(12) United States Patent
Matteucci et al.

(10) Patent No.: US 8,003,625 B2
(45) Date of Patent: Aug. 23, 2011

(54) PHOSPHORAMIDATE ALKYLATOR PRODRUGS

(75) Inventors: Mark Matteucci, Portola Valley, CA (US); Jian-Xin Duan, South San Francisco, CA (US); Hailong Jiao, Foster City, CA (US); Jacob Kaizerman, Menlo Park, CA (US)

(73) Assignee: Threshold Pharmaceuticals, Inc., Redwood CIty, CA (US)

( * ) Notice: Subject to any disclaimer, the term of this patent is extended or adjusted under 35 U.S.C. 154(b) by 146 days.

(21) Appl. No.: 11/993,822

(22) PCT Filed: Jun. 29, 2006

(86) PCT No.: PCT/US2006/025881
§ 371 (c)(1),
(2), (4) Date: Aug. 28, 2009

(87) PCT Pub. No.: WO2007/002931
PCT Pub. Date: Jan. 4, 2007

(65) Prior Publication Data
US 2010/0137254 A1    Jun. 3, 2010

Related U.S. Application Data

(60) Provisional application No. 60/695,755, filed on Jun. 29, 2005.

(51) Int. Cl.
*A61K 31/675* (2006.01)
*A61K 31/665* (2006.01)
*C07F 9/22* (2006.01)
*A61P 35/00* (2006.01)

(52) U.S. Cl. .............. 514/94; 514/95; 514/99; 548/119; 549/6; 549/218

(58) Field of Classification Search ........................ None
See application file for complete search history.

(56) References Cited

U.S. PATENT DOCUMENTS

| | | | |
|---|---|---|---|
| 3,652,579 A | 3/1972 | Hoffer et al. | |
| 4,908,356 A | 3/1990 | Borch et al. | |
| 4,921,963 A | 5/1990 | Skov et al. | |
| 4,945,102 A | 7/1990 | Suzuki et al. | |
| 5,190,929 A | 3/1993 | Borch et al. | |
| 5,233,031 A | 8/1993 | Borch et al. | |
| 5,270,330 A | 12/1993 | Suzuki et al. | |
| 5,306,727 A | 4/1994 | Borch | |
| 5,403,932 A | 4/1995 | Borch et al. | |
| 5,472,956 A | 12/1995 | Borch et al. | |
| 5,622,936 A | 4/1997 | Wiessler et al. | |
| 5,703,080 A | 12/1997 | Nakakura et al. | |
| 5,750,782 A | 5/1998 | Denny et al. | |
| 5,780,585 A | 7/1998 | Anlezark et al. | |
| 5,872,129 A | 2/1999 | Denny et al. | |
| 5,877,158 A | 3/1999 | Bosslet et al. | |
| 5,985,909 A | 11/1999 | Denny et al. | |
| 6,020,315 A | 2/2000 | Bosslet et al. | |
| 6,130,237 A | 10/2000 | Denny et al. | |
| 6,197,760 B1 | 3/2001 | Struck | |
| 6,218,519 B1 | 4/2001 | Kenten et al. | |
| 6,240,925 B1 | 6/2001 | McMillan et al. | |
| 6,251,933 B1 | 6/2001 | Denny et al. | |
| 6,506,739 B1 | 1/2003 | Herr et al. | |
| 6,656,926 B2 | 12/2003 | Borch et al. | |
| 6,855,695 B2 | 2/2005 | Lin et al. | |
| 6,903,081 B2 | 6/2005 | Borch et al. | |
| 7,173,020 B2 | 2/2007 | Borch et al. | |
| 7,304,046 B2 | 12/2007 | Borch et al. | |
| 2003/0008850 A1 | 1/2003 | Borch et al. | |
| 2003/0050331 A1 | 3/2003 | Ng et al. | |
| 2003/0096743 A1 | 5/2003 | Sender et al. | |
| 2003/0130189 A1 | 7/2003 | Sender et al. | |
| 2004/0121940 A1 | 6/2004 | De Groot et al. | |
| 2004/0176332 A1 | 9/2004 | Borch et al. | |
| 2004/0254103 A1 | 12/2004 | Lin et al. | |
| 2005/0043244 A1 | 2/2005 | Lin et al. | |
| 2006/0258656 A1 | 11/2006 | Matteucci | |

FOREIGN PATENT DOCUMENTS

| | | |
|---|---|---|
| DE | 2229223 | 2/1973 |
| EP | 312 858 B1 | 2/1992 |
| EP | 648 503 A1 | 4/1995 |
| JP | 8-509727 A | 10/1996 |
| JP | 2002-543059 A | 12/2002 |
| WO | WO 94/25471 A1 | 11/1994 |
| WO | WO 97/39007 A1 | 10/1997 |
| WO | WO 00/64864 A1 | 11/2000 |
| WO | WO 02/096910 A1 | 12/2002 |
| WO | WO 03/066052 A1 | 8/2003 |
| WO | WO 2004/085361 A1 | 10/2004 |
| WO | WO 2004/085421 A2 | 10/2004 |
| WO | WO 2004/087075 A2 | 10/2004 |
| WO | WO 2005/076888 A1 | 8/2005 |
| WO | WO 2006/057946 A2 | 6/2006 |
| WO | WO 2008/011588 A2 | 1/2008 |
| WO | WO 2008/076826 A2 | 6/2008 |
| WO | WO 2008/083101 A1 | 7/2008 |

OTHER PUBLICATIONS

Misiura et al., caplus an 2002:311287.*
Misiura et al., Acta Biochim. Polonica, vol. 49, 2002, pp. 169-176.*
Berry et al., "5-Nitrofuran-2-ylmethyl group as a potential bioreductively activated pro-drug system," *J. Chem. Soc. Perkin Trans.*, 1997, 1:1147-1156.
Borch, RF, et al., "Antitumor activity and toxicity of novel nitroheterocyclic phosphoramidates," *J Med Chem*, 2001, 44(1): 74-77.
Borch, RF, et al., "Synthesis and evaluation of nitroheterocyclic phosphoramidates as hypoxia-selective alkylating agents," *J Med Chem*, 2000, 43(11): 2258-2265.
De Jaeger et al., "Relationship of hypoxia to metastatic ability in rodent tumours," *Br. J. Cancer*, 2001, 84(9):1280-1285.

(Continued)

*Primary Examiner* — Sun Jae Y Loewe
(74) *Attorney, Agent, or Firm* — Kilpatrick Townsend Stockton LLP

(57) ABSTRACT

Phosphoramidate alkylator prodrugs can be used to treat cancer when administered alone or in combination with one or more anti-neoplastic agents.

20 Claims, 7 Drawing Sheets

OTHER PUBLICATIONS

DeGroot, et al. "Anticancer Prodrugs for Application in Monotherapy: Targeting Hypoxia, Tumor-Associated Enzymes, and Receptors," *Current Med Chem*, 2001, 8:1093-1122.

Denny, W.A., "Prodrug strategies in cancer therapy," Eur. J. Med. Chem., 2001, 36:577-595.

Duan, Jian-Xin, "Potent and Highly Selective Hypoxia-Activated Achiral Phosphoramidate Mustards as Anticancer Drugs," *J. Med. Chem.*, 2008, 51(8): 2412-2420.

Engle et al., "$^{31}$P NMR Kinetic Studies of the Intra- and Intermolecular Alkylation Chemistry of Phosphoramide Mustard and Cognate N-Phosphorylated Derivatives of N,N-Bis(2-chlorethyl)amine$^{1,2}$," *J. Med. Chem.*, 1982, 25:1347-1357.

Everett et al., "Bioreductively-Activated Prodrugs for Targeting Hypoxic Tissues: Elimination of Aspirin from 2-Nitroimidazole Derivatives," *Bioorganic Med. & Chem. Ltrs.*, 1999, 9:1267-1272.

Everett et al., "Modifying rates of reductive elimination of leaving groups from indolequinone prodrugs: a key factor in controlling hypoxia-selective drug release," *Biochemical Pharmacology*, 2002, 63:1629-1639.

Garsky Publication, "The Synthesis of a Prodrug of Doxorubicin Designed to Provide Reduced Greater Targeting Efficacy," *J. Med. Chem*. 2001, 44(24), 4216-4224. (Abstract).

Glazman-Kusnierczyk, et al. "Antitumor activity evaluation of bromine-substituted analogues of ifosfamide. 1. Stereodifferentiation of biological effects and selection of the most potent compounds," *Immunopharmacology and Immunotoxicology*, 1992, 14(4): 883-911.

Hay et al., "A 2-Nitroimidazole Carbamate Prodrug of 5-Amino-1-(Chloromethyl)-3-[(5,6,7-Trimethoxyindol-2-YL)Carbonyl]-1,2-Dihydro-3H-Benz[E]Indole (Amino-*Seco*- CBI-TMI) for Use With Adept and Gdept," *Biooganic Med. & Chem. Ltrs.*, 1999, 9:2237-2242.

Hernick et al., "Studies on the Mechanisms of Activation of Indolequinone Phosphoramidate Prodrugs," *J. Med. Chem.*, 46:148-154 (2003).

Hernick, et al., "Design, Synthesis, and Biological Evaluation, of Indolequinone Phosphormamidate Prodrugs Targeted to DT-diaphorase," 2002, *J. Med Chem*. 45: 3540-3548.

Kyle et al., "Direct Assessment of Drug Penetration into Tissue Using a Novel Application of Three-Dimensional Cell Culture," *Cancer Research*, 2004, 64:6304-6309.

Lee, et al., "Synthesis and Hypoxia-Selective Cytotoxicity of a 2-Nitroimidazole Mustard," Bioorganic & Med. Chem. Ltrs., 1998, 8:1741-1744.

Lin et al., "(*o*- and *p*- Nitrobenzyloxycarbobyl)—5-fluorouracil Derivatives as Potential Conjugated Bioreductive Alkylating Agents," 1986, *J. Med. Chem.*, 29:84-89.

Naylor et al., "Recent Advances in Bioreductive Drug Targeting," *Mini Reviews in Med. Chem.*, 2001, 1:17-29.

Papot, S. et al. "Design of Selectively activated anticancer prodrugs: elimination and cyclization strategies," *Curr Med Chem Anticancer Agents*, 2002, 2(2): 155-85.

Parveen et al., "2-Nitroinnidazol-5-Ylmethyl as a Potential Bioreductively Activated Prodrug System: Reductively Triggered Release of the Parp Inhibitor 5-Bromoisoquinolinone," *Bioorganic Med. & Chem. Ltrs.*, 1999, 9:2031-2036.

Rofstad et al., "Hypoxia-induced metastasis of human melanoma cells: involvement of vascular endothelial growth factor-mediated angiogenesis," *Br. J. Cancer*, 1999, 80(11):1697-1707.

Rosen et al., "Phase 1 Study of TLK286 (Telcyta) Administered Weekly in Advanced Malignancies," *Clin. Cancer Res.*, 2004, 10:3689-3698.

Steinberg, G., et al., "Synthesis and evaluation of pteroic acid-conjugated nitroheterocyclic phosphoramidates as folate receptor-targeted alkylating agents," *J Med Chem*, 2001, 44(1): 69-73.

Struck, et al. "Antitumor activity of halogen analogs of phosphoramide, isophosphoramide, and triphosphoramide mustards, the cytotoxic metabolites of cyclophosphamide, ifosfamide, and trofosfamide," *Cancer Chemo. Pharma.*, 1994, 34(3): 191-6.

Studzian, et al. "Effects of alkylating metabolites of ifosfamide and its bromo analogues on DNA of HELA cells," *Biochem, Pharm*. 1992, 43(5):937-943.

Wakselman, M., "1,4- and 1,6- Eliminations from Hydroxy- and Amino-Substituted Benzyl Systems: Chemical and Biochemical Applications," *Nouv. J. Chim.*, 1983, 7(7):439-447.

West et al., "A comparison of adriamycin and mAMSA, II. Studies with V79 and human tumour multicellular spheroids," *Cancer Chemother. Pharmacol.*, 1987, 20:109-114.

Workman et al., "The experimental development of bioreductive drugs and their role in cancer therapy," *Cancer and Metastasis Rev.*, 1993, 12:73-82.

Denny, W.A., "Nitroreductase-Based GDEPT," *Current Pharmaceutical Design*, 8(15):1349-1361 (2002).

Hay, M.P. et al., "Structure-Activity Relationships of 1,2,4-Benzotriazine 1,4-Dioxides as Hypoxia-Selective Analogues of Tirapazamine," *J. Med. Chem.*, 46(1):169-182 (2003).

Mauger, A.B. et al., "Self-Immolative Prodrugs: Candidates for Antibody-Directed Enzyme Prodrug Therapy in Conjunction with a Nitroreductase Enzyme," *Journal of Medicinal Chemistry*, 37(21):3452-3458 (1994).

Stewart, D.J. et al., "Doxorubicin plus metronidazole in the treatment of recurrent or metastatic squamous cell carcinoma of the head and neck ," *Am. J. Clin. Oncol.*, 16(2):113-116 (Apr. 1993), Abstract.

Tannock, I.F., "In Vivo Interaction of Anti-Cancer Drugs with Misonidazole or Metronidazole: Methotrexate, 5-Flurouracil and Adriamycin," *Br. J. Cancer*, 42:861 (1980).

Tercel, M. et al., "Hypoxia-Selective Antitumor Agents, 16. Nitroarylmethyl Quaternary Salts as Bioreductive Prodrugs of the Alkylating Agent Mechlorethamine," *J. Med. Chem.*, 44(21):3511-3522.

\* cited by examiner

PHOSPHORAMIDATE ALKYLATOR PRODRUGS

CROSS-REFERENCES TO RELATED APPLICATIONS

This application claims benefit of U.S. provisional patent application No. 60/695,755 filed 29 Jun. 2005, which is incorporated herein by reference.

BACKGROUND OF THE INVENTION

1. Field of Invention

The present invention provides compositions and methods for treating cancer and other hyperproliferative disease conditions with phosphoramidate alkylator prodrugs. The present invention generally relates to the fields of chemistry, biology, molecular biology, pharmacology, and medicine.

2. Description of Related Art

Alkylating agents ("alkylators" or "mustards") used in cancer chemotherapy encompass a diverse group of chemicals that have the ability to alkylate biologically vital macromolecules such as DNA under physiological conditions (see Hardman et al., *The Pharmacological Basis of Therapeutics*, 2001, 1389-1399, McGraw-Hill, New York, USA). DNA alkylation is postulated to be an important mechanism in the antitumor activity of alkylators. The chemotherapeutic alkylators act as strong electrophiles, for example, through the formation of neighboring-heteroatom-stabilized onium intermediates such as an aziridine or an aziridinium cation.

Phosphoramidate based alkylators used in cancer therapy, such as Cyclophosphamide and Ifosfamide, are an important subclass of chemotherapeutic alkylators. Cyclophosphamide and Ifosfamide are each activated in the liver and the active alkylator released alkylates nucleophilic moieties such as the DNA within the tumor cells to act as a chemotherapeutic agent. If the active alkylators are released away from the tumor, DNA and other nucleophilic moieties such as the phosphate, amino, sulfhydryl, hydroxyl, carboxyl and imidazo groups of biomolecules of healthy non-cancerous cells, can get alkylated. Such alkylation of healthy cells can result in unwanted toxic events in patients (see Hardman et al., supra).

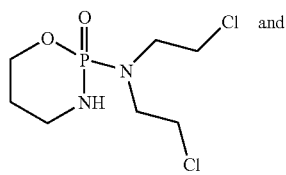

Cyclophosphamide

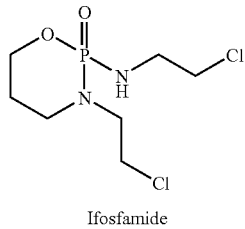

Ifosfamide

There remains a need for new phosphoramidate based alkylators that can be used to treat cancer or other hyperproliferative disease conditions, preferably compounds less toxic to normal cells. The present invention meets these needs and provides novel phosphoramidate alkylator prodrugs as well as methods of therapy employing them, as summarized in the following section.

BRIEF SUMMARY OF THE INVENTION

In one aspect the present invention provides compounds which are hypoxia activated phosphoramidate alkylator prodrugs and methods for their synthesis. The phosphoramidate alkylator prodrugs of the present invention can have the formula Alk-T wherein Alk is a phosphoramidate alkylator, T is $L-Z_3$ wherein L is a linker, and $Z_3$ is a bioreductive group.

In one aspect, the present invention provides phosphoramidate alkylator prodrugs of formula (I):

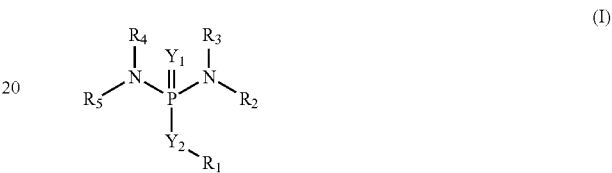

wherein $Y_1$ is O, S, $NR_6$, or $NSO_2R_6$ wherein each $R_6$ is independently $C_1$-$C_6$ alkyl, $C_1$-$C_6$ heteroalkyl, aryl, or heteroaryl;

$Y_2$ is O, S, $NR_6$, $NCOR_6$, or $NSO_2R_6$;

each of $R_1$-$R_5$ independently is hydrogen, hydroxyl, amino, $C_1$-$C_6$ alkyl, $C_1$-$C_6$ heteroalkyl, $C_3$-$C_8$ cycloalkyl, heterocyclyl, $C_1$-$C_6$ alkoxy, $C_1$-$C_6$ alkylamino, $C_1$-$C_6$ dialkylamino, aryl, heteroaryl, $C_1$-$C_6$ acyl, $C_1$-$C_6$heteroacyl, aroyl, or heteroaroyl; or together any two of $R_1$-$R_5$ form a $C_3$-$C_{10}$ heterocycle; or each of $R_1$-$R_5$ independently is a Trigger, T, wherein T is $L-Z_3$;

L is selected from
—[C(Z$_1$)$_2$—Y$_3$]$_v$[C(=O)—O]$_q$—[C(Z$_1$)$_2$—Z$_2$—Y$_4$]$_u$—[C(Z$_1$)$_2$]$_z$—[—C(Z$_1$)=C(Z$_1$)]$_g$—Z$_3$ and
—[C(Z$_1$)$_2$—Y$_3$]$_v$—(S(=O)$_2$)$_q$—[C(Z$_1$)$_2$—Z$_2$—Y$_4$]$_u$[C(Z$_1$)$_2$]$_z$—[C(Z$_1$)=C(Z$_1$)]$_g$—Z$_3$; wherein each z, v, q, u, and g independently is 0 or 1;

$Y_3$ is S, O, or $NR_7$ wherein each $R_7$ is independently hydrogen, hydroxyl, $C_1$-$C_6$ alkyl, $C_1$-$C_6$ heteroalkyl, $C_3$-$C_8$ cycloalkyl, heterocyclyl, $C_1$-$C_6$ alkoxy, $C_1$-$C_6$ alkylamino, $C_1$-$C_6$ dialkylamino, aryl, heteroaryl, $C_1$-$C_6$ acyl, $C_1$-$C_6$heteroacyl, aroyl, or heteroaroyl;

$Y_4$ is O, S, or —NR$_7$—C(=O)—O—;

each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$heteroacyl, aroyl, or heteroaroyl;

$Z_2$ is $C_1$-$C_6$ alkylene, $C_1$-$C_6$ heteroalkylene,

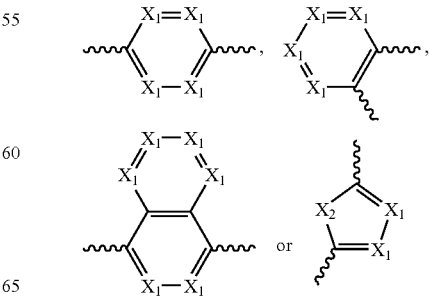

wherein each $X_1$ is independently N or $CR_8$, each $R_8$ is independently hydrogen, halogen, nitro, cyano, $CO_2H$, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$ heteroacyl, aroyl, or heteroaroyl;

$X_2$ is $NR_7$, S, or O; and $Z_3$ is selected from the group consisting of:

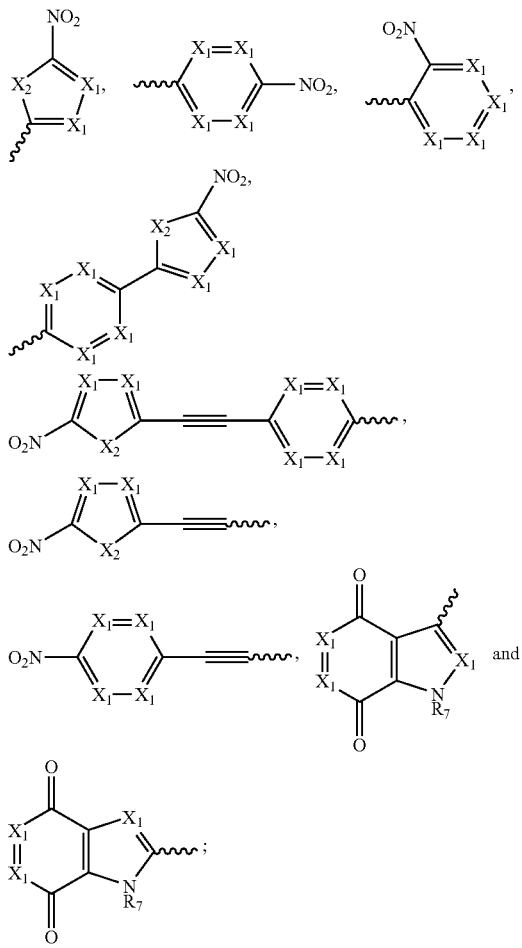

with the proviso that in formula (I):

(i) at least two of $R_1$-$R_5$ are selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl;

(ii) at least one of $R_1$-$R_5$ is selected from the group consisting of 2-haloalkyl, 2-$C_1$-$C_6$ alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

or (iii) $NR_2R_3$ and $NR_4R_5$ both together are

and an individual isomer or a racemic or non-racemic mixture of isomers, bioisosteres, pharmacophores, a pharmaceutically acceptable salt, solvate, hydrate, or a prodrug thereof.

In one embodiment, $Z_3$ is a bioreductive group that can accept one or more electrons in an oxidation-reduction reaction.

In a related embodiment, the present invention provides phosphoramidate alkylator prodrugs having $IC_{50}$ or $GI_{50}$, in cells under hypoxia, of 50 µM to 0.01 nM. In a related embodiment, the present invention provides phosphoramidate alkylator prodrugs having hypoxic cytotoxicity which are up to a million fold, up to 10,000 fold, and up to 1000 fold less toxic in corresponding normoxic cells. In a related embodiment, the cellular cytotoxicity is measured by antiproliferation assays and using the relative $IC_{50}$ value of a compound in hypoxic and normoxic cells. In a related embodiment, the cellular cytotoxicity is measured by clonogenic assays and using the relative $C_{10}$, $C_{50}$, or $C_{90}$ values of the compounds in hypoxic and normoxic cells.

In another related embodiment, the present invention provides phosphoramidate alkylator prodrugs having $IC_{50}$ values, in cells under hypoxia, of 50 µM to 0.01 nM. In another related embodiment, the present invention provides phosphoramidate alkylator prodrugs which are up to 5000 fold less toxic in corresponding normoxic cells as measured by the relative $IC_{50}$ values in hypoxic and normoxic cells. In another related embodiment, the present invention provides phosphoramidate alkylator prodrugs having an $IC_{50}$ in cells in hypoxia of 50 µM to 0.01 nM and which is up to 1000 fold less toxic in corresponding normoxic cells as measured by the relative $IC_{50}$ values in hypoxic and normoxic cells.

In a related embodiment, a phosphoramidate alkylator prodrug of the present invention has a hypoxic cytotoxicity of 0.1 nM to 50 µM and a hypoxia cytotoxicity ratio, HCR, measured by the ratio of normoxic and hypoxic cytotoxicities, and defined in greater detail further below, of 10 to 100,000. In a related embodiment, the phosphoramidate alkylator prodrug of the present invention has a hypoxic cytotoxicity of 0.1 nM to 50 µM and an HCR of 25 to 100,000. In another related embodiment, a phosphoramidate alkylator prodrug of the present invention has a hypoxic cytotoxicity of 0.1 nM to 5 µM and an HCR of 50 to 10,000.

In one aspect, the present invention provides novel phosphoramidate alkylators for treatment of cancer and other hyperproliferative diseases.

In one aspect, the present invention provides a pharmaceutical formulation comprising the phosphoramidate alkylator prodrugs of the invention and a pharmaceutically acceptable excipient, carrier, or diluent.

In one aspect, the present invention provides a method of treating cancer and other hyperproliferative diseases comprising administering a therapeutically effective amount of a phosphoramidate alkylator prodrug of the invention or one that is known, to a patient in need of such therapy. In one embodiment, the cancer treated is resistant to first line, second line, or third line therapy, or is a relapsed cancer. In another embodiment, the cancer treated is a metastatic cancer. In another embodiment, the phosphoramidate alkylator prodrug of the invention, or one that is known, is administered in combination with at least another anti-cancer agent.

DETAILED DESCRIPTION OF THE INVENTION

Figure 1:
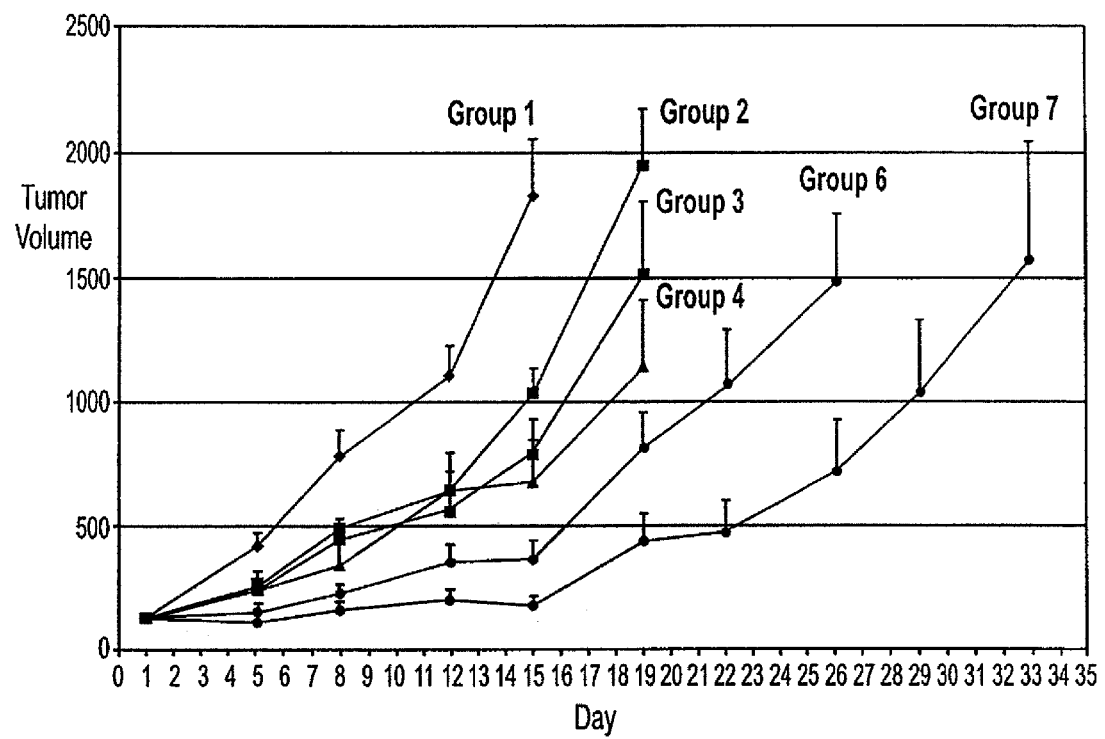
FIG. 1 demonstrates the effect of Compound 25 (50 mg/kg) on tumor growth in the H460 xenograft mouse model.

The detailed description of the different aspects and embodiments of the present invention is organized as follows: Section I provides useful definitions; Section IIa and b describes the compounds of the invention and methods for making them; Section IIIa, b and c describes methods of treatment, therapies, administrations, and formulations employing the compounds of the invention alone or in combination; and Section IV provides examples of synthetic methods and biological assays for the compounds of the invention. This detailed description is organized into sections only for the convenience of the reader, and disclosure found in any section is applicable to any aspect of the invention.

I. DEFINITIONS

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "a" or "an" means "at least one" or "one or more."

"Alkyl" means a linear saturated monovalent hydrocarbon radical or a branched saturated monovalent hydrocarbon radical having the number of carbon atoms indicated in the prefix. As used in this disclosure, the prefixes ($C_1$-$C_{qq}$), $C_1$-$C_{qq}$, or $C_1$-$C_{qq}$, wherein qq is an integer from 2-20, have the same meaning. For example, ($C_1$-$C_8$) alkyl, $C_{1-8}$ alkyl, or $C_1$-$C_8$ alkyl includes methyl, ethyl, n-propyl, 2-propyl, n-butyl, 2-butyl, tert-butyl, pentyl, and the like. For each of the definitions herein (e.g., alkyl, alkenyl, alkoxy, aralkyloxy), when a prefix is not included to indicate the number of main chain carbon atoms in an alkyl portion, the radical or portion thereof will have six or fewer main chain carbon atoms. ($C_1$-$C_6$) alkyl can be further optionally be substituted with substituents, including for example, deuterium ("D"), hydroxyl, amino, mono or di($C_1$-$C_6$) alkyl amino, halo, $C_2$-$C_6$ alkenyl ether, cyano, nitro, ethenyl, ethynyl, $C_1$-$C_6$ alkoxy, $C_1$-$C_6$ alkylthio, —COOH, —CONH$_2$, mono- or di($C_1$-$C_6$) alkylcarboxyamido, —SO$_2$NH$_2$, —OSO$_2$—($C_1$-$C_6$) alkyl, mono or di($C_1$-$C_6$) alkylsulfonamido, aryl, heteroaryl, alkylsulfonyloxy, heteroalkylsulfonyloxy, arylsulfonyloxy or heteroarylsulfonyloxy.

"Alkenyl" means a linear monovalent hydrocarbon radical or a branched monovalent hydrocarbon radical having the number of carbon atoms indicated in the prefix and containing at least one double bond, but no more than three double bonds. For example, ($C_2$-$C_6$) alkenyl includes, ethenyl, propenyl, 1,3-butadienyl and the like. Alkenyl can be further optionally be substituted with substituents, including for example, deuterium ("D"), hydroxyl, amino, mono or di($C_1$-$C_6$) alkyl amino, halo, $C_2$-$C_6$ alkenyl ether, cyano, nitro, ethenyl, ethynyl, $C_1$-$C_6$ alkoxy, $C_1$-$C_6$ alkylthio, —COOH, —CONH$_2$, mono- or di($C_1$-$C_6$) alkyl-carboxamido, —SO$_2$NH$_2$, —OSO$_2$—($C_1$-$C_6$) alkyl, mono or di($C_1$-$C_6$) alkylsulfonamido, aryl, heteroaryl, alkyl or heteroalkylsulfonyloxy, and aryl or heteroarylsulfonyloxy.

"Alkylator" means a reactive moiety capable of forming a covalent alkyl linkage to macromolecules via an electrophilic reaction with a nucleophile on the macromolecule.

"Phosphoramidate alkylator" means an alkylator for which an aziridine or aziridinium electrophile is present or generated by intramolecular cyclization.

"Alkylene" means a linear saturated divalent hydrocarbon radical having from one to twelve carbon atoms or a branched saturated divalent hydrocarbon radical having from one to twelve carbon atoms optionally substituted with substituents including for example, deuterium ("D"), hydroxyl, amino, mono or di($C_1$-$C_6$)alkyl amino, halo, $C_2$-$C_6$ alkenyl ether, cyano, nitro, ethenyl, ethynyl, $C_1$-$C_6$ alkoxy, $C_1$-$C_6$ alkylthio, —COOH, —CONH$_2$, mono- or di-($C_1$-$C_6$)alkyl-carboxamido, —SO$_2$NH$_2$, —OSO$_2$—($C_1$-$C_6$) alkyl, mono or di($C_1$-$C_6$) alkylsulfonamido, aryl, heteroaryl, alkyl or heteroalkylsulfonyloxy, and aryl or heteroarylsulfonyloxy. For example, alkylene includes methylene, ethylene, propylene, 2-methylpropylene, pentylene, hexylene, and the like.

"Heteroalkylene" has essentially the meaning given above for an alkylene except that one or more heteroatoms (i.e. oxygen, sulfur, nitrogen and/or phosphorous) may be present in the alkylene biradical. For example, heteroalkylene includes, —CH$_2$OCH$_2$O—, —CH$_2$CH$_2$OCH$_2$CH$_2$—, —CH$_2$CH$_2$N(CH$_3$)CH$_2$CH$_2$—, —CH$_2$CH$_2$SCH$_2$CH$_2$—, and the like.

"Aryl" refers to a monovalent monocyclic or bicyclic aromatic hydrocarbon radical of 6 to 10 ring atoms which is substituted independently with one to eight substituents, preferably one, two, three, four or five substituents selected from deuterium ("D"), alkyl, cycloalkyl, cycloalkylalkyl, halo, nitro, cyano, hydroxyl, alkoxy, amino, acylamino, monoalkylamino, di-alkylamino, haloalkyl, haloalkoxy, heteroalkyl, COR (where R is hydrogen, alkyl, cycloalkyl, cycloalkyl-alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^x$R$^y$ (where n is an integer from 0 to 5, R' and R" are independently hydrogen or alkyl, and R$^x$ and R$^y$ are independently selected from hydrogen, alkyl, cycloalkyl, cycloalkylalkyl, phenyl or phenylalkyl). In one embodiment, R$^x$ and R$^y$ together are cycloalkyl or heterocyclyl. More specifically, the term aryl includes, but is not limited to, phenyl, biphenyl, 1-naphthyl, and 2-naphthyl, and the substituted forms thereof.

"Cycloalkyl" refers to a monovalent cyclic hydrocarbon radical of three to seven ring carbons. The cycloalkyl group can have one or more double bonds and can also be optionally substituted independently with one, two, three or four substituents selected from alkyl, optionally substituted phenyl, or —C(O)R$^z$ (where R$^z$ is hydrogen, alkyl, haloalkyl, amino, mono-alkylamino, di-alkylamino, hydroxyl, alkoxy, or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl, and the like.

"Heteroalkyl" means an alkyl radical as defined herein with one, two or three substituents independently selected from cyano, —OR$^w$, —NR$^x$R$^y$, and —S(O)$_p$R$^z$ (where p is an integer from 0 to 2), with the understanding that the point of attachment of the heteroalkyl radical is through a carbon atom of the heteroalkyl radical. $R^w$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. $R^x$ is hydrogen, alkyl, cycloalkyl, cycloalkyl-alkyl, aryl or aralkyl. $R^y$ is hydrogen, alkyl, cycloalkyl, cycloalkyl-alkyl, aryl, aryalkyl, alkoxycarbonyl, aryloxycarbonyl, carboxamido, mono- or di-alkylcarbamoyl or alkylsulfonyl. $R^z$ is hydrogen (provided that n is 0), alkyl, cycloalkyl, cycloalkyl-alkyl, aryl, aryalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^w$, $R^x$, $R^y$, and $R^z$ can be further substituted by amino, halo, fluoro, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^w$, —$NR^xR^y$, or —$S(O)_p R^z$ portions. In one embodiment, $R^x$ and $R^y$ together are cycloalkyl or heterocyclyl.

"Heteroaryl" means a monovalent monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to eight substituents, preferably one, two, three or four substituents, selected from alkyl, cycloalkyl, cycloalkyl-alkyl, halo, nitro, cyano, hydroxyl, alkoxy, amino, acylamino, mono-alkylamino, di-alkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^x$R$^y$ (where n is an integer from 0 to 5, R' and R" are independently hydrogen or alkyl, and R$^x$ and R$^y$ are, independently of each other, hydrogen, alkyl, cycloalkyl, cycloalkyl-alkyl, phenyl or phenylalkyl). In one embodiment, $R^x$ and $R^y$ together are cycloalkyl or heterocyclyl. More specifically, the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, indazolyl, pyrrolopyrymidinyl, indolizinyl, pyrazolopyridinyl, triazolopyridinyl, pyrazolopyrimidinyl, triazolopyrimidinyl, pyrrolotriazinyl, pyrazolotriazinyl, triazolotriazinyl, pyrazolotetrazinyl, hexaaza-indenyl, and heptaaza-indenyl and derivatives thereof. Unless indicated otherwise, the arrangement of the hetero atoms within the ring can be any arrangement allowed by the bonding characteristics of the constituent ring atoms.

"Heterocyclyl" or "cycloheteroalkyl" means a saturated or unsaturated non-aromatic cyclic radical of 3 to 8 ring atoms in which one to four ring atoms are heteroatoms selected from O, NR (where R is hydrogen, alkyl, cycloalkyl, cycloalkylalkyl, phenyl or phenylalkyl), P(=O)OR$^w$, or S(O)$_p$ (where p is an integer from 0 to 2), the remaining ring atoms being C, where one or two C atoms can optionally be replaced by a carbonyl group. The heterocyclyl ring can be optionally substituted independently with one, two, three or four substituents selected from alkyl, aryl, arylalkyl, heteroaryl, heteroarylalkyl, cycloalkyl, cycloalkylalkyl, halo, nitro, cyano, hydroxyl, alkoxy, amino, mono-alkylamino, di-alkylamino, haloalkyl, haloalkoxy, —COR (where R is hydrogen, alkyl, cycloalkyl, cycloalkylalkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^x$R$^y$ (where n is an integer from 0 to 5, R' and R" are independently hydrogen or alkyl, R$^x$ and R$^y$ are, independently of each other, hydrogen, alkyl, cycloalkyl, cycloalkylalkyl, phenyl or phenylalkyl). More specifically the term heterocyclyl includes, but is not limited to, pyridyl, tetrahydropyranyl, N-methylpiperidin-3-yl, N-methylpyrrolidin-3-yl, 2-pyrrolidon-1-yl, furyl, quinolyl, thienyl, benzothienyl, pyrrolidinyl, piperidinyl, morpholinyl, pyrrolidinyl, tetrahydrofuranyl, tetrahydrothiofuranyl, 1,1-dioxohexahydro-1Δ$^6$-thiopyran-4-yl, tetrahydroimidazo[4,5-c]pyridinyl, imidazolinyl, piperazinyl, and piperidin-2-yl and the derivatives thereof. The prefix indicating the number of carbon atoms (e.g., $C_3$-$C_{10}$) refers to the total number of carbon atoms in the portion of the cycloheteroalkyl or heterocyclyl group exclusive of the number of heteroatoms.

"$C_1$-$C_6$ Acyl" means —CO—($C_1$-$C_6$ alkyl), wherein the term alkyl is as defined above.

"$C_1$-$C_6$ Heteroacyl" means —CO—($C_1$-$C_6$ heteroalkyl), wherein the term heteroalkyl is as defined above.

"Aroyl" means —CO-aryl, wherein the term aryl is as defined above.

"Heteroaroyl" means —CO-heteroaryl, wherein the term heteroaryl is as defined above.

"$R_{sul}$sulfonyloxy" means $R_{sul}$—S(=O)$_2$—O— including alkylsulfonyloxy, heteroakylsulfonyloxy, cycloalkylsulfonyloxy, heterocyclylsulfonyloxy, arylsulfonyloxy and heteroarylsulfonyloxy wherein $R_{sul}$ is alkyl, heteroalkyl, cycloalkyl, heterocyclyl, aryl and heteroaryl respectively, and wherein alkyl, heteroalkyl, cycloalkyl, heterocyclyl, aryl and heteroaryl are defined above. Examples of alkylsulfonyloxy include Me-S(=O)$_2$—O—, Et-S(=O)$_2$—O—, CF$_3$—S(=O)$_2$—O— and the like, and examples of arylsulfonyloxy include

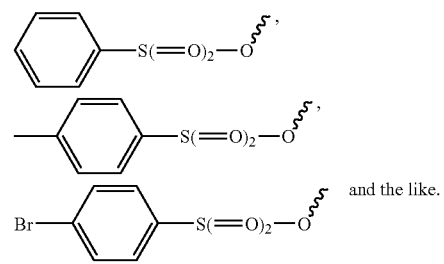

and the like.

Alkylsulfonyloxy, heteroakylsulfonyloxy, cycloalkylsulfonyloxy, heterocyclylsulfonyloxy, arylsulfonyloxy, and heteroarylsulfonyloxy groups can be leaving groups in phosphoramidate alkylators and can be replaced in a cell by nucleic acids such as DNA or RNA, and imidazoles, carboxylates, or thiols of proteins, causing alkylation and cell death. The rate of reaction of various $R_{sul}$sulfonyloxy groups with nucleic acids, proteins or water can be modulated depending on, for example, the electron withdrawing nature and the steric bulk of the $R_{sul}$ moiety and can provide phosphoramidate alkylators and prodrugs thereof which are more toxic to tumors in general and hypoxic zones of tumor in particular over healthy cells.

"Substituents" mean, along with substituents particularly described in the definition of each of the groups above, those selected from: deuterium, -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$, —R', —N₃, perfluoro(C₁-C₄) alkoxy, and perfluoro(C₁-C₄) alkyl, in a number ranging from zero to the total number of open valences on the radical; and where R', R" and R'" are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and (unsubstituted aryloxy)-$C_{1-4}$ alkyl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other suitable substituents include each of the above aryl substituents attached to a ring atom by an alkylene tether of from 1-4 carbon atoms. Two of the substituents on adjacent atoms of the aryl or heteroaryl ring may optionally be replaced with a substituent of the formula -T²-C(O)—(CH₂)$_q$—U³—, wherein T² and U³ are independently —NH—, —O—, —CH₂— or a single bond, and q is an integer of from 0 to 2. Alternatively, two of the substituents on adjacent atoms of the aryl or heteroaryl ring may optionally be replaced with a substituent of the formula -A-(CH₂)$_r$—B—, wherein A and B are independently —CH₂—, —O—, —NH—, —S—, —S(O)—, —S(O)₂—, —S(O)₂NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH₂)$_s$—X⁵—(CH₂)$_t$—, where s and t are independently integers of from 0 to 3, and X⁵ is —O—, —NR'—, —S—, —S(O)—, —S(O)₂—, or —S(O)₂NR'—. The substituent R' in —NR'- and —S(O)₂NR'— is selected from hydrogen or unsubstituted $C_{1-6}$ alkyl.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium (³H), iodine-125 (¹²⁵I) or carbon-14 (¹⁴C). All isotopic variations of the compounds of the present invention, whether radioactive or not, are intended to be encompassed within the scope of the present invention.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al, "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, a "glucose analog" includes mono-, di- and tri-saccharides. The glucose analog includes sacchrides comprising glucosamine, N-acetyl-glucosamine; fructose; mannose and mannose derivatives; glucose and glucose derivatives, including but not limited to 2-deoxyglucose (2-DG), N-acetyl-2-amino-2-deoxyglucose, 3-amino-3-deoxy-glucose, 2-amino-2-deoxy-glucose; and galactose and galactose derivatives including but not limited to D-2-deoxy-D-galactose, D-4-amino-4-deoxy-galactose and D-2-amino-2-deoxy-galactose. Thus, the glucose analog can differ from glucose or a derivative such as DG and glucosamine in that it is an epimer thereof. In addition, the glucose analog can be a fluorinated derivative of any of the foregoing compounds. Moreover, the oxygen in the ring of any of the foregoing compounds can be substituted with an isostere selected from the group consisting of S, sulfone, and the like. For example, glucose analog can be 5-thio-D-glucose or a derivative thereof A wavy line

"∿∿"

means the point of attachment of one group or moiety to another. For example, both

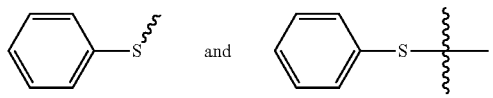

indicate that the thio group is the point of attachment to another group or moiety.

The terms CO, C(O), C(=O), —CO— are used interchangeably herein. The terms $CO_2$ and COO are used interchangeably herein. The terms; $SO_2$, $S(O)_2$ are used interchangeably herein. The terms SO and S(=O) are used interchangeably herein. The terms PO and P(=O) are used interchangeably herein.

As used herein, a "bioisostere" of a chemical moiety such as molecule, group, or atom means another chemical moiety having similar size and spatial disposition of electron pair or pairs. Bioisosteres and bioisosterism are well-known tools for predicting the biological activity of compounds, based upon the premise that compounds with similar size, shape, and electron density can have similar biological activity. Known bioisosteric replacements include, for example, the interchangeability of —F, —OH, —$NH_2$, —Cl, and —$CH_3$; the interchangeability of —Br and -i-$C_3H_7$; the interchangeability of —I and -t-$C_4H_9$; the interchangeability of —O—, —S—, —NH—, —$CH_2$, and —Se—; the interchangeability of —N=, —CH=, and —P=(in cyclic or noncyclic moieties); the interchangeability of phenyl and pyridyl groups; the interchangeability of —C=C— and —S-(for example, benzene and thiophene); the interchangeability of an aromatic nitrogen ($R_{ar}$—N($R_{ar}$)—$R_{ar}$) for an unsaturated carbon ($R_{ar}$—C(=$R_{ar}$)—$R_{ar}$); and the interchangeability of —CO—, —SO—, and —$SO_2$—. These examples are not limiting on the range of bioisosteric equivalents and one of skill in the art will be able to identify other bioisosteric replacements known in the art. See, for example, Patani et al., 1996, *Chem. Rev.* 96:3147-76; and Burger, 1991, *A. Prog. Drug Res.* 37:287-371.

A reasonable quantitative prediction of the binding ability or the function of a known molecule can be made based on the spatial arrangement of a small number of atoms or functional groups in the molecule. As used herein, such an arrangement is called a "pharmacophore", and once the pharmacophore or pharmacophores in a molecule have been identified, this information can be used to identify other molecules containing the same or similar pharmacophores. Such methods are well known to persons of ordinary skill in the art of medicinal chemistry, and the structural information described in this application identifies the pharmacophore of phosphoramidate alkylator prodrugs and phosphoramidate alkylators. An example of programs available to perform pharmacophore-related searches is the program 3D Pharmacophore search from the Chemical Computing Group (see http://www.chemcomp.com/fdept/prodinfo.htm).

"Optional" or "optionally" means that the subsequently described event or circumstance can, but need not, occur, and that the description includes instances where the event or circumstance occurs and instances in which it does not. For example, "heterocyclo group optionally mono- or di-substituted with an alkyl group" means that the alkyl can, but need not be, present, and the description includes situations where the heterocyclo group is mono- or disubstituted with an alkyl group and situations where the heterocyclo group is not substituted with an alkyl group.

A combination of substituents or variables is permissible only if such a combination results in a stable or chemically feasible compound. A stable compound or chemically feasible compound is one in which the chemical structure is not substantially altered when kept at a temperature of 4° C. or less, in the absence of moisture or other chemically reactive conditions, for at least a week.

As used herein, a "prodrug" means a compound that, after administration, is metabolized or otherwise converted to an active or more active form with respect to at least one biological property, relative to itself. To produce a prodrug, a pharmaceutically active compound (or a suitable precursor thereof) is modified chemically such that the modified form is less active or inactive, but the chemical modification is effectively reversible under certain biological conditions such that a pharmaceutically active form of the compound is generated by metabolic or other biological processes. A prodrug can have, relative to the drug, altered metabolic stability or transport characteristics, fewer side effects or lower toxicity, or improved flavor, for example (see the reference Nogrady, 1985, *Medicinal Chemistry A Biochemical Approach*, Oxford University Press, New York, pages 388-392). Prodrugs can also be prepared using compounds that are not drugs but which upon activation under certain biological conditions generate a pharmaceutically active compound. As used herein a phosphoramidate alkylator prodrug is a prodrug that upon activation releases the active phosphoramidate alkylator.

As used herein, a "cytotoxic agent" is an agent or compound that produces a toxic effect on cells. As used herein, a "cytostatic agent" is an agent that inhibits or suppresses cellular growth and multiplication.

As used herein "hypoxic cells" are cells residing in a hypoxic environment in vivo such as, for example, in a hypoxic tumor zone, or in vitro. As used herein "normoxic cells" are cells residing in a normoxic environment in vivo or in vitro. As used herein "hypoxic cytotoxicity" of a compound or agent is its cytotoxicity on hypoxic cells. As used herein "normoxic cytotoxicity" of a compound or agent is its cytotoxicity on normoxic cells.

As used herein, a "bioreductive group" refers to a group that accepts electrons in an oxidation-reduction reaction. The bioreductive group is a group (1) that can be reduced, i.e., a group that can accept electrons, hydrogen, and/or or an hydride ion; (2) that can be reduced in vivo and/or in vitro; (3) that can be reduced in vivo and/or in vitro under hypoxia; (4) that can be reduced in vivo and/or in vitro by DT-diaphorase, thiols, or by photochemical or electrochemical means; or (5) that can be eliminated and/or cleaved by a biological process, such as by enzymatic hydrolysis, metabolism, etc.

For example, and as described in more detail below, one bioreductive group is a nitroimidazole that may be substituted with a variety of groups. Other examples of bioreductive groups include, but are not limited to, groups based on electron deficient nitrobenzenes, electron deficient nitrobenzoic acid amides, nitroazoles, nitroimidazoles, nitrothiophenes, nitrothiazoles, nitrooxazoles, nitrofurans, and nitropyrroles, where each of these classes of moieties may be optionally substituted, such that the redox potential for the bioreductive group lies within a range where the group can undergo reduction in the hypoxic conditions of a tumor, by DT-diaphorase, and/or by a thiol. One of skill in the art will understand, in view of the disclosure herein, how to substitute these and other bioreductive groups to provide a a bioreductive group having a redox potential that lies within said range.

Generally, one of skill in the art can "tune" the redox potential of a bioreductive group by modifying that group to contain electron withdrawing groups, electron donating groups, or some combination of such groups. For example, nitrothiophene, nitrofuran, and nitrothiazole groups may be substituted with one or more electron donating groups, including but not limited to methyl, methoxy, or amine groups, to achieve the desired redox potential. In another example, the nitropyrrole moiety can be substituted with an electron withdrawing group, including but not limited to cyano, carboxamide, —$CF_3$, and sulfonamide groups, to achieve the desired redox potential. For this purpose, strong electron withdrawing groups such as cyano, sulfone, sulfonamide, carboxamide, or —$CF_3$, and milder electron withdrawing groups such as —$CH_2$-halogen where halogen is —F, —Cl, or —Br, can be used.

As used herein, an "anti-neoplastic agent", "anti-tumor agent", or "anti-cancer agent", refers to any agent used in the treatment of cancer. Such agents can be used alone or in combination with other compounds and can alleviate, reduce, ameliorate, prevent, or place or maintain in a state of remission of clinical symptoms or diagnostic markers associated with neoplasm, tumor or cancer. Anti-neoplastic agents include, but are not limited to, anti-angiogenic agents, alkylating agents or alkylators, antimetabolites, certain natural products, platinum coordination complexes, anthracenediones, substituted ureas, methylhydrazine derivatives, adrenocortical suppressants, certain hormones and antagonists, anticancer polysaccharides, chemoprotectants, and certain herb or other plant extracts.

As used herein, "cancer" refers to one of a group of more than 100 diseases caused by the uncontrolled growth and spread of abnormal cells that can take the form of solid tumors, lymphomas, and non-solid cancers such as leukemia.

As used herein, "malignant cancer" refers to cancer cells or cancers that have the capacity of metastasis, with loss of both growth and positional control.

As used herein, "neoplasm" (neoplasia) or "tumor" refers to abnormal new cell or tissue growth, which can be benign or malignant.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of cancer or other hyperproliferative disease conditions, diminishment of extent of disease, delay or slowing of disease progression, amelioration, palliation or stabilization of the disease state, and other beneficial results described below.

As used herein, "reduction" of a symptom or symptoms (and grammatical equivalents of this phrase) means decreasing the severity or frequency of the symptom(s), or elimination of the symptom(s).

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "therapeutically effective amount" of a drug is an amount of a drug that, when administered to a subject with cancer, will have the intended therapeutic effect, e.g., alleviation, amelioration, palliation or elimination of one or more manifestations of cancer in the subject. The full therapeutic effect does not necessarily occur by administration of one dose, and can occur only after administration of a series of doses. Thus, a therapeutically effective amount can be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose, and can occur only after administration of a series of doses. Thus, a prophylactically effective amount can be administered in one or more administrations.

As used herein, a "second line" therapy refers to therapy that is given for the treatment of a cancer which has failed to respond to a first chemotherapy regimen or "first line" chemotherapy. "Third line" therapy refers to therapy that is given for the treatment of a cancer when both initial treatment, first-line therapy, and subsequent treatment, second-line therapy, don't work, or stop working.

As used herein "LogP" means a measure of lipophilicity of a substance determined based on the partitioning of the substance between octanol and water.

IIa. Compounds

Most drug-mediated cancer therapies, including phosphoramidate alkylator-based therapies, rely on poisons, called cytotoxic agents, selective for dividing cells and targeting, for example, their replicating DNA, microtubule, and various growth factors and growth factor receptors. These drugs are effective, because cancer cells generally divide more frequently than normal cells. However, such drugs almost inevitably do not kill all of the cancer cells in the patient. One reason is that cancer cells can mutate and develop drug resistance. Another is that not all cancer cells divide more frequently than normal cells and slowly-dividing cancer cells can be as, or even more, insensitive to such cytotoxic agents as normal cells.

Some cancer cells reside in a poorly vascularized solid tumor, are unable to generate the energy required for cell division, and divide slowly. As a tumor grows, it requires a blood supply and, consequently, growth of new vasculature. The new vasculature that supports tumor growth is often disordered, leaving significant regions of the tumor under-vascularized and even the vascularized regions subject to intermittent blockage. These under-vascularized and blocked regions of the tumor become hypoxic—they have a lower oxygen concentration or a lower oxygen partial pressure than the corresponding normal tissue, and the cells in them exhibit slower rates of division. Thus, the median oxygen concentration of only ten percent of solid tumors falls in the normal range of 40 to 60 mm Hg, and fifty percent of solid tumors exhibit median oxygen concentrations of less than 10 mm Hg.

The hypoxic areas of the tumor represent a significant source of metastases and cancer cells resistant to therapy (see for example, De Jaeger et al., Br J Cancer. 2001, 84(9):1280-5 and Rofstad et al., Br J Cancer. 1999, 80(11):1697-707). Not surprisingly, then, low tumor oxygen levels are associated with a poor response to therapy, increased metastases, and poor survival. The mechanisms of activation and action of Cyclophosphamide and Ifosfamide can exemplify how these agents cannot specifically target the difficult to kill hypoxic zone of a tumor.

Both Cyclophosphamide and Ifosfamide are prodrugs and can be oxidatively activated in the liver via intermediates to yield active phosphoramidate alkylators, Alkylators 1 (cylophosphamide mustard) and 2 (ifosfamide mustard), respectively (see below). The charge neutral Hemiacetals 1 and 2, below, can have a half life of many minutes and can permeate in and out of the cell. In contrast, the anionic Alkylators 1 and 2 are much less cell membrane permeable and once formed extracellularly inefficiently kill the cell by alkylating cellular DNA.

When the phosphoramidate alkylators reach the tumor, they generally kill cells in the fast growing, well vascularized, normoxic, outer zone of the tumor. However, these phosphoramidate alkylators are not as effective in permeating into the less vascularized, slower growing, progressively hypoxic inner tumor zones and in killing tumor cells therein. Before any of these active alkylators reach the tumor, they can react with healthy cells and result in toxicity and/or cell death.

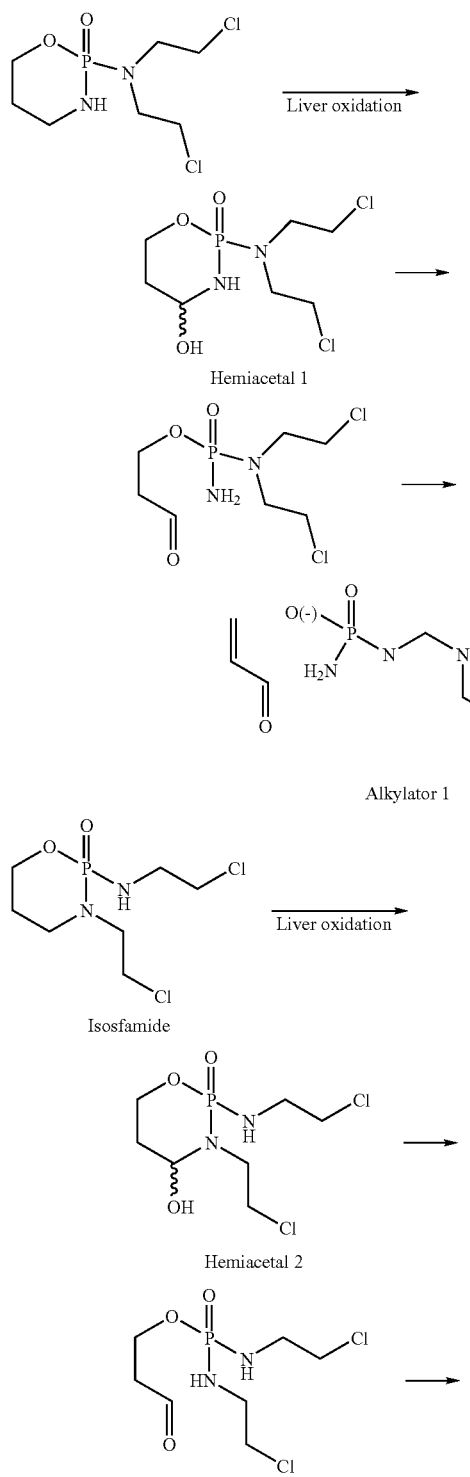

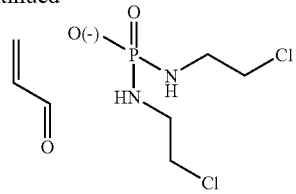

Alkylator 2

While the hypoxic tumor is difficult to treat, the hypoxic tumor zone can generate reduced derivatives of a variety of chemical groups (see the reference Workman et al., 1993, Cancer and Metast. Rev. 12: 73-82), and prodrugs of cytotoxins can be developed to exploit such bioreductive environments (PCT Application Nos. US04/009667 and US05/08161; PCT/US2005/041959 and PCT/US2005/042095, all Matteucci et al.). Such a hypoxia reducible (or hypoxia activated) prodrug can be constructed by employing a bioreductive group ($Z_3$) together with an alkylator. The bioreductive group is employed as part of a Trigger moiety covalently bonded or attached to the phosphoramidate alkylator.

The compounds of the invention can generally be described as phosphoramidate alkylator prodrugs. In general, the phosphoramidate alkylator prodrugs of the invention have the following structure Alk-Trigger wherein Alk is a phosphoramidate alkylator and Trigger, T, has a structure L-$Z_3$, wherein the linker L is bonded to a bioreductive group $Z_3$. In one embodiment, the Trigger, T, is a hypoxia activated trigger.

Phosphoramidate alkylator derivatives are reported in the references Borch et al., J. Med. Chem. 2000, 43: 2258-65; 2001, 44: 69-73; 2001, 44: 74-7; Hernick et al. J. Med. Chem. 2002, 45: 3540-8; Hernick et al., J. Med. Chem. 2003, 46: 148-54; U.S. Pat. Nos. 4,908,356; 5,306,727; 5,403,932; 5,190,929; 5,472,956; and 6,656,926; US Patent Application Publication No. US 2003/0008850; and Papot et al., Curr. Med. Chem., 2002, 2, 155-85. Isolated compounds disclosed therein are not the subject of the present invention. In some embodiments, the phosphoramidate alkylator prodrugs of the present invention have one or more of the following characteristics: (i) a higher hypoxic toxicity or lower value of $IC_{50}$ or $IC_{90}$, in hypoxic tissue, (ii) lower normoxic cytotoxicity, and (iii) less toxic side effect profile, or some combination of these attributes. In some embodiments, the phosphoramidate alkylator prodrugs of the present invention differ from known phosphoramidate alkylator derivatives by: (i) the nature of the phosphoramidate alkylator released, (ii) the nature of the linker (L) and/or the bioreductive group $Z_3$, (iii) the presence of more than one bioreductive group moiety, or some combination of these attributes, (iv) increased hypoxia selective cytoxicity measured by larger HCR values, (v) increased aqueous solubility, (vi) increased stability to liver microsomal degradation, and/or (vii) providing effective phosphoramide alkylator prodrugs that are achiral and avoid enantiomer specific in vivo metabolism.

To understand why the prodrug compounds of the present invention represent a significant advance over known anti-cancer phosphoramidate alkylator derivatives, an understanding of tumor biology, particularly under hypoxia, pharmacokinetics, and pharmacodynamics of prodrugs provided herein, in particular, is helpful.

For effective tumor therapy, a hypoxia activated prodrug should be much less toxic to healthy normoxic cells compared to hypoxic tumor cells. In some embodiments, the hypoxia activated prodrugs of the invention are less active and less toxic to normoxic cells than hypoxic cells. When such a prodrug of the invention encounters the hypoxic, reducing environment within solid tumor tissue, reduction of the bioreductive group causes dissociation of the phosphoramidate alkylator or the active cytotoxin. The phosphoramidate alkylator is released within the tumor zone and can more easily penetrate the hypoxic region of the solid tumor. These phosphoramidate alkylators can kill cells in the difficult to reach hypoxic region of the solid tumor while minimizing death of non-cancerous healthy cells and toxic side effects to the patient. Thus the present invention provides hypoxia activated prodrugs that are much less toxic to healthy, normoxic cells compared to hypoxic, tumor cells.

In certain embodiments, the phosphoramidate alkylator prodrugs of the present invention employ nitro containing aromatic or indole quinone moieties as bioreductive groups in the Trigger, T. In the hypoxic tumor, the nitro group is reduced to a hydroxylamino or an amino group, and flow of an electron pair from the amino or hydroxylamino group through the conjugated π electron system of the Trigger, T, releases the phosphoramidate alkylator. In another embodiment, in a hypoxic tumor, an indole quinone is reduced to an indole hydroquinone, and flow of an electron pair from the hydroquinone through the Trigger, T, releases the phosphoramidate alkylator. The released phosphoramidate alkylator kills cells in and/or near the hypoxic tumor.

A number of enzymes can be responsible for the reduction of the bioreductive group $Z_3$ in the Trigger. For example, cytochrome P450 reductase enzymes can reduce the nitro or a quinone moiety in a bioreductive group in a first step respectively to a $NO_2(-)$ or a semiquinone radical anion. The hypoxic tumor zone can have a higher concentration of the reductase enzyme compared to normoxic tissue. Under normoxia, as in well vascularized healthy tissue, in the presence of oxygen, the $NO_2(-)$ or the semiquinone radical anion formed can react with oxygen to revert back to the bioreductive group and not ultimately generate or release the phosphoramidate alkylator. The aryl or heteroaryl moiety covalently bonded to the $NO_2(-)$ or the semiquinone radical anion modulates the oxygen sensitivity of the radical anion.

The oxygen sensitivity of the bioreductive group varies, depending partly on the reduction potential of the bioreductive group. Thus, for example, one bioreductive group can get reduced in a hypoxic tumor zone having 1% oxygen, another in a zone having 0.1% oxygen, and yet another in a zone having 0.01% oxygen.

A bioreductive group loses some or all of its hypoxic specificity when it is so easily reduced that the cytochrome P450 reductase enzyme or other reducing agents ("reducing agents") in healthy normoxic tissue can reduce it in the presence of oxygen. If a $NO_2(-)$ or a semiquinone radical anion in a bioreductive group does not react or reacts slowly with oxygen, the radical anion itself can release the phosphoramidate alkylator, or can be further reduced and release the phosphoramidate alkylator, causing toxicity to healthy normoxic cells and tissue. The novel phosphoramidate alkylator prodrugs of the present invention are more toxic to the hypoxic cancer cells and tissue compared to the healthy normoxic cells and tissue.

The ease or difficulty of reducing the bioreductive group $Z_3$ can be measured by the reduction potential of the bioreductive group and is influenced by the linker (L), and the phosphoramidate alkylator (Alk-H). For example, attachment of the bioreductive group to an electron withdrawing linker or an electron withdrawing phosphoramidate alkylator can make the bioreductive group easier to reduce compared to when it is covalently bonded to an electron rich linker or an electron rich phosphoramidate alkylator.

The Trigger, T, can be oxidized, hydrolyzed, or thiolyzed and can release the phosphoramidate alkylator in a hypoxia non-senselective manner. Telcyta™, a phosphoramidate alkyltor prodrug that is in the clinic, can release an active toxin in absence of hypoxia by the action of glutathione transferase (see, e.g., phosphoramidate alkylator if in the "Methods of Treatment" section). The chemical nature of the linker and/or the phosphoramidate alkylator can influence the oxidative, hydrolytic, or thiolytic stability of the prodrug with respect to phosphoramidate alkylator release. In one embodiment of the present invention a hypoxia activated phosphoramidate alkylator prodrug does not release the phosphoramidate alkylator in a hypoxia non-specific, oxidation, hydrolysis, or thiolysis.

According to the present invention, a properly employed Trigger in a phosphoramidate alkylator prodrug can be used to "tune" the pharmacokinetic property of the prodrug without altering its cytotoxic properties. For example, a high volume of distribution of an anticancer agent ensures that the prodrug is absorbed in the tissue quickly. According to the present invention, in one embodiment, the volume of distribution of a phosphoramidate alkylator prodrug can be modulated by employing a Trigger, T, containing an amino group capable of forming an ammonium cation under physiological conditions. In one embodiment, a Trigger, T, containing a quaternary ammonium group can yield a prodrug compound of the invention having a high volume of distribution while avoiding possible endosomal trapping. In another embodiment, a Trigger, T, comprising a carboxyl functionality will exist as the anionic carboxylate anion form. $CO_2(-)$ in the extracellular space outside of normal healthy tissue and not pass easily through the normal cell membrane. The lower pH in tumor extracellular space can convert the $CO_2(-)$ to the uncharged "$CO_2H$" form allowing the prodrug to pass through tumor cell membrane.

A phosphoramidate alkylator containing a hydroxyl, amino, mercapto, and/or a carboxyl group can be transformed into a prodrug by covalently attaching a Trigger, T, to one or more of these functional groups. During the transformation from a phosphoramidate alkylator to a prodrug, a hydroxyl group in the phosphoramidate alkylator can be transformed, for example, to an ether or an acetal; an amino to an alkylamino, a carbamate, or an amide; a carboxyl group to an ester; and a mercapto group to a thioether or a thioacyl, as described in greater detail in the Method of Synthesis and the Experimental sections below. These transformations can yield a prodrug which is less polar or more lipophilic than the corresponding phosphoramidate alkylator. Non polar phosphoramidate alkylator prodrugs may not be readily soluble in aqueous pharmaceutical carriers or diluents. Solubility enhancer groups like $CO_2H$, amino, alkylamino, dialylamino, and hydroxyl can be employed in the Trigger, T, to modulate the solubility of the prodrug and overcome any problems encountered in preparing aqueous formulations of the phosphoramidate alkylator prodrugs.

Phosphoramidate alkylators of the present invention can have one or more N-(2-haloalkyl) or N-(2-haloethyl) and/or one or more aziridine

moiety covalently bonded to a P=O moiety as shown below. Upon release of the anionic phosphoramidate alkylator moiety an aziridine or aziridium species forms which can alkylate DNA (See EXAMPLE section, Example 36). Depending upon the electron withdrawing nature of $R_2$ and $R_3$ substituents, the aziridinium formation kinetics can vary. For example, as shown in the reaction sequence below, the rate of alkylation can increase when the $NR_2R_3$ moiety is changed from $NH_2$ to

(see Engle et al., *J. Med. Chem.*, 1987, 25:1347-57). Substituents on the nitrogen atoms can alter the geometry of the phosphoramidate alkylator, the delocalization of the lone electron pair on this nitrogen atom in the P=O moiety, the availability of the nitrogen lone electron pairs for aziridinium or subsequent aziridine formation, and the aqueous solubility of the phosphoramidate alkylator prodrug and the phosphoramidate alkylator.

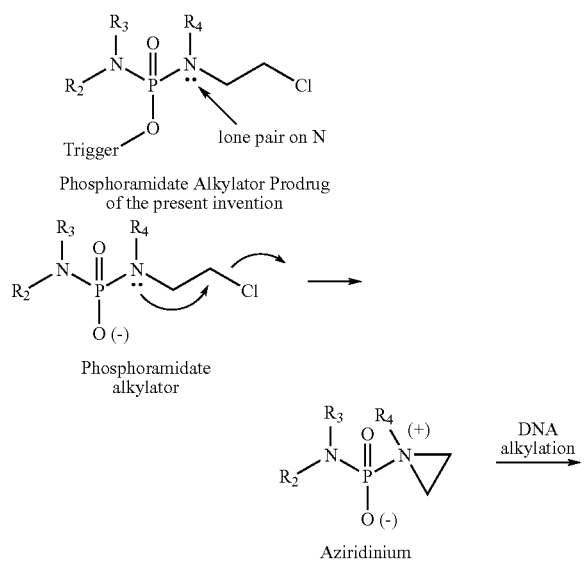

The present invention arises in part out of the discovery that phosphoramidate alkylator prodrugs employing 2-nitroimidazole-bioreductive group show unexpectedly high hypoxic cytotoxicity, low normoxic toxicity and high HCR and improved solubility. For example, Compounds 24 and 25 were respectively, 400 to 1000 fold more toxic in hypoxic cells than in normoxic cells in an anti-proliferation cytotoxicity assay with a $IC_{50}$ of 0.05 μM in cells under hypoxia. (See EXAMPLE section). Phosphoramidate alkylator prodrugs containing ifosfamide mustard or ifosfamide mustard analogs and having formulas:

$Z_3$—$CH_2$—O—P(=O)(NHCH$_2$CH$_2$X$_4$)$_2$, $Z_3$—$CH_2$—O—P(=O)(NHCH(R$_9$)CH$_2$X$_4$)$_2$, and
$Z_3$—CH(Z$_2$)—O—P(=O)(NHCH(R$_9$)CH$_2$X$_4$)$_2$;

wherein $Z_2$ is methyl; $R_9$ is hydrogen, methyl, or isopropyl; $Z_3$ is 1-N-methyl-2-nitroimidazol-5-yl), 2-nitrothiophen-5-yl, or 2-nitrofuran-5-yl; and each $X_4$ is Cl or Br were unexpectedly more toxic in hypoxic cells compared to normoxic cells, and/or possessed unexpectedly high HCR values, in anti-proliferation cell cytotoxicity assays, in contrast to the HCR values of known phosphoramidate alkylator derivatives having 2-nitrothiophene-5-yl, 2-nitrofuran-5-yl, or 5-nitro imidazolyl, bioreductive groups ($Z_3$), and N,N'(tetrakis-2-chloroethyl) phosphoramidate mustard or cyclofosfamide mustard; or an indole quinonyl group as $Z_3$ and ifosfamide mustard (see e.g., compounds P4, P14-17, P19, and P21-22, in Borch et al., *J. Med. Chem.*, and U.S. Pat. No. 6,656,926 both supra).

In one aspect, the present invention provides phosphoramidate alkylators prodrugs of formula (I):

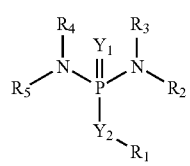

(I)

wherein $Y_1$ is O, S, $NR_6$ or $NSO_2R_6$ wherein each $R_6$ is independently $C_1$-$C_6$ alkyl, $C_1$-$C_6$ heteroalkyl, aryl, or heteroaryl;

$Y_2$ is O, S, $NR_6$, $NCOR_6$, or $NSO_2R_6$;

each of $R_1$-$R_5$ independently is hydrogen, hydroxyl, amino, $C_1$-$C_6$ alkyl, $C_1$-$C_6$ heteroalkyl, $C_3$-$C_8$ cycloalkyl, heterocyclyl, $C_1$-$C_6$ alkoxy, $C_1$-$C_6$ alkylamino, $C_1$-$C_6$ dialkylamino, aryl, heteroaryl, $C_1$-$C_6$ acyl, $C_1$-$C_6$ heteroacyl, aroyl, or heteroaroyl; or together any two of $R_1$-$R_5$ form a $C_3$-$C_{10}$ heterocycle; or each of $R_1$-$R_5$ independently is a Trigger, T, wherein T is L-$Z_3$;

L is selected from

—[C($Z_1$)$_2$—$Y_3$]$_v$—[C(=O)—O]$_q$—[C($Z_1$)$_2$—$Z_2$—$Y_4$]$_u$—[C($Z_1$)$_2$]$_z$—[—C($Z_1$)=C($Z_1$)]$_g$—; and —[C($Z_1$)$_2$—$Y_3$]$_v$—(S(=O)$_2$)$_q$—[C($Z_1$)$_2$—$Z_2$—$Y_4$]$_u$—[C($Z_1$)$_2$]$_z$—[C($Z_1$)=C($Z_1$)]$_g$—;

wherein each z, v, q, u, and g independently is 0 or 1;

$Y_3$ is S, O, or $NR_7$ wherein each $R_7$ is independently hydrogen, hydroxyl, $C_1$-$C_6$ alkyl, $C_1$-$C_6$ heteroalkyl, $C_3$-$C_8$ cycloalkyl, heterocyclyl, $C_1$-$C_6$ alkoxy, $C_1$-$C_6$ alkylamino, $C_1$-$C_6$ dialkylamino, aryl, heteroaryl, $C_1$-$C_6$ acyl, $C_1$-$C_6$heteroacyl, aroyl, or heteroaroyl;

$Y_4$ is O, S, or —$NR_7$—C(=O)—O—;

each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$heteroacyl, aroyl, or heteroaroyl;

$Z_2$ is $C_1$-$C_6$ alkylene, $C_1$-$C_6$ heteroalkylene,

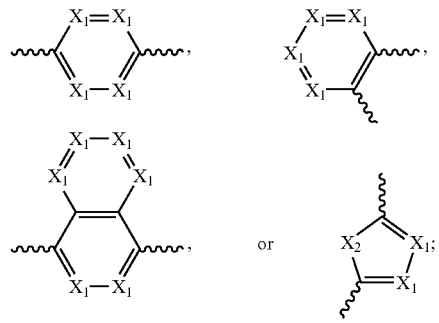

each $X_1$ is independently N or $CR_8$ wherein $R_8$ is independently hydrogen, halogen, OH, OP(=O)(OH)$_2$, nitro, cyano, $CO_2H$, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$heteroacyl, aroyl, or heteroaroyl;

$X_2$ is $NR_7$, S, or O; and $Z_3$ is a bioreductive group selected from the group consisting of:

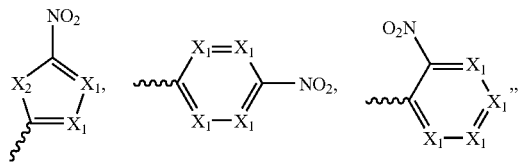

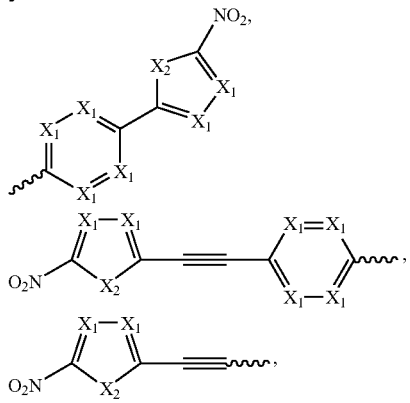

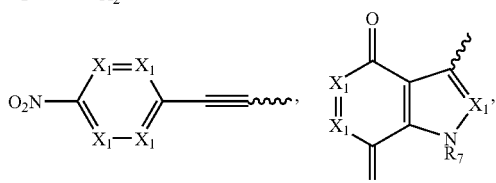

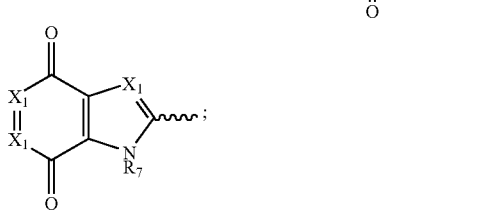

with the proviso that in formula (I):
(i) at least two of $R_1$-$R_5$ are selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl;
(ii) at least one of $R_1$-$R_5$ is selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

or
(iii) each of $NR_2R_3$ and $NR_4R_5$ are

and
an individual isomer or a racemic or non-racemic mixture of isomers, bioisosteres, pharmacophores, a pharmaceutically acceptable salt, solvate, hydrate, or a prodrug thereof.

In one embodiment, z is 1.
In one embodiment, $R^2$—$R^5$ are not the same.
In one embodiment, any one of $R^2$—$R^5$ is

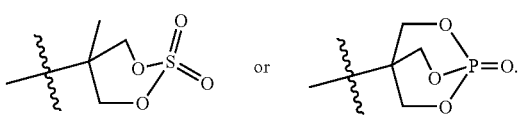

In one embodiment, the present invention provides hypoxia activated phosphoramidate alkylator prodrugs each employing two phosphoramidate alkylators. In one embodiment, the phosphoramidate alkylator prodrug of the present invention employs an 1-N-alkyl-2-nitroimidazol-5-yl moiety or a 1-N-methyl-2-nitroimidazol-5-yl moiety as a bioreductive group or $Z_3$. In one embodiment, the phosphoramidate alkylator prodrug of the present invention employs a 2-nitrofuran moiety as a bioreductive group or $Z_3$.

In one embodiment, the present invention excludes the compounds:

P1
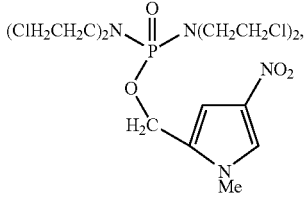

P2
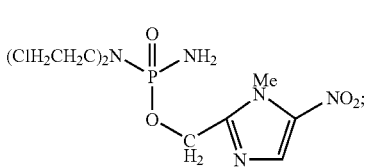

P3
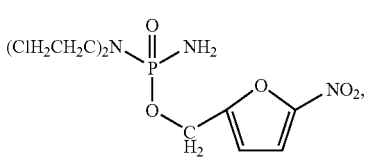

P4
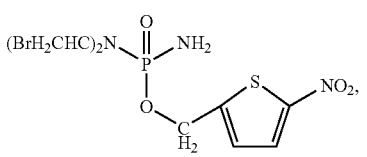

P5
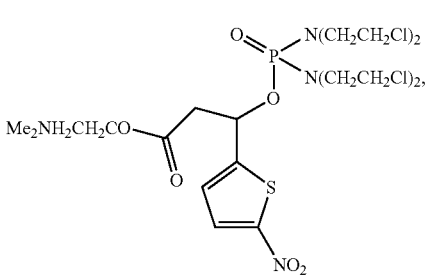

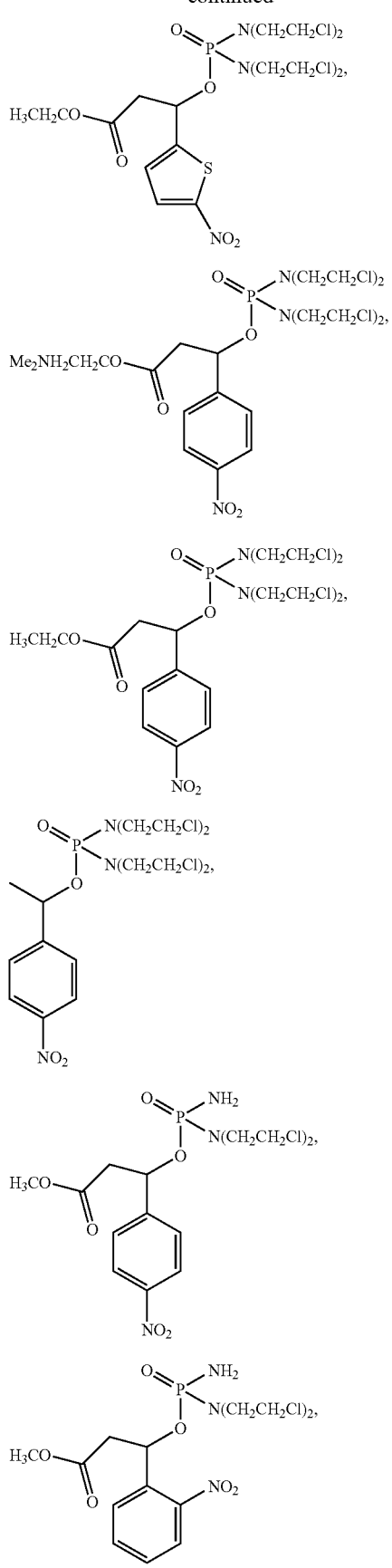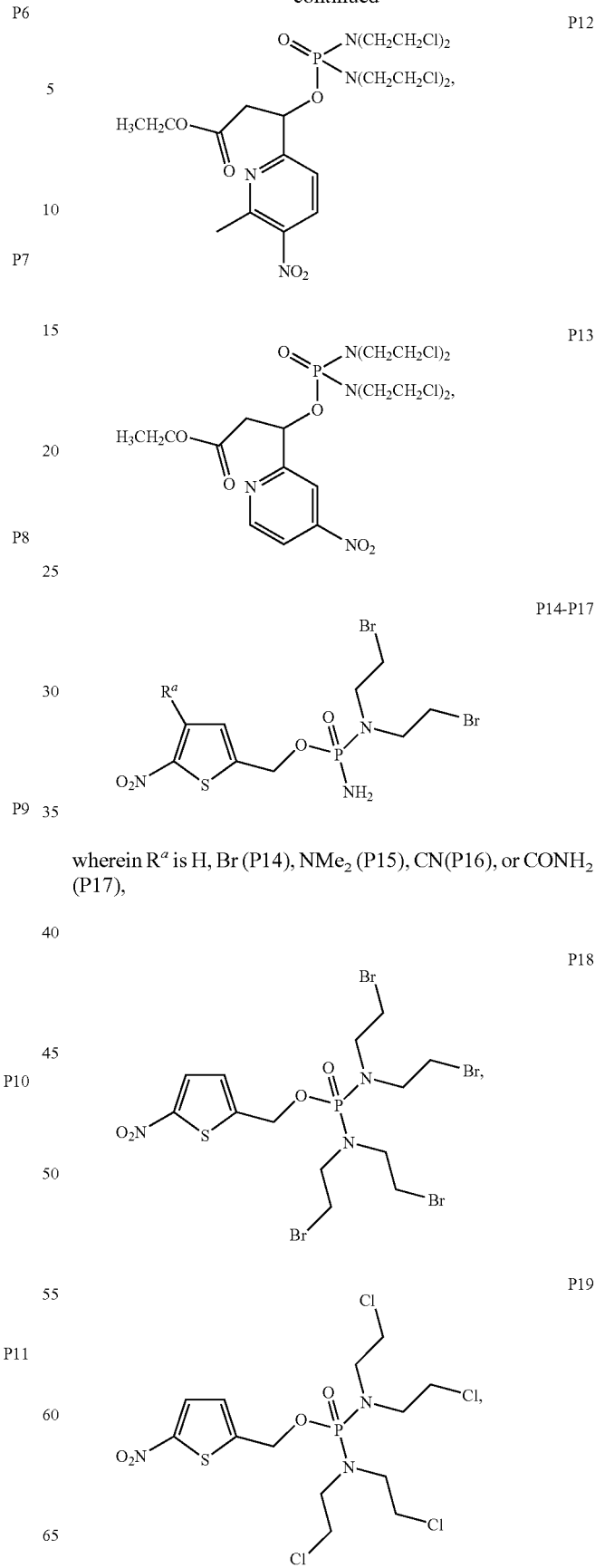
wherein $R^a$ is H, Br (P14), $NMe_2$ (P15), CN(P16), or $CONH_2$ (P17), -continued

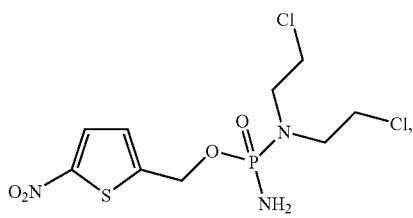
P20

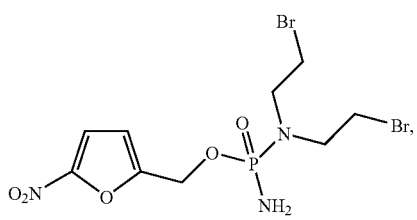
P21

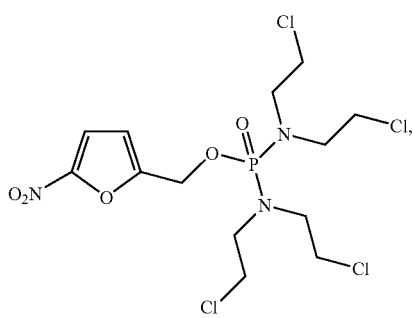
P22

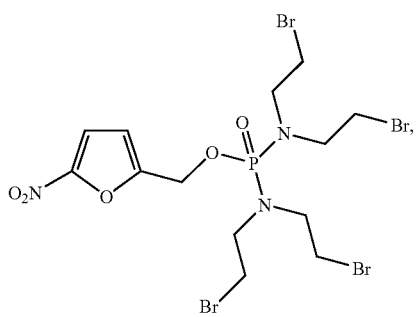
P23

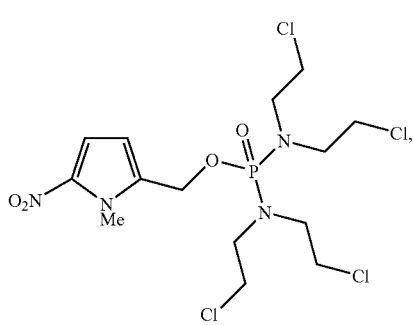
P24

-continued

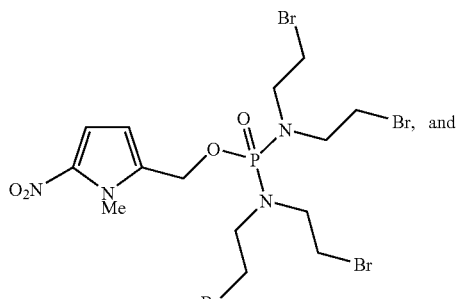
P25

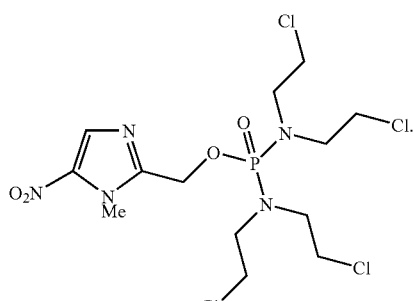
P26

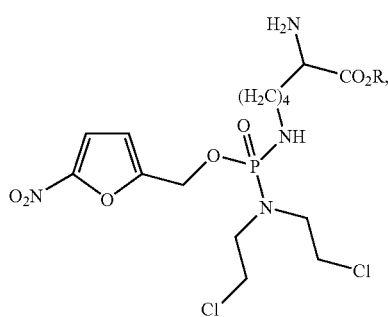
P36

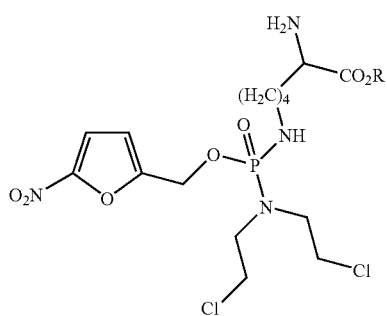
P37 wherein R is H, Me or allyl;

3-(5-Methoxy-1-methyl-4,7-indolequinonyl)-methyl bis[N-methyl-N-(2-bromoethyl)]phosphorodiamidate (P27), 3-(5-Methoxy-1-methyl-4,7-indolequinonyl)methyl N,N-bis(2-bromoethyl)-phosphorodiamidate (P28), 2-(5-Methoxy-1-methyl-4,7-indolequinonyl)methyl bis[N-methyl-N-(2-bromoethyl)]phosphorodiamidate (P29), 2-(5-Methoxy-1-methyl-4,7-indolequinonyl)methyl N,N-bis(2-chloroethyl) phosphorodiamidate (P30), 2-(5-Methoxy-1-methyl-4,7-indolequinonyl)methyl N,N-bis(2-bromoethyl)-phosphorodiamidate (P31), 3-(5-Methoxy-1-methyl-4,7-indolequinonyl)methyl N,N-bis(2-bromoethyl)-phosphorodiamidate (P32), 2-(5-Methoxy-1-methyl-4,7-indolequinonyl)methyl bis[N-methyl-N-(2-bromoethyl)]phosphorodiamidate (P33), 2-(5-Methoxy-1-methyl-4,7-indolequinonyl)methyl N,N-bis (2-chloroethyl)-phosphorodiamidate (P34), and
2-(5-Methoxy-1-methyl-4,7-indolequinonyl)methyl N,N-bis (2-bromoethyl)-phosphorodiamidate (P35)

In a related embodiment, the present invention provides a compound of formula (I) with the proviso that (i) at least one of $R_1$-$R_5$ is selected from the group consisting of 2-alkylsulfonyloxyalkyl, 2-heteroalkylsulfonyloxyalkyl, 2-arylsulfonyloxyalkyl, and 2-heteroalkylsulfonyloxyalkyl and at least one of $R_1$-$R_5$ is selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl; or (ii) at least one of $R_1$-$R_5$ is selected from the group consisting of 2-haloalkyl, 2-$C_1$-$C_6$ alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

or (iii) each $NR_2R_3$ and $NR_4R_5$ is

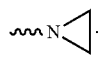

In another related embodiment, the present invention provides a compound of formula (I) with the proviso that the formula (I) excludes $R_2$ and $R_3$ together forming a morpholine ring or $R_4$ and $R_5$ together forming a morpholine ring.

In one embodiment, the present invention excludes a compound of the following structure:

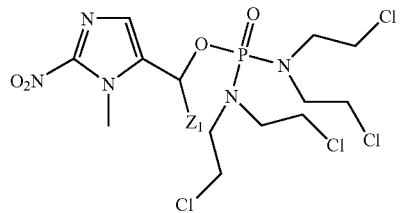

wherein $Z_1$ is hydrogen or $C_1$-$C_6$ alkyl.

In one embodiment, the present invention provides compounds wherein the Trigger, T, is:

[C($Z_1$)$_2$—$Y_3$]—(C(=O)—O)—[C($Z_1$)$_2$—$Z_2$—$Y_4$]—[C($Z_1$)$_2$]$_z$—[C($Z_1$)=C($Z_1$)]—$Z_3$;

[C($Z_1$)$_2$—$Y_3$]—[C($Z_1$)$_2$—$Z_2$—$Y_4$]—[C($Z_1$)$_2$]$_z$—[C($Z_1$)=C($Z_1$)]—$Z_3$;

[C($Z_1$)$_2$—$Y_3$]—[C($Z_1$)$_2$]$_z$—[C($Z_1$)=C($Z_1$)]—$Z_3$;

[C($Z_1$)$_2$—$Y_3$]—[C($Z_1$)$_2$]$_z$—$Z_3$;

[C($Z_1$)$_2$—$Y_3$]—(C(=O)—O)—[C($Z_1$)$_2$]$_z$—[C($Z_1$)=C($Z_1$)]—$Z_3$;

[C($Z_1$)$_2$—$Y_3$]—(C(=O)—O)—[C($Z_1$)$_2$]—$Z_3$;

[C($Z_1$)$_2$—$Y_3$]—(C(=O)—O)—[C($Z_1$)$_2$]$_z$—[C($Z_1$)=C($Z_1$)]—$Z_3$;

[C($Z_1$)$_2$—$Z_2$—$Y_4$]—[C($Z_1$)$_2$]$_z$—[C($Z_1$)=C($Z_1$)]—$Z_3$;

—[C($Z_1$)$_2$]$_z$—[C($Z_1$)=C($Z_1$)]—$Z_3$;

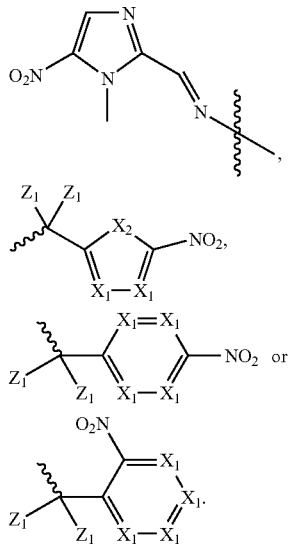

In an additional embodiment, $Z_3$ is:

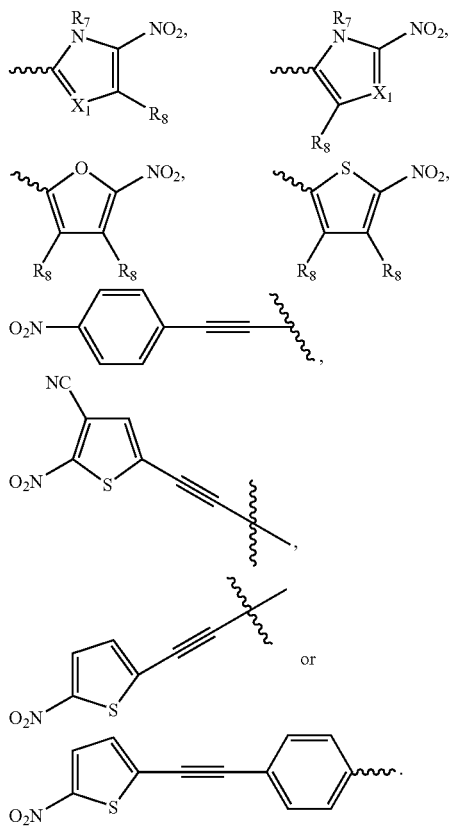

In one embodiment, each —C($Z_1$)$_2$— is: —CH$_2$—, —CHMe—, —CH(CN)—, —CH(CO$_2$H)—, —CH(CONH$_2$)—, —CH(CF$_3$)—, —CHF$_2$)—, —C(Me)$_2$-, —C(Et)$_2$-, —CH(CH$_2$NMe$_2$)—, —CH(CH$_2$NMe$_2$)—, —C(CH$_2$NMe$_2$)$_2$—, or —C(CH$_2$CO$_2$H)$_2$—.

In one embodiment, —C($Z_1$)$_2$—$Y_3$— is: —CH$_2$—O—, —CH$_2$—S—, —CH$_2$—NMe, —CH$_2$—NH—, CH(Me)—

O—, CH(Me)—S—; —CH(Me)—NMe—, —CH(Me)—NH—; —CMe₂-NMe—, —CMe₂-NMe—, or —CMe₂-NMe—.

In one embodiment —Z₂—Y₄— together is:

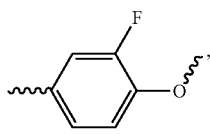 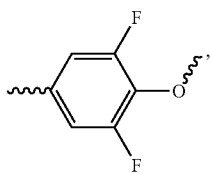

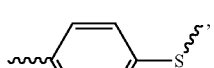 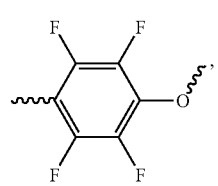

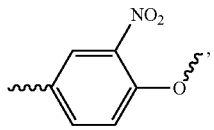 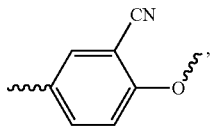

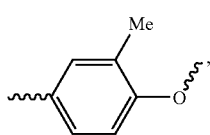 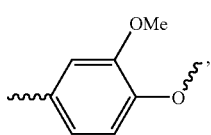

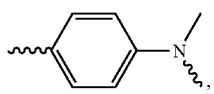 or 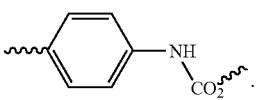

In one embodiment, —[C(Z₁)=C(Z₁)]— is: —CH=CH—, —C(CN)=CH—, —CH=C(CN)—, —C(Ar)=CH—, —CH=CAr—, —C(COAr)=CH—, —CH=C(COAr)—, —C(COR₁₂)=CH— or —CH=C(COR₁₂)—, wherein Ar is aryl optionally substituted with up to five substituents selected from the group consisting of OH, OMe, CF₃, O—CHF₂, OCF₃, NO₂, CN, halo, halomethyl, dihalomethyl, trihalomethyl, hydroxymethyl, CO₂H, CONH₂, CONMe₂, and CONHMe; and R₁₂ is independently hydrogen, $C_1$-$C_6$ alkyl, $C_1$-$C_6$ heteroalkyl, $C_3$-$C_8$ cycloalkyl, or heterocyclyl.

In another embodiment, Trigger is:

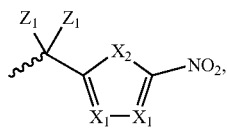

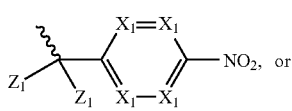

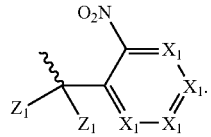

In another embodiment, Trigger is

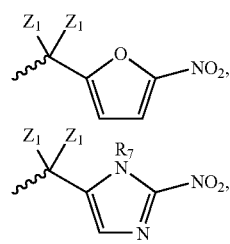 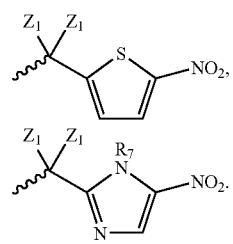

wherein each $Z_1$ independently is H or $C_1$-$C_6$ alkyl.

In another embodiment, Trigger is:

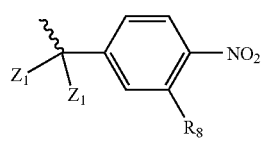

wherein each $Z_1$ is hydrogen or $C_1$-$C_6$ alkyl and $R_8$ is H, OH, or —OP(=O)(OH)₂.

In one embodiment, the present invention provides compounds of formulas (II) and (III):

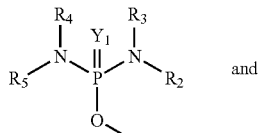 (II)

and

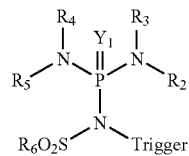 (III)

wherein each $R_2$-$R_5$ independently is selected from the group consisting of hydrogen, hydroxyl, $C_1$-$C_6$ alkyl, $C_1$-$C_6$ heteroalkyl, $C_3$-$C_8$ cycloalkyl, heterocyclyl, $C_1$-$C_6$ alkoxy, $C_1$-$C_6$ alkylamino, $C_1$-$C_6$ dialkylamino, aryl and heteroaryl; or together any two of $R_2$-$R_5$ form a $C_3$-$C_{10}$ heterocycle; each $Y_1$ independently is S or O; and each Trigger, T, is defined as in formula (I);

with the proviso that in formulas (II) or (III):

(i) at least two of $R_1$-$R_5$ are selected from the group consisting of 2-haloalkyl, 2-alkylsulfonyloxyalkyl, 2_heteroalkylsulfonyloxyalkyl, 2-arylsulfonyloxyalkyl, and 2 heteroalkylsulfonyloxyalkyl; or (ii) at least one of $R_1$-$R_5$ is selected from the group consisting of 2-haloalkyl, 2-$C_1$-$C_6$ alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

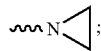

or (iii) each $NR_2R_3$ and $NR_4R_5$ are

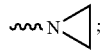

and an individual isomer or a racemic or non-racemic mixture of isomers, bioisosteres, pharmacophores, a pharmaceutically acceptable salt, solvate, hydrate, or a prodrug thereof.

In one embodiment, the present invention provides a compound of formula (II) wherein Trigger, T, is $-CH_2-Z_3$, $-CH(Z_1)-Z_3$, or $-C(Z_1)_2-Z_3$ wherein $Z_1$ is $C_1$-alkyl and $Z_3$ is:

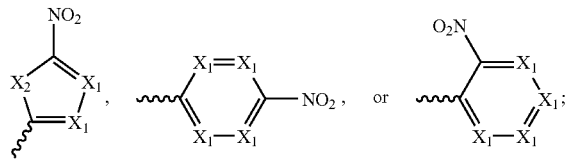

with the proviso that in formula (II):
(i) one of $R_2$ and $R_3$ is H and one of $R_4$ and $R_5$ is H;
(ii) one of $R_2$ and $R_3$ is $C_1$-alkyl and one of $R_4$ and $R_5$ is $C_1$-alkyl; or
(iii) at least one of $R_2$-$R_5$ is hydroxyl, amino, $C_3$-$C_8$ cycloalkyl, heterocyclyl, $C_1$-$C_6$ alkoxy, $C_1$-$C_6$ alkylamino, $C_1$-$C_6$ dialkylamino, aryl, heteroaryl, $C_1$-$C_6$ acyl, $C_1$-$C_6$ heteroacyl, or aroyl or heteroaroyl.

In one embodiment, the present invention provides a compound of formula (II) wherein $Z_3$ is a bioreductive group selected from:

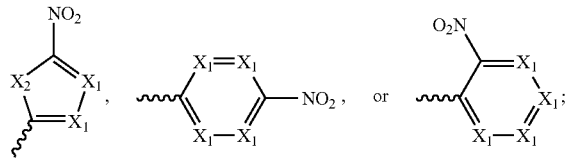

with the proviso that in formula (II):
(i) at least one of $R_1$-$R_5$ are selected from the group consisting of 2-alkylsulfonyloxyalkyl, 2-heteroalkylsulfonyloxyalkyl, 2-arylsulfonyloxyalkyl, and 2-heteroalkylsulfonyloxyalkyl and
at least one of $R_1$-$R_5$ are selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl; or
(ii) at least one of $R_1$-$R_5$ is selected from the group consisting of 2-haloalkyl, 2-$C_1$-$C_6$ alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

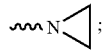

or (iii) each $NR_2R_3$ and $NR_4R_5$ are

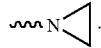

In one aspect, the present invention provides phosphoramidate alkylator prodrugs of formula (I):

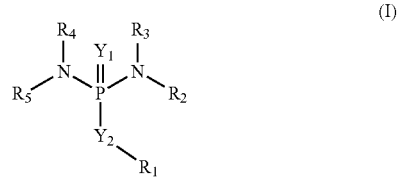

(I)

wherein $R_1$ is a $-[C(Z_1)_2-Y_3]_v-[C(=O)-O]_q-[C(Z_1)_2-Z_2-Y_4]_u-Z_3$ or $-[C(Z_1)_2-Y_3]_v-(S(=O)_2)_q-[C(Z_1)_2-Z_2-Y_4]_u-Z_3$, wherein each v, q, and u independently is 0 or 1; and $Z_3$ is a glucose or an analog thereof with the proviso that it excludes glucose conjugates of phosphoramidate alkylators described in the reference Wiessler et al., U.S. Pat. No. 5,622,936;

each of $R_2$-$R_5$ independently is hydrogen, hydroxyl, amino, $C_1$-$C_6$ alkyl, $C_1$-$C_6$ heteroalkyl, $C_3$-$C_8$ cycloalkyl, heterocyclyl, $C_1$-$C_6$ alkoxy, $C_1$-$C_6$ alkylamino, $C_1$-$C_6$ dialkylamino, aryl and heteroaryl, $C_1$-$C_6$ acyl, $C_1$-$C_6$ heteroacyl, aroyl, or heteroaroyl; or together any two of $R_1$-$R_5$ form a $C_3$-$C_{10}$ heterocycle;

with the proviso that in formula (I):
(i) at least two of $R_2$-$R_5$ are selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl;
(ii) at least one of $R_2$-$R_5$ is selected from the group consisting of 2-haloalkyl, 2-$C_1$-$C_6$ alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

or (iii) each $NR_2R_3$ and $NR_4R_5$ are

and an individual isomer or a racemic or non-racemic mixture of isomers, bioisosteres, pharmacophores, a pharmaceutically acceptable salt, solvate, hydrate, or a prodrug thereof.

In another embodiment, the present invention provides the compounds:

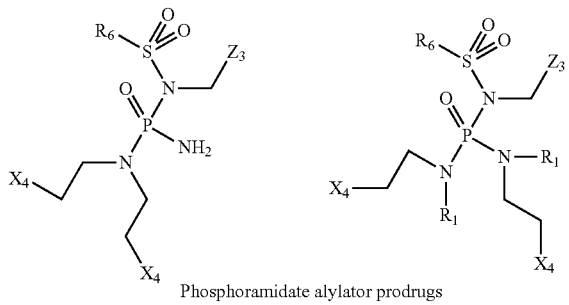

Phosphoramidate alylator prodrugs

↓ reductive activation ↓

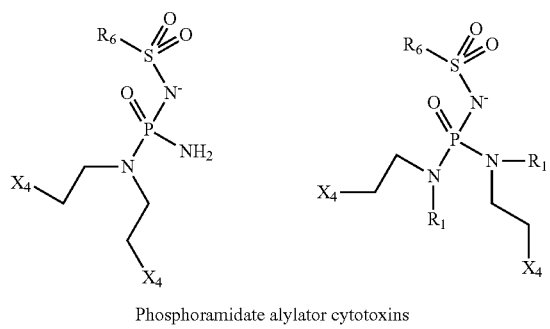

Phosphoramidate alylator cytotoxins

In another embodiment, the present invention provides the compounds:

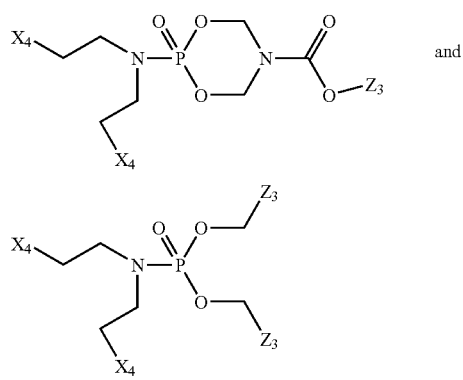

wherein $X_4$ and $Z_3$ are defined as above.

In another embodiment, the present invention provides the compounds:

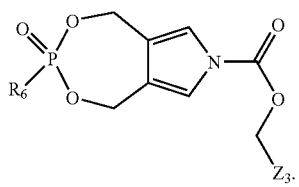

In one embodiment, $R_6$ is —(N—CH$_2$CH$_2$X$_4$)$_2$.

In another embodiment, the present invention provides the compounds:

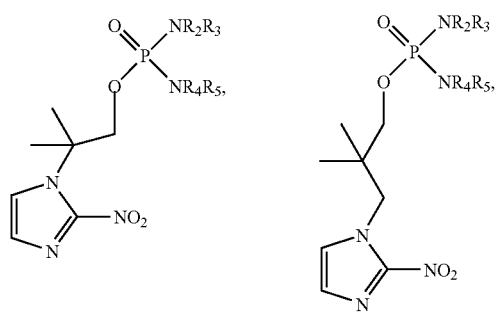

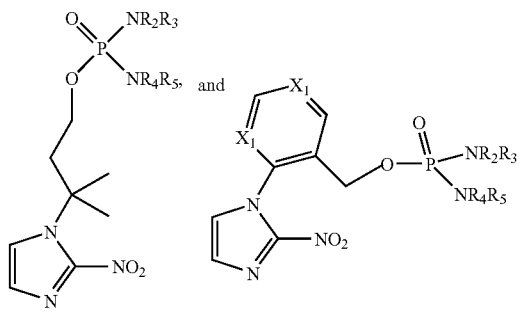

wherein $R_2$-$R_5$ are defined as in formula (II).

The following scheme exemplifies hypoxic reduction of the phosphoramidate alkylator prodrug to yield the corresponding phosphoramidate alkylator.

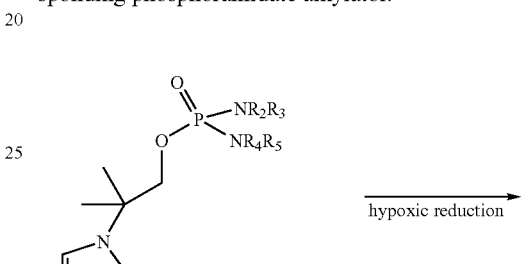

Phosphoramidate alkylator prodrugs

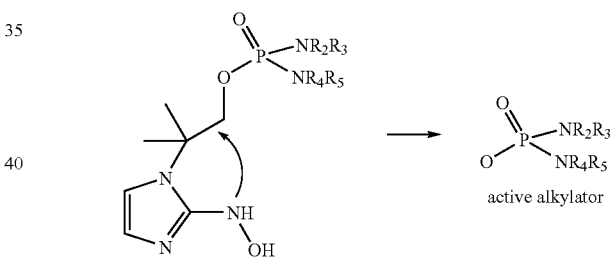

active alkylator

In another embodiment, the present invention provides the compounds:

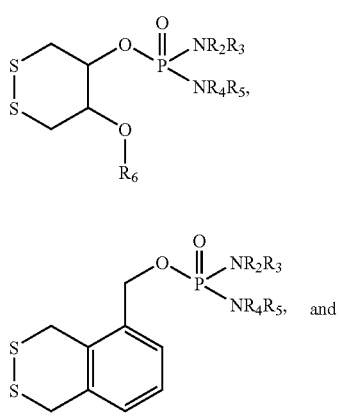

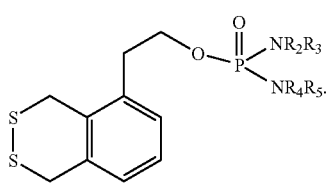

wherein R$_2$-R$_5$ are defined as in formula (II).

The following scheme exemplifies hypoxic reduction of the phosphoramidate alkylator prodrug to yield the corresponding phosphoramidate alkylator.

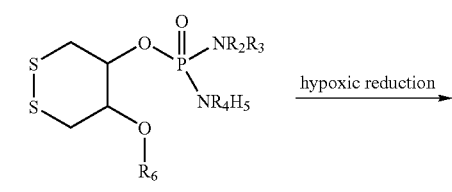

Phosphoramidate alkylator prodrugs

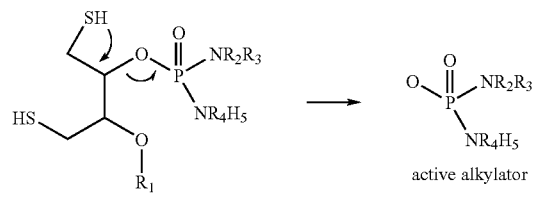

active alkylator

In one embodiment, the present invention provides the compounds of the formulas (IV)-(VII)

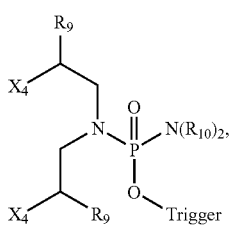
(IV)

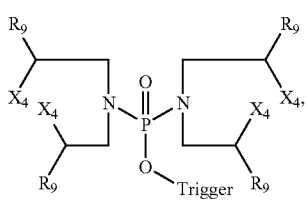
(V)

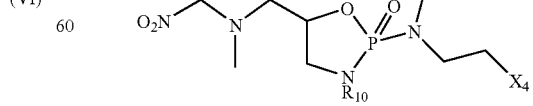
(VI)

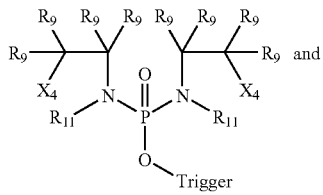
and

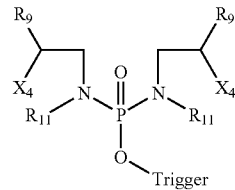
(VII)

wherein each R$_9$ independently is hydrogen, deuterium, aryl, heteroaryl, C$_1$-C$_6$ alkyl, C$_1$-C$_6$ heteroalkyl, C$_3$-C$_8$ cycloalkyl, heterocyclyl, C$_1$-C$_6$ acyl, C$_1$-C$_6$ heteroacyl, aroyl, heteroaroyl, C$_1$-C$_6$ alkoxycarbonyl, C$_1$-C$_6$ alkylaminocarbonyl, di C$_1$-C$_6$ alkylaminocarbonyl, or C$_1$-C$_6$ alkoxy; or together two R$_9$ groups form a heterocycle; each R$_{10}$ is hydrogen, C$_1$-C$_6$ alkyl, C$_1$-C$_6$ heteroalkyl, C$_3$-C$_8$ cycloalkyl, heterocyclyl, aroyl or heteroaroyl, or together two R$_{10}$ groups form a heterocycle;

R$_{11}$ is independently hydrogen, deuterium, aryl, heteroaryl, C$_1$-C$_6$ alkyl, C$_1$-C$_6$ heteroalkyl, C$_3$-C$_8$ cycloalkyl, heterocyclyl, C$_1$-C$_6$ acyl, C$_1$-C$_6$ heteroacyl, aroyl, heteroaroyl, C$_1$-C$_6$ alkoxycarbonyl, C$_1$-C$_6$ alkylaminocarbonyl, di C$_1$-C$_6$ alkylaminocarbonyl, or C$_1$-C$_6$ alkoxy; or together two R$_9$ groups form a heterocycle with the proviso that when R$_{11}$ is C$_1$-C$_6$alkyl or C$_1$-C$_6$ heteroalkyl then R$_{11}$ excludes

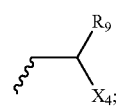

or together two R$_{11}$ groups form a heterocycle;

X$_4$ is Cl, Br, alkylsulfonyloxy, heteroalkylsulfonyloxy, arylsulfonyloxy, or heteroalkylsulfonyloxy; and Trigger, T, is [C(Z$_1$)$_2$—Y$_3$]$_v$—(C(=O)—O)$_q$—[C(Z$_1$)$_2$—Z$_2$—Y$_4$]$_u$[C(Z$_1$)$_2$]$_z$—[C(Z$_1$)=C(Z$_1$)]$_g$—Z$_3$.

In a related embodiment, in formulas (IV)-(VII), each R$_9$ is independently hydrogen, deuterium, C$_1$-C$_3$ alkyl, C$_1$-C$_6$ heteroalkyl, C$_3$-C$_6$ cycloalkyl, heterocyclyl, aryl or heteroaryl. In another embodiment, each R$_9$ is independently hydrogen, deuterium, or C$_1$-C$_6$ alkyl. In another related embodiment, each R$_9$ is independently methyl, ethyl, propyl, isopropyl, isobutyl, tertiary butyl, or cyclopropyl.

In one embodiment, the present invention provides a compound of formula (IV) wherein one of R$_{10}$ is —(CH$_2$)$_e$-Intercalator wherein an Intercalator is an aromatic or heteroaromatic moiety capable of intercalating between a nucleic acid base pair and e is 1-6.

In another embodiment, the present invention provides the compound:

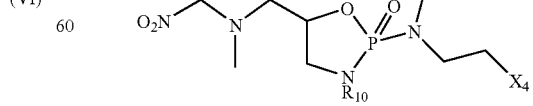

wherein X$_4$ and R$_{10}$ are defined as in formula (IV).

In another embodiment, the present invention provides the compounds:

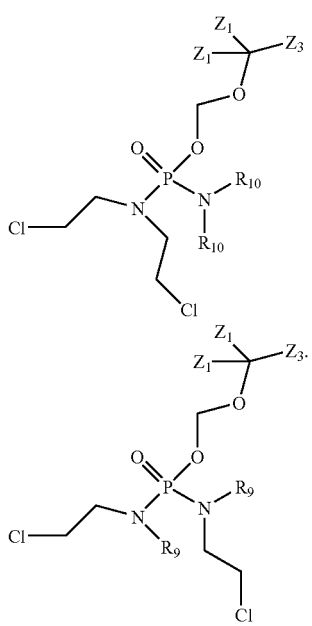

In one embodiment, the present invention provides the compound of formula (VIII):

(VIII)

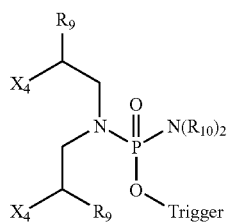

wherein each $R_9$ is independently hydrogen, methyl, ethyl, propyl, isopropyl, or cyclopropyl; and $N(R_{10})_2$ is selected from $NH_2$, NHMe, $NMe_2$, $NEt_2$,

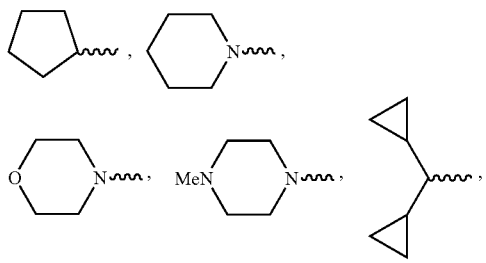

NHOMe, and NHOH.

In one embodiment, the present invention provides the compound of formula (IX):

(IX)

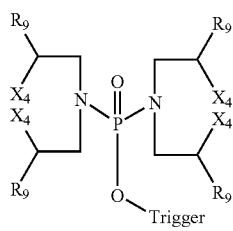

wherein each $R_9$ independently is hydrogen, methyl, ethyl, propyl, isopropyl, or cyclopropyl.

In one embodiment, the present invention provides the compound of formula (X):

(X)

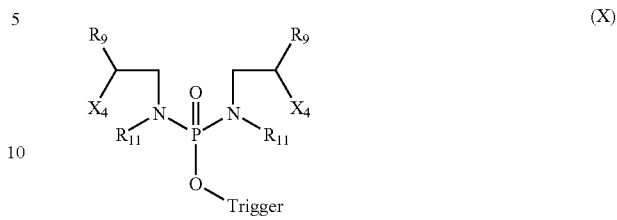

wherein each $R_9$ independently is hydrogen, methyl, ethyl, propyl, isopropyl, or cyclopropyl; and each $R_{11}$ is independently hydrogen, methyl, ethyl, propyl, isopropyl, benzyl, substituted methyl, cyclopropyl, methoxy, and hydroxyl; or together two $R_{11}$ form a heterocycle.

In one embodiment, the present invention provides the compounds of formulas (X-A), (X-B) and (X-C):

(X-A)

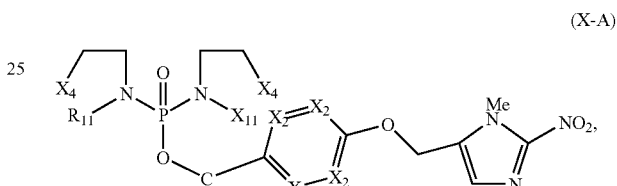

(X-B)

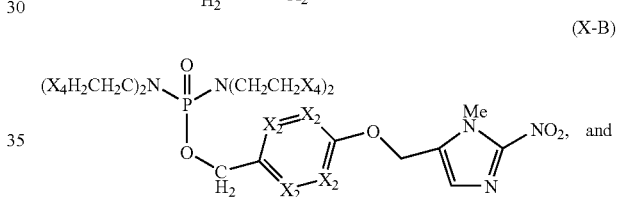

(X-C)

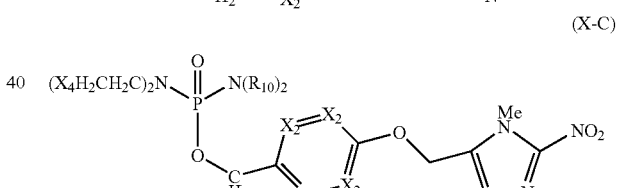

wherein $X_2$ and $X_4$, are defined as in formula (I), and $R_{10}$, and $R_{11}$ are defined as in formulas (IV), (VI) and (VII).

In one embodiment, the present invention provides the compounds of the formula (XI)-(XV):

(XI)

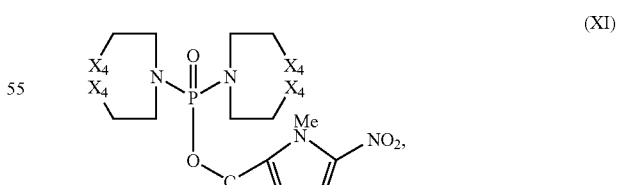

(XII)

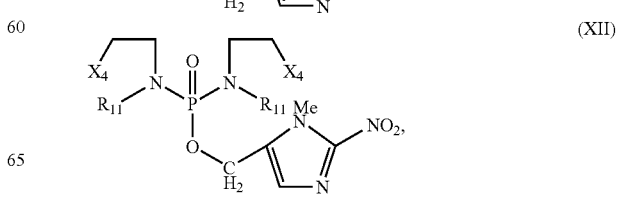

-continued (XIII)

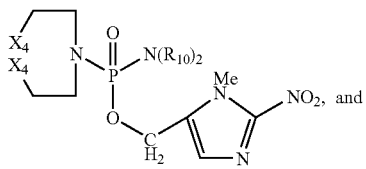

(XIV)

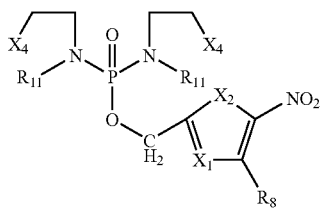

(XV)

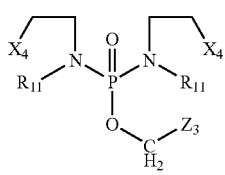

wherein each $R_{11}$ independently is hydrogen, methyl or substituted methyl, benzyl, isopropyl, propyl, cyclopropyl, methoxy, and hydroxyl; and $X_1$, $X_2$, and $Z_3$ are defined as above; and $X_4$ is Cl, Br, alkylsulfonyloxy, heteroalkylsulfonyloxy, cycloalkylsulfonyloxy, heterocycloalkylsulfonyloxy, arylsulfonyloxy, or heteroarylsulfonyloxy. In one embodiment, in compounds of formulas (XII), (XIV), and (XV), when $X_4$ is Cl or Br then $R_{11}$ excludes isopropyl. In one embodiment, a compound of formula (X) excludes a compound wherein $Z_3$ is

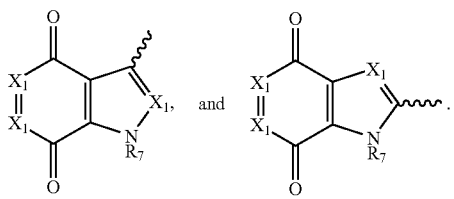

In one embodiment, the present invention provides a compound of formula (XII), (XIV), or (XV) wherein each $R_{11}$ is hydrogen. Examples of compounds of formula XII, XIV, or XV include compounds 5, 7, 8, 9, 10, 13, 14, 15, 19, 23, 24, 25, 26, 32, 34, and 36. In one embodiment, the present invention provides phosphoramidate alkylator prodrugs of formulas XII, XIV, or XV wherein $R_{11}$ excludes propyl or isopropyl. In another embodiment, the present invention excludes the compound:

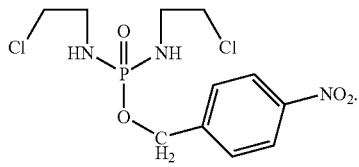

In one embodiment the present invention provides a phosphoramidate alkylator prodrug wherein $R_{11}$ is $C_3$-$C_s$ cycloalkyl. In another embodiment, the cycloalkyl is cyclopropyl. In general, a cyclopropyl group can be more stable than an alkyl group to oxidatively metabolizing proteins in the cell, particularly in the liver. The prodrug compounds of the invention provide a pharmacokinetically improved phopsphoramidate alkylator prodrug compared to known phosphoramidate alkylator prodrugs.

In one embodiment, the present invention provides compounds of formula (XVI)

(XVI)

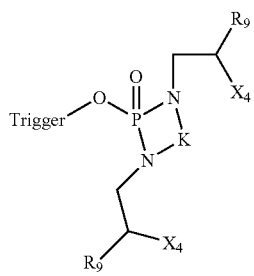

wherein K is $C_1$-$C_6$ alkylene or $C_1$-$C_6$ heteroalkylene. In one embodiment K is $(C(R_{12})_2)_e$, $CH_2CH_2(-X_6-CH_2CH_2)_f$, or $CH_2(-X_6-CH_2)_f$ wherein e is 1-10, f is 0-3, and $X_6$ is O, S, or $NR_{12}$ wherein each $R_{12}$ is independently defined as above.

In one embodiment, the present invention provides compounds of formula (XVII-(XVIII)

(XVII)

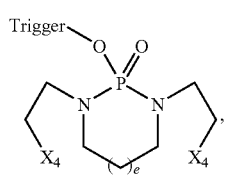

(XVIII)

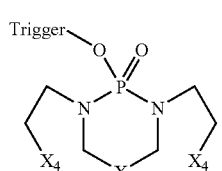

wherein e is 0-4, $X_4$ is Cl or Br, alkylsulfonyloxy, heteroalkylsulfonyloxy, arylsulfonyloxy, or heteroarylsulfonyloxy; $X_6$ is O, S, or $NR_{12}$ wherein $R_{12}$ is defined as above.

In one embodiment, the present invention provides the compound of formula (XIX):

(XIX)

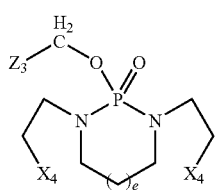

wherein e is 0-4, and $X_4$ is Cl, Br, alkylsulfonyloxy, heteroalkylsulfonyloxy, arylsulfonyloxy, or heteroarylsulfonyloxy. In a related embodiment, the present invention provides a compound of formula (XIX) wherein e is 1. See EXAMPLE section for examples of compounds of formulas described herein.

In one embodiment, the present invention provides the compound of formula (XX):

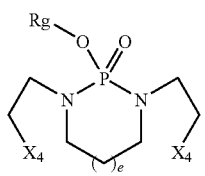

(XX)

wherein $R_g$ is glucose or a glucose analog; e is 0-4, and $X_4$ is Cl, Br, alkylsulfonyloxy, heteroalkylsulfonyloxy, arylsulfonyloxy, or heteroarylsulfonyloxy. As used herein, a glucose analog includes mono, di and tri saccharides. In a related embodiment, the present invention provides a compound of formula XX wherein e is 1.

In one embodiment, the present invention provides the compounds:

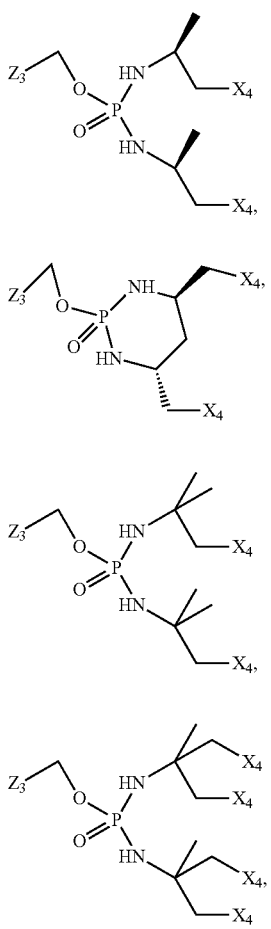

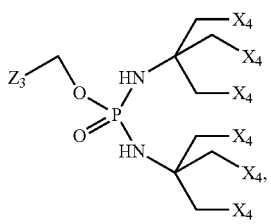

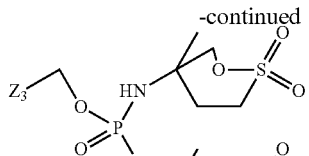

-continued

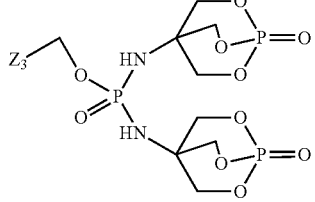

wherein $X_4$ is Cl, Br, or alkylsulfonyloxy.

In one embodiment, the present invention provides the compounds:

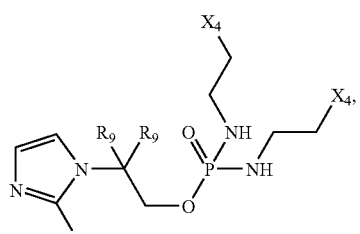

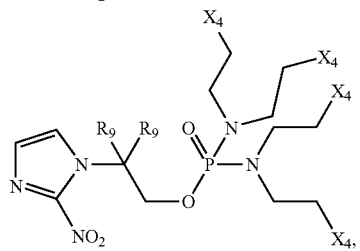

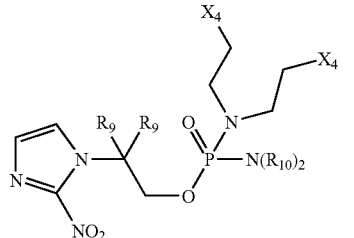

wherein $R_9$ and $X_4$ are defined as in formula VI.

In one embodiment, the present invention provides the compound of formula (XXI)

(XXI)

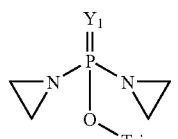

wherein $Y_1$ is S or O; and Trigger, T, is defined as in formula (I).

In another embodiment, the present invention provides the oxime-phosphoramidate alkylator conjugate:

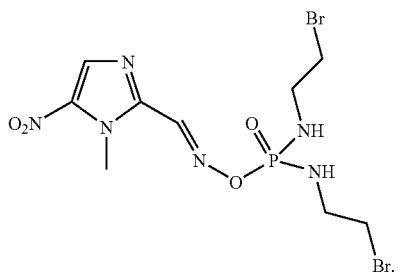

In one embodiment, such an oxime-phosphoramidate alkylator conjugate can be hydrolyzed enzymatically to produce

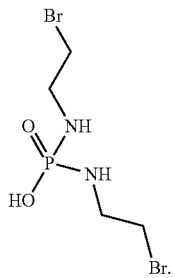

In another aspect, the present invention provides compounds of formula (XXII):

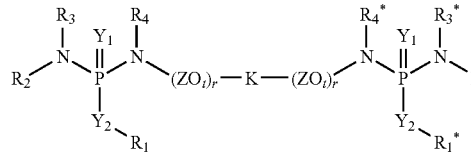

(XXII)

wherein $R_1$-$R_5$, $Y_1$, and $Y_2$ are defined as in formula (I);

each $R_1$-$R_5$ and $R_1^*$-$R_5^*$ independently is selected from the group consisting of hydrogen, hydroxyl, $C_1$-$C_6$ alkyl, $C_1$-$C_6$ alkoxy, $C_1$-$C_6$ alkylamino, $C_1$-$C_6$ dialkylamino, aryl, heteroaryl; or together $R_2$ and $R_2^*$ form a heterocycle; or each $R_1$-$R_5$ and $R_1^*$-$R_5^*$ independently is a Trigger, T, selected from the group consisting of —[C($Z_1$)$_2$—$Y_3$]$_v$—[C(=O)—O]$_1$—[C($Z_1$)$_2$—$Z_2$—$Y_4$]$_u$—[C($Z_1$)$_2$]$_z$—[—C($Z_1$)=C($Z_1$)]$_g$—$Z_3$ and —[C($Z_1$)$_2$—$Y_3$]$_v$—(S(=O)$_2$)$_4$[C($Z_1$)$_2$—$Z_2$—$Y_4$]$_u$—[C($Z_1$)$_2$]$_z$—[C($Z_1$)=C($Z_1$)]$_g$—$Z_3$—; with the proviso that in formula (XXII):

(i) at least two of $R_1$-$R_5$ and $R_1^*$-$R_5^*$ are 2-haloalkyl, 2-alkylsulfonyloxyalkyl, 2_heteroalkylsulfonyloxyalkyl, 2-arylsulfonyloxyalkyl, or 2 heteroalkylsulfonyloxyalkyl; or (ii) at least one of $R_1$-$R_5$ and $R_1^*$-$R_5^*$ is 2-haloalkyl, 2-$C_1$-$C_6$ alkylsulfonyloxyalkyl, 2-heteroalkylsulfonyloxyalkyl, 2-arylsulfonyloxyalkyl, or 2-heteroalkylsulfonyloxyalkyl; and at least one of $NR_2R_3$ and $NR_2^*R_3^*$ is

or (iii) each $NR_2R_3$ and $NR_2^*R_3^*$ both

and an individual isomer or a racemic or non-racemic mixture of isomers, bioisosteres, pharmacophores, a pharmaceutically acceptable salt, solvate, hydrate, or a prodrug thereof.

each Z independently is C, S, or P;

each t independently is 1 or 2;

each r independently is 0 or 1;

K is selected from the group consisting of $C_1$-$C_6$ alkylene, $C_1$-$C_6$ heteroalkylene, arylene, or heteroarylene, (C($R_9$)$_2$)$_n$; and (Y$_5$—(C($R_9$)$_2$)$_m$—Y$_4$—(C($R_9$)$_2$)$_m$—Y$_6$)$_n$ wherein n is 1-8;

each m independently is 1-4;

each $R_9$ is independently $C_1$-$C_6$ alkyl or heteroalkyl, or together when covalently bonded to the same carbon atom or adjacent carbon atoms are cycloalkyl or heterocyclyl; and each $Y_4$, $Y_5$, and $Y_6$ independently is O, S, $NR_7$, or a bond; with the proviso that one of $Y_4$, $Y_5$, and $Y_6$ has to be O, S, or $NR_7$.

In another aspect, the present invention provides compounds of formula (XXIII):

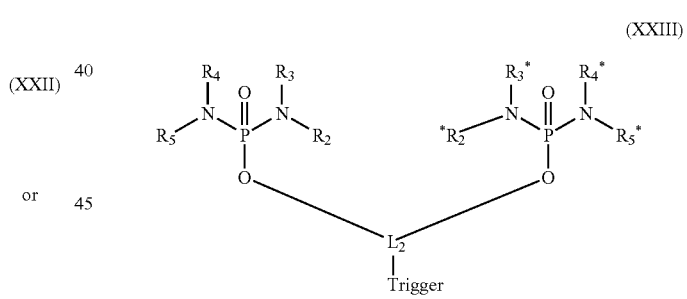

(XXIII)

wherein $R_1$-$R_5$, $Y_1$, and $Y_2$ are defined as in formula (I);

each $R_1$-$R_5$ and $R_1^*$-$R_5^*$ independently is selected from the group consisting of hydrogen, hydroxyl, $C_1$-$C_6$ alkyl, $C_1$-$C_6$ alkoxy, $C_1$-$C_6$ alkylamino, $C_1$-$C_6$ dialkylamino, aryl, heteroaryl; or together $R_2$ and $R_2^*$ form a heterocycle; or each $R_1$-$R_5^*$ independently is a Trigger, T, selected from the group consisting of —[C($Z_1$)$_2$—$Y_3$]$_v$—[C(=O)—O]$_q$—[C($Z_1$)$_2$—$Z_2$—$Y_4$]$_u$—[C($Z_1$)$_2$]$_z$—[—C($Z_1$)=C($Z_1$)]$_g$—$Z_3$ and —[C($Z_1$)$_2$—$Y_3$]$_v$—(S(=O)$_2$)$_q$—[C($Z_1$)$_2$—$Z_2$—$Y_4$]$_u$—[C($Z_1$)$_2$]$Z_4$]$_u$—[C($Z_1$)=C($Z_1$)]$_g$—$Z_3$—;

with the proviso that in formula (XXIII)

(i) at least two of $R_2$-$R_5$ and $R_2^*$-$R_5^*$ are 2-haloalkyl, 2-alkylsulfonyloxyalkyl, 2-heteroalkylsulfonyloxyalkyl, 2-arylsulfonyloxyalkyl, or 2 heteroalkyl-sulfonyloxyalkyl;

(ii) at least one of $R_2$-$R_5$ and $R_2^*$-$R_5^*$ is 2-haloalkyl, 2-$C_1$-$C_6$ alkylsulfonyloxyalkyl, 2-heteroalkylsulfonyloxyalkyl, 2-arylsulfonyloxyalkyl, or 2-heteroalkylsulfonyloxyalkyl; and one of $NR_2R_3$ and $NR_2^*R_3^*$ is

or (iii) $NR_2R_3$ and $NR_2^*R_3^*$ together are both

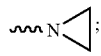

or $NR_4R_5$ and $NR_4^*R_5^*$ together are both

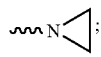

and an individual isomer or a racemic or non-racemic mixture of isomers, bioisosteres, pharmacophores, a pharmaceutically acceptable salt, solvate, hydrate, or a prodrug thereof.

$L^2$ is

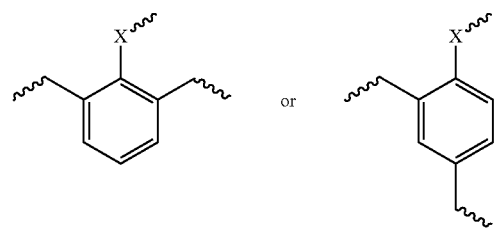

wherein X is defined as above.

In another embodiment, the present invention provides compounds of formula (XXIV):

(XXIV)

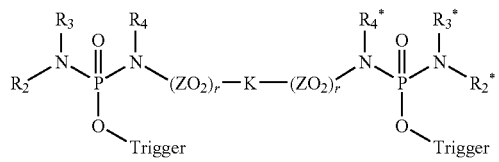

wherein $R_2$, $R_3$, $R_4$, $R_2^*$, $R_3^*$, $R_4^*$, Z, K and Trigger are as defined in Formula (XXII).

In another embodiment, the present invention provides compounds of formula (XXIV) having the structure of formula (XXV) or (XXVI):

(XXV)

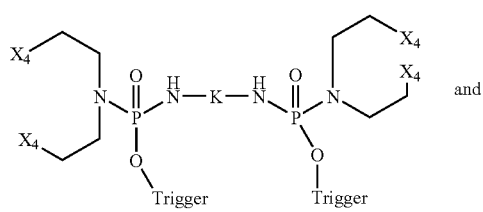

and (XXVI)

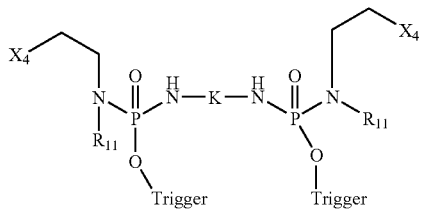

In another embodiment, the present invention provides compounds of formula (XXVI):

(XXVI)

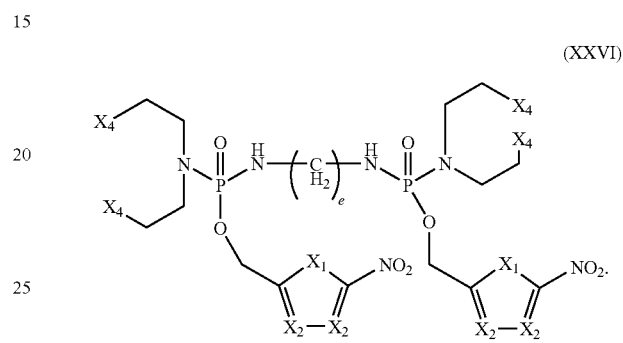

wherein $X_1$, $X_2$, $X_4$, and e are defined as in formula (XXV).

In another aspect, the present invention provides compounds of formula (XXVII):

(XXVII)

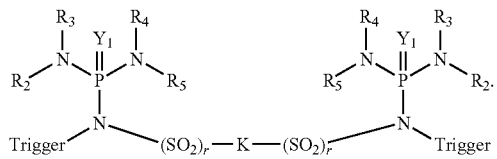

wherein $R_2$-$R_5$, r, k, $Y_1$, and Trigger, T, are defined as in formula (XXIV).

In one embodiment, the present invention provides a compound of formula:

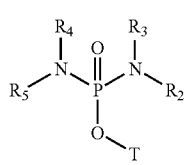

wherein T is L-$Z_3$;

$L_1$ is $CH_2$, CHMe, $C(Me)_2$, $CH_2OCH_2$, $(CH_2)_3$, $CH_2S(CH_2)_2$, $CH_2S(CH_2)_3$,

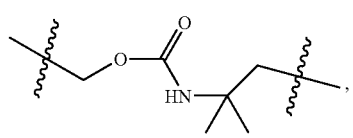

-continued
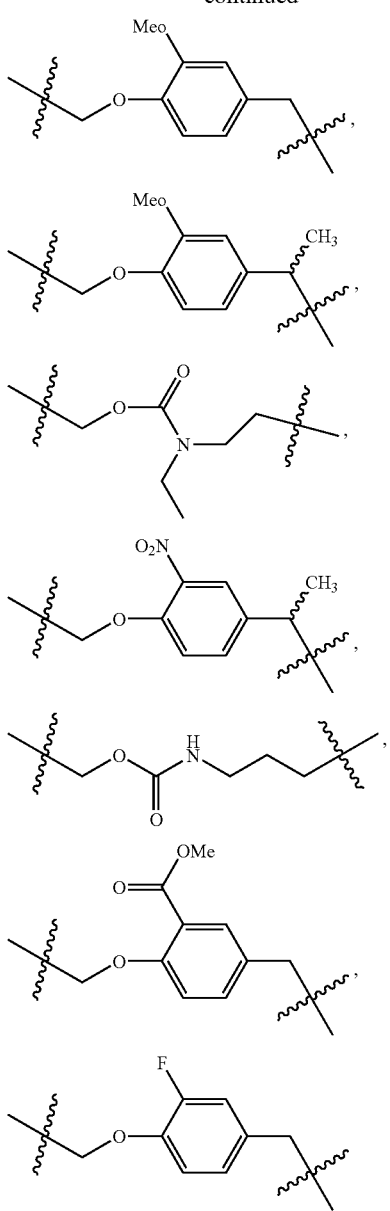
In another embodiment, the present invention provides a compound in which $Z_3$ is selected from the group consisting of:
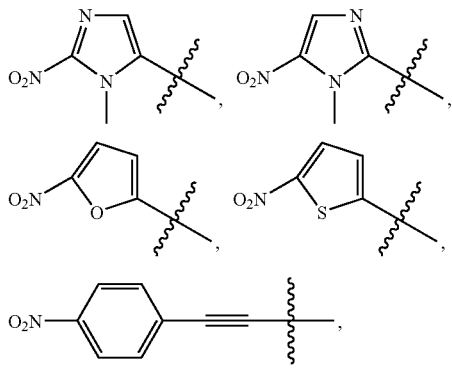
-continued
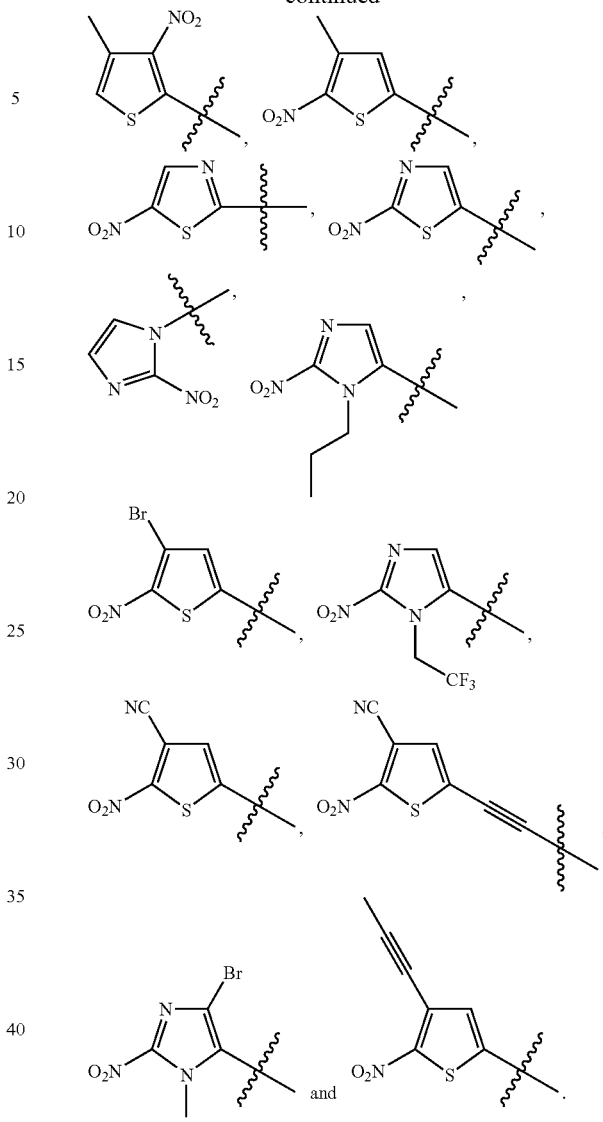
In another embodiment, the present invention provides a moiety having the formula:
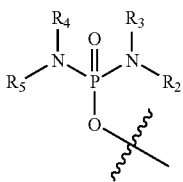
selected from the group consisting of:
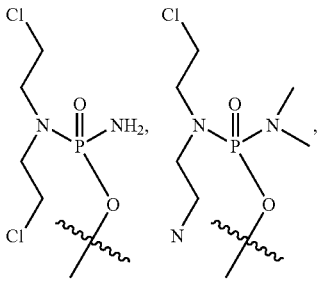

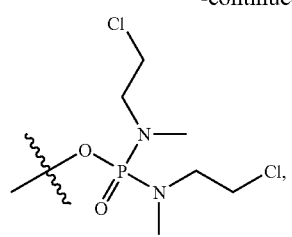
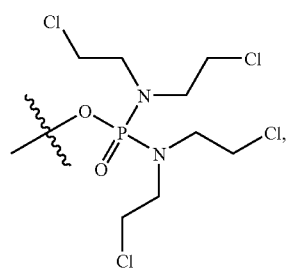
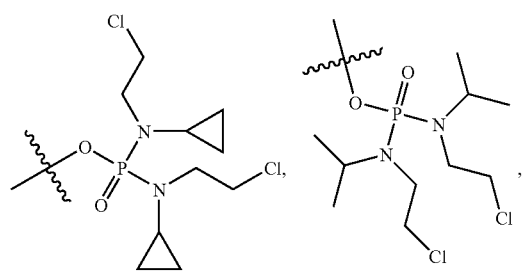
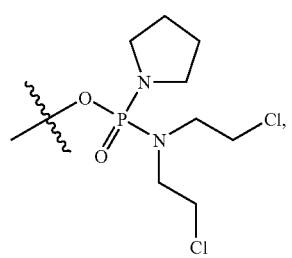
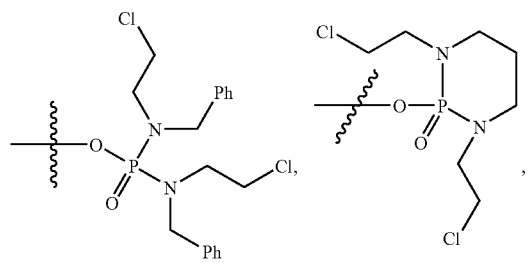
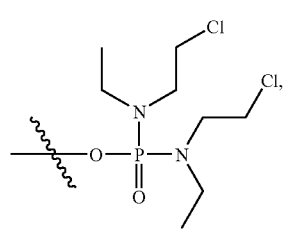
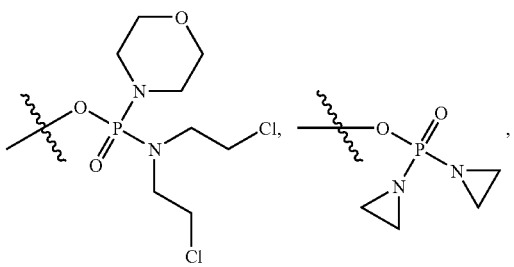
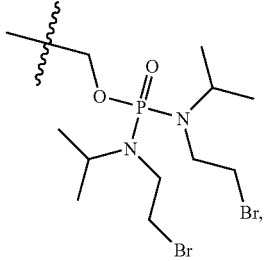
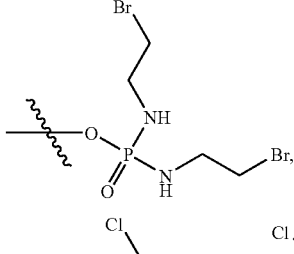
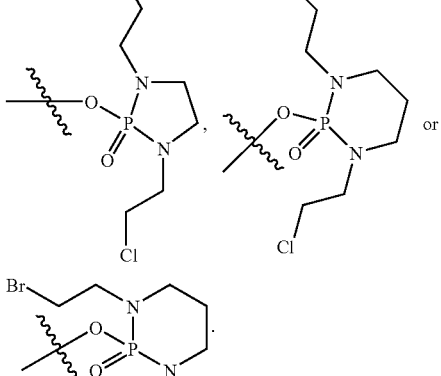
In another embodiment, the present invention provides a T selected from the group consisting of:
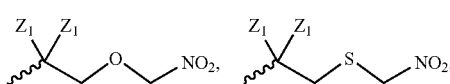
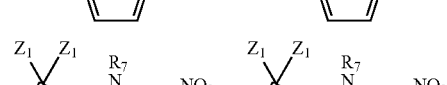

-continued

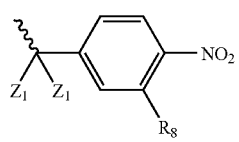

wherein each $Z_1$, $R_7$, and $R_8$ is defined as above. Within this embodiment, $Z_1$ is hydrogen, methyl, or ethyl; $R_7$ is methyl, trifluoroethyl, ethyl, propyl, and cyclohexyl; and $R_8$ is OH or $OP(=O)(OH)_2$. Within this embodiment,

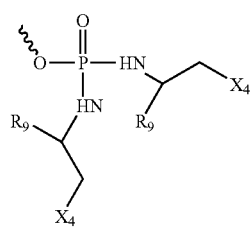

wherein each $R_9$ is hydrogen or $C_1$-$C_6$ alkyl and each $X_4$ is halo or $R_{sul}S(=O)_2O$—. In another embodiment, $R_9$ is hydrogen, methyl, ethyl, isopropyl, or isobutyl; and $X_4$ is chloro, bromo, or methanesulfonyloxy.

In another embodiment, the present invention provides a compound of formula:

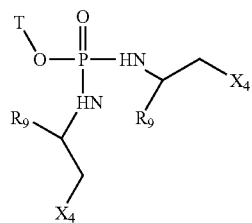

wherein T is defined as above or more particularly T is L-$Z_3$ wherein L is $CH_2$, CHMe, $CMe_2$,

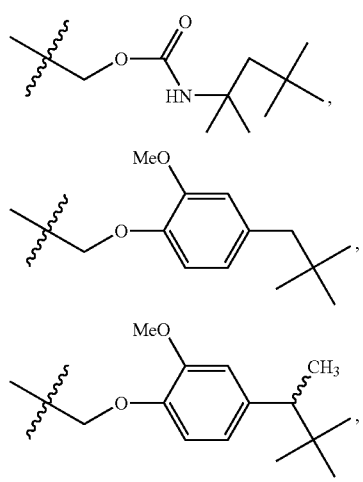

-continued

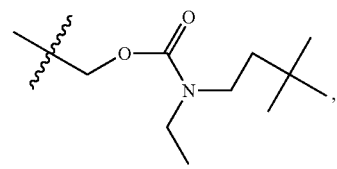

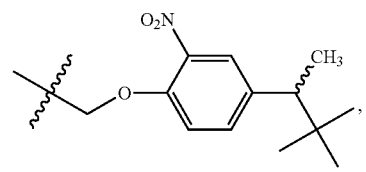

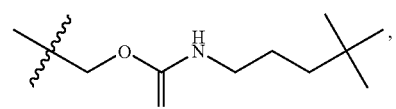

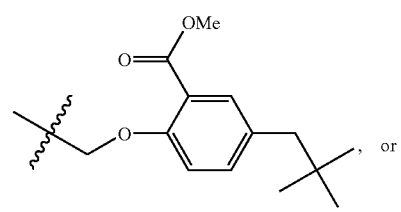

, or

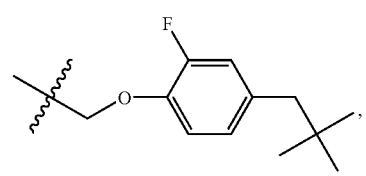

and $Z_3$ is

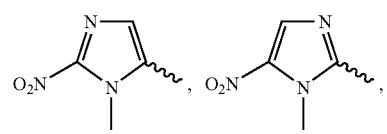

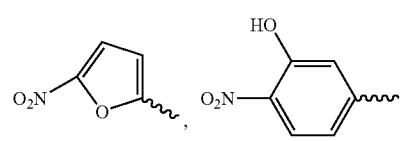

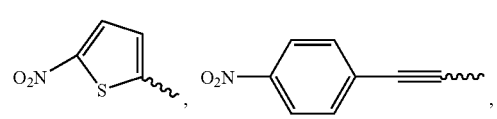

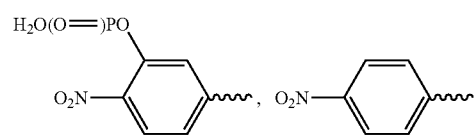

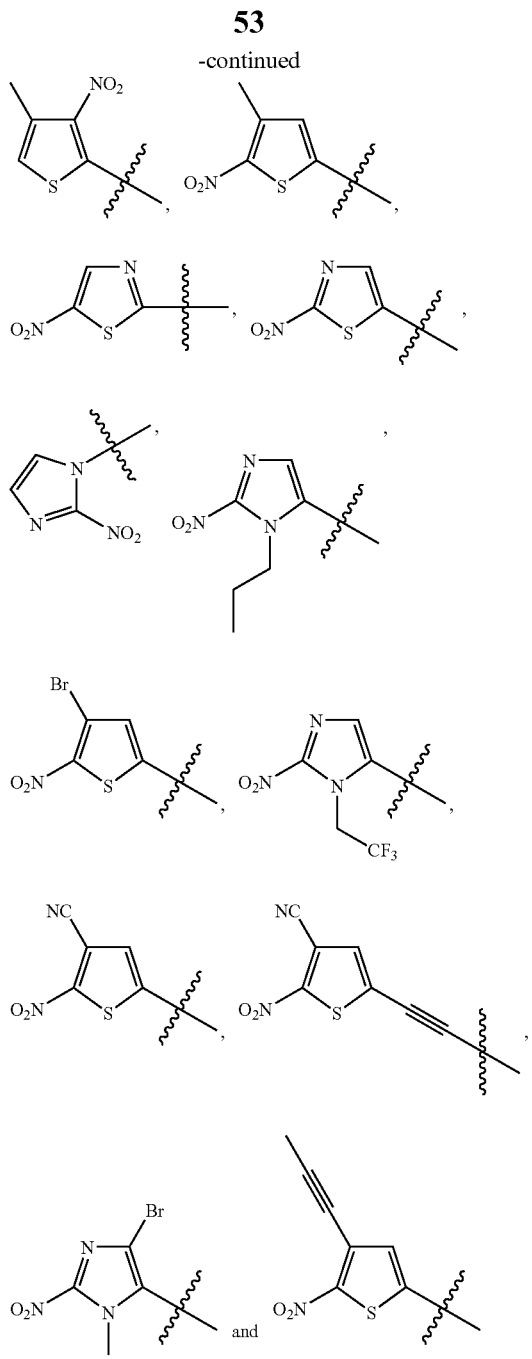

In one aspect the present invention provides deuterated phosphoramidate alkylators and deuterated phosphoramidate alkylator prodrugs of formula wherein $X_4$ is halo or $R_{sul}S(=O)_2O$. In another embodiment, $X_4$ is Cl or Br. Such deuterated phosphoramidate alkylators and their prodrugs are equally cytotoxic with respect to hypoxic tumor tissue as their non-deuterated or hydrogenated analogs, such as compounds 25, 36 and the like. However, the presence of such deuterated analogs in vivo, for example in blood plasma, can be determined more efficiently compared to their corresponding phosphoramidate alkylators and/or phosphoramidate alkylator prodrugs by nuclear magnetic resonance methods and such deuterated analogs can be useful in determining pharmacokinetic or pharmacodynamic properties of the phosphoramidate alkylators and/or phosphoramidate alkylator prodrugs. Pharmacokinetic and or pharmacodynamic information of phosphoramidate alkylators and/or phosphoramidate alkylator prodrugs is used in determining dosage, frequency of dosing, and similar administration related parameters. The synthesis of an octadeuterated-compound 25 and octadeuterated isofosfamide alkylator is described in the EXAMPLE section.

In another group of embodiments, the present invention provides the individual and selective groupings of the compounds of the EXAMPLES. Examples of compounds of the invention include:

1

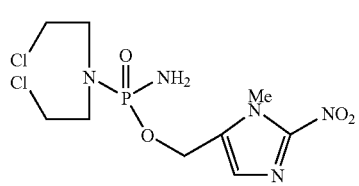

2

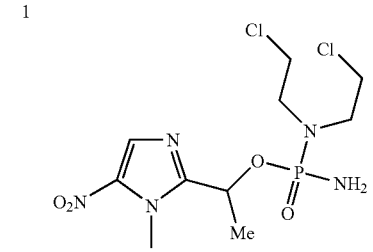

-continued
3
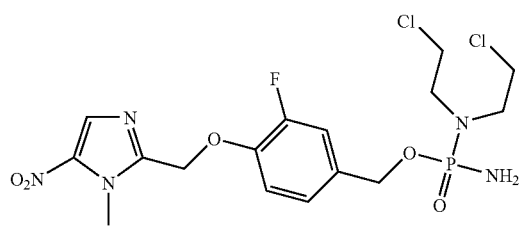
4
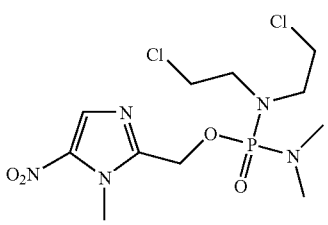
5
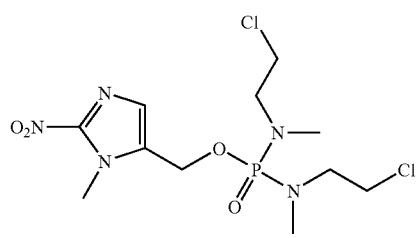
6
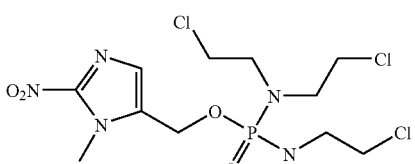
7
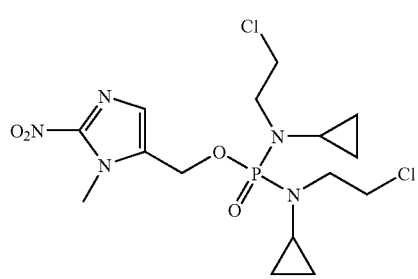
8
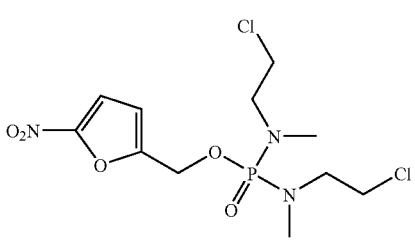
9
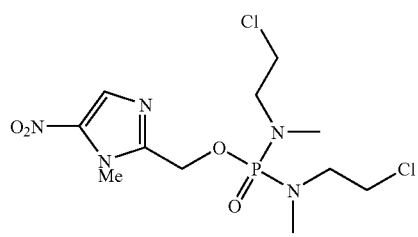
10
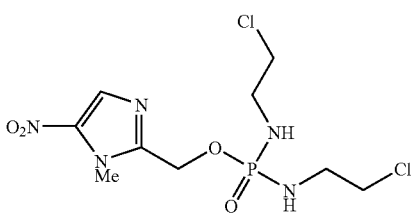
11
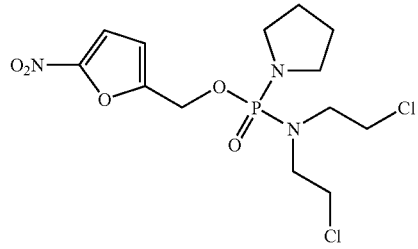
12
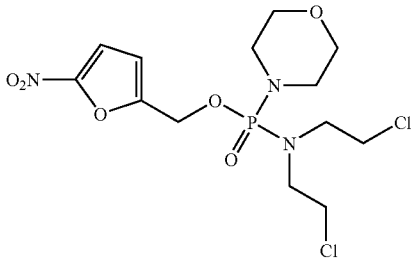
13
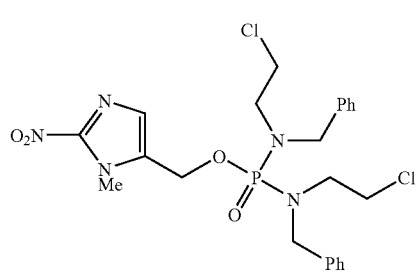
14
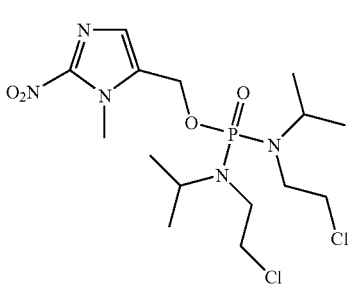

-continued
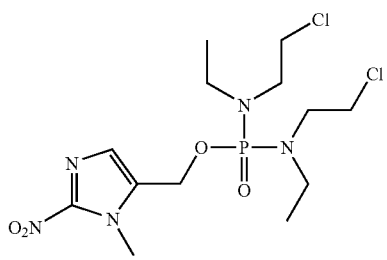 15
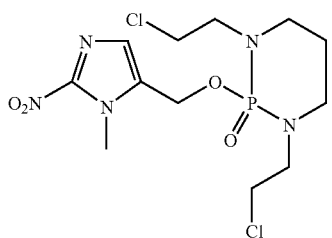 16
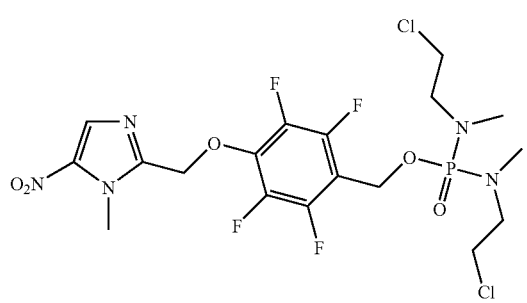 17
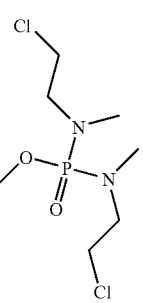 18
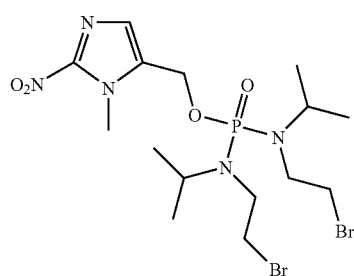 19
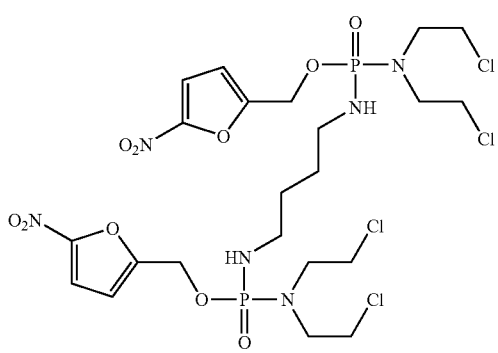 20
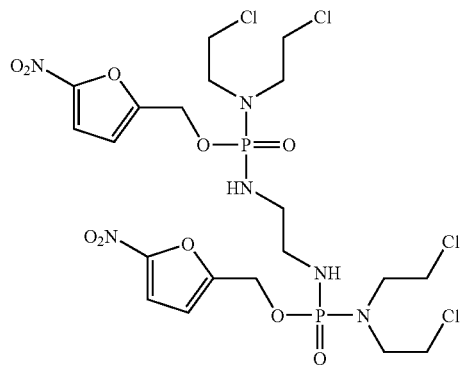 21
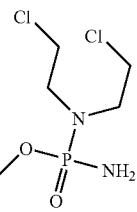 22
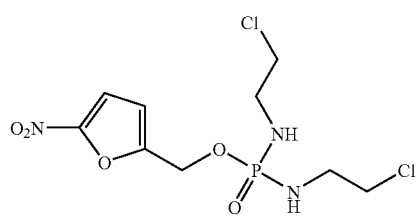 23
 24

25 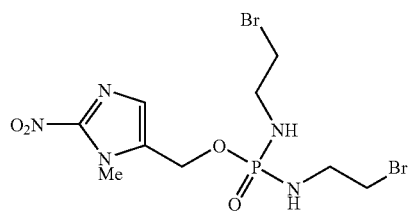
26 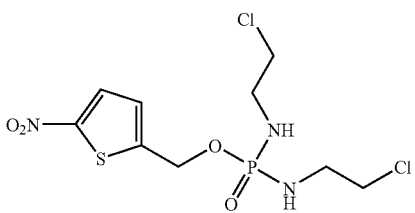
27 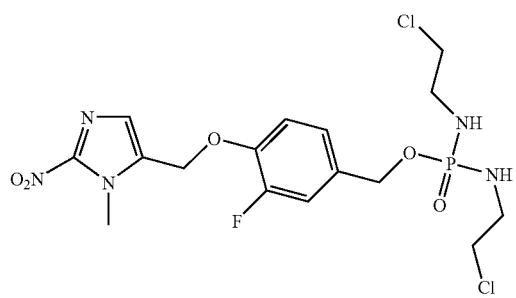
28 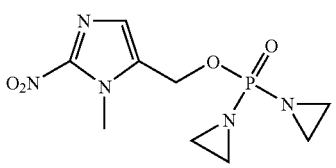
29 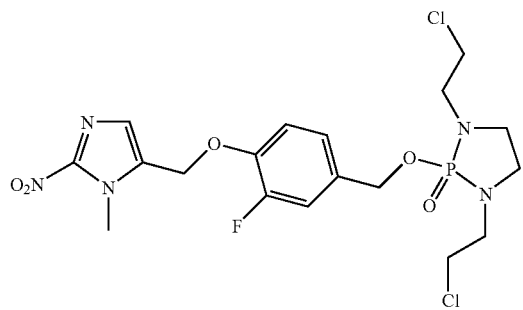
30 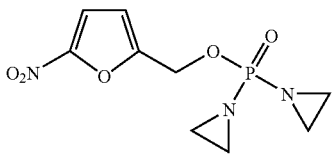
31 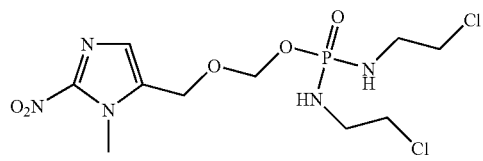
32 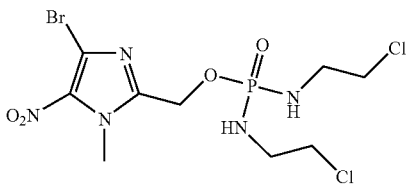
33 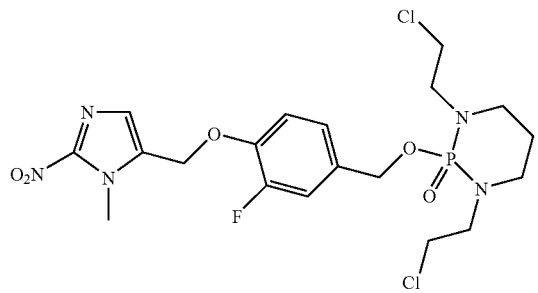
34 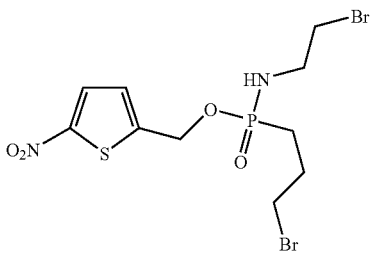
35 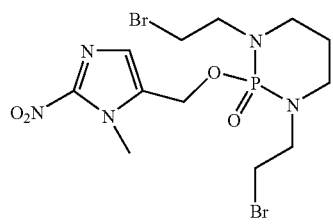
36

-continued
134
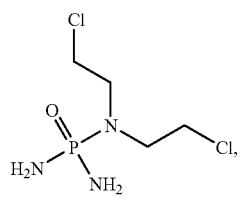
135
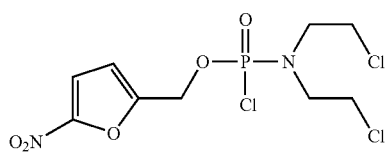
136
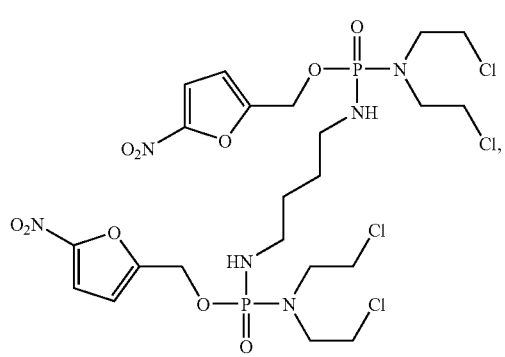
137
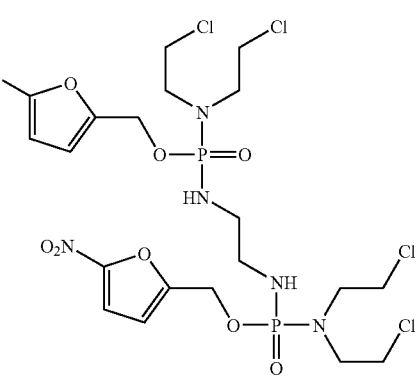
138
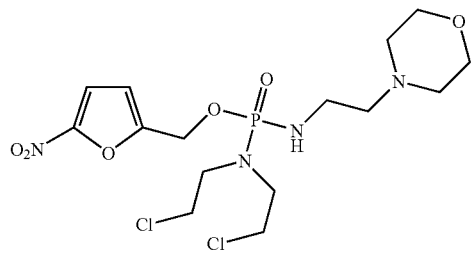
139
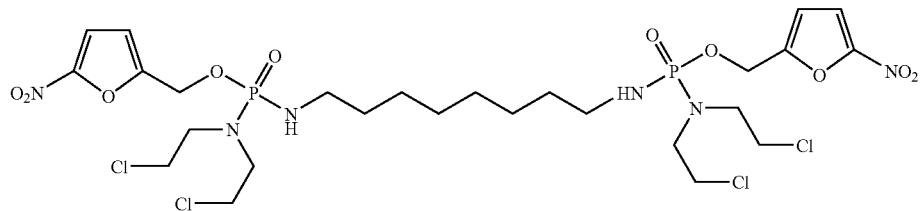
140
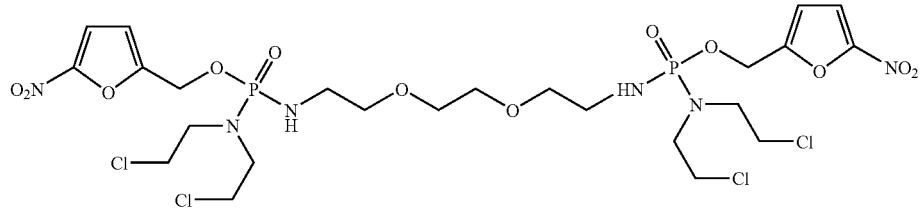
141
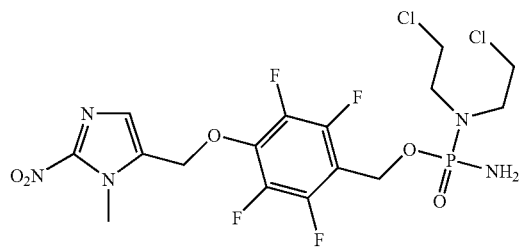
142
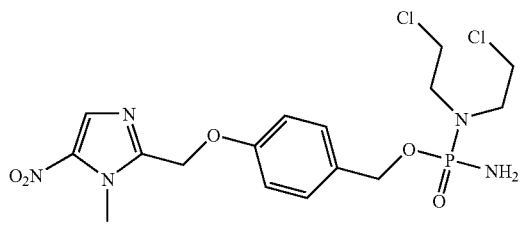

-continued
| | |
|---|---|
| 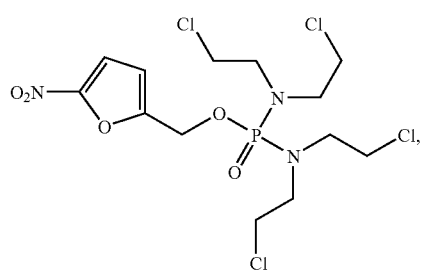 143 | 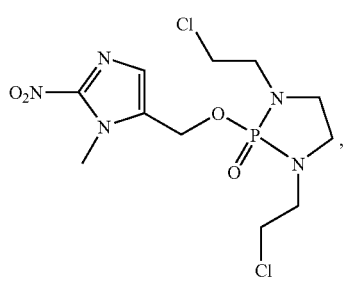 144 |
| 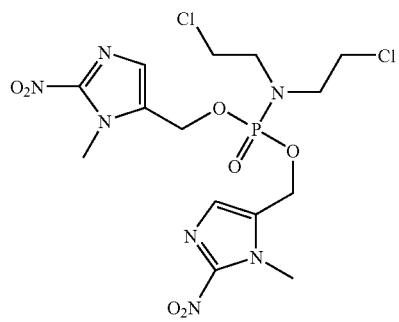 145 | 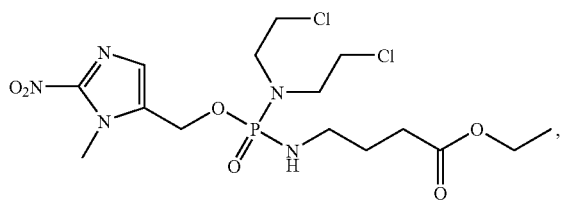 146 |
| 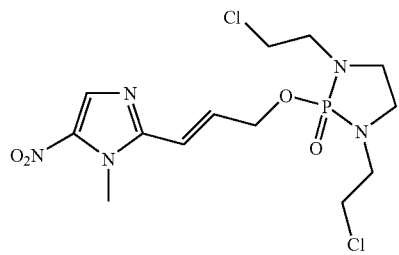 147 | 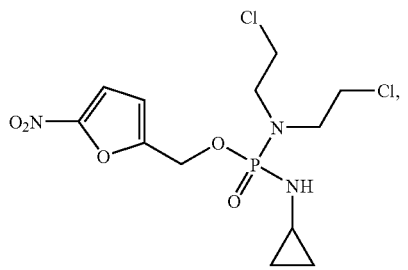 148 |
| 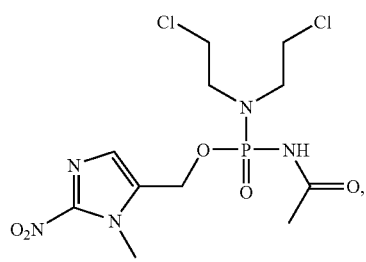 149 | 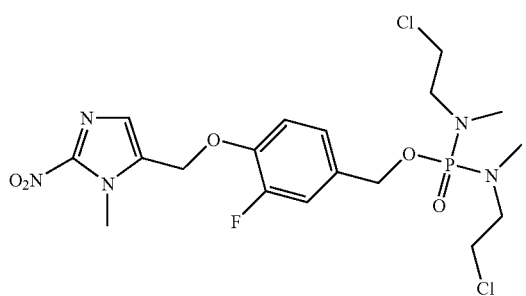 150 |
| 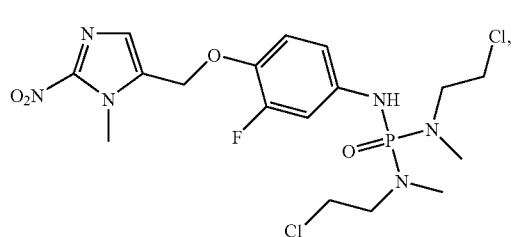 151 | 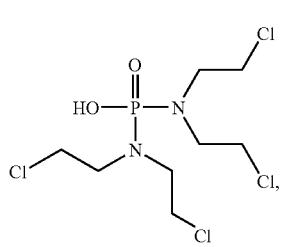 152 |

153
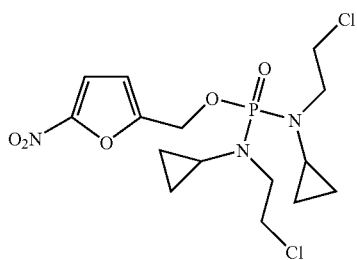

154
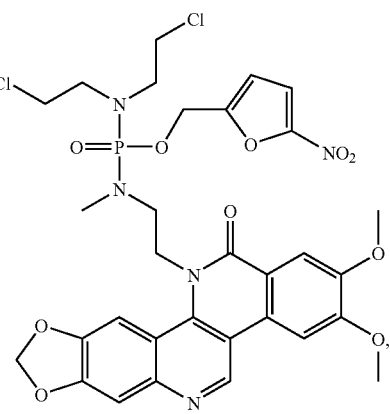

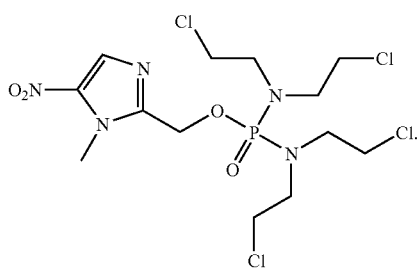

In one embodiment, the phosphoramidate alkylator prodrug contains

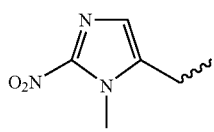

as $Z_3$ and shows hypoxic tumor specific toxicity while being much less toxic to healthy, normoxic tissue.

In one embodiment, the present invention provides a novel phosphoramidate alkylator prodrug which upon bioreduction releases the corresponding novel or known phosphoramidate alkylator 1a
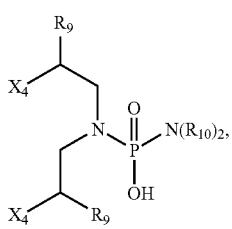

1b
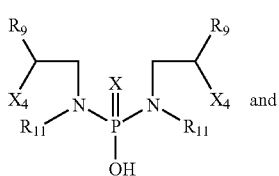

1c
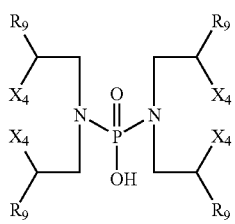

wherein $X_4$ is defined as in formula (I), and $R_9$, $R_{10}$, and $R_{11}$, are defined as in formulas (IV)-(VII), and ionized forms thereof. In a related embodiment, $X_4$ is Cl, Br, methanesulfonyloxy, benzenesulfonyloxy, or para-toluenesulfonyloxy.

In one embodiment, the present invention provides a novel phosphoramidate alkylator prodrug which upon bioreduction releases the corresponding novel or known phosphoramidate alkylators 1d
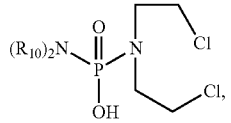

1e
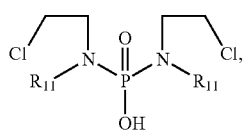

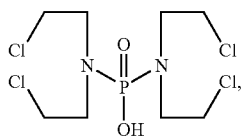
1f

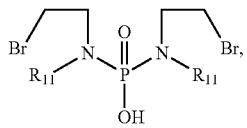
1g

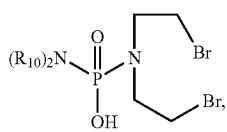
1h

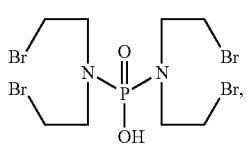
1i

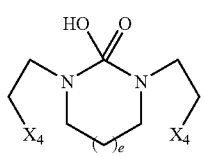
1j and ionized forms thereof;
wherein $N(R_{10})_2$ is selected from the group consisting of $NH_2$, NHMe, $NMe_2$, $NEt_2$,

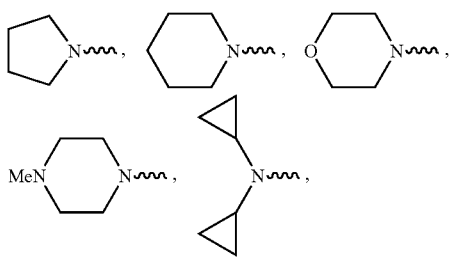

NHOMe and NHOH; each $R_{11}$ is independently hydrogen, Me, ethyl, cyclopropyl, isopropyl, propyl, benzyl, substituted methyl, cyclopropyl, methoxy, and hydroxyl; or together two $R_{11}$ form a heterocycle.

The anti-cancer agent cyclophosphamide metabolizes to 1d ($R_{10}$ is hydrogen) and Ifosfamide metabolizes to 1e (each $R_{11}$ is hydrogen), when used in cancer treatment glufosfamide, which is being evaluated in the clinic for cancer treatment, releases an alkylator of formula 1e (each $R_{11}$ is hydrogen, see Wiessler et al., U.S. Pat. No. 5,622,936; PCT application No. US05/03370 entitled "Anti Cancer Therapies", U.S. Pat. Appl. No. 60/638,995 entitled "Glufosfamide Combination Therapy" and U.S. Pat. Appl. No. 60/683,087 filed on 11 May 2005 entitled "Glufosfamide Combination Therapy"). Telcyta™ which is being evaluated in the clinic for cancer treatment, releases if (Rosen et al., *Clin Cancer Res.* 2004, 10(11):3689-98).

Known phosphoramidate alkylator prodrugs such as ifosfamide and cyclophosphamide metabolize to produce cytotoxic by products such as acrolein and chloroacetaldehyde which cause undesirable patient side-effects such as hemorrhagic cystitis, coma or death. In one embodiment, the present invention provides a phosphoramidate alkylator prodrug which upon metabolism produces less toxic by products per treatment as compared to those produced by the metabolism of ifosfamide and/or cyclophosphamide. In one embodiment, the phosphoramidate alkylator prodrugs of the present invention do not produce acrolein by in vivo metabolism. Examples of toxic by products resulting from metabolism of the prodrugs of the invention include chloro, bromo, alkylsulfonyloxy, heteroalkylsulfonyloxy, arylsulfonyloxy, or heteroarylsulfonyloxy-acetaldehyde, (for metabolic production of chloroacetaldehyde from ifosfamide see the reference Hardman et al., supra, page 1396). In another embodiment, the present invention provides a phosphoramidate alkylator prodrug which upon oxidative metabolism produces 5-95% as much chloroacetaldehyde or an equivalent as defined above, per treatment, as produced by ifosfamide metabolism.

The phosphoramidate alkylator derivative formed upon the reduction of $Z_3$ can be different from the phosphoramidate alkylator being protected and the phosphoramidate alkylator prodrug and is termed a modified phosphoramidate alkylator prodrug. For example, a phosphoramidate alkylator prodrug can yield a modified phosphoramidate alkylator prodrug Alk-Trigger$_{mod}$ upon reduction of the bioreductive group ($Z_3$). When reduction of the bioreductive group forms a modified phosphoramidate alkylator prodrug, the linker (L) bonded to the phosphoramidate alkylator can undergo degradation to yield either the phosphoramidate alkylator or some other modified phosphoramidate alkylator prodrug.

In one embodiment, the present invention provides a compound which demonstrates a bystander effect upon activation in hypoxic tissue by incorporating a linker (L) as described above. In one embodiment, the bystander effect allows a modified phosphoramidate alkylator of the present invention to diffuse or penetrate into tumor zones which are not hypoxic enough to activate the prodrug compounds of the invention but reside nearby the hypoxic tumor zone which can activate these prodrugs.

Upon reduction of the bioreductive group ($Z_3$) within the Trigger, T, is modified to $Z_{3\text{-}mod}$, to yield a modified phosphoramidate alkylator prodrug such as phosphoramidate alkylator-$T_M$ or Alk-$T_M$ conjugate. In one embodiment the $T_M$ is selected from:

$[C(Z_1)_2-Y_3]-(C(=O)-O)-[C(Z_1)_2-Z_2-Y_4]-[C(Z_1)_2]_z-[C(Z_1)=C(Z_1)]-Z_{3\text{-}mod}$;
$[C(Z_1)_2-Y_3]-[C(Z_1)_2-Z_2-Y_4]-[C(Z_1)_2]_z-[C(Z_1)=C(Z_1)]-Z_{3\text{-}mod}$;
$[C(Z_1)_2-Y_3]-[C(Z_1)_2]_z-[C(Z_1)=C(Z_1)]-Z_{3\text{-}mod}$;
$[C(Z_1)_2-Y_3]-[C(Z_1)_2]_z-Z_{3\text{-}mod}$;
$[C(Z_1)_2-Y_3]-(C(=O)-O)-[C(Z_1)_2]_z-[C(Z_1)=C(Z_1)]-Z_{3\text{-}mod}$;
$[C(Z_1)_2-Y_3]-(C(=O)-O)-[C(Z_1)_2]_z-Z_{3\text{-}mod}$;
$[C(Z_1)_2-Y_3]-(C(=O)-O)-[C(Z_1)_2]_z-[C(Z_1)=C(Z_1)]-Z_{3\text{-}mod}$;
$[C(Z_1)_2-Z_2-Y_4]-[C(Z_1)_2]z-[C(Z_1)=C(Z_1)]-Z_{3\text{-}mod}$; and
$-[C(Z_1)]_z-[C(Z_1)=C(Z_1)]-Z_{3\text{-}mod}$ wherein $Z_{3\text{-}mod}$ is bioreduced or otherwise reduced or modified $Z_3$.

In another embodiment, the $T_M$ is selected from:
$[C(Z_1)_2-Y_3]-(C(=O)-O)-[C(Z_1)_2-Z_2-Y_4]-H$;
$[C(Z_1)_2-Y_3]-[C(Z_1)_2-Z_2-Y_4]-H$; and $[C(Z_1)_2-Y_3]-H$.

In one embodiment, Trigger, T, includes the following linkers (L) having the formula:
$-[C(Z_1)_2-Y_3]-(=O)-O)-[C(Z_1)_2-Z_2-Y_4]-[C(Z_1)_2]_z-[C(Z_1)=C(Z_1)]-$;

—[C(Z$_1$)$_2$—Y$_3$]—[C(Z$_1$)$_2$—Z$_2$—Y$_4$]—[C(Z$_1$)$_2$]$_z$—[C(Z$_1$)=C(Z$_1$)]—;

—[C(Z$_1$)$_2$—Y$_3$]—[C(Z$_1$)$_2$]$_z$—[C(Z$_1$)=C(Z$_1$)]—; —[C(Z$_1$)$_2$—Y$_3$]—[C(Z$_1$)$_2$]$_z$—; —[C(Z$_1$)$_2$—Y$_3$]—(=O)—O)—[C(Z$_1$)$_2$]$_z$—[C(Z$_1$)=C(Z$_1$)]—; —[C(Z$_1$)$_2$—Y$_3$]—(C(=O)—O)—C(Z$_1$)$_2$—;

—[C(Z$_1$)$_2$—Y$_3$]—(=O)—O)—[C(Z$_1$)$_2$]$_z$—[C(Z$_1$)=C(Z$_1$)]—; and

—[C(Z$_1$)$_2$—Z$_2$—Y$_4$]—[C(Z$_1$)$_2$]$_z$—[C(Z$_1$)=C(Z$_1$)]—; —[C(Z$_1$)$_2$]$_z$—[C(Z$_1$)=C(Z$_1$)]— and —[C(Z$_1$)$_2$]$_z$—.

In one embodiment, the present invention provides a Trigger, T, which upon bioreduction is modified to Trigger$_{Mod}$ or T$_M$ and the phosphoramidate alkylator is separated from T$_M$ in less than 0.1 second. In another embodiment, the phosphoramidate alkylator is separated from T$_M$ in between 0.01 to 0.10 second. In another embodiment, the phosphoramidate alkylator is separated from T$_M$ in between 0.1 to 1.0 second. In another embodiment, the active phosphoramidate is separated from T$_M$ in between 1.0 to 10.0 seconds. In another embodiment, the phosphoramidate alkylator is separated from T$_M$ in between 10.0 to 100.0 seconds.

In a related embodiment, upon activation or reduction, a phosphoramidate alkylator prodrug yields a prodrug with a modified Trigger (T$_M$) which subsequently releases the phosphoramidate alkylator 20 to 500 µm from the site of activation or reduction; or 20 to 100 µm from the site of activation or reduction. Bystander effect of a phosphoramidate alkylator prodrug of the present invention can be measured using cellular spheroids and multilayer cellular assay (for example of such assays see Kyle et al., Cancer Res. 2004, 64(17):6304-9 and West et al., Cancer Chemother. Pharmacol., 1987, 20(2): 109-14); and as described in greater detail in Examples 35 and 37. Tumor cells can be grown in culture as multicellular spheroids to create an in vitro model of the tumor microenvironment in solid tumors containing a hypoxic region and a quiescent cell population responding to the environmental stresses of limited nutrients and increased waste production. These spheroids have the unique property of developing gradients of oxygen and nutrients as the aggregate of cells continues to divide and grow outward. After the viable rim reaches approximately 150 µm in size, a hypoxic region develops, that drives the cells in this region into a quiescent state and eventually to cell death. A necrotic core develops as a result of the dying cells. The spheroid can be divided into 4 distinct compartments for modeling the effectiveness of a hypoxic activated prodrug: 1) the outer aerobic and actively dividing region; 2) a region of intermediate hypoxia; 3) a region of hypoxia where cells are not cycling; 4) and a necrotic core containing dead cells and cellular debris. The response to a drug will depend on a number of factors; the ability of compound to penetrate into the deepest regions of the spheroid. The activation of hypoxic activated prodrug (HAP) by nitroreductases; the reactivity of the activated drug in the cell in which it was activated; and the ability of the activated drug to leave the site from where it was activated and kill nearby cells (bystander effect). The assessment of the effectiveness of a compound can therefore be evaluated on a number of different levels. The effect of the compound alone can be compared to cells in monolayer culture versus intact spheroids. The HAP can used as a monotherapy. The hypoxic fraction of the spheroid can be modulated by varying the concentration of O$_2$ of the equilibrating gas and therefore change the ratio of the aerobic and hypoxic compartments. HAP's can be combined with other chemotherapeutic agents that either target only the outer aerobic cells or are able to target the entire spheroid. The expected cell kill can be predicted by knowing the hypoxic fraction and the expected cell kill of each of the monotherapies.

In one embodiment, the present invention provides a phosphoramidate alkylator prodrug which upon activation such as bioreduction releases the phosphoramidate alkylator with a half life of less than 0.1 second; between 0.01 to 0.10 second, between 0.1 to 1.0 second, between 1.0 to 10.0 seconds, and between 10.0 to 100.0 seconds.

Anti cancers drugs can bind to tissue surrounding the vasculature and/or have high molecular weights that impede diffusion and not reach in therapeutically effective concentrations hypoxic tumor zones that can be up to 150-200 µM away from the vasculature. In one embodiment, the present invention provides phosphoramidate alkylator prodrugs that can reach hypoxic cancer cells away from the vasculature. Some methods for determining the bystander effect are described in greater detail in Examples 35 and 37. The phosphoramidate alkylator used in a hypoxia activated prodrug plays an important role to efficiently kill tumor cells. For example, for a hypoxia activated phosphoramidate alkylator prodrug, the cytoxicity of the phosphoramidate alkylator and its rate of cellular alkylation, and the cell membrane permeability of the prodrug and the phosphoramidate alkylator impact the hypoxic selectivity and hypoxic cytotoxicity of the phosphoramidate alkylator prodrug.

In one embodiment, the present invention provides phosphoramidate alkylator prodrugs that are safer than the corresponding phosphoramidate alkylators formed in vivo (at least ten and up to one million-fold safer. In one embodiment, the increased safety results from a modification at the site of attachment of the Trigger, T, (activation of the phosphoramidate alkylator prodrug releases the alkylator/cytotoxic agent). In either event, the phosphoramidate alkylator prodrugs are converted into the corresponding alkylator in hypoxic tissues by virtue of the activation or reduction of the bioreductive group ($Z_3$), resulting in its removal and the concomitant or subsequent release or generation of the phosphoramidate alkylator.

In one embodiment, the Trigger, T, is covalently bonded to the phosphoramidate alkylator, in a manner that masks or reduces the cytotoxic activity of the phosphoramidate alkylator. This masking effect can vary and can depend on the cytotoxic activity of the phosphoramidate alkylator. Typically, the phosphoramidate alkylator prodrug will show at least about 10 fold less cytotoxic activity than the corresponding phosphoramidate alkylator, and can show up to about a million fold or less cytotoxic activity. In one version, the cytotoxic activity of the phosphoramidate alkylator prodrug is about 100 fold to about 10,000 fold less than the cytotoxic activity of the corresponding phosphoramidate alkylator. As one example, for a phosphoramidate alkylator with an IC$_{50}$, IC$_{90}$, or LC$_{50}$ of 1 nM, the IC$_{50}$, IC$_{90}$, or LC$_{50}$ of the corresponding phosphoramidate alkylator prodrug can be 1 µM or greater.

In one version, compounds provided herein include as phosphoramidate alkylator prodrug, any phosphoramidate alkylator that can be linked to a Trigger, T, in a manner that yields a phosphoramidate alkylator prodrug that is at least about 10-fold to about 1,000,000-fold, and typically about 100 to about 10.000-fold, less active as a cytotoxic agent than the corresponding phosphoramidate alkylator or modified phosphoramidate alkylator that is released from the compounds under hypoxic conditions.

To determine if a phosphoramidate alkylator prodrug is selectively active under anoxic or hypoxic conditions, cells are exposed to the drug either with air (normoxic) or without oxygen (anoxia) or with very little oxygen (hypoxia). One of skill in the art will recognize that cytotoxicity of a phosphoramidate alkylator prodrug as measured in an anti-proliferation assay is expressed by the $IC_{50}$; and the cytotoxicity of a phosphoramidate alkylator prodrug as measured in a clonogenic survival experiment is expressed as $IC_{10}$ or $LC_{10}$, $IC_{90}$ or $LC_{90}$, or $IC_{99}$ or $LC_{99}$. The ratio of cytotoxicity as measured for example by $IC_{50}$, $IC_{90}$, $LC_{50}$, $LC_{90}$, or $LC_{99}$ determined in normoxia and hypoxia is called hypoxia cytotoxicity ratio (HCR) and can be a measure of the hypoxia selective cytotoxicity of the prodrugs of the present invention. The larger the HCR of the phosphoramidate alkylator prodrug the higher is its hypoxic cell selective toxicity and greater the hypoxic tumor killing ability of the prodrug relative to healthy normoxic cells. The HCR determined based on $IC_{99}$ or $LC_{99}$ is larger than that determined based on $IC_{90}$ or $LC_{90}$.

In a related embodiment, the phosphoramidate alkylator prodrug of the present invention has a hypoxic cytotoxicity of 0.1 nM to 50 μM and an HCR of 10 to 100,000. In a related embodiment, the phosphoramidate alkylator prodrug of the present invention has a hypoxic cytotoxicity of 0.1 nM to 50 μM and an HCR of 25 to 100,000 (see EXAMPLE section). In another related embodiment, the phosphoramidate alkylator prodrug of the present invention has a hypoxic cytotoxicity of 0.1 nM to 5 μM and an HCR of 50 to 10,000 such as, for example, the compounds described in Examples 29, 30 and 31.

In one embodiment, the present invention provides a phosphoramidate alkylator prodrug having hypoxic toxicity which is 5 to 1,000,000 fold more than the corresponding normoxic toxicity. In another embodiment, the present invention provides a phosphoramidate alkylator prodrug having hypoxic toxicity which is 10 to 10,000 fold more than the corresponding normoxic toxicity. In another embodiment, the present invention provides a phosphoramidate alkylator prodrug having hypoxic toxicity which is 25 to 5,000 fold more than the corresponding normoxic toxicity.

Tumors have a gradient of oxygen concentration that can vary from 10%, in tissues adjacent to the vasculature, to 0.5% in tissues about 150 μM away, and lower in tissues further away from the vasculature and near the necrotic core. In one embodiment, the present invention provides phosphoramidate alkylator prodrugs that can generate phosphoramidate alkylators, 5-1,000,00; 10-10,00; and 25-5,000 fold more toxic than the corresponding prodrug, under a variety of oxygen concentrations. In one embodiment, the present invention provides phosphoramidate alkylator prodrugs generate phosphoramidate alkylators, 5-1,000,00; 10-10,00; and 25-5,000 fold more toxic than the corresponding prodrug, under about 0.5-0.6% oxygen concentrations.

The logP of a phopsphramidate alkylator prodrug of the present invention can measure the lipophilicity or the hydrophilicity of the prodrug. In one embodiment, the present invention provides a phosphoramidate alkylator prodrug having a logP less than 0, Such phosphoramidate alkylator prodrugs can be hydrophilic, such as a prodrug having formula XV wherein each $R_{11}$ is H and can be easily formulated as an aqueous formulation for i.v. or i.p. injection. Another example of such prodrugs are compounds 24, 25 and 36.

In one embodiment, the present invention provides a phosphoramidate alkylator prodrug having a logP greater than 0. In one embodiment, the present invention provides a phosphoramidate alkylator prodrug having a logP between 0 and 4 such as those exemplified by formulas XIV; XX and XV wherein each $R_{11}$ is methyl or, cyclopropyl, and administered in a patient can pass the cell membrane to penetrate inside cancer cells. Another example a prodrug having a logP between 0 and is 5, 6, 7, or 16. (for measured logP of phopsphramidate alkylator prodrugs of the present invention see EXAMPLES section).

IIb. Methods of Synthesis

The present invention arises in part out of the discovery that compound 36, which could not be isolated by reacting

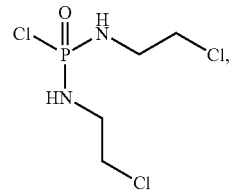

1-N-methyl-2-nitroimidazole-5-methanol, and n-butyl lithium in a suitable solvent, was readily synthesized by employing a Mitsunobu-type reaction wherein 1-N-methyl-2-nitroimidazole-5-methanol was activated by the addition of triphenylphosphine and diisopropyl azodicarboxylate, and reacted with

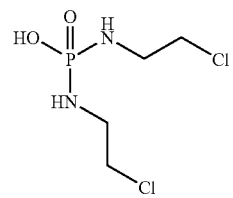

to yield compound 36.

Thus, in one aspect the present invention provides a method of synthesizing a phosphoramidate compound comprising reacting a phosphoramidic or a phosphordiamidic acid and an alcohol to yield a phosphoramidate. In another aspect, the present invention provides methods of synthesizing the novel phosphoramidate alkylator prodrug compounds of the invention or those that are known. In one embodiment, the present invention provides a method of synthesizing a phosphoramidate alkylator prodrug comprising reacting a novel or known phosphoramidate alkylator, a Trigger-OH, a trisubstituted phosphine, and a dialkyl azodicarboxylate to yield a novel or known phosphoramidate alkylator prodrug. In one embodiment of the method, in a first step the Trigger-OH is reacted with the trisubstituted phosphine and the dialkyl azodicarboxylate to yield an intermediate, and in a second step, the phosphoramidate alkylator is added to the intermediate obtained from the first step to yield the product. Such a Mitsunobu type reaction is particularly suitable for synthesis of novel or known phosphoramidate alkylator prodrugs or derivatives, Alk-Trigger, wherein Trigger is L-$Z_3$, wherein $Z_3$ is:

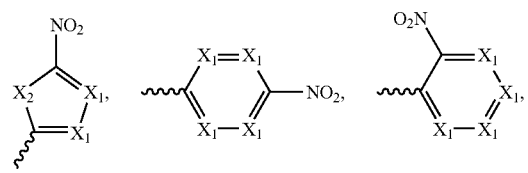

-continued

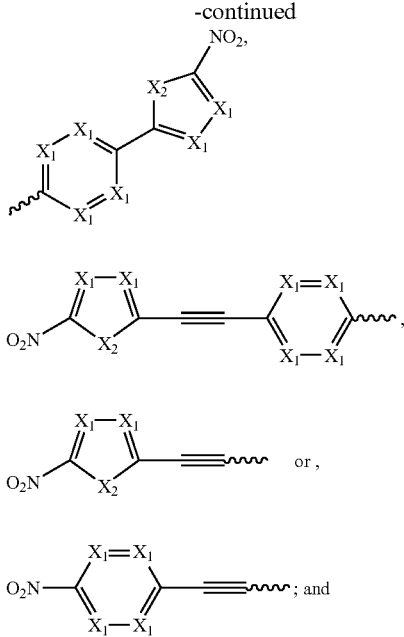

Alk is

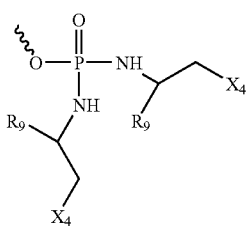

wherein $R_9$ is as defined above.

In one embodiment, the present invention provides a method of synthesizing a phosphoramidate alkylator prodrug comprising reacting each of novel or known phosphoramidate alkylators:

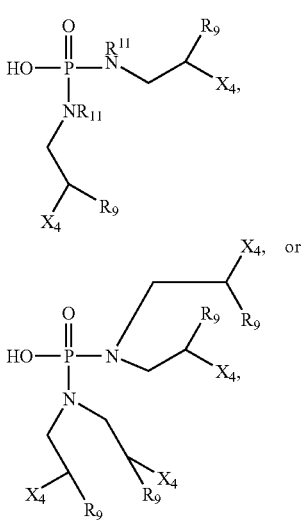

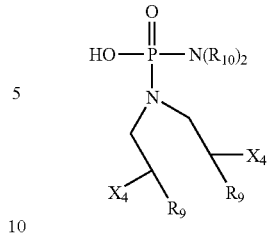

with a Trigger-OH, a trisubstituted phosphine, and a dialkyl azodicarboxylate to yield respectively,

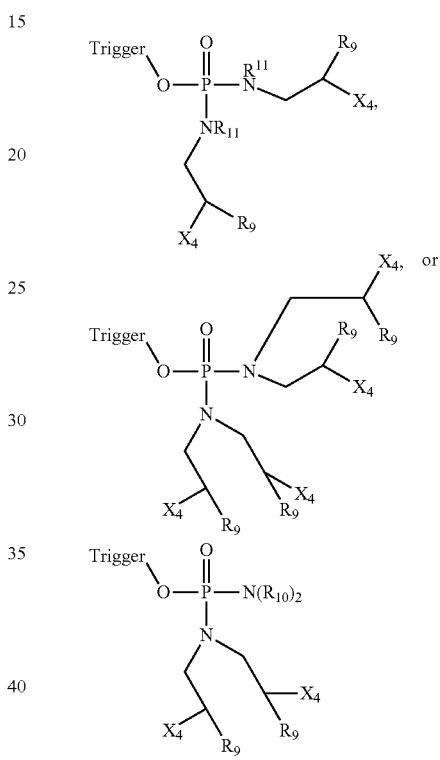

wherein $X_4$, $R_5$, $R_7$, and $R_8$ are as defined as in formula (I) and $R_9$, $R_{10}$ and $R_{11}$ are as defined above.

In one embodiment, the present invention provides a method to synthesize a compound of formula:

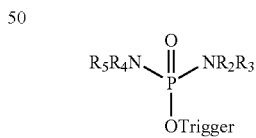

comprising reacting (a) a novel or known phosphoramidate alkylator of formula:

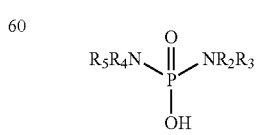

wherein $R_2$-$R_5$ are defined as in formula (I) with the proviso that (i) at least two of $R_1$-$R_5$ are selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl;

(ii) at least one of $R_1$-$R_5$ is selected from the group consisting of 2-haloalkyl, 2-$C_1$-$C_6$ alkylsulfonyloxyalkyl, 2-heteroalkylsulfonyloxyalkyl, 2-arylsulfonyloxyalkyl, and 2-heteroalkylsulfonyloxyalkyl; and at least one of $NR_2R_3$ and $NR_4R_5$ is

or (iii) $NR_2R_3$ and $NR_4R_5$ both together are

(b) a Trigger-OH wherein Trigger is defined as in Formula (I), a trisubstituted phosphine, and (c) a dialkyl azodicarboxylate to yield the compound of formula:

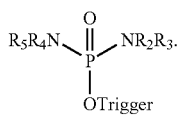

In one embodiment, the compound of formula:

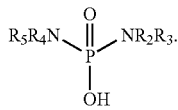

is selected from the group consisting of:

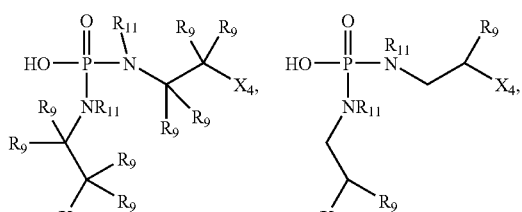
, and
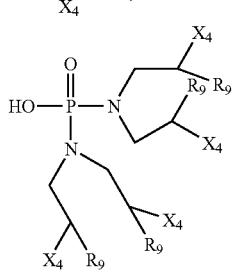
.

In another embodiment, the group of formula:

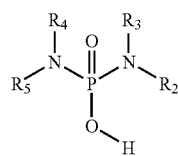

is selected from the group consisting of:

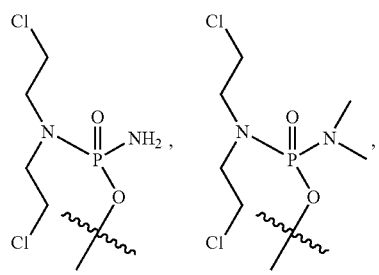

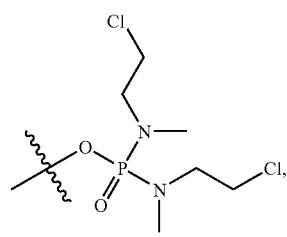

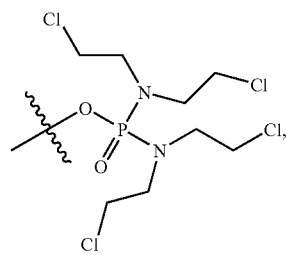

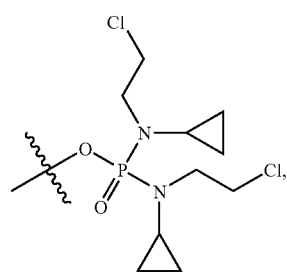

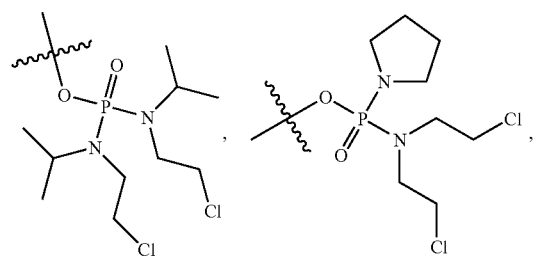

-continued

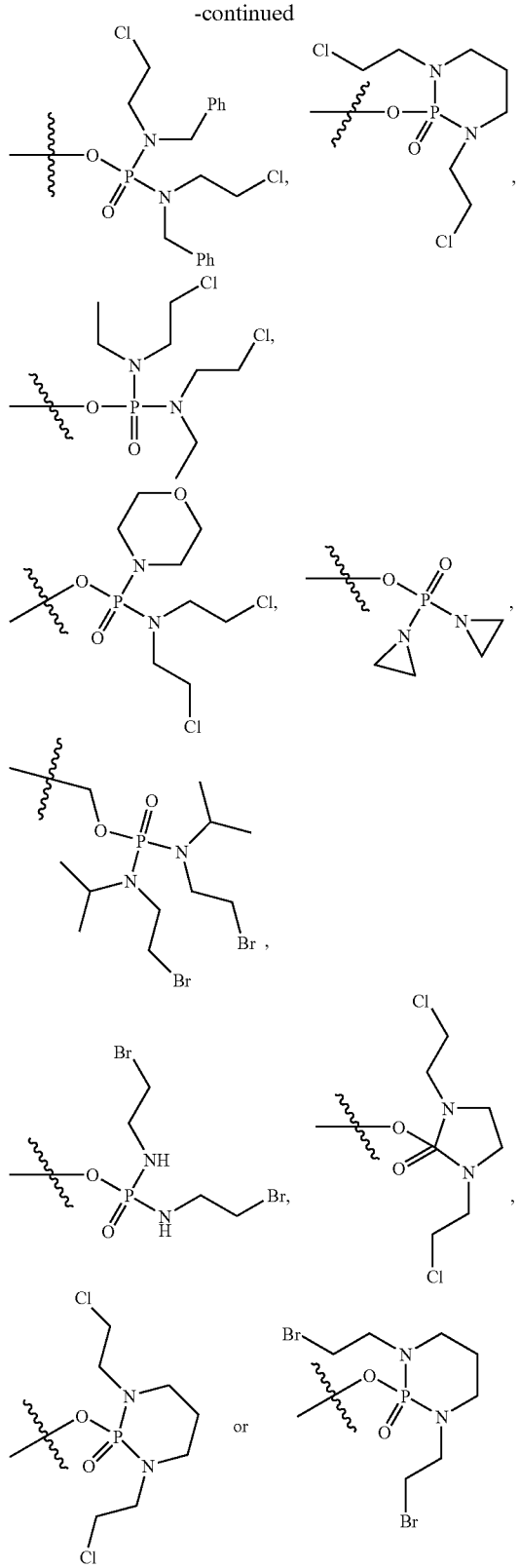

In another embodiment, the reaction includes a solvent such as THF, dioxane, a $C_1$-$C_6$ alkyl acetate, chloroform, dichloromethane, acetonitrile and the like. In another embodiment, each substituent in the trisubstituted phosphine is independently selected from a $C_1$-$C_6$ alkyl, $C_1$-$C_6$ heteroalkyl, $C_3$-$C_8$ cycloalkyl, heterocyclyl, aryl, heteroaryl, and $C_1$-$C_6$ alkoxy substituent. In another embodiment, Trigger, T, is

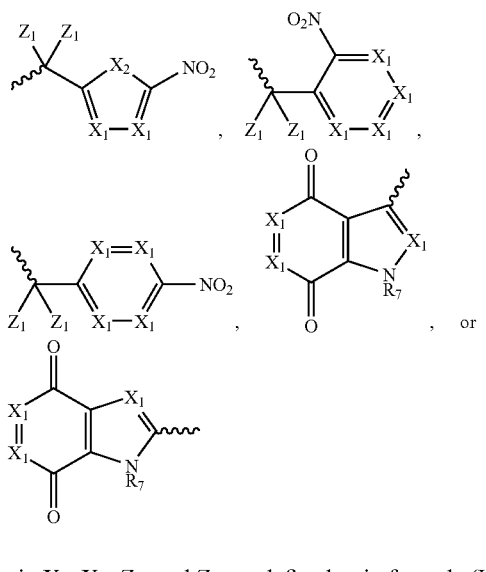

wherein $X_1$, $X_2$, $Z_1$, and $Z_2$ are defined as in formula (I).

In another embodiment, the present invention provides a method to synthesize a phosphoramidate alkylator prodrug comprising (i) reacting in a solvent selected from THF, dioxane, dichloromethane, chloroform, ethyl acetate, propyl acetate, butyl acetate, or acetonitrile a compoumd of formula:

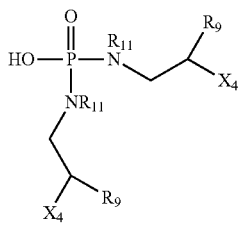

wherein each $R_{11}$ is independently hydrogen, cyclopropyl, methyl, ethyl, benzyl, or methoxy; each $R_9$ is independently hydrogen, methyl, ethyl, propyl, or cyclopropyl; and $X_4$ is halo, methylsulfonyloxy, phenylsulfonyloxy, 4-methylphenylsulfonyloxy, and 4-halophenylsulfonyloxy;

(ii) a trisubstituted phosphine selected from triphenylphosphine, tributylphosphine, tributylphosphite; and (iii) diethyl or diisopropyl azodicarboxylate;

to yield a product of formula:

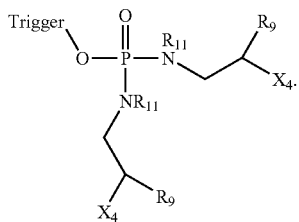

In another embodiment, the present invention provides a method of synthesizing a compound of formula:

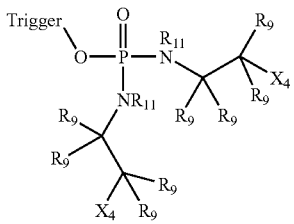

comprising the steps of:
(i) reacting in an aprotic solvent, a Trigger-OH, wherein Trigger is defined as in Formula (I); a trisubstituted phosphine; and a dialkyl azodicarboxylate to yield an Intermediate (i);
(ii) reacting the Intermediate (i) obtained from step (i) with a compound of formula

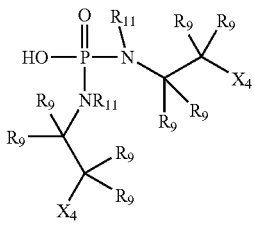

wherein each $R_9$, $R_{11}$, and $X_4$ is defined as in Formula (I), to yield the compound of formula:

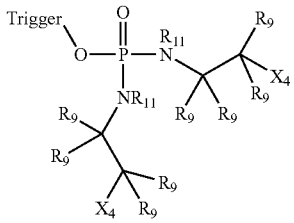

In another embodiment, the trisubstituted phosphine is $P(R_{12})_3$ wherein each $R_{12}$ is H, $C_1$-$C_6$ alkyl, $C_1$-$C_6$ heteroalkyl, $C_3$-$C_8$ cycloalkyl, heterocyclyl, aryl, or heteroaryl. In another embodiment, the trisubstituted phosphine is a polymer supported trisubstituted phosphine. In another embodiment, the trisubstituted phosphine is triphenylphosphine, tributylphosphine, tripropylphosphine, triethylphosphine, or trimethylphosphine. In another embodiment, the trisubstituted phosphine is a polymer supported triphenyl phosphine. Polymer supported trisubstituted phosphines are commercially available, for example, from Varian Inc. of Palo Alto, Calif. In another embodiment, the present invention provides a method of synthesizing the compounds wherein each $R_{11}$ is hydrogen. In another embodiment, the present invention provides a method of synthesizing the compounds

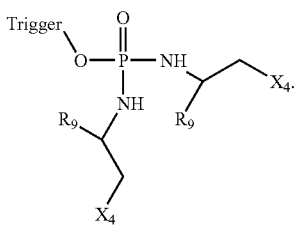

In another embodiment, the present invention provides the method of making a compound wherein the Trigger selected from the group consisting of:

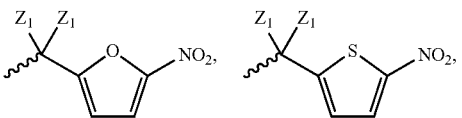

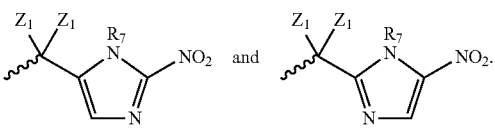

In another embodiment, the present invention provides the method of making a compound wherein $Z_3$ is:

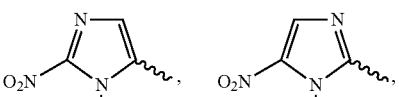

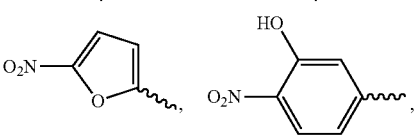

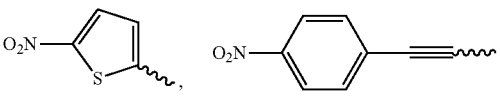

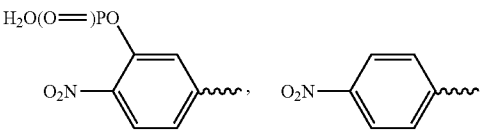

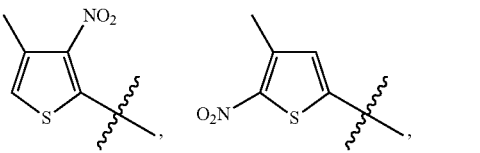

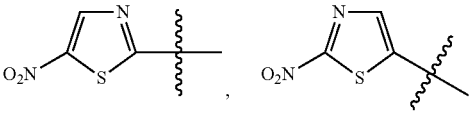

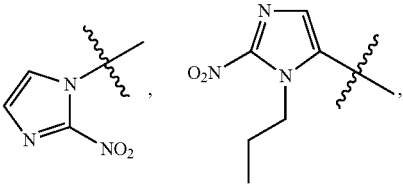

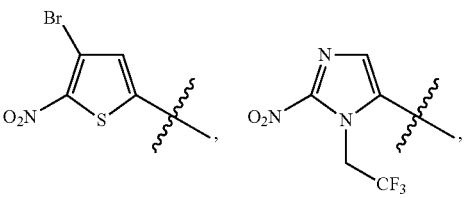

-continued

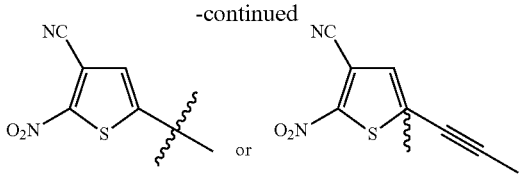
or

In one embodiment, the present invention provides a method to synthesize a phosphoramidate alkylator prodrug comprising the steps of:

(a) refluxing $POCl_3$ with an N-2-haloethyl-N—($R_{13}$)ammonium salt, wherein $R_{13}$ is hydrogen, $C_1$-$C_6$ alkyl, $C_1$-$C_6$ heteroalkyl, $C_3$-$C_8$ cycloalkyl, heterocyclyl, aryl, or heteroaryl, to yield a dichlorophosphoramidate intermediate;

(b) reacting the dichlorophosphoramidate intermediate in step (a) with an N-2-haloethyl-N—($R_{13}$)ammonium salt, wherein $R_{13}$ is hydrogen, $C_1$-$C_6$ alkyl, $C_1$-$C_6$ heteroalkyl, $C_3$-$C_8$ cycloalkyl, heterocyclyl, aryl, or heteroaryl, and a base in a solvent to yield a monochlorophosphoramidate intermediate; and (c) reacting the monochlorophosphoramidate intermediate obtained in step (b) with Trigger-OH and a base in a solvent to yield the phosphoramidate alkylator prodrug.

In one embodiment, the dichlorophosphoramidate intermediate of step (a) is separated from the rest of the reaction mixture before subjecting it to the reaction in step (b).

In another embodiment, the separation is performed by first removing excess $POCl_3$ in vacuo and then distilling the dichlorophosphoramidate under reduced pressure.

In one embodiment, the phosphoramidate alkylator prodrug of step (c) is separated from the rest of the reaction mixture by flash column chromatography on silica gel. In one embodiment, the base employed in step (b) is a tertiary amine. Suitable tertiary amines employed in step (b) include trialkyl amines, such as, triethyl amine or diisopropylethylamine. In one embodiment, the solvent employed in step (b) is tetrahydrofuran (THF) or dioxane.

In one embodiment, the monochlorophosphoramidate intermediate of step (b) is separated from the rest of the reaction mixture by flash column chromatography on silica gel before subjecting it to the reaction in step (c). In one embodiment, the base useful in step (c) is lithium, sodium, or potassium hexaalkyldisilazide; sodium or potassium hydride; or lithium diisopropylamide. In one embodiment, the solvent employed in step (c) is dimethoxyethane, diglyme, diethylether, or THF.

In one embodiment, the present invention provides a method to synthesize a phosphoramidate alkylator prodrug comprising the steps of:

(a) reacting in a solvent about 1 equivalent each of $POCl_3$, a Trigger-OH, and a base to yield a dichlorophosphate intermediate; and (b) reacting the dichlorophosphate intermediate in step (a) with a N-2-haloethyl-N—($R_{13}$)ammonium salt, wherein $R_{13}$ is hydrogen, $C_1$-$C_6$ alkyl, $C_1$-$C_6$ heteroalkyl, $C_3$-$C_8$ cycloalkyl, heterocyclyl, aryl, heteroaryl, and a base in a solvent to yield the phosphoramidate alkylator prodrug.

In one embodiment, steps (a) and (b) are performed at temperatures below 0° C. In another embodiment, step (b) is performed at a temperature between 20-100° C. higher than the temperature of step (a).

In another embodiment, the present invention provides a method for synthesizing heterocyclic phopspphoramidate alkylator prodrugs of the present invention as shown below:

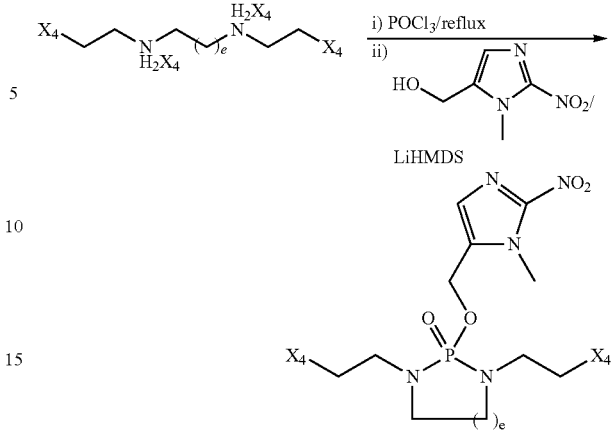

wherein $X_4$=Br or Cl; e=1-3

In one embodiment, the present invention provides a method to synthesize a phosphoramidate alkylator prodrug comprising the steps of:

(a) reacting $PCl_3$ with a N,N-di(2-haloethyl)ammonium salt and a base in a solvent to yield a monochlorophosphamide derivative;

(b) reacting the monochlorophosphamide derivative with Trigger-OH to yield an intermediate; and (c) oxidizing the intermediate in step (b) to yield the phosphoramidate alkylator prodrug.

In one embodiment, the base used in step (b) is triethylamine. In another embodiment, the solvent used in step (c) is dimethoxyethane, diglyme, or a $C_1$-$C_6$ alkyl acetate. In another embodiment, Trigger-OH is step (c) is

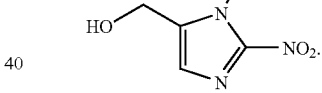

Various 1-N-alkyl-2-aminoimidazole-5-carboxylate can be synthesized as described schematically below:

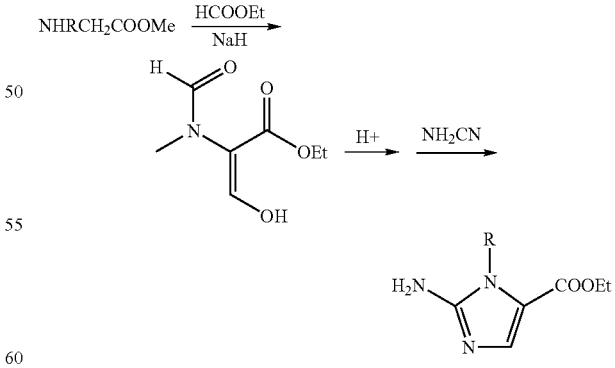

The 1-N-alkyl-2-aminoimidazole-5-carboxylates can be reduced to yield various 1-N-alkyl-2-amino-5-hydroxymethylimidazole derivatives employed in the present invention as bioreductive group $Z_3$.

The synthetic methods are provided in further detail in the EXAMPLES section below.

Synthesis of bioreductive groups and phosphoramidate alkylator prodrugs, and methods of the present invention can be adapted from the references Matteucci et al., PCT Appl. Pub. No. WO 04/009667, and Hypoxia activated prodrugs US Pat. Appl. entitled. "Hypoxia Activated anti-Cancer Agents"; deGroot et al., 2001, *Current Med. Chem.* 8:1093-1122; Denny et al., U.S. Pat. Nos. 5,750,782; 5,780,585; 5,872,129; and 6,251,933; Davis et al., PCT Appl. Pub. Nos. WO 04/85421 and WO 04/85361; and Lin et al., US Pat. Appl. Pub. Nos. 2004/0254103 and 2005/0043244, and Borch et al. (supra).

Examples of methods to synthesize phosphoramidate alkylator prodrugs of the present invention are provided in further detail in the "EXAMPLES" section below.

IIIa. Methods of Treatment

In one embodiment, the present invention provides a method of treating cancer in a patient in need of therapy thereof by administering to the patient a phosphoramidate alkylator prodrug of the present invention or one that is known. Known phosphoramidate alkylators are provided by the references Borch et al., supra. In one embodiment, the phosphoramidate alkylator prodrug employed in treating cancer according to the methods provided by the present invention has the formula selected from (I)-(XXVII). In one embodiment, the phosphoramidate alkylator prodrug employed in treating cancer according to the methods provided by the present invention is selected from the compounds exemplified in the EXAMPLE section.

Cancer therapy with alkylating agents can lead to development of cancers that are resistant to these alkylating agents. Alkylating agents can kill cancer cells in the more rapidly dividing or higher oxygen containing cancer region as compared to the cancer cells in the slower growing hypoxic cancer region. The latter cells survive the treatment by alkylators and can produce cells resistant to such alkylators. Increased activity of guanine-$O^6$-Alkyltransferase, glutathione, glutathione transferases, the nucleotide excision repair pathway, and/or the mismatch repair proteins, and decreased permeation of actively transported drugs such as mechlorethamine and melphalan, are postulated to be responsible for cancer resistance to alkylators (for example, see, Hardman et al., pages 1393 and 1433, supra).

The prodrugs of the present invention are effective in treating cancers resistant to other therapies. Slowly dividing cancer cells in the hypoxic cancer zone act as a source of resistant cancer cells and strains and are killed by the prodrugs of the present invention. In one embodiment, the present invention provides a method of treating a cancer resistant to treatment by one or more alkylators by administering the compounds of the present invention alone or in combination with another anticancer agent. In one embodiment, a phosphoramidate alkylator prodrug of the invention is administered in combination with a drug having substantially no nephrotoxicity. In one embodiment the phosphoramidate alkylators prodrug is administered with carboplatin.

In one embodiment, the present invention provides phosphoramidate alkylators prodrugs which are not cross-resistant with known alkylators. In another embodiment, present invention provides phosphoramidate alkylators prodrugs which are not cross-resistant with the alkylators cyclophosphamide, ifosfamide, glufosfamide, mechlorethamine, melphalan, chlorambucil, dacarbazine, temozolomide, carmustine, streptozocin, bendamustin, busulfan, thiotepa, cisplatin, carboplatin, and oxaliplatin.

In one embodiment, the present invention provides a method of treating cancer by administering as a first line therapy the compounds of the present invention alone or in combination with other anti-cancer agents. In another embodiment, the present invention provides a method of treating a metastatic cancer by administering as a first line therapy the compounds of the present invention alone or in combination with other anti-cancer agents. In one embodiment, the present invention provides a method of treating cancer by administering as a second line therapy the compounds of the present invention alone or in combination with other anti-cancer agents. In one embodiment, the present invention provides a method of treating cancer by administering as a third line therapy the compounds of the present invention alone or in combination with other anti-cancer agents. In one embodiment, the present invention provides a method of treating cancer by administering after a prior treatment with surgery and/or radiation therapy the compounds of the present invention alone or in combination with other anti-cancer agents. In one embodiment, the present invention provides a method of treating cancer, the cancer having relapsed after prior chemotherapy, surgery, radiation or any combination of them, by administering the compounds of the present invention alone or in combination with other anti-cancer agents.

In methods for treating cancer provided by the present invention, an effective amount of phosphoramidate alkylator prodrug is administered to the subject. Generally, the subject can be any human or non-human mammal. The preferred subject is a human subject. Other particular subjects include but are not limited to non-human primates, dogs, cats, farm animals and horses. In one version, the phosphoramidate alkylator prodrug is administered alone. In one version, the phosphoramidate alkylator prodrug is administered in combination with one or more additional anti-cancer agents. In one version, the phosphoramidate alkylator prodrug is administered in conjunction with a therapeutic cancer treatment, including but not limited to surgery and radiation. The phosphoramidate alkylator prodrug will typically be administered in a pharmaceutical composition. Various pharmaceutical compositions that can be used are described in the Formulations section infra.

The phosphoramidate alkylator prodrugs and their pharmaceutical compositions can be used to treat any type of cancer in a subject, particularly in a human subject. Cancers that can be treated include but are not limited to leukemia, breast cancer, skin cancer, bone cancer, liver cancer, brain cancer; cancer of the larynx, gallbladder, pancreas, rectum, parathyroid, thyroid, adrenal, neural tissue, head and neck, stomach, bronchi, and kidneys; basal cell carcinoma, squamous cell carcinoma of both ulcerating and papillary type, metastatic skin carcinoma, osteosarcoma, Ewing's sarcoma, veticulum cell sarcoma, myeloma, giant cell tumor, small-cell lung tumor, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, and epidermoid carcinomas.

The phosphoramidate alkylator prodrug can particularly be used in the treatment of cancers containing significant areas of hypoxic tissue. Such cancers include but are not limited to lung cancer, especially non-small cell lung cancer, breast cancer, colon cancer, head and neck cancer, ovarian cancer, pancreatic cancer, and prostate cancer. Examples of types of cancers that can be treated with the phosphoramidate alkylator prodrugs of the invention are provided in the following references, each of which is incorporated in its entirety herein by reference Tidmarsh et al., PCT Pat. Appl. No. PCT/US2005/047314 filed on 22 Dec. 2005, and PCT Pat. Appl. entitled "Glufosfamide combination therapy", PCT Pat. Appln No. PCT/US06/18191; and U.S. Pat. App. No. 60/760,599 and 60/719,787 and PCT Pat. Pub. No. WO 2005/076888. Several of these cancers are discussed for illustrative purposes below. Those of skill in the art will appreciate that cancer chemotherapy often involves the simultaneous or successive administration of a variety of anti-cancer agents, and as discussed further below, a phosphoramidate alkylator prodrug can be used in combination therapies as provided by the methods described herein. Thus, in the description of illustrative cancers containing hypoxic regions amenable to treatment with a phosphoramidate alkylator prodrug, examples of combination therapies are also described.

Lung cancer affects more than 100,000 males and 50,000 females in the United States, most of whom die within 1 year of diagnosis, making it the leading cause of cancer death. Current protocols for the treatment of lung cancer involve the integration of chemotherapy with or without radiotherapy or surgery. A phosphoramidate alkylator prodrug can be used as a single agent or in combination with existing combination therapies. A variety of combination chemotherapy regimens have been reported for small cell lung cancer, including the combinations consisting of cyclophosphamide, doxorubicin and vincristine (CAV); etoposide and cisplatin (VP-16); and cyclophosphamide, doxorubicin and VP-16 (CAVP-16). Modest survival benefits from combination chemotherapy (etoposide plus cisplatin) treatment have been reported for non-small cell lung cancer.

Likewise, several different cytotoxic drugs have produced at least temporary regression of ovarian cancer. The most active drugs in the treatment of ovarian cancer have been alkylating agents, including cyclophosphamide, ifosfamide, melphalan, chlorambucil, thiotepa, cisplatin, and carboplatin. Current combination therapies for ovarian cancer include cisplatin or carboplatin in combination with cyclophosphamide at 3- to 4-week intervals for six to eight cycles. The compounds and methods described herein provide prodrug forms and methods for treating ovarian cancer in which a phosphoramidate alkylator prodrug as described herein is used as a single agent or in existing such combination therapy, either to replace an agent or in addition to the agent(s) currently used.

Cancer of the prostate is the most common malignancy in men in the United States and is the second most common cause of cancer death in men above age 55, and this cancer has been reported to consist primarily of hypoxic tissue. Several chemotherapy protocols have been reported for use in late stage disease following relapse after hormonal treatment. Agents for the treatment of prostate cancer include the alkylators estramustine phosphate, prednimustine, and cisplatin. Combination chemotherapy is also used to treat prostate cancer, including treatment with estramustine phosphate plus prednimustine and cisplatin, and 5-fluorouracil, melphalan, and hydroxyurea. The present invention provides methods for treating prostate cancer in which a phosphoramidate alkylator prodrug of the present invention is used in such combinations, either to replace an agent or in addition to the agent(s) currently used.

Cancer of the large bowel is the second most common cause of cancer death in the United States and is likewise a cancer characterized by hypoxic regions. While chemotherapy in patients with advanced colorectal cancer has proven to be of only marginal benefit, 5-fluorouracil is the most effective treatment for this disease. 5-Fluorouracil is useful alone or in combination with other drugs, but is associated with only a 15 to 20 percent likelihood of reducing measurable tumor masses by 50 percent or more. Using 5-FU in combination with the compounds and methods described herein, and the methods for treating colon cancer using a prodrug, can offer significant therapeutic benefit and potential for meeting the unmet need for better treatment methods for this disease.

In one version of the treatment methods, a phosphoramidate alkylator prodrug can be used in various known approaches to cancer therapy including but not limited to "anti-body-directed enzyme prodrug therapy" (ADEPT), "virus-directed enzyme prodrug therapy (VDEPT), "gene-directed enzyme prodrug therapy" (GDEPT), and "bacteria-directed enzyme prodrug therapy" (BDEPT). The general uses of a phosphoramidate alkylator prodrug are not limited to the foregoing treatment methods.

In another aspect, the present invention provides a method of treatment of non-cancer hyperproliferative diseases characterized by cellular hyperproliferation (e.g., an abnormally increased rate or amount of cellular proliferation). In one embodiment, the hyperproliferative disease treated according to the present method is selected from the group consisting of allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

In some embodiments of the invention, a compound of the present invention is administered to treat a hyperproliferative disease selected from the group consisting of psoriasis, multiple sclerosis, rheumatoid arthritis, restenosis, and benign prostatic hyperplasia. In one embodiment, the hyperproliferative disease treated is psoriasis, a disease characterized by the cellular hyperproliferation of keratinocytes which builds up on the skin to form elevated, scaly lesions. In another embodiment, the hyperproliferative disease treated is multiple sclerosis, a disease characterized by progressive demyelination in the brain. In another embodiment, the hyperproliferative diseases treated is rheumatoid arthritis, a multisystem chronic, relapsing, inflammatory disease that can lead to destruction and ankylosis of joints affected. In another embodiment, the compounds of the present invention are administered to prevent a hyperproliferative disease resulting from cellular proliferation on a prosthesis implanted in a subject by coating the prosthesis with a composition containing a compound of the present invention. In another embodiment, the hyperproliferative disease treated is benign prostatic hyperplasia, a disease in which prostate epithelial cells grow abnormally and thereby block urine flow.

IIIb. Formulations, Modes of Administration, Dosages

A phosphoramidate alkylator prodrug will typically be formulated as pharmaceutical formulations for administration to a subject. Described in this section are modes of administration, formulations, and dosages that can be used when treating cancers using a phosphoramidate alkylator prodrug described herein.

Administration of a phosphoramidate alkylator prodrug for the treatment of cancer can be effected by any method that enables delivery of the prodrugs to the site of action, the hypoxic region of a tumor. Many cancer drugs are administered by intravenous injection, and a phosphoramidate alkylator prodrug can be formulated for such administration, including not only ready-for-injection formulations but also lyophilized or concentrated formulations that must be rehydrated or diluted, respectively, prior to injection. In addition to these formulations, a phosphoramidate alkylator prodrug can be formulated for administration by oral routes, intraduodenal routes, parenteral injection (including intravenous, subcutaneous, intramuscular, intravascular or infusion), topical, and rectal routes. Those of skill in the art will recognize that a phosphoramidate alkylator prodrug may be activated by bacteria in the gut. If such activation is not desired, then the practitioner can employ a route of administration or a formulation that results in absorption of a phosphoramidate alkylator prodrug prior to its entry into the large intestine or colon. The actual route of administration and corresponding formulation of the phosphoramidate alkylator prodrug will depend on the type of cancer being treated, the phosphoramidate alkylator prodrug selected for administration, the severity of the cancer, and the age, weight, and condition of the patient, among other factors.

The amount of a phosphoramidate alkylator prodrug administered, and thus the amount of the phosphoramidate alkylator prodrug contained in the dose administered and the product comprising that dose, will be dependent on the subject being treated, the severity of the cancer, localization of the cancer, the rate of administration, the disposition of the prodrug (e.g., molecular weight, solubility and hypoxic and normoxic cytotoxicity), the cytotoxic agent released by a phosphoramidate alkylator prodrug, and the discretion of the prescribing physician.

In one embodiment, the present invention provides a method of cancer treatment in a patient wherein an effective dosage is typically in the range of about 0.001 to about 0.1 g per kg body weight, or about 0.1 to about 35 mg/kg/day in single or divided doses. For a 70 kg human, this would amount to about 0.05 to about 7 g/day, for example, about 0.2 to about 2.5 g/day. In some instances, dosage levels below the lower limit of the aforesaid range can be more than adequate, while in other cases still larger doses can be employed without causing any harmful side effect; larger doses can also be divided into several small doses for administration throughout the day by infusion for an hour or continuously using a peripherally inserted central catheter (PICC line) and portable intravenous bag and pump.

In one embodiment, the effective dose of a compound of the present invention for treatment of cancer and other hyperproliferative diseases is in the range of about 0.1 to about 35 mg/kg/day; about 0.5 to about 20 mg/kg/day; about 0.5 to about 15 mg/kg/day; about 0.5 to about 10 mg/kg/day; about 0.5 to about 8 mg/kg/day; and about 1 to about 5 mg/kg/day in single or divided doses. In one embodiment, the effective dose of a compound of the present invention for treatment of cancer and other hyperproliferative diseases is in the range of about 2 to about 8 mg/kg/day; about 2 to about 4 mg/kg/day; and about 2 mg/kg/day in single or divided doses. In one embodiment, the effective dose of a compound of the present invention for treatment of cancer and other hyperproliferative diseases is in the range of about 0.25 to about 2.5 mg/kg/day; about 0.25 to about 1 mg/kg/day; and about 0.25 to about 0.5 mg/kg/day in single or divided doses. In one embodiment, the dose is administered i.v. daily, either as a monotherapy (compound of the present invention alone) or in conjunction (combination) with standard of care therapies. In one embodiment, the effective dose for treatment of cancer and other hyperproliferative diseases is in the range as described earlier administered once a week.

In one embodiment, a larger dose is administered intermittently (less frequently); a dose in the range of about 3 to about 20 mg/kg; about 6 to about 10 mg/kg; or 8 mg/kg is administered once every three days for two weeks. In another embodiment, a dose in the range of about 5 to about 30 mg/kg; about 10 to about 15 mg/kg; or 12.5 mg/kg of the phosphoramidate alkylator prodrug is administered once a week for four weeks. In one embodiment, a dose in the range of about 0.5 to about 8 mg/kg/day is administered for 5 days over two weekly cycles.

In another embodiment, for treatment of human patients, the maximum daily dose of a phosphoramidate alkylator prodrug is not greater than 500 mg/kg patient weight and, accordingly, a phosphoramidate alkylator prodrug is administered in a daily dose in the range of about 1 mg of a phosphoramidate alkylator prodrug/kg of patient weight to about 500 mg of a phosphoramidate alkylator prodrug/kg of patient weight. In one embodiment, a phosphoramidate alkylator prodrug is administered in a daily dose in the range of about 5 mg/kg to about 500 mg/kg of the body weight of the patient to be treated. In another embodiment, the therapeutically effective dose is a daily dose of a phosphoramidate alkylator prodrug is about 10 mg/kg to about 250 mg/kg of the body weight of the patient to be treated. In another embodiment, the therapeutically effective dose of a phosphoramidate alkylator prodrug is about 25 mg/kg to about 150 mg/kg of the body weight of the patient to be treated. In another embodiment, the therapeutically effective dose of a phosphoramidate alkylator prodrug is about 25 mg/kg to about 50 mg/kg of body weight of the patient to be treated. In another embodiment, the therapeutically effective dose of a phosphoramidate alkylator prodrug is about 1.25 mg/kg to about 12.5 mg/kg of body weight of the patient to be treated.

Guidance concerning administration can also be provided by and from studies in humans and other mammalian animals. A therapeutically effective dose determined for an animal can be converted to the corresponding human equivalent dose (HED) as described in the table below:

| Animal | Human Equivalent Dose (HED) conversion factor[a] |
|---|---|
| Mouse | 12.3 |
| Hamster | 7.4 |
| Rat | 6.2 |
| Ferret | 5.3 |
| Guinea pig | 4.6 |
| Micro-pig | 1.4 |

-continued

| Animal | Human Equivalent Dose (HED) conversion factor[a] |
|---|---|
| Mini-pig | 1.1 |
| Rabbit | 3.1 |
| Dog | 1.8 |
| Monkeys[b] | 3.1 |
| Marmoset | 6.2 |
| Squirrel monkey | 5.3 |
| Baboon | 1.8 |

[a]To convert animal dose in mg/kg to HED (assumes a 60 kg human) in mg/kg, divide animal dose by HED convertion factor. For species not listed or for weights outside the standard ranges, human equivalent dose (HED) can be calculated from the formula: HED = animal dose in mg/kg × (animal weight in kg/human weight in kg)$^{0.33}$.
[b]For example, cynomolgus, rhesus, or stumptail.

To achieve therapeutic effectiveness, the therapeutically effective daily dose of a phosphoramidate alkylator prodrug is usually administered multiple times to the patient. In one embodiment, a phosphoramidate alkylator prodrug is administered daily for a period of time. Typically, daily administration for at least 3 consecutive days will be employed. In related embodiments, administration is for at least 5 consecutive days, at least 7 consecutive days, or at least 10 consecutive days. Depending on the dose, formulation, and route of administration selected by the practitioner and the convenience of the patient, the entire daily dose can be administered once daily, or the daily dose can be administered in multiple smaller doses through the course of a day (including by infusion with a pump or intravenous administration). For example, the dose can be divided into two smaller doses and administered twice daily, or divided into three smaller doses and administered thrice daily. It will be apparent to one of skill in the art of cancer treatment that, as used herein, "daily" administration is not limited to one administration per day but can include multiple administrations.

Administration schedules other than consecutive daily administration can also be used. Administration once every other day (qod) is particularly convenient, and administration once every third day, or once a week can be appropriate in some instances, but in any event, a phosphoramidate alkylator prodrug is repeatedly administered over a period of time. For example, whether administration is daily (including, as noted, a divided daily dose), every other day, or less frequently, in one embodiment a phosphoramidate alkylator prodrug is administered at least 2 days per week for at least two, three, four, five or at least six consecutive weeks, or, alternatively, for at least two, three, four, five or at least six weeks within a six-month period, or, alternatively, for at least two, three, four, five or at least six weeks within a twelve-month period. In one embodiment, a phosphoramidate alkylator prodrug is administered at least 3 days per week for at least two, three, four, five or at least six consecutive weeks, or, alternatively, for at least two, three, four, five or at least six weeks within a six-month period, or, alternatively, for at least two, three, four, five or at least six weeks within a twelve-month period. In one embodiment a phosphoramidate alkylator prodrug is administered at least 10 days per month, optionally at least 20 days per month, for at least one month or at least two, three, four, five or at least six consecutive months, or, alternatively, at least one, two, three, four, five or at least six months in a 6-month period.

In one embodiment, the administration of the therapeutically effective dose is continued for multiple days, typically for at least three consecutive days, and often for at least five to ten consecutive days, or for a week, or for several weeks or more. Thus, a patient can be administered a phosphoramidate alkylator prodrug in accordance with the present methods for several days, a week, a month, two months, three months, six months, or a year or longer.

Consistent with administration regimens of other anticancer agents, a phosphoramidate alkylator prodrug can be administered in multiple "rounds" of administration. For example, in some embodiments, a phosphoramidate alkylator prodrug can be administered once daily for at least three to ten, or at least five to ten consecutive days, and such three to ten or five to ten day treatments can be repeated once, twice, or three or more times, sometimes with a no-treatment (with a phosphoramidate alkylator prodrug) period ranging from one to several weeks between each multiple-day treatment. Similarly, in some embodiments, a phosphoramidate alkylator prodrug is administered every other day for two to ten administrations, more often three to ten administrations, or five to ten administrations, and such two, three or five to ten administrations qod can be repeated once, twice, or three or more times with a no-treatment (with a phosphoramidate alkylator prodrug) period ranging from one to several weeks between each multiple-day treatment. Other multiple-round schedules for administration will be apparent to the skilled practitioner guided by this disclosure.

In one aspect, "administering a therapeutically effective dose or regimen of a phosphoramidate alkylator prodrug" refers to (i) administering a phosphoramidate alkylator prodrug in the ranges stated (e.g., 1 mg to 1 g of a phosphoramidate alkylator prodrug per kg of patient weight, typically 25 to 150 mg of a phosphoramidate alkylator prodrug per kg of patient weight) for a specified minimum number of days within a specified time period, wherein the administration of a phosphoramidate alkylator prodrug has a therapeutic effect on the cancer in the patient. Illustrative therapeutically effective dose regimens for a phosphoramidate alkylator prodrug include those described herein, such as administration of a phosphoramidate alkylator prodrug for 3 consecutive days, 5 consecutive days, 7 consecutive days, 10 consecutive days, at least 3 days per week, at least 3 days per week for one month, at least 10 days per month, and at least 20 days per month.

In optimizing a phosphoramidate alkylator prodrug treatment regimen according to the present invention, the dose and frequency of a phosphoramidate alkylator prodrug administration can be selected to achieve a maximal sustained area under the plasma concentration curve (AUC) over the course of treatment. The theoretically optimal dosing regimen will result in a maximal exposure of the tumor cells to a phosphoramidate alkylator prodrug, as measured by AUC, while minimizing the maximal plasma concentration ($C_{max}$) for any single administration. A higher $C_{max}$ will contribute to toxicity while the AUC will determine efficacy. As is understood in the art for other cancer therapeutic drugs, treatment with a phosphoramidate alkylator prodrug can be suspended temporarily if toxicity is observed, or for the convenience of the patient, without departing from the scope of the invention, and then resumed.

In one embodiment, the pharmacokinetics of the phosphoramidate alkylator prodrug of the present invention employed for the treatment of cancer can determine the dose, the method of administration, and the kind of cancer that is treated with the phosphoramidate alkylator prodrug. In one embodiment, the phosphoramidate alkylator prodrug of the present invention can have an in vivo half life of between 1 to 300 minutes. In one embodiment, the compounds of the present invention can have an in vivo half life of between 3 to 10 minutes. In one embodiment, the compounds of the present invention can have an in vivo half life of between 10 to 30 minutes. A short half life of the phosphoramidate alkylator prodrug can require an infusion time in treatment that is longer than that required for a phosphoramidate alkylator prodrug having a longer half life. A short half life of the phosphoramidate alkylator prodrug can increase the maximum tolerated dose (MTD) for that prodrug.

In another embodiment, the present invention provides phosphoramidate alkylator prodrugs that remain up to 20% unchanged when incubated with mouse liver microsomal protein for 30 minutes. In another embodiment, the present invention provides phosphoramidate alkylator prodrugs that remain 20-80% unchanged when incubated with mouse liver microsomal protein for 30 minutes. In another embodiment, the present invention provides phosphoramidate alkylator prodrugs that remain greater than 80% unchanged when incubated with mouse liver microsomal protein for 30 minutes. In another embodiment, examples of phosphoramidate alkylator prodrugs of the present invention which when incubated with mouse liver microsomal protein for 30 minutes remain greater than 80% unchanged include 1, 25, and 36. The higher the MLM stability of a prodrug of the invention, the lower the therapeutically effective dose and undesirable patient side effects of that prodrug.

In a related embodiment, the bioreductive group of the phosphoramidate alkylator prodrugs of the present invention upon reduction/activation in a hypoxic tumor zone form a phosphoramidate alkylator-$T_M$ conjugate. The phosphoramidate alkylator-$T_M$ conjugate can diffuse and reach other parts of the tumor or other tumors in the case of a metastatic disease. Various pharmacokinetic parameters such as volume of distribution under steady state (Vss), clearance (CL), area under curve (AUC), mouse liver microsomal stability (MLM stability), plasma stability, and $C_{max}$ of phosphoramidate alkylator prodrugs of the present invention were measured and listed in the EXAMPLES section (see also Hardman et al., supra).

In re-treatment regimens, the dose can be adjusted to reflect patient tolerance of the prior treatment. In any event, as toxicity is observed during repeat administration, dosing can be temporarily stopped as severe symptoms are observed. The period of temporary halting of administration (drug holiday) can be ended at the time when the first organ of toxicity no longer contains significant concentrations of a phosphoramidate alkylator prodrug or a phosphoramidate alkylator released therefrom (which can be measured or determined indirectly by cessation of symptoms). Therefore, an intermittent dosing period can be defined not only by specific days but individualized by drug holidays that are based on symptoms and normal organ clearance of a phosphoramidate alkylator prodrug or a phosphoramidate alkylator released therefrom.

A formulation of a phosphoramidate alkylator prodrug can, for example, be in a form suitable for oral administration as a tablet, capsule, pill powder, sustained release formulation, solution, and suspension; for parenteral injection as a sterile solution, suspension or emulsion; for topical administration as an ointment or cream; and for rectal administration as a suppository. A formulation of a phosphoramidate alkylator prodrug can be in unit dosage forms suitable for single administration of precise dosages and will typically include a conventional pharmaceutical carrier or excipient.

Suitable pharmaceutical carriers include inert diluents or fillers, water and various organic solvents. The pharmaceutical compositions can, if desired, contain additional ingredients such as flavorings, binders, excipients, and the like. Thus for oral administration, tablets containing various excipients, such as citric acid, can be employed together with various disintegrants, such as starch, alginic acid, and certain complex silicates, and with binding agents such as sucrose, gelatin and acacia. Additionally, lubricating agents such as magnesium stearate, sodium lauryl sulfate, and talc can be used to prepare the tablet forms of formulations of a phosphoramidate alkylator prodrug described herein. Solid compositions of a similar type can be employed in soft and hard filled gelatin capsules. Preferred materials, therefore, include lactose or milk sugar and high molecular weight polyethylene glycols. When aqueous suspensions or elixirs are desired for oral administration, the prodrug therein can be combined with various sweetening or flavoring agents, coloring matters or dyes and, if desired, emulsifying agents or suspending agents, together with diluents such as water, ethanol, propylene glycol, glycerin, or combinations thereof.

Exemplary parenteral administration forms include solutions or suspensions of a phosphoramidate alkylator prodrug in sterile aqueous solutions, for example, aqueous polyethylene glycols, propylene glycol or dextrose solutions. Such dosage forms can be suitably buffered, if desired.

Methods of preparing various pharmaceutical compositions with a specific amount of active drug are known, or will be apparent, to those skilled in this art in view of this disclosure. For examples, see Remington's Pharmaceutical Sciences, Mack Publishing Company, Philadelphia, Pa., 17$^{th}$ Edition (1984).

The methods of cancer treatment employing a phosphoramidate alkylator prodrug of the present invention are effective in killing the most difficult to kill cancer cells growing in the hypoxic region of a tumor. Once released in the hypoxic region a phosphoramidate prodrug can diffuse from the hypoxic cells and kill the cancer cells in adjacent regions containing increasing populations of rapidly dividing cells. The hypoxic region acts as a drug-factory to produce within a tumor an alkylator for killing adjacent normoxic cancer cells leading to a higher concentration of the phosphoramidate alkylator within the tumor, relative to normal tissues. The use of the prodrug to generate the phosphoramidate alkylator within the tumor can reduce toxic side-effects arising due to normal cell toxicity. After cancer cells in the normoxic region of the tumor are destroyed, a hypoxic region can become normoxic and start to divide. At this point, such cells can be killed by the phosphoramidate alkylators generated from a phosphoramidate alkylator prodrug of this invention or those known, or by other anticancer agents or cytoxins administered in combination with the phosphoramidate alkylator prodrug, as described in the following section.

IIIc. Combination Therapies

In accordance with the methods of the invention, a phosphoramidate alkylator prodrug can be co-administered in combination with other anti-cancer agents ("anticancer agent"). Without intending to be bound by any particular mechanism or effect, such co-administration can in some cases provide one or more of several advantages over known cancer therapies, such as, for example, co-administration of a phosphoramidate alkylator prodrug and the anticancer agent has a synergistic effect on induction of cancer cell death. Co-administration provides a better therapeutic result than administration of the anticancer agent alone, e.g., greater alleviation or amelioration of one or more symptoms of the cancer, diminishment of extent of disease, delay or slowing of disease progression, amelioration, palliation or stabilization of the disease state, partial or complete remission, prolonged survival or other beneficial therapeutic results.

The co-administration of a phosphoramidate alkylator prodrug increases the sensitivity of cancer cells to the anticancer agent, allowing lower doses of the anticancer agent to be administered to the patient or allowing an anticancer agent to be used for treatment of cells otherwise resistant to the anticancer agent or otherwise refractory to treatment. While the known anti-cancer agents in general target the rapidly dividing cells in the normoxic region, the phosphoramidate alkylator prodrugs of the invention target the hypoxic cells in the regions of tumors that are not efficiently killed by the anti-cancer agent alone.

As used herein, a phosphoramidate alkylator prodrug is "co-administered" with another anticancer agent (also referred to herein as "Agent") when a phosphoramidate alkylator prodrug and Agent are administered as part of the same course of therapy. In one embodiment, a phosphoramidate alkylator prodrug is first administered prior to administration of the Agent, (i.e., the initiation of the other cancer therapy), and treatment with a phosphoramidate alkylator prodrug is continued throughout the course of administration of the Agent (i.e., the course of the other therapy). In another embodiment, a phosphoramidate alkylator prodrug is administered after the initiation or completion of the other cancer therapy. In other embodiments, a phosphoramidate alkylator prodrug is first administered contemporaneously with the initiation of the other cancer therapy. See, for example combination therapies as described in the EXAMPLE section.

In one embodiment, a phosphoramidate alkylator prodrug is first administered prior to administration of the Agent, and treatment with a phosphoramidate alkylator prodrug is continued after the cessation of administration of the Agent. In one embodiment, a phosphoramidate alkylator prodrug is first administered prior to administration of the Agent, and treatment with a phosphoramidate alkylator prodrug is continued during part of the period of administration of the Agent. For certain drugs, such as certain topoisomerase inhibitors, a phosphoramidate alkylator prodrug administration can be initiated and completed prior to the administration of the second drug.

In the presence of oxygen, the radical anion formed upon the reduction of $Z_3$ reacts with oxygen to yield superoxide and $Z_3$. Superoxide is a cytotoxin and the production of superoxide in normoxic tissues can lead to unwanted side effects. In one embodiment, the present invention provides a phosphoramidate alkylator prodrug administered in combination with a chemoprotective agent or a chemoprotectant. Chemoprotective agents protect healthy tissue from the toxic effects of anticancer drugs. In one embodiment, the chemoprotective agent is a thiol or a disulfide. In one embodiment, the chemoprotectant can reduce superoxide. In another embodiment, the chemoprotectant can react with the "Michael-receptor" generated from a phosphoramidate alkylator prodrug and prevent "Michael-receptor" from reacting with proteins and nucleic acid (see below).

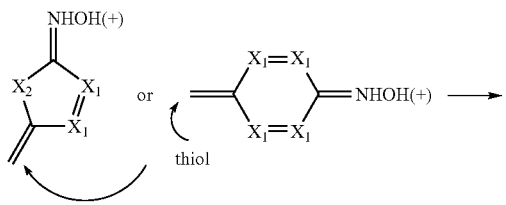

Anticancer drug therapy today typically involves multiple rounds, or "cycles," of administration of the anti-cancer agent(s). In the context of administering a phosphoramidate alkylator prodrug, each cycle of administration (as well as a complete set of cycles) can be viewed as administration of a second drug. A phosphoramidate alkylator prodrug can be administered in any or all of the multiple cycles of treatment with the other Agent; in general, a phosphoramidate alkylator prodrug is administered on a daily basis for at least two or more days during each cycle. In one aspect of the invention, a phosphoramidate alkylator prodrug is co-administered with the Agent according to a schedule repeated at each round.

In one version of the method of treating cancer using a phosphoramidate alkylator prodrug, a phosphoramidate alkylator prodrug is administered in combination with an effective amount of one or more chemotherapeutic agents, an effective amount of radiotherapy, an appropriate surgery procedure, or any combination of such additional therapies.

When a phosphoramidate alkylator prodrug is used in combination with one or more of the additional therapies, a phosphoramidate alkylator prodrug and additional therapy can be administered at the same time or can be administered separately. For example, if a phosphoramidate alkylator prodrug is administered with an additional chemotherapeutic agent, the two agents can be administered simultaneously or can be administered sequentially with some time between administrations. One of skill in the art will understand methods of administering the agents simultaneously and sequentially and possible time periods between administration. See for example combination therapies as described in the EXAMPLE section.

The Agents can be administered as the same or different formulations and can be administered via the same or different routes.

Chemotherapeutic agents that can be used in combination with a phosphoramidate alkylator prodrug of the invention include, but are not limited to, busulfan, improsulfan, pipo-sulfan, benzodepa, carboquone, 2-deoxy-D-glucose, lonidamine and analogs thereof, glufosfamide, gemcitibine, erlotinib, meturedepa, uredepa, altretamine, imatinib, triethylenemelamine, triethylenephosphoramide, triethylenethiophosphoramide, trimethylolomelamine, chlorambucil, chlornaphazine, estramustine, ifosfamide, gefitinib, mechlorethamine, mechlorethamine oxide hydrochloride, melphalan, novembichin, phenesterine, prednimustine, trofosfamide, uracil mustard, carmustine, chlorozotocin, fotemustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, mycophenolic acid, nogalamycin, olivomycin, peplomycin, plicamycin, porfiromycin, puromycin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, 5-fluorouracil, tegafur, L-asparaginase, pulmozyme, aceglatone, aldophosphamide glycoside, aminolevulinic acid, amsacrine, bestrabucil, bisantrene, carboplatin, defofamide, demecolcine, diaziquone, elformithine, elliptinium acetate, etoglucid, flutamide, gallium nitrate, hydroxyurea, interferon-alpha, interferon-beta, interferon-gamma, interleukin-2, lentinan, mitoguazone, mitoxantrone, mopidamol, nitracrine, pentostatin, phenamet, pirarubicin, podophyllinic acid, 2-ethylhydrazide, procarbazine, razoxane, sizofuran, spirogermanium, paclitaxel, tamoxifen, erlotinib, teniposide, tenuazonic acid, triaziquone, 2,2',2"-trichlorotriethylamine, urethan, vinblastine, cyclophosphamide, and vincristine. Other chemotherapeutic agents that can be used include platinum derivatives, including but not limited to cis platinum, carboplatin, and oxoplatin.

In one version, a phosphoramidate alkylator prodrug described herein can be used in combination with an antiangeogenisis inhibitor including but not limited to Avastin and similar therapeutics. In one version of the combination treatment methods, a subject is treated with an antiangeogenisis inhibitor and subsequently treated with a phosphoramidate alkylator prodrug. In one version of the combination treatment methods, a subject is treated with an antiangeogenisis inhibitor and subsequently treated with a phosphoramidate alkylator prodrug and another chemotherapeutic agent, including but not limited to cisplatin and carboplatin. In one version of these combination methods of treatment using an antiangeogenisis inhibitor, the method is used to treat breast cancer.

In another embodiment, a phosphoramidate alkylator prodrug is administered with an anti-cancer agent that acts, either directly or indirectly, to inhibit the epidermal growth factor or EGFR receptor. EGFR inhibitors suitable for coadministration with a phosphoramidate alkylator prodrug of the invention include gefitinib and erlotonib.

In another version, a phosphoramidate alkylator prodrug is administered with an anti-cancer agent that acts, either directly or indirectly, to inhibit hypoxia-inducible factor 1 alpha (HIF1a) or to inhibit a protein or enzyme, such as a glucose transporter or VEGF, whose expression or activity is increased upon increased HIF1a levels. HIF1a inhibitors suitable for use in this version of the methods and compositions described herein include P13 kinase inhibitors; LY294002; rapamycin; histone deacetylase inhibitors such as [(E)-(1S,4S,10S,21R)-7-[(Z)-ethylidene]-4,21-diisopropyl-2-oxa-12,13-dithia-5,8,20,23-tetraazabicyclo-[8,7,6]-tricos-16-ene-3,6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-1) inhibitors such as PD98059 (2'-amino-3'-methoxyflavone); PX-12 (1-methylpropyl 2-imidazolyl disulfide); pleurotin PX-478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; camptothecins; and YC-1, a compound described in Biochem. Pharmacol., 15 Apr. 2001, 61(8):947-954, incorporated herein by reference, and its derivatives.

In another version, a phosphoramidate alkylator prodrug is administered with an anti-angiogenic agent, including but not limited to anti-angiogenic agents selected from the group consisting of angiostatin, an agent that inhibits or otherwise antagonizes the action of VEGF, batimastat, captopril, cartilage derived inhibitor, genistein, endostatin, interleukin, lavendustin A, medroxypregesterone acetate, recombinant human platelet factor 4, Taxol, tecogalan, thalidomide, thrombospondin, TNP-470, and Avastin. Other useful angiogenesis inhibitors for purposes of the combination therapies provided by the present methods and compositions described herein include Cox-2 inhibitors like celecoxib (Celebrex), diclofenac (Voltaren), etodolac (Lodine), fenoprofen (Nalfon), indomethacin (Indocin), ketoprofen (Orudis, Oruvail), ketoralac (Toradol), oxaprozin (Daypro), nabumetone (Relafen), sulindac (Clinoril), tolmetin (Tolectin), rofecoxib (Vioxx), ibuprofen (Advil), naproxen (Aleve, Naprosyn), aspirin, and acetaminophen (Tylenol).

In addition, because pyruvic acid plays an important role in angiogenesis, pyruvate mimics and glycolytic inhibitors like halopyruvates, including bromopyruvate, can be used in combination with an anti-angiogenic compound and a phosphoramidate alkylator prodrug to treat cancer. In another version, a phosphoramidate alkylator prodrug is administered with an anti-angiogenic agent and another anti-cancer agent, including but not limited to a cytotoxic agent selected from the group consisting of alkylators, Cisplatin, Carboplatin, and inhibitors of microtubule assembly, to treat cancer.

In addition to the combination of a phosphoramidate alkylator prodrug with the Agents described above, the present methods and compositions described herein provides a variety of synergistic combinations of a phosphoramidate alkylator prodrug and other anti-cancer drugs. Those of skill in the art can readily determine the anti-cancer drugs that act "synergistically" with a phosphoramidate alkylator prodrug as described herein. For example, the reference Vendetti, "Relevance of Transplantable Animal-Tumor Systems to the Selection of New Agents for Clinical Trial," Pharmacological Basis of Cancer Chemotherapy, Williams and Wilkins, Baltimore, 1975, and Simpson Herren et al., 1985, "Evaluation of In Vivo Tumor Models for Predicting Clinical Activity for Anticancer Drugs," Proc. Am. Assoc. Cancer Res. 26: 330, each of which is incorporated herein by reference, describe methods to aid in the determination of whether two drugs act synergistically.

While synergy is not required for therapeutic benefit in accordance with the methods of described herein, in one embodiment, the present invention provides a method of cancer treatment, wherein there is synergy between a phosphoramidate alkylator prodrug and another anticancer agent. Two drugs can be said to possess therapeutic synergy if a combination dose regimen of the two drugs produces a significantly better tumor cell kill than the sum of the single Agents at optimal or maximum tolerated doses. The "degree of synergy" can be defined as net log of tumor cell kill by the optimum combination regimen minus net log of tumor cell kill by the optimal dose of the most active single Agent. Differences in cell kill of greater than ten-fold (one log) are considered conclusively indicative of therapeutic synergy.

When a phosphoramidate alkylator prodrug is used with another anti-cancer agent, a phosphoramidate alkylator prodrug will, at least in some embodiments, be administered prior to the initiation of therapy with the other drug or drugs and administration will typically be continued throughout the course of treatment with the other drug or drugs. In some embodiments, the drug co-administered with a phosphoramidate alkylator prodrug will be delivered at a lower dose, and optionally for longer periods, than would be the case in the absence of a phosphoramidate alkylator prodrug administration. Such "low dose" therapies can involve, for example, administering an anti-cancer drug, including but not limited to paclitaxel, docetaxel, doxorubicin, cisplatin, or carboplatin, at a lower than approved dose and for a longer period of time together with a phosphoramidate alkylator prodrug administered in accordance with the methods described herein.

These methods can be used to improve patient outcomes over currently practiced therapies by more effectively killing cancer cells or stopping growth of cancer cell as well as diminishing unwanted side effects of the other therapy. When employed in combination with a phosphoramidate alkylator prodrug, the additional anti-cancer agent(s) is dosed using either the standard dosages employed for those Agents (i.e., when used without a phosphoramidate alkylator prodrug) or are less than those standard dosages.

The administration of a phosphoramidate alkylator prodrug in accordance with the methods described herein can therefore allow the physician to treat cancer with existing (or later approved) drugs at lower doses (than currently used), thus ameliorating some or all of the toxic side effects of such drugs. The exact dosage for a given patient varies from patient to patient, depending on a number of factors including the drug combination employed, the particular disease being treated, and the condition and prior history of the patient, but can be determined using only the skill of the ordinarily skilled artisan in view of the teachings herein.

Specific dose regimens for known and approved chemotherapeutic agents or antineoplastic agents (i.e., the recommended effective dose) are known to physicians and are given, for example, in the product descriptions found in the Physician's Desk Reference 2003, (Physicians' Desk Reference, 57th Ed) Medical Economics Company, Inc., Oradell, N.J. and/or are available from the Federal Drug Administration. Illustrative dosage regimens for certain anti-cancer drugs are also provided below.

Cancer drugs can be classified generally as alkylators, anthracyclines, antibiotics, aromatase inhibitors, bisphosphonates, cyclo-oxygenase inhibitors, estrogen receptor modulators, folate antagonists, inorganic aresenates, microtubule inhibitors, modifiers, nitrosoureas, nucleoside analogs, osteoclast inhibitors, platinum containing compounds, retinoids, topoisomerase 1 inhibitors, topoisomerase 2 inhibitors, and tyrosine kinase inhibitors. In accordance with the methods described herein, a phosphoramidate alkylator prodrug can be co-administered with any anti-cancer drug from any of these classes or can be administered prior to or after treatment with any such drug or combination of such drugs. In addition, a phosphoramidate alkylator prodrug can be administered in combination with a biologic therapy (e.g., treatment with interferons, interleukins, colony stimulating factors and monoclonal antibodies). Biologics used for treatment of cancer are known in the art and include, for example, trastuzumab (Herceptin), tositumomab and $^{131}$I Tositumomab (Bexxar), rituximab (Rituxan).

Alkylators useful in the practice of the methods described herein include but are not limited to busulfan (Myleran, Busulfex), chlorambucil (Leukeran), ifosfamide (with or without MESNA), cyclophosphamide (Cytoxan, Neosar), glufosfamide, melphalan, L-PAM (Alkeran), dacarbazine (DTIC-Dome), and temozolamide (Temodar). In accordance with the methods described herein a phosphoramidate alkylator prodrug is co-administered with an alkylator to treat cancer. In one version, the cancer is chronic myelogenous leukemia, multiple myeloma, or anaplastic astrocytoma.

In one embodiment, the present invention provides a method of treating cancer treatable by administering an alkylator by administering the phosphoramidate alkylator prodrugs of the present invention alone or in combination with at least another alkylator or a prodrug thereof. Alkylators, such as, for example, cyclophosphamide, ifosfamide, glufosfamide, mechlorethamine, melphalan, chlorambucil, dacarbazine, temozolomide, carmustine, streptozocin, bendamustin, busulfan, thiotepa, cisplatin, carboplatin, and oxaliplatin, and types of cancers treated using any one of such alkylators alone or in combination with other anti cancer or chemoprotective agents are described, for example, in the reference Hardman et al. (supra).

In one embodiment, the present invention provides a method of treating cancer by coadministering a phosphoramidate alkylator prodrug with at least the alkylator Cyclophosphamide, in the treatment of Stages III and IV malignant lymphomas, multiple myeloma, leukemia, mycosis fungoides, neuroblastoma, ovarian adenocarcinoma, retinoblastoma, and carcinoma of the breast. Cyclophosphamide is administered for induction therapy in doses of 1500-1800 mg/m$^2$ that are administered intravenously in divided doses over a period of three to five days; for maintenance therapy, 350-550 mg/m$^2$ are administered every 7-10 days, or 110-185 mg/m$^2$ are administered intravenously twice weekly. In accordance with the methods described herein, a phosphoramidate alkylator prodrug is co-administered with cyclophosphamide administered at such doses or at lower doses and/or for a longer duration than normal for administration of Cyclosphosphamide alone.

In one embodiment, the present invention provides a method of treating cancer by administering a phosphoramidate alkylator prodrug of the invention together with a cancer treatment regimen using at least the alkylator Mechlorethamine. For example, Mechlorethamine is used in the combination chemotherapy regimen MOPP (mechlorethamine, Oncovin (vincristine), procarbazine, and prednisone) in patients with Hodgkin's disease and administered by intravenous bolus administration in doses of 6 mg/m$^2$ on days 1 and 8 of the 28 day cycles of each course of treatment.

In one embodiment, the present invention provides a method of treating cancer by administering a phosphoramidate alkylator prodrug of the invention with a cancer treatment regimen using at least the alkylator Ifosfamide. Ifosfamide is used to treat pediatric and adult sarcomas, carcinomas of cervix and lung, and in combination with other drugs for germ cell testicular cancer. Ifosfamide is used as part of the ICE (Ifosfamide, Carboplatin, and Etoposide) and RICE (Rituxan and ICE) regimens for treating lymphomas (see Hardman et al., supra).

In one embodiment, the present invention provides a method of treating cancer by administering a phosphoramidate alkylator prodrug of the invention with a cancer treatment regimen using at least the alkylator Glufosfamide. Glufosfamide is in the clinic for the treatment of pancreatic cancer or Gemzar resistant pancreatic cancer. Glufosfamide can be used for treating breast cancer, Morbus Hodgkin, gastrointestinal tract cancer, or as part of the GCE (Glufosfamide, Carboplatin, and Etoposide) or RGCE (Rituxan and GCE) regimen, for treating lymphomas. (Tidmarsh et al., PCT Pat. Appl. No. PCT/US2005/047314 filed on 22 Dec. 2005, and PCT Pat. Appl. entitled "Glufosfamide combination therapy", PCT Pat. Appl. PCT/US06/18191; and U.S. Pat. App. No. 60/760,599 and 60/719,787 and PCT Pat. Pub. No. WO 2005/076888, incorporated in their entirety herein by reference).

In one embodiment, the present invention provides a method of treating cancer by administering a phosphoramidate alkylator prodrug of the invention with a cancer treatment regimen using at least an alkylator selected from the group consisting of ethylenimines and methylmelamines. In another embodiment, the ethylenimine is Triethylenemelamine or Thiotepa.

Thiotepa can be used to treat adenocarcinomas of the breast, ovary, and bladder, malignant lymphomas, bronchiogenic carcinomas, and Wilms' tumor. Thiotepa was used at high doses in combination chemotherapy with cyclophosphamide in patients with refractory malignancies treated with autologous bone transplantation and to treat a variety of cancers including bladder, ovarian, breast, lung, brain, and lymphomas (see, *International Agency for Research on Cancer Monographs on the Evaluation of Carcinogenic Risk of Chemicals to Humans,* 1975, 9: 286, Lyon, France; *International Agency for Research on Cancer*

Monographs on the Evaluation of Carcinogenic Risk of Chemicals to Humans, 1990, 50: 415, Lyon, France; and *MEDLINEplus,* 2003, Drug Information: Thiotepa, National Library of Medicine). The methylmelamine Altretamine is used to treat advanced ovarian cancer after failure of first round therapies.

In one embodiment, the present invention provides a method of treating cancer by administering a phosphoramidate alkylator prodrug of the invention with a cancer treatment regimen using at least the alkylator Melphalan, Chlorambucil, or Bendamustine. Melphalan is used to treat multiple myolema and can be administered orally. Chlorambucil is used to treat chronic lyphocytic leukemia and primary macroblobulinemia. Bendamustine, developed by Salmedix, Inc., can be used to treat hematological malignancies, such as, for example, non-Hodgkin's lymphoma, chronis lymphocytic leukemia, and multiple myeloma.

In one embodiment, the present invention provides a method of treating cancer by administering a phosphoramidate alkylator prodrug of the invention with a cancer treatment regimen using at least the alkylator Busulfan. Busulfan is used to treat chronic granulocytic leukemia and chronic myelogenous leukemia. High doses of busulfan can be used in combination with Cyclophosphamide to treat patients with acute myelogenous leukemia before bone marrow transplantation.

In one embodiment, the present invention provides a method of treating cancer by administering a phosphoramidate alkylator prodrug of the invention with a cancer treatment regimen using at least a nitrosourea alkylator. In another embodiment, the nitrosourea alkylator is Carmustine. Carmustine can be used to treat Hodgkin's disease, lymphomas, myelomas, malignant astrocytomas, metastatic tumors of the brain, melanoma, and gastrointestinal tumors. In another embodiment, the nitrosourea is Streptozocin which is used to treat pancreatic islet cell carcinoma.

In one embodiment, the present invention provides a method of treating cancer by administering a phosphoramidate alkylator prodrug of the invention with a cancer treatment regimen using at least a triazene alkylator. In one embodiment, the triazene alkylator is Dacarbazine. Dacarbazine is used to treat malignant melanoma, Hodgkin's disease, and adult sarcoma. In another embodiment, the triazene alkylator is Temozolomide. Temozolomide can be used to treat malignant gliomas.

In one embodiment, the present invention provides a method of treating cancer by administering a phosphoramidate alkylator prodrug of the invention with a cancer treatment regimen using at least a platinum coordination complex alkylator. In one embodiment, the platinum coordination complex alkylator is Cisplatin. Cisplatin can be used to treat cancer of bladder, head and neck, endometrium, small cell carcinoma of the lung, and some neoplasms of childhood. Cisplatin alone or with cyclophosphamide is used to treat advanced ovarian cancer. Combination chemotherapy of Cisplatin with Bleomycin, Etoposide, and Vinblastine is used to treat advanced testicular cancer; and with one of Paclitaxel, Cyclophosphamide, or Doxorubicin to treat ovarian carcinoma.

Anthracyclines useful in the practice of the methods described herein include but are not limited to, doxorubicin (Adriamycin, Doxil, Rubex), mitoxantrone (Novantrone), idarubicin (Idamycin), valrubicin (Valstar), and epirubicin (Ellence). In accordance with the methods described herein a phosphoramidate alkylator prodrug is co-administered with an anthracycline to treat cancer. In one version, the cancer is acute nonlymphocytic leukemia, Kaposi's sarcoma, prostate cancer, bladder cancer, metastatic carcinoma of the ovary, and breast cancer.

As one example the compound (8S,10S)-10-[(3-Amino-2,3,6-trideoxy-alpha.-L-lyxo-hexopyranosyl)oxy]-8-glycoloyl-7,8,9,10-tetrahydro-6,8,11-trihydroxy-1-methoxy-5,12-naphthacenedione, more commonly known as doxorubicin, is a cytotoxic anthracycline antibiotic isolated from cultures of Streptomyces peucetius var. caesius. Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma. Doxorubicin is typically administered in a dose in the range of 30-75 mg/m$^2$ as a single intravenous injection administered at 21-day intervals; weekly intravenous injection at doses of 20 mg/m$^2$; or 30 mg/m$^2$ doses on each of three successive days repeated every four weeks. In accordance with the methods of the methods described herein, a phosphoramidate alkylator prodrug is co-administered starting prior to and continuing after the administration of doxorubicin at such doses (or at lower doses). Cyclic Anthracycline cytotoxin prodrugs useful in the practice of the methods described herein are provided by the reference Matteuci et al., PCT Patent Application No. US05/008161.

Antibiotics useful in the practice of the methods described herein include but are not limited to dactinomycin, actinomycin D (Cosmegen), bleomycin (Blenoxane), daunorubicin, and daunomycin (Cerubidine, DanuoXome). In accordance with the methods described herein a phosphoramidate alkylator prodrug is co-administered with an antibiotic to treat cancer. In one version, the cancer is a cancer selected from the group consisting of acute lymphocytic leukemia, other leukemias, and Kaposi's sarcoma.

Aromatase inhibitors useful in the practice of the methods described herein include but are not limited to anastrozole (Arimidex) and letroazole (Femara). In accordance with the methods described herein a phosphoramidate alkylator prodrug is co-administered with an aromatase inhibitor to treat cancer. In one version, the cancer is breast cancer.

Bisphosphonate inhibitors useful in the practice of the methods described herein include but are not limited to zoledronate (Zometa). In accordance with the methods described herein a phosphoramidate alkylator prodrug is co-administered with a bisphosphonate inhibitor to treat cancer. In one version, the cancer is a cancer selected from the group consisting of multiple myeloma, bone metastases from solid tumors, or prostate cancer.

Cyclo-oxygenase inhibitors useful in the practice of the methods described herein include but are not limited to celecoxib (Celebrex). In accordance with the methods described herein a phosphoramidate alkylator prodrug is co-administered with a cyclo-oxygenase inhibitor to treat cancer. In one version, the cancer is colon cancer or a pre-cancerous condition known as familial adenomatous polyposis.

Estrogen receptor modulators useful in the practice of the methods described herein include but are not limited to tamoxifen (Nolvadex) and fulvestrant (Faslodex). In accordance with the methods described herein a phosphoramidate alkylator prodrug is co-administered with an estrogen receptor modulator to treat cancer. In one version, the cancer is breast cancer or the treatment is administered to prevent the occurrence or reoccurrence of breast cancer.

Folate antagonists useful in the practice of the methods described herein include but are not limited to methotrexate and tremetrexate. In accordance with the methods described herein a phosphoramidate alkylator prodrug is co-administered with a folate antagonist to treat cancer. In one version, the cancer is osteosarcoma.

As one example, the compound N-[4-[[(2,4-diamino-6-pteridinyl)methyl methylamino]benzoyl]-L-glutamic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides. Methotrexate is administered as follows. For choriocarcinoma, intramuscular injections of doses of 15 to 30 mg are administered daily for a five-day course, such courses repeated as needed with rest period of one or more weeks interposed between courses of therapy. For leukemias, twice weekly intramuscular injections are administered in doses of 30 mg/m$^2$. For mycosis fungoides, weekly intramuscular injections of doses of 50 mg or, alternatively, of 25 mg are administered twice weekly. In accordance with the methods described herein, a phosphoramidate alkylator prodrug is co-administered with methotrexate administered at such doses (or at lower doses). 5-Methyl-6-[[(3,4,5-trimethoxyphenyl)-amino]methyl]-2,4-quinazolinediamine (commonly known as trimetrexate) is another antifolate drug that can be co-administered with a phosphoramidate alkylator prodrug.

Inorganic arsenates useful in the practice of the methods described herein include but are not limited to arsenic trioxide (Trisenox). In accordance with the methods described herein a phosphoramidate alkylator prodrug is co-administered with an inorganic arsenate to treat cancer. In one version, the cancer is refractory acute promyelocytic leukemia (APL).

Microtubule inhibitors (as used herein, a "microtubule inhibitor" is any agent that interferes with the assembly or disassembly of microtubules) useful in the practice of the methods described herein include but are not limited to vincristine (Oncovin), vinblastine (Velban), paclitaxel (Taxol, Paxene), vinorelbine (Navelbine), docetaxel (Taxotere), epothilone B or D or a derivative of either, and discodermolide or its derivatives. Tubulin binding anticancer drugs and prodrugs thereof which can be used in the practice of the methods of the present invention are provided in the reference Matteucci et al., PCT Patent Application No. PCT/US2005/042095; US Patent Applications entitled "Tubulin Binding Anti Cancer Agents and Prodrugs Thereof" (U.S. Pat. Appl. No. 60/802,971, U.S. Pat. Appl. No. 60/802,184 and U.S. Pat. Appl. No. 60/802,267). In accordance with the methods described herein a phosphoramidate alkylator prodrug is co-administered with a microtubule inhibitor to treat cancer. In one version, the cancer is ovarian cancer, breast cancer, non-small cell lung cancer, Kaposi's sarcoma, and metastatic cancer of breast or ovary origin. As one example, the compound 22-oxo-vincaleukoblastine, also commonly known as vincristine, is an alkaloid obtained from the common periwinkle plant (Vinca rosea, Linn.) and is useful in the treatment of acute leukemia. It has also been shown to be useful in combination with other oncolytic agents in the treatment of Hodgkin's disease, lymphosarcoma, reticulum-cell sarcoma, rhabdomyosarcoma, neuroblastoma, and Wilm's tumor. Vincristine is administered in weekly intravenous doses of 2 mg/m$^2$ for children and 1.4 mg/m$^2$ for adults. In accordance with the methods described herein, a phosphoramidate alkylator prodrug is co-administered with vincristine administered at such doses. In one version, a phosphoramidate alkylator prodrug is not administered prior to treatment with a microtubule inhibitor, such as a taxane, but rather, a phosphoramidate alkylator prodrug is administered simultaneously with or within a few days to a week after initiation of treatment with a microtubule inhibitor.

Modifiers useful in the practice of the methods described herein include but are not limited to Leucovorin (Wellcovorin), which is used with other drugs such as 5-fluorouracil to treat colorectal cancer. In accordance with the methods described herein a phosphoramidate alkylator prodrug is co-administered with a modifier and another anti-cancer agent to treat cancer. In one version, the cancer is colon cancer. In one version, the modifier is a compound that increases the ability of a cell to take up glucose, including but not limited to the compound N-hydroxyurea. N-hydroxyurea has been reported to enhance the ability of a cell to take up 2-deoxyglucose (see the reference Smith et al., 1999, Cancer Letters 141: 85, incorporated herein by reference), and administration of N-hydroxyurea at levels reported to increase 2-deoxyglucose uptake or to treat leukemia together with administration of 2-deoxyglucose and a phosphoramidate alkylator prodrug as described herein is one version of the therapeutic methods provided herein. In another such version, a phosphoramidate alkylator prodrug is co-administered with nitric oxide or a nitric oxide precursor, such as an organic nitrite or a spermineNONOate, to treat cancer, as the latter compounds stimulate the uptake of glucose.

Nitrosoureas useful in the practice of the methods described herein include but are not limited to procarbazine (Matulane), lomustine, CCNU (CeeBU), carmustine (BCNU, BiCNU, Gliadel Wafer), and estramustine (Emcyt). In accordance with the methods described herein a phosphoramidate alkylator prodrug is co-administered with a nitrosourea to treat cancer. In one version, the cancer is prostate cancer or glioblastoma, including recurrent glioblastoma multiforme.

Nucleoside analogs useful in the practice of the methods described herein include but are not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), azacytidine (Vidaza), pentostatin (Nipent), cladribine (Leustatin, 2-CdA), gemcitabine (Gemzar), and capecitabine (Xeloda). In accordance with the methods described herein a phosphoramidate alkylator prodrug is co-administered with a nucleoside analog to treat cancer. In one version, the cancer is B-cell lymphocytic leukemia (CLL), hairy cell leukemia, adenocarcinoma of the pancreas, metastatic breast cancer, non-small cell lung cancer, or metastatic colorectal carcinoma. As one example, the compound 5-fluoro-2,4(1H,3H)-pyrimidinedione, also commonly known as 5-fluorouracil, is an antimetabolite nucleoside analog effective in the palliative management of carcinoma of the colon, rectum, breast, stomach, and pancreas in patients who are considered incurable by surgical or other means. 5-Fluorouracil is administered in initial therapy in doses of 12 mg/m$^2$ given intravenously once daily for 4 successive days with the daily dose not exceeding 800 mg. If no toxicity is observed at any time during the course of the therapy, 6 mg/kg are given intravenously on the 6th, 8th, 10th, and 12th days. No therapy is given on the 5th, 7th, 9th, or 11th days. In poor risk patients or those who are not in an adequate nutritional state, a daily dose of 6 mg/kg is administered for three days, with the daily dose not exceeding 400 mg. If no toxicity is observed at any time during the treatment, 3 mg/kg can be given on the 5th, 7th, and 9th days. No therapy is given on the 4th, 6th, or 8th days. A sequence of injections on either schedule constitutes a course of therapy. In accordance with the methods described herein, a phosphoramidate alkylator prodrug is co-administered with 5-FU administered at such doses or with the prodrug form Xeloda with correspondingly adjusted doses. As another example, the compound 2-amino-1,7-dihydro-6H-purine-6-thione, also commonly known as 6-thioguanine, is a nucleoside analog effective in the therapy of acute non-lymphocytic leukemias. 6-Thioguanine is orally administered in doses of about 2 mg/kg of body weight per day. The total daily dose can be given at one time. If after four weeks of dosage at this level there is no improvement, the dosage can be cautiously increased to 3 mg/kg/day. In accordance with the methods described herein, a phosphoramidate alkylator prodrug is co-administered with 6-TG administered at such doses (or at lower doses).

Osteoclast inhibitors useful in the practice of the methods described herein include but are not limited to pamidronate (Aredia). In accordance with the methods described herein a phosphoramidate alkylator prodrug is co-administered with an osteoclast inhibitor to treat cancer. In one version, the cancer is osteolytic bone metastases of breast cancer, and one or more additional anti-cancer agents are also co-administered with a phosphoramidate alkylator prodrug.

Platinum compounds useful in the practice of the methods described herein include but are not limited to cisplatin (Platinol) and carboplatin (Paraplatin). In accordance with the methods described herein a phosphoramidate alkylator prodrug is co-administered with a platinum compound to treat cancer. In one version, the cancer is metastatic testicular cancer, metastatic ovarian cancer, ovarian carcinoma, and transitional cell bladder cancer. As one example, the compound cis-Diaminedichloroplatinum (II), commonly known as cisplatin, is useful in the palliative treatment of metastatic testicular and ovarian tumors, and for the treatment of transitional cell bladder cancer which is not amenable to surgery or radiotherapy. Cisplatin, when used for advanced bladder cancer, is administered in intravenous injections of doses of 50-70 mg/m$^2$ once every three to four weeks. In accordance with the methods described herein, a phosphoramidate alkylator prodrug is co-administered with cisplatin administered at these doses (or at lower doses). One or more additional anti-cancer agents can be co-administered with the platinum compound and a phosphoramidate alkylator prodrug. As one example, Platinol, Blenoxane, and Velbam can be co-administered with a phosphoramidate alkylator prodrug. As another example, Platinol and Adriamycin can be co-administered with a phosphoramidate alkylator prodrug.

Retinoids useful in the practice of the methods described herein include but are not limited to tretinoin, ATRA (Vesanoid), alitretinoin (Panretin), and bexarotene (Targretin). In accordance with the methods described herein a phosphoramidate alkylator prodrug is co-administered with a retinoid to treat cancer. In one version, the cancer is a cancer selected from the group consisting of APL, Kaposi's sarcoma, and T-cell lymphoma.

Topoisomerase 1 inhibitors useful in the practice of the methods described herein include but are not limited to topotecan (Hycamtin) and irinotecan (Camptostar). In accordance with the methods described herein a phosphoramidate alkylator prodrug is co-administered with a topoisomerase 1 inhibitor to treat cancer. Topoisomerase inhibitors and prodrugs thereof useful in the practice of the methods of the present invention are provided in the reference Matteucci et al., PCT Patent Application No. PCT/US2005/041959. In one version, the cancer is metastatic carcinoma of the ovary, colon, or rectum, or small cell lung cancer. As noted above, however, in one version of the methods described herein, administration of a phosphoramidate alkylator prodrug either precedes or follows, or both, administration of a topoisomerase 1 inhibitor but is not administered concurrently therewith.

Topoisomerase 2 inhibitors useful in the practice of the methods described herein include but are not limited to etoposide, VP-16 (Vepesid), teniposide, VM-26 (Vumon), and etoposide phosphate (Etopophos). In accordance with the methods described herein a phosphoramidate alkylator prodrug is co-administered with a topoisomerase 2 inhibitor to treat cancer. In one version, the cancer is a cancer selected from the group consisting of refractory testicular tumors, refractory acute lymphoblastic leukemia (ALL), and small cell lung cancer. As noted above, however, in one version of the methods described herein, administration of a phosphoramidate alkylator prodrug either precedes or follows, or both, administration of a topoisomerase 2 inhibitor but is not administered concurrently therewith.

Tyrosine kinase inhibitors useful in the practice of the methods described herein include but are not limited to imatinib (Gleevec). In accordance with the methods described herein a phosphoramidate alkylator prodrug is co-administered with a tyrosine kinase inhibitor to treat cancer. In one version, the cancer is CML or a metastatic or unresectable malignant gastrointestinal stromal tumor.

Lonidamine analogs useful in the practice of the present invention are provided in the Matteucci et al. U.S. patent application Ser. Nos. 11/346,632; 60/764,427; 60/764,438; and applications entitled "Heterocyclic Lonidamine Analogs" (US Publication No. US 2007 0015771 A1; U.S. Pat. Appl. No. 60/771,928) and PCT Publication Nos. WO 2006/015191, WO 2006/015263 and WO 2006/01007 A2.

Thus, described herein are methods of treating cancer in which a phosphoramidate alkylator prodrug or a pharmaceutically acceptable salt thereof and one or more additional anti-cancer agents are administered to a patient. Specific versions of such other anti-cancer agents include without limitation 5-methyl-6-[[(3,4,5-trimethoxyphenyl)amino]-methyl]-2, 4-quinazolinediamine or a pharmaceutically acceptable salt thereof, (8S,10S)-10-(3-amino-2,3,6-trideoxy-alpha-L-lyxo-hexopyranosyl)oxy]-8-glycoloyl-7, 8,9,10-tetrahydro-6,8,11-trihydroxy-1-methoxy-5,12-naphthacenedione or a pharmaceutically acceptable salt thereof; 5-fluoro-2,4(1H,3H)-pyrimidinedione or a pharmaceutically acceptable salt thereof; 2-amino-1,7-dihydro-6H-purine-6-thione or a pharmaceutically acceptable salt thereof; 22-oxo-vincaleukoblastine or a pharmaceutically acceptable salt thereof; 2-bis[(2-chloroethyl)amino]tetrahydro-2H-1,3,2-oxazaphosphorine, 2-oxide, or a pharmaceutically acceptable salt thereof; N-[4-[[(2,4-diamino-6-pteridinyl)methyl]-methylamino]benzoyl]-L-glutamic acid, or a pharmaceutically acceptable salt thereof; or cisdiamminedichloro-platinum (II).

IV. EXAMPLES

In the following examples, any reference to a compound designated by a letter is a reference to the structure shown next to or above that letter in the corresponding reaction schemes.

Synthesis

Methods to synthesize the phosphoramidate alkylator prodrugs of the present invention are provided in section IIb. Starting materials used in the synthesis of the phosphoramidate alkylator prodrugs of the present invention were bought, when available, from commercial manufacturers, such as, for example, the Sigma-Aldrich Co. 1-N-Methyl-2-nitroimidazole-5-methanol was purchased from Syngene, India. Non-commercially available starting materials can be synthesized via standard literature procedures. Such procedures can be identified via literature search tools such as SciFinder available from the American Chemical Society or Beilstein, available from MDL Software.

Reactions with moisture sensitive compounds, such as, for example, POCl$_3$ and PCl$_3$, and their mono and dichloro derivatives were performed employing anhydrous solvents and under nitrogen or argon. Separation of a product from the reaction mixture was performed employing a work-up where necessary, followed by vacuum distillation, crystallization, column chromatography, or preparative thick layer chromatography. A suitable eluent for the column chromatography of a compound can be determined by reading this disclosure and/or by determining the R$_f$ of the compound by thin layer chromatography and choosing a solvent which allows separation of the desired compound from undesired compounds. The choice of a particular eluent can depend, among other factors, on the polar nature of the compound, existence of other closely eluting compounds, type of stationary phase such as silica gel or alumina used, and the amount of pressure used to elute the solvent through the stationary phase. In practice, different compositions of solvents can be used to separate the same compound.

Separated compounds were analyzed for their purity by standard analytical techniques, such as, TLC, NMR spectroscopy, and LC-MS, and stored in a freezer or a fridge, avoiding moisture, light, or air. Stock solutions of phosphoramidate alkylator prodrug compounds were prepared in DMSO and stored in a freezer.

Example 1

Synthesis of Compound 23

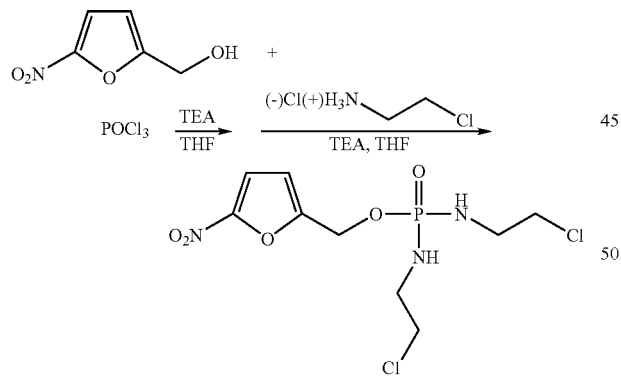

To a solution of 5-nitrofurfuryl alcohol (200 mg, 1.4 mmol) in THF (10 ml) at −78° C. POCl$_3$ was added in one portion followed by a dropwise addition of triethylamine (TEA, 0.22 ml, 1.54 mmol). Temperature was increased to −30° C. in one hour and then 2-chloroethylamine hydrochloride was added followed by TEA (1 ml, 7 mmol). After the temperature was raised to room temperature (rt), the reaction was continued for one more hour, the reaction mixture was quenched with water and the organic layer was separated. The aqueous layer was extracted with DCM and the combined organic solution was dried and concentrated. Compound 23 was separated by flash column chromatography and analyzed by LC/MS and NMR spectroscopy to be pure.

Example 2

Synthesis of Compound 5

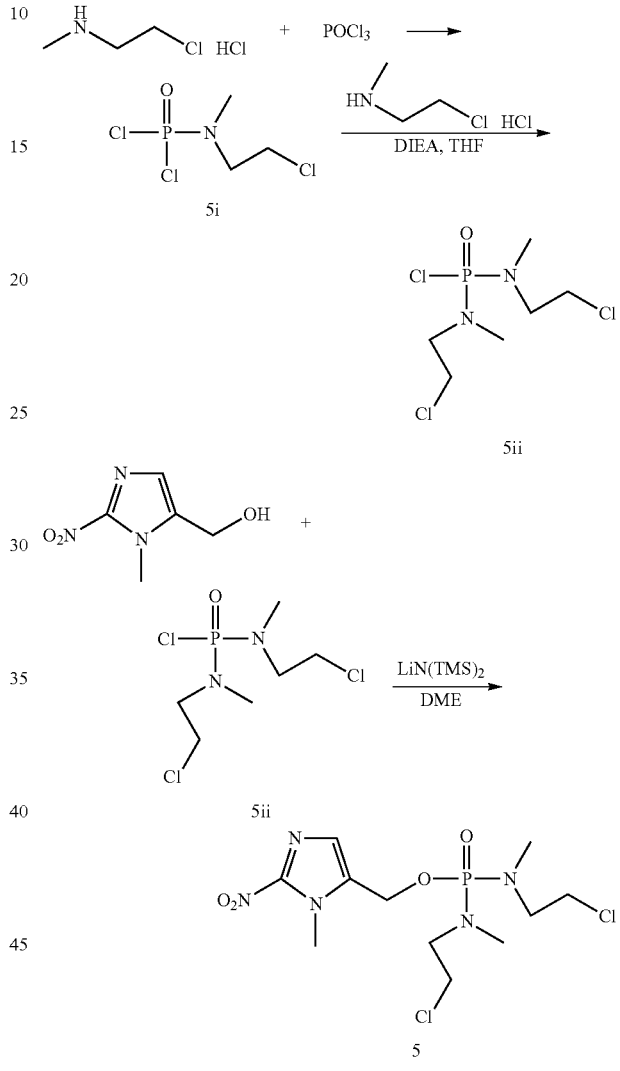

A suspension of N-Methyl-2-chloroethylammonium chloride (10 gm) in POCl$_3$ (40 ml) was refluxed (135° C.) over night. After removing excess POCl$_3$ under vacuum product 51 was distilled out under vacuum as light yellow oil and analyzed by $^1$H and $^{31}$P NMR spectroscopy to be pure.

To a solution of 5i (1 gm, 4.75 mmol) and N-Methyl-2-chloroethylammonium chloride (0.62 gm, 4.75 mmol) in THF at −78° C., diisopropylethylamine (DIEA, 1.65 ml, 9.5 mmol) was slowly added and the reaction mixture was warmed to rt. After stirring at rt for one hour, the reaction mixture was diluted with ethyl acetate and washed with brine. The organic layer was dried over MgSO$_4$ and concentrated to yield a residue which was separated by flash chromatography yielding compound 5ii as oil.

To a solution of N-methyl 2-nitroimidazole-5-methanol (0.5 g, 3.2 mmol) in dimethoxyethane (DME), lithium bis (trimethylsilyl)amide (3.2 mmol, 3.2 ml, 1 M in THF) was added at −78° C. After 5 min, 5ii (2.9 mmol, 770 mg) was added and the reaction mixture was warmed to −20° C., diluted with ethyl acetate and washed with brine. The organic layer was dried over MgSO$_4$ and concentrated. Purification by flash chromatography with 6-12% methanol in DCM yielded 5.

Compounds of 8 and 16 were synthesized employing the procedure used for the preparation of compound 5.

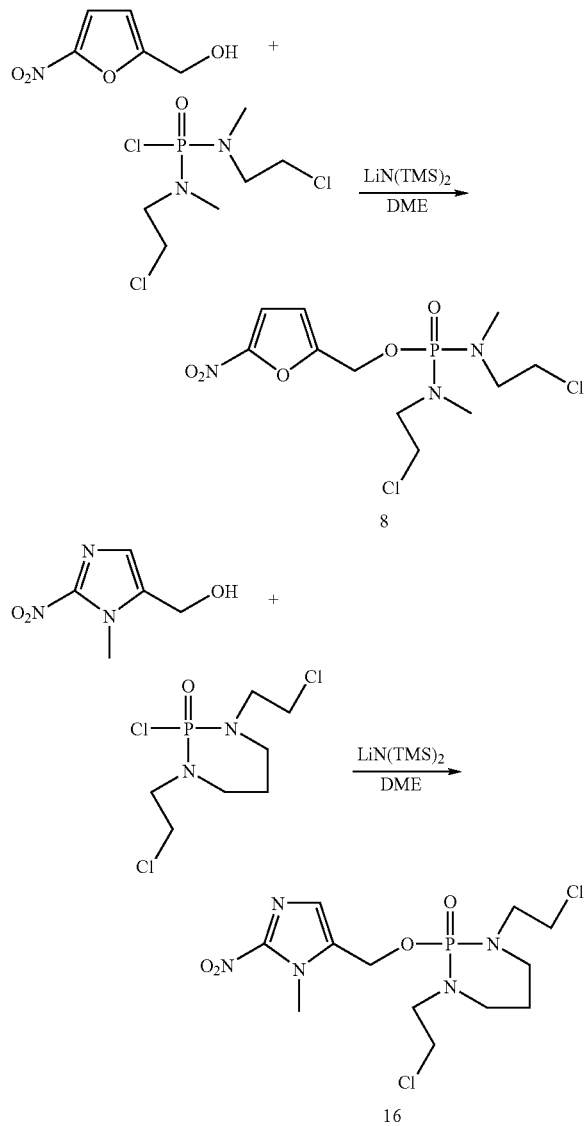

Example 3

Synthesis of Compound 35

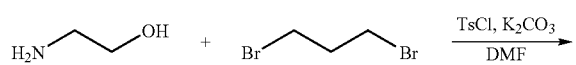

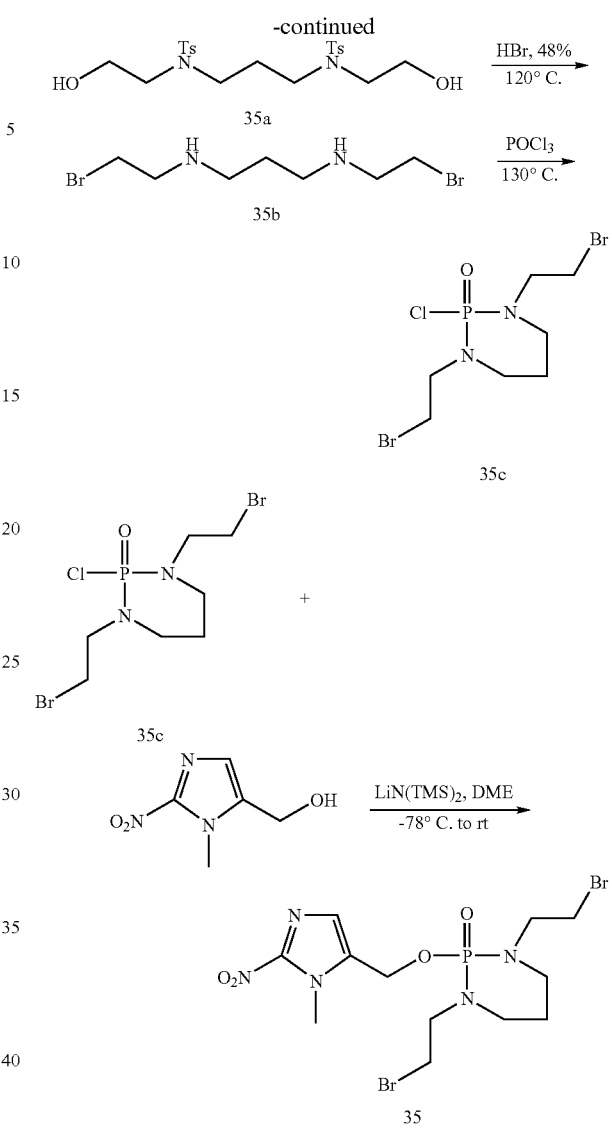

To a solution of ethanolamine (6.03 mL, 100 mmol) and K$_2$CO$_3$ (13.8 g, 100 mmol) in DMF (38 mL), a solution of p-toluenesulfonyl chloride (19 g, 100 mmol) was added drop wise at rt and the reaction mixture was heated to 120° C. (bath temperature). K$_2$CO$_3$ (27.6 g, 200 mmol) was added to the reaction mixture, followed by dropwise addition of 1,3-dibromopropane (10 g, 50 mmol). After heating for two more hours, the reaction was cooled to rt, poured into water (250 mL), and extracted with ethyl acetate. The organic layer was dried with Na$_2$SO$_4$ and concentrated to yield compound 35a as yellow oil which was employed in the next reaction.

A solution of compound 35a (5 g) in aqueous HBr (48%, 50 ml) was distilled to remove the aqueous portion (about 20 ml), and the reaction mixture was refluxed for 40 h. Additional aqueous portion (5 ml) was removed by distillation and the reaction mixture was refluxed (4 h). The reaction mixture was cooled to rt, diluted with water (20 mL), and filtered through a celite pad. The filtrate was concentrated to dryness to yield a residue which was coevaporated with ethanol thrice, and following addition of a large volume of acetone, a white solid product 35b was filtered and washed with acetone twice and employed in the phosphorylation provided below.

A suspension of compound 35b (1 g) in POCl₃ (14 mL) was heated at 130° C. for about 14 h and excess POCl₃ removed under vacuum at 130° C. (bath temperature). The residue was purified by column chromatography on silica gel employing 10-80% ETOAc/hexane to yield product 35c which was convereted to compound 35 of the present invention employing the same procedure as provided in Example 2 employing for column chromatographic separation silica gel and 10-80% acetone/toluene as the eluent.

Example 4

Synthesis of Compound 7

Compound 7 was prepared by employing N-cyclopropyl-2-chloroethylammonium chloride as provided below

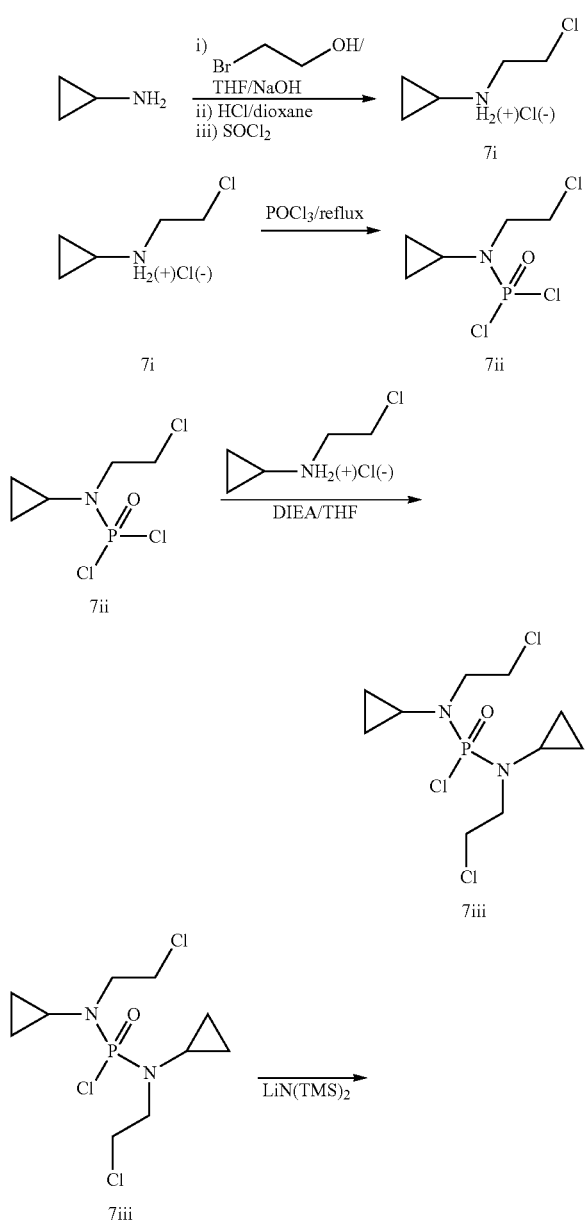

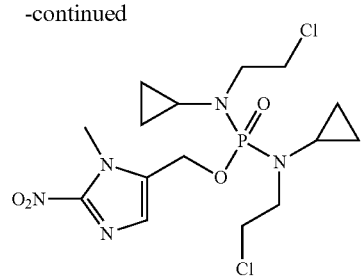

To a solution of cyclopropylamine (25 g) in dry THF (30 ml) a solution of 2-bromoethanol (17.6 g, 0.141 mol) in 30 ml THF was added dropwise over 35 minutes. The reaction mixture was stirred for 1 hour at rt, and heated at 50° C. for 75 minutes. After cooling, the reaction mixture was concentrated to yield an orange oil to which was added a solution of sodium hydroxide (7 g) in water (50 ml). The reaction mixture was stirred for 10 minutes, and extracted 4 times with ethyl acetate (75 ml). The combined organic layer was dried (MgSO₄) and evaporated to give an orange oily residue. The residue was distilled in vacuo at 53-56° C. (1 mm Hg) to yield an intermediate alcohol (5.94 g, 42% yield) as a clear, colorless liquid which was analyzed by LC/MS and ¹H NMR to be pure.

To a solution of the intermediate alcohol (3.7 g, 36.6 mmol) in dry THF (30 ml) a solution of HCl in dioxane (4.0M, 18.3 ml, 73.2 mmol) was added. The reaction mixture was cooled to 0° C. and SOCl₂ (6.50 g, 54.9 mmol) was added by syringe. The reaction mixture was refluxed (6 h), cooled, and concentrated to yield a residue. The residue was triturated with dry ether (100 ml), filtered, and residual volatiles removed in vacuo to yield 7i (5.42 g, 95% yield) which was analyzed by ¹H NMR to be pure.

7i (3.00 g, 19.2 mmol) was added to POCl₃ (15 ml) and refluxed under nitrogen for 7.5 hours. The reaction mixture was concentrated and the resulting oil distilled in vacuo through a short path distillation apparatus to yield 7ii as a clear, pale yellow oil (3.6 g, 79% yield) which was analyzed by ¹H NMR to be pure.

7ii (0.50 g, 2.11 mmol) and N-cyclopropyl-2-chloroethylamine hydrochloride (0.33 g, 2.11 mmol) were combined in dry THF under argon. The reaction mixture was cooled to −78° C. and DIEA (0.545 g, 4.22 mmol) added slowly by syringe, warmed to rt slowly, stirred for 1.5 hours and concentrated to give an orange oily residue. The residue was separated by flash chromatography over silica using 0-50% of hexane in ethyl acetate to give 315 mg (47% of theoretical) of pale yellow oil which was analyzed to be 7iii by MS.

N-methyl-2-nitroimidazole-5-methanol (76.8 mg, 0.489 mmol) was partially dissolved in dry THF (2 ml) under argon. The reaction mixture was cooled to −78° C. and a solution of lithium bis(trimethylsilyl)amide in THF (1.6M, 0.306 ml, 0.489 mmol) was added. After 15 minutes, a solution of 7iii (172 mg, 0.538 mmol) in 2 ml THF was added. After 15 minutes the reaction mixture was slowly warmed to rt, stirred for 2 hours, poured into 25 ml water and extracted 3 times with ethyl acetate (30 ml). The combined organic layers were dried over MgSO₄ and concentrated to give a yellow oily residue. The residue was separated by flash chromatography in 0-10% methanol in DCM to yield compound 7 (110 mg, 51% yield) as a yellow oil which was analyzed by LC-MS and $^1$H NMR to be pure.

Example 5

Synthesis of Compounds 6 and 15

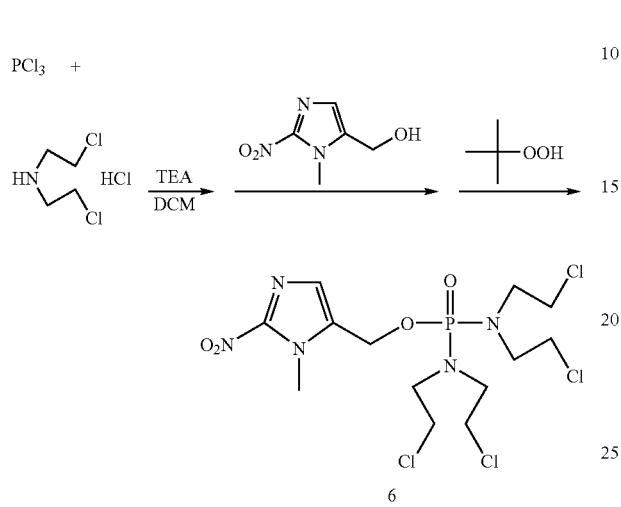

6

To a suspension of bis(2-chloroethyl)ammonium chloride (1.43 g, 8.01 mmol) in dichloromethane (DCM), phosphorus trichloride (0.32 ml, 3.64 mmol) was added at rt followed by addition of TEA (3.05 ml, 21.84 mmol). The reaction mixture was stirred at rt for 30 minutes and then N-methyl 2-nitroimidazolyl methanol (0.474 g, 3.31 mmol) in DME was added. After stirring for 0.5 hour, the reaction mixture was cooled to −20° C. and tert-butyl hydroperoxide (0.7 ml, 3.82 mmol, 5.5 M in Decane) was added. The reaction mixture was warmed to rt over a period of one hour, and poured into 10% aqueous HCl. The organic layer was separated and the aqueous layer was extracted with DCM. The combined organic solution was dried with MgSO$_4$ and concentrated to yield a residue which was purified by flash chromatography with 6-12% methanol in DCM yielding 6.

Compound 15 was synthesized using the method described for the synthesis of Compound 6 above.

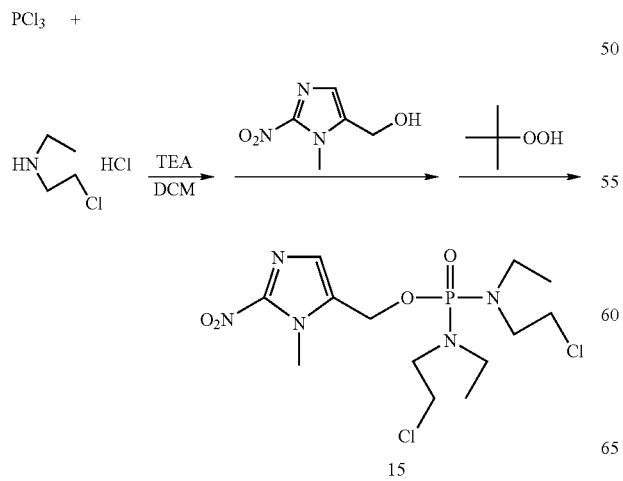

15

Example 6

Synthesis of Compounds 23, 26 and 36

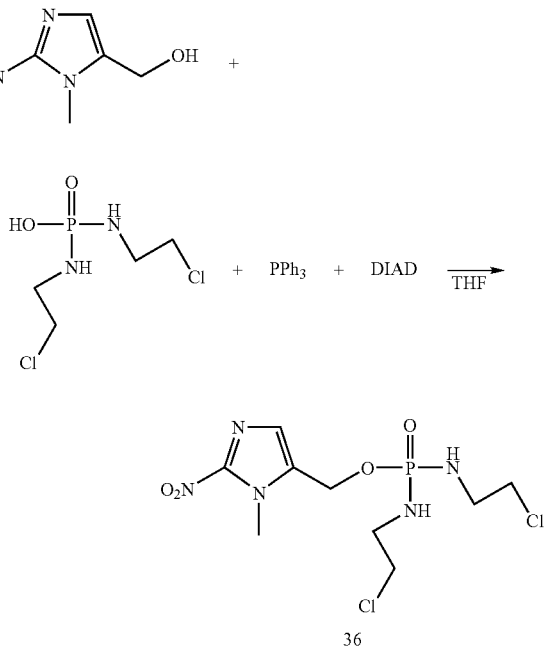

36

To a solution of N-methyl-2-nitroimidazole-5-methanol (180 mg, 1.14 mmol), triphenylphosphine (300 mg, 1.14 mmol), and isophosphoramide mustard (1c, 127 mg, 0.57 mmol) in THF (10 ml), diisopropyl azodicarboxylate (DIAD, 0.22 ml, 1.14 mmol) was added dropwise at rt. After two hours, the reaction mixture was concentrated and the residue separated by flash chromatography with 30-100% acetone in toluene yielding compound 36.

Compounds 23 and 26 were synthesized employing the procedure of Example 6.

Example 7

Synthesis of Compound 1

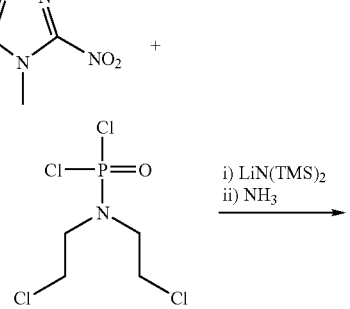

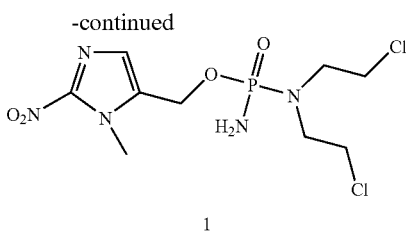

1

N-methyl-2-nitroimidazole-5-methanol (50 mg, 0.318 mmol) was dissolved in dry THF (2 ml) under nitrogen. The solution was cooled to −78° C. and a solution of lithium bis(trimethylsilyl)amide (1M in toluene, 0.35 ml, 0.35 mmol) was added by syringe. After 5 minutes a solution of bis (chloroethyl) phosphoramidic dichloride (91 mg, 0.35 mmol) in THF (2 ml) was added. After stirring at 78° C. for 30 minutes, the temperature was reduced to −20° C. employing a NaCl/ice bath and anhydrous ammonia was bubbled through the reaction mixture for 5 minutes. The reaction mixture was purged with nitrogen, warmed to rt, poured into 25 ml water and extracted with ethyl acetate (4×25 ml). The combined organic layers were dried (MgSO$_4$) and concentrated to give pale yellow oil which was separated by flash chromatography over silica gel using 0-10% methanol in dichloromethane yielding compound 1 (32 mg, 28% yield) of an oil which soldified on standing and was analyzed by LC/MS and $^1$H NMR to be pure.

Example 8

Synthesis of Compounds 24 and 25

To a solution of 2-bromoethylammonium bromide (19.4 g) in DCM (90 mL) at −10° C. was added a solution of POCl$_3$ (2.3 mL) in DCM (4 mL) followed by addition of a solution of TEA (14.1 mL) in DCM (25 mL). The reaction mixture was filtered, the filtrate concentrated to ca. 30% of the original volume and filtered. The residue was washed with DCM (3×25 mL) and the combined DCM portions concentrated to yield a solid to which a mixture of THF (6 mL) and water (8 mL) was added. THF was removed in a rotary evaporator, and the resulting solution chilled overnight in a fridge. The precipitate obtained was filtered, washed with water (10 mL) and ether (30 mL), and dried in vacuo to yield 2.1 g of:

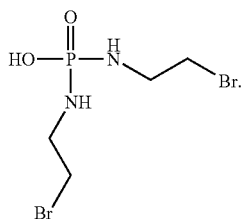

Isophosphoramide mustard

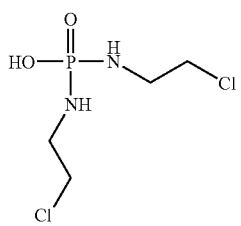

can be synthesized employing the method provided in Example 8, substituting 2-bromoethylammonium bromide with 2-chloroethylammonium chloride. Synthesis of Isophosphoramide mustard has been described (see for example Wiessler et al., supra).

The phosphoramidate alkylator toxin:

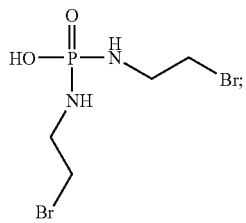

was transformed into compounds 24 and 25, employing the method provided in Example 6 and the appropriate Trigger-OH.

Example 9

Synthesis of Compounds 37-105

The following compounds 37-105 were synthesized employing the Mitsunobu type coupling described for the synthesis of 25 or 36 above, and upon appropriate substitution of the Trigger-OH and the ifosfamide mustard analog employed. For example, for the synthesis of compounds 40, 81, 83, 87, 89, 95, 96, 100, and 104, the ifosfamide mustard analog employed was HOP(=O)(NHCH$_2$CH$_2$Cl)$_2$; in compounds 50, 53, 55, 56, 58-65, 68-71, 73-75, 77-80, 82, 84-86, 88, 90-92, 94, 97-99, 101-103, and 105, the ifosfamide mustard analog employed is HOP(=O)(NHCH$_2$CH$_2$Br)$_2$; in compounds 37, 39, 52, 54, and 93, the ifosfamide mustard analog employed is the R enantiomer of HOP(=O)(NHCHMeCH$_2$Cl)$_2$; in compounds 38, 41, 51, and 57 the ifosfamide mustard analog employed is the S enantiomer of HOP(=O)(NHCHMeCH$_2$Cl)$_2$; in compounds 43-45 and 49 the ifosfamide mustard analog employed was the R enantiomer of HOP(=O)(NHCH(CHMe$_2$)CH$_2$Cl)$_2$; and in compounds 46-48, the ifosfamide mustard analog employed was the S enantiomer of HOP(=O)(NHCH(CHMe$_2$)CH$_2$Cl)$_2$.

The various Trigger-OH compounds employed in the synthesis of Compounds 37-105, included the following Trigger-OH compounds: 1-N-methyl-2-nitroimidazole-5-methanol, 1-N-methyl-5-nitroimidazole-2-methanol, 5-nitrofuran-2-methanol, 5-nitrothiophene-2-methanol;

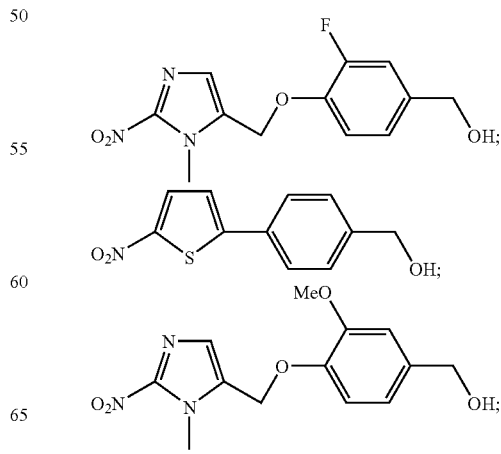

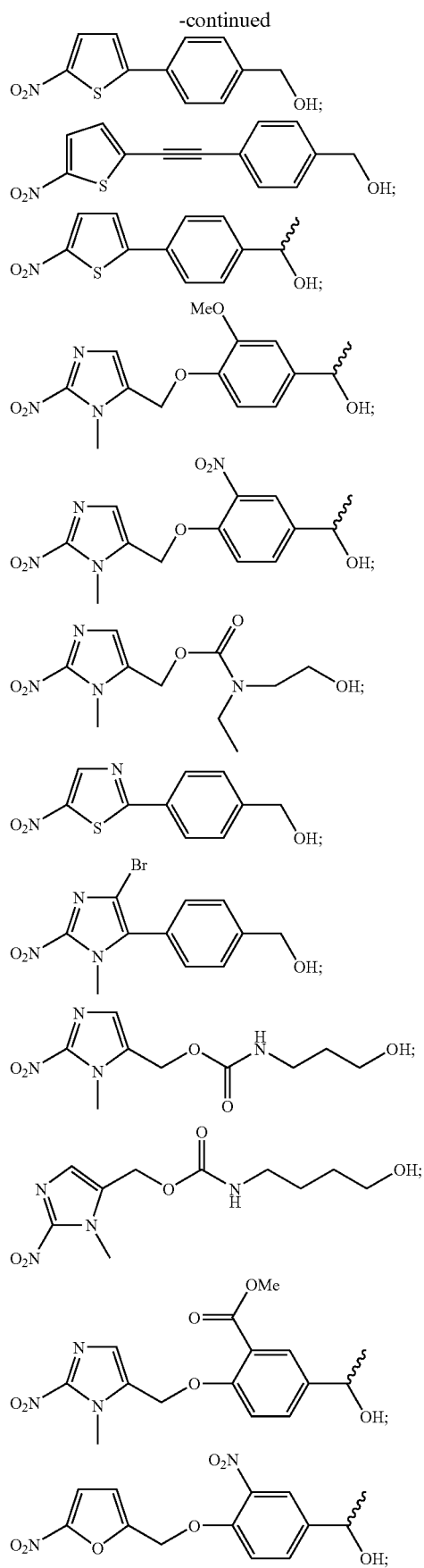
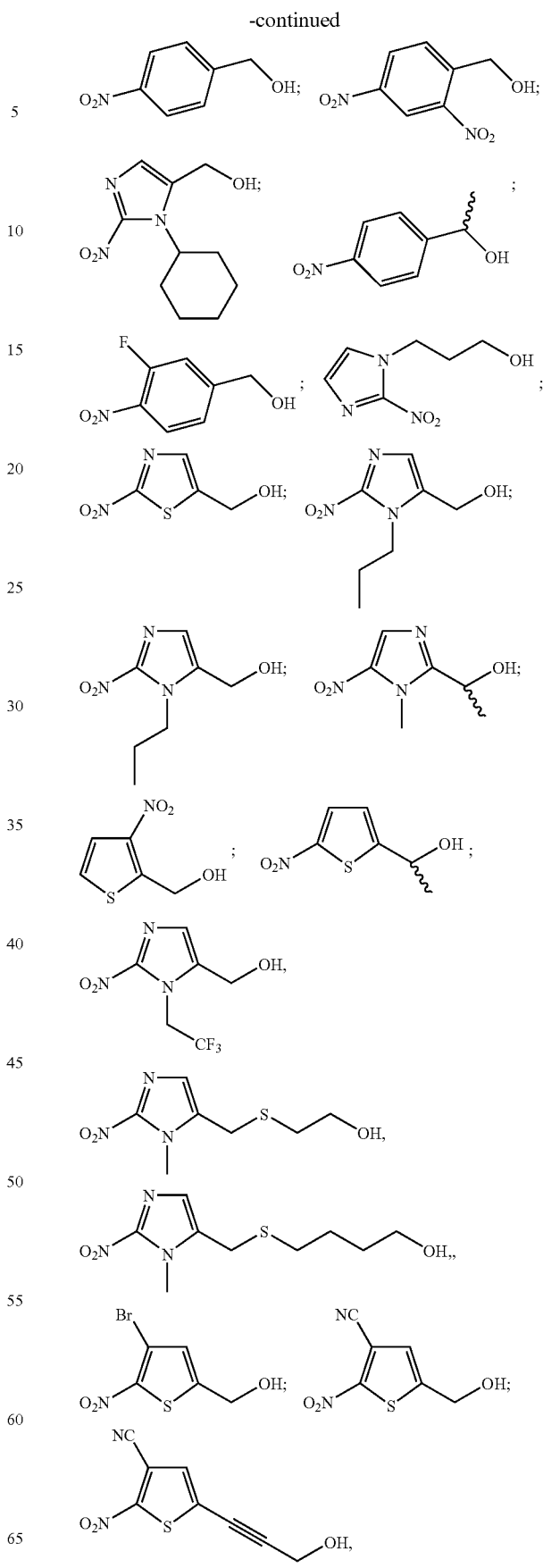

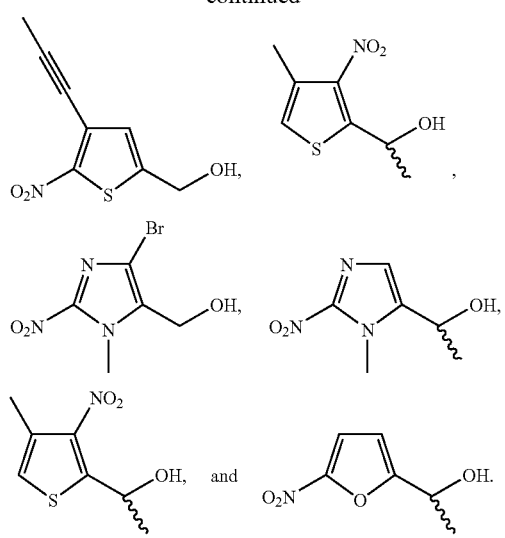
The following compounds were made according to the method described in Example 6.
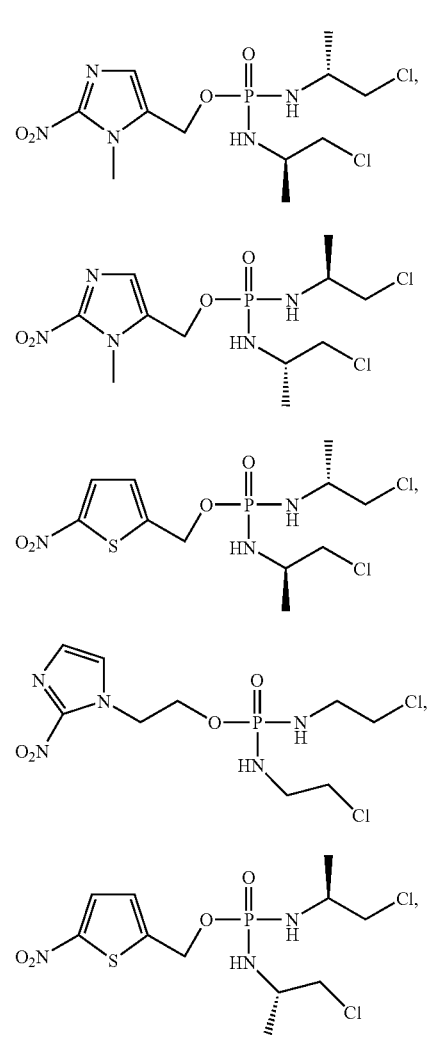
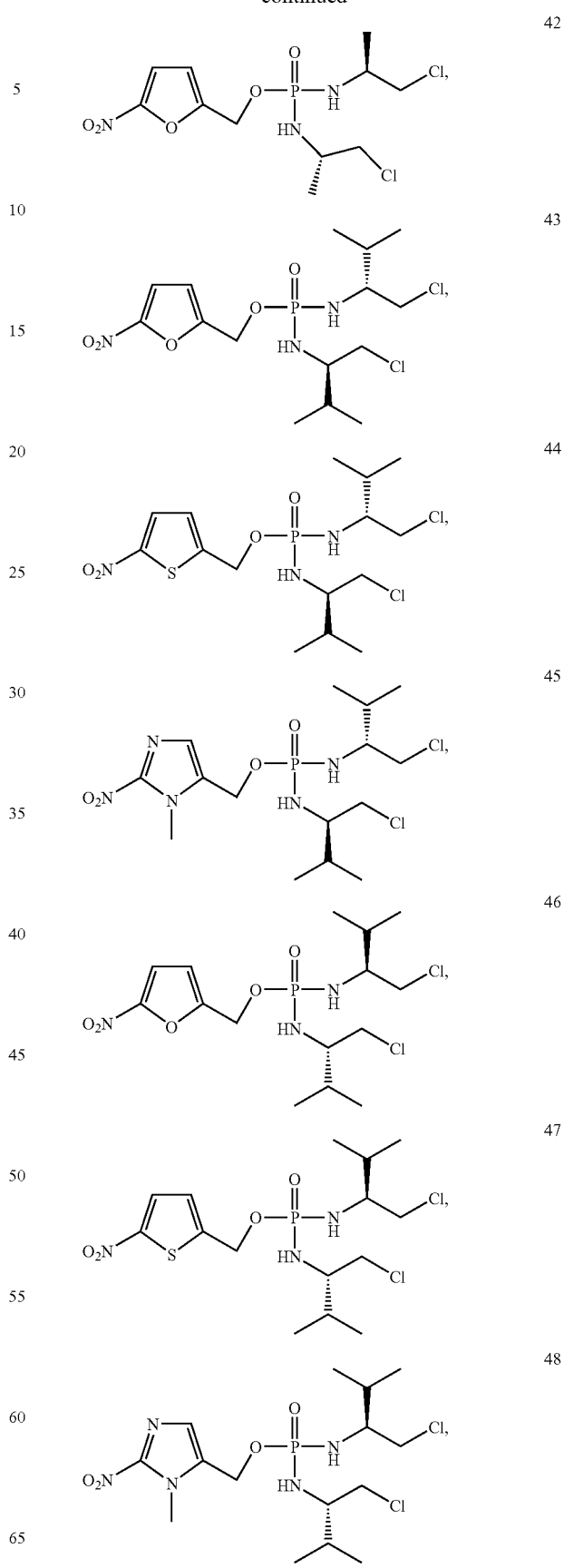

49
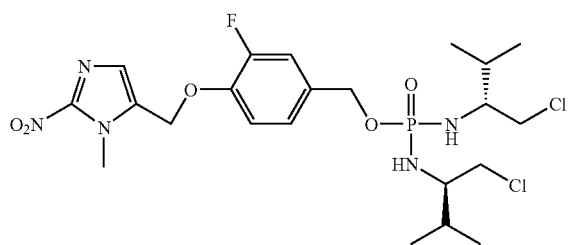
50
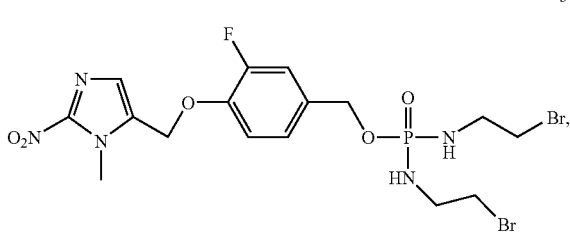
51
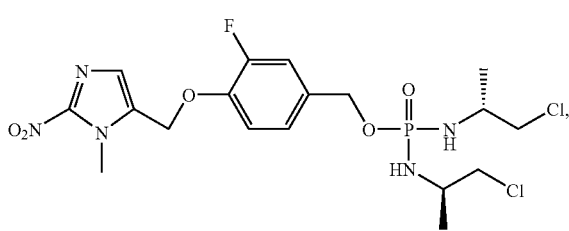
52
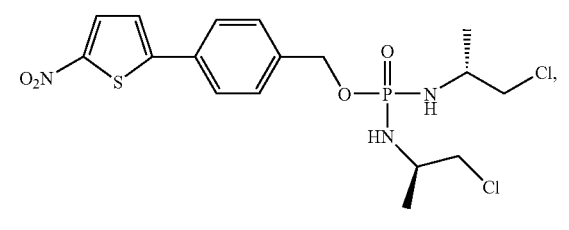
53
54
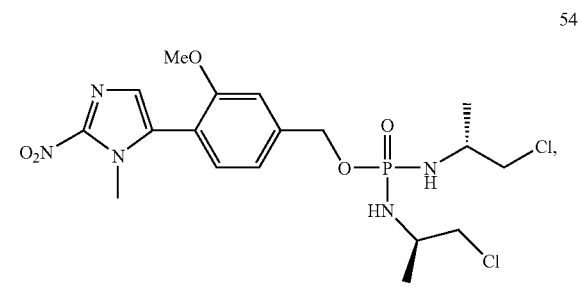
55
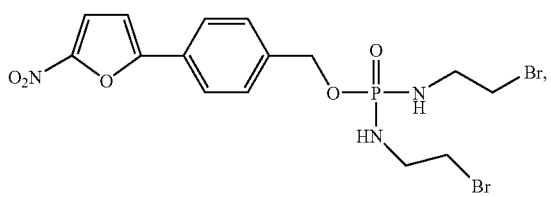
56
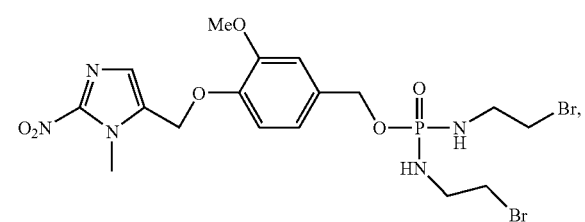
57
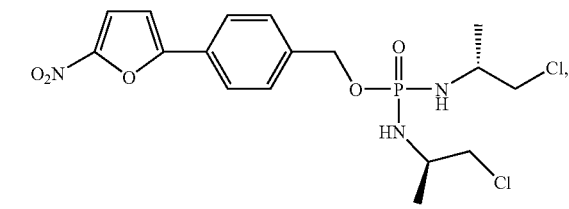
58
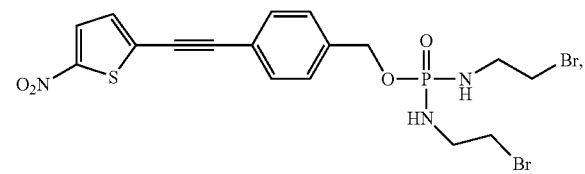
59
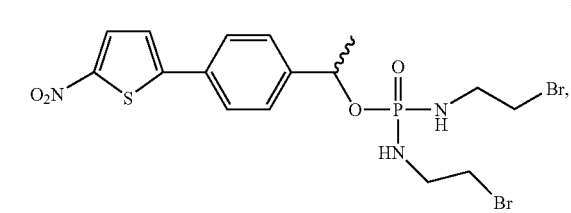
60
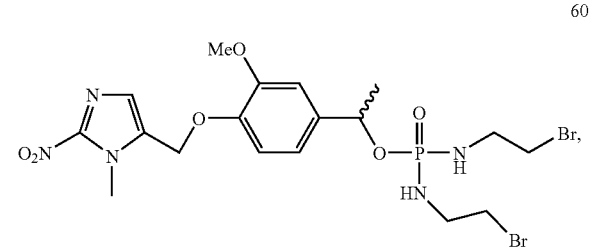
61
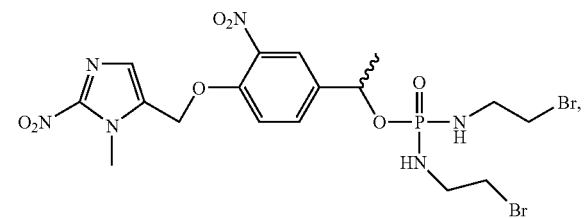

-continued
62
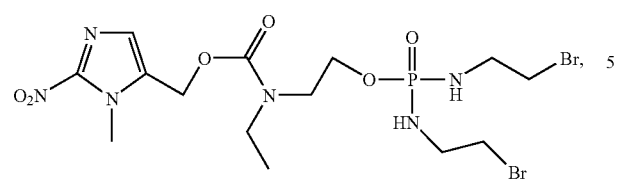
63
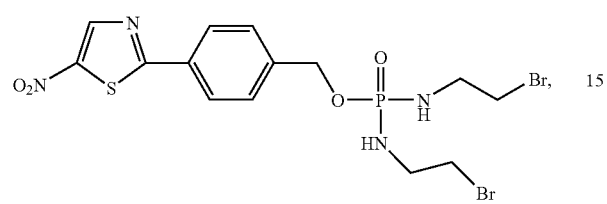
64
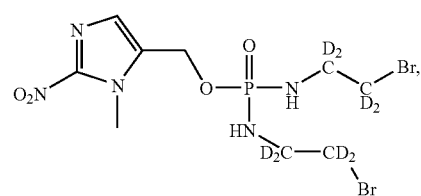
65
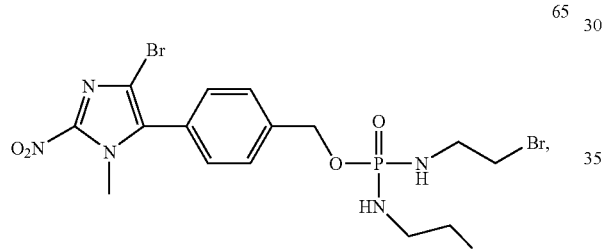
66
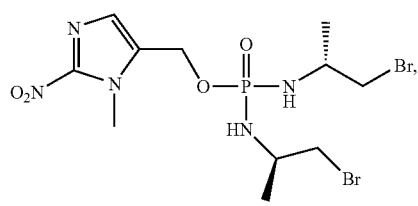
67
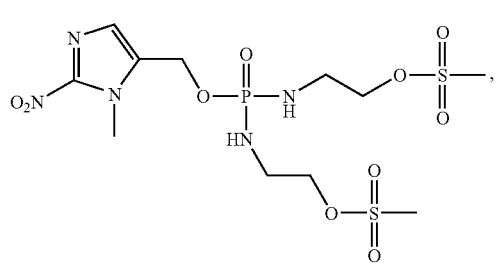
68
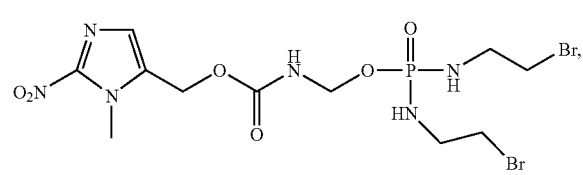
-continued
69
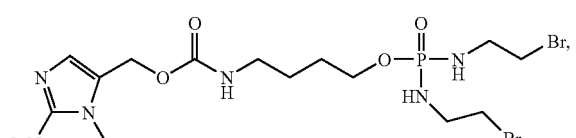
70
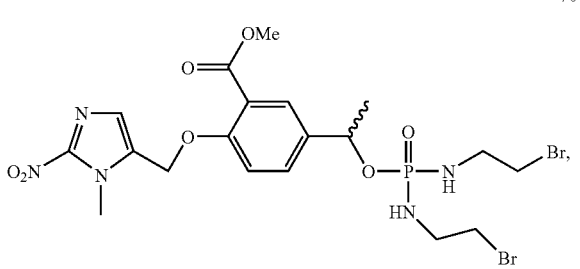
71
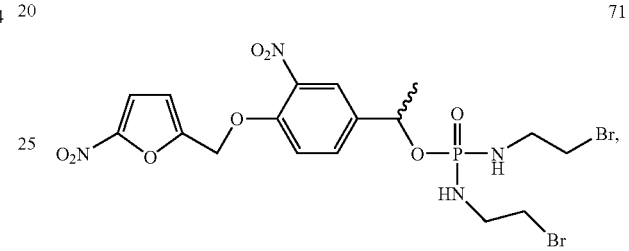
72
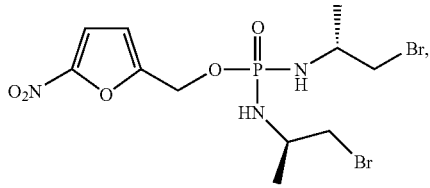
73
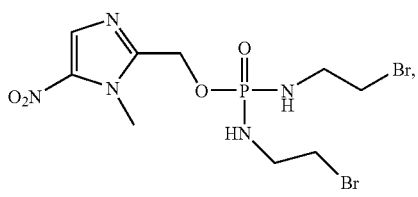
74
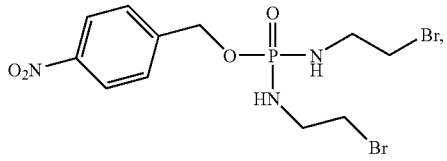
75
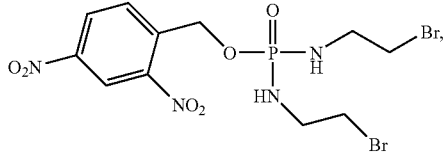
76
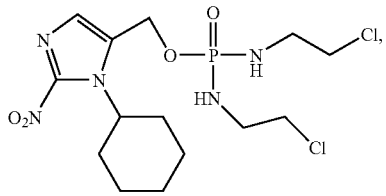

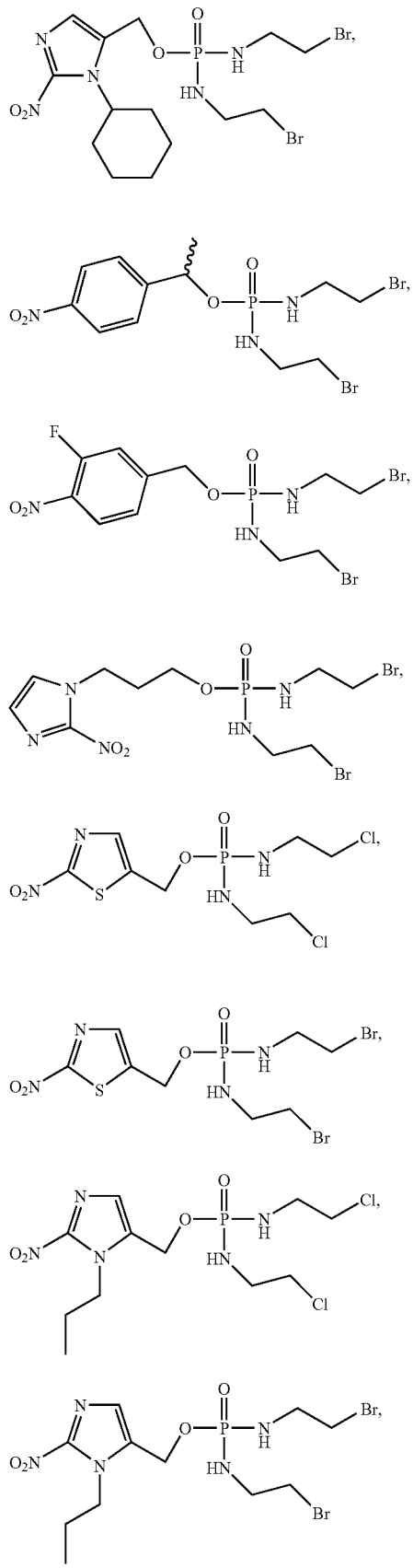
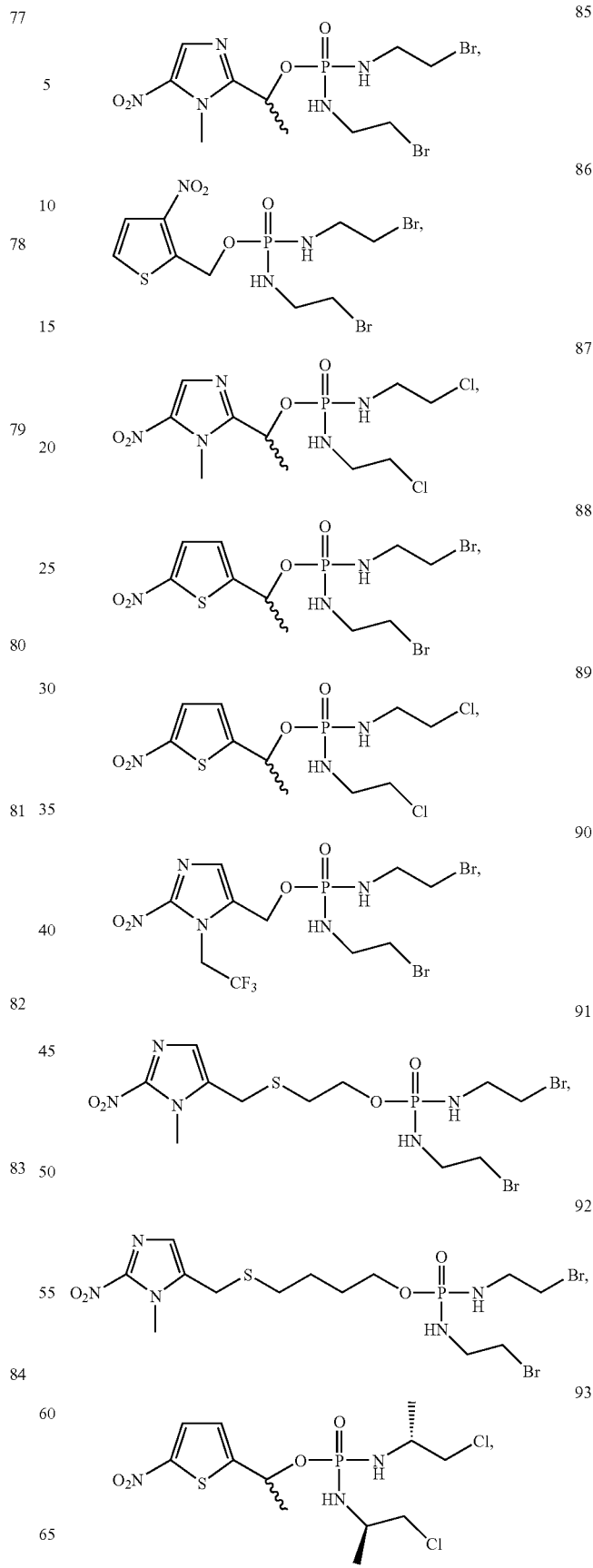

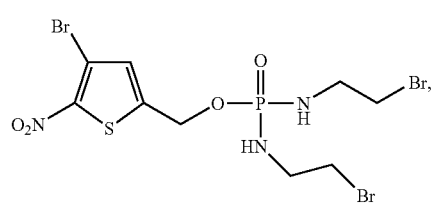
94

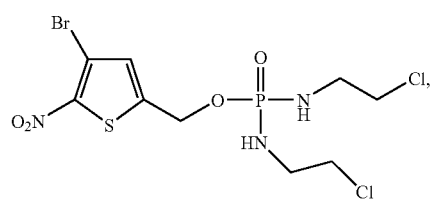
95

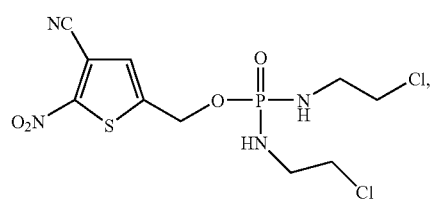
96

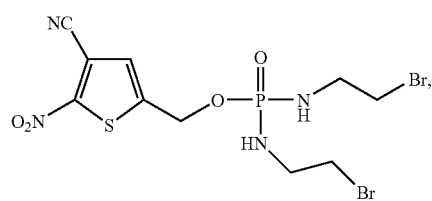
97

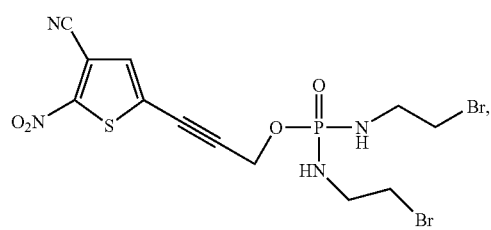
98

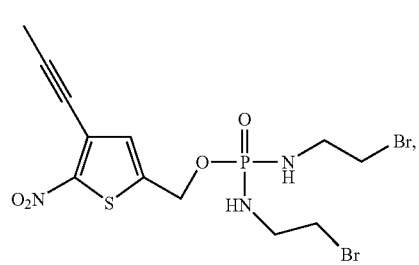
99

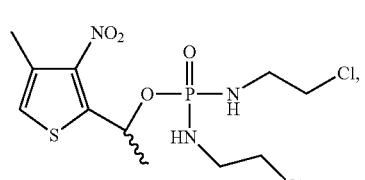
100

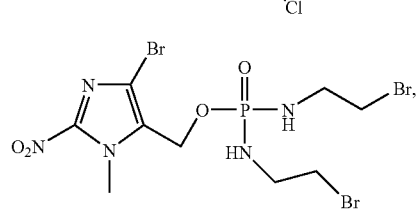
101

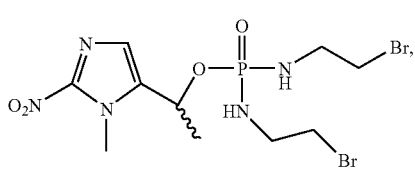
102

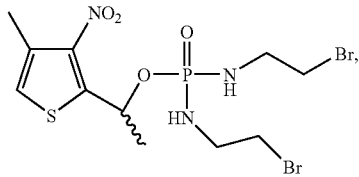
103

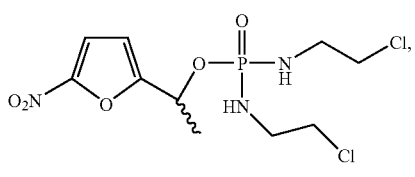
104

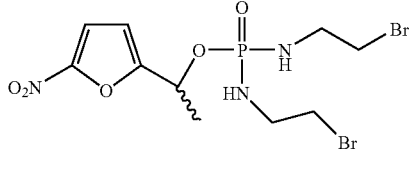
105

Examples 10-26 describe the synthesis of various Trigger-OH compounds employed in the synthesis of phosphoramidate alkylator prodrugs of the invention.

Example 10

Synthesis of Compound 52i

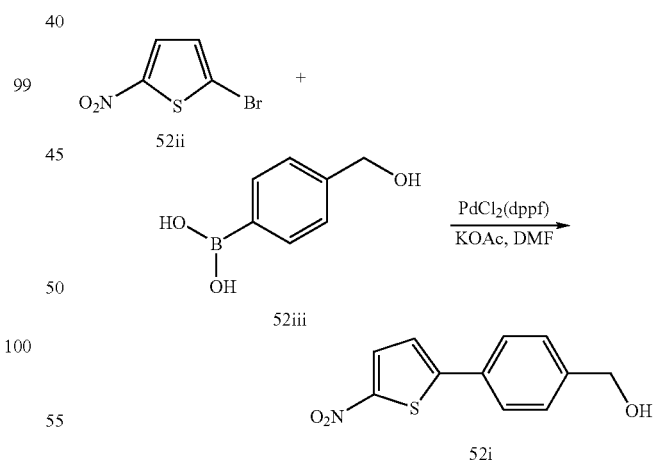

A solution of compound 52ii (100 mg, 0.48 mmol), 52iii (73 mg, 0.48 mmol), and KOAc (190 mg, 1.92 mmol) in DMF (5 ml) was degassed thrice and PdCl$_2$(dppf) (36 mg, 0.048 mmol) added to it at rt under an argon atmosphere. The reaction mixture was heated at 60° C. for two hours, diluted with ethyl acetate (EA) and washed with brine. The organic layer was dried, concentrated, and the residue separated by column chromatography on silica gel employing as eluent EA/Hex (0-80%) to yield 52i.

Compounds 55i, 63i, 59i, 65i, and 68i were prepared in a similar manner as described schematically below:

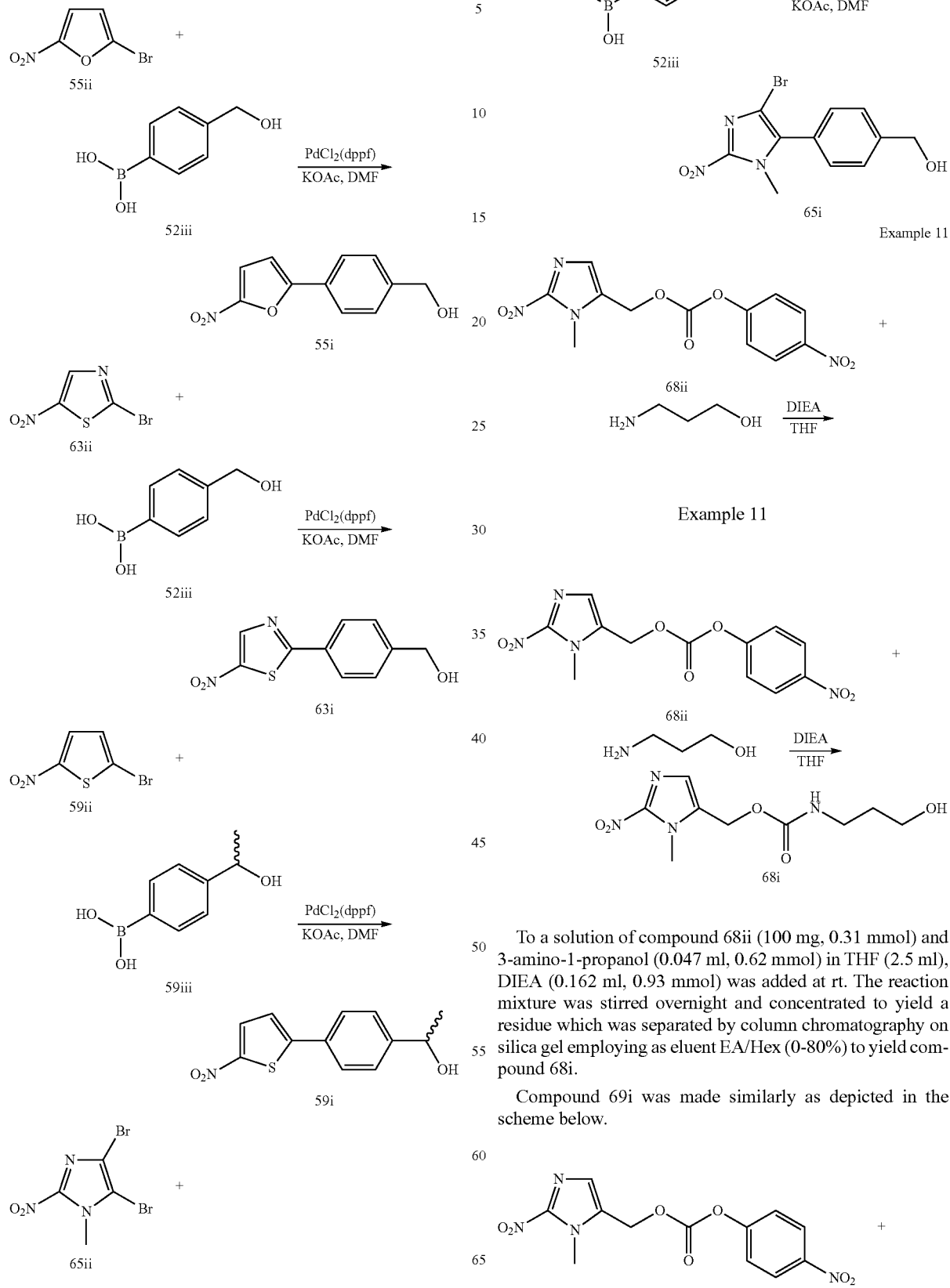

To a solution of compound 68ii (100 mg, 0.31 mmol) and 3-amino-1-propanol (0.047 ml, 0.62 mmol) in THF (2.5 ml), DIEA (0.162 ml, 0.93 mmol) was added at rt. The reaction mixture was stirred overnight and concentrated to yield a residue which was separated by column chromatography on silica gel employing as eluent EA/Hex (0-80%) to yield compound 68i.

Compound 69i was made similarly as depicted in the scheme below.

-continued

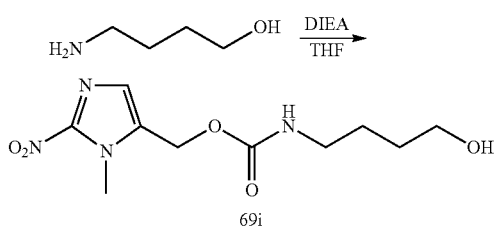

Example 12

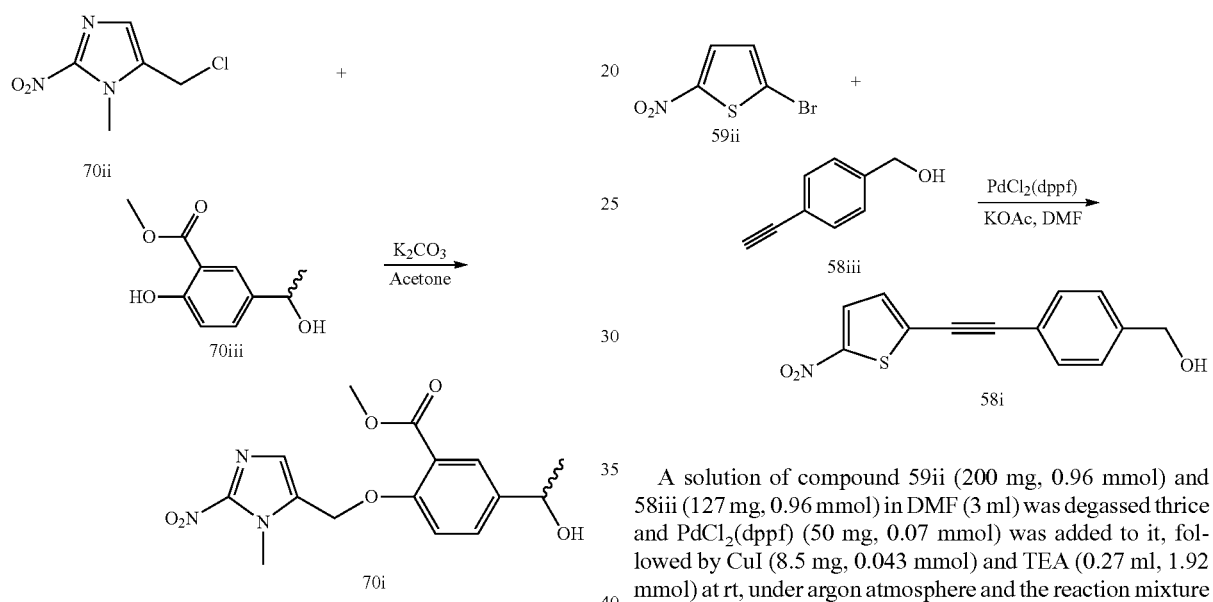

To a solution of compound 70ii (100 mg, 0.87 mmol) and compound 70iii (112 mg, 0.87 mmol) in acetone (8 ml), was added K$_2$CO$_3$ (78.6 mg, 0.87 mmol) at rt. The reaction mixture was heated at 60° C. with stirring for 1 h, filtered, and concentrated to yield a residue which was separated by column chromatography on silica gel employing as eluent EA\Hex(0-60%) to yield compound 70i.

Compound 51i was made similarly as depicted in the scheme below.

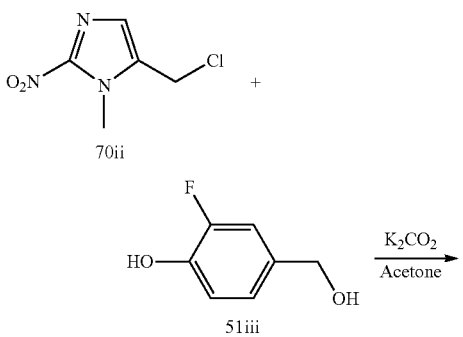

-continued

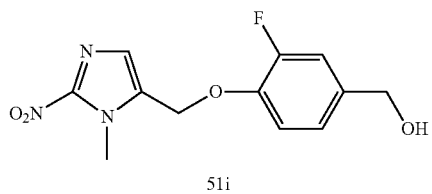

Example 13

HAP Triggers

A solution of compound 59ii (200 mg, 0.96 mmol) and 58iii (127 mg, 0.96 mmol) in DMF (3 ml) was degassed thrice and PdCl$_2$(dppf) (50 mg, 0.07 mmol) was added to it, followed by CuI (8.5 mg, 0.043 mmol) and TEA (0.27 ml, 1.92 mmol) at rt, under argon atmosphere and the reaction mixture was heated at 60° C. for two hours. The reaction mixture was diluted with EA, washed with brine, the organic layer separated, dried, and concentrated to yield a residue which was separated by column chromatography on silica gel employing as eluent EA\Hex (0-70%) to yield compound 58i.

Example 14

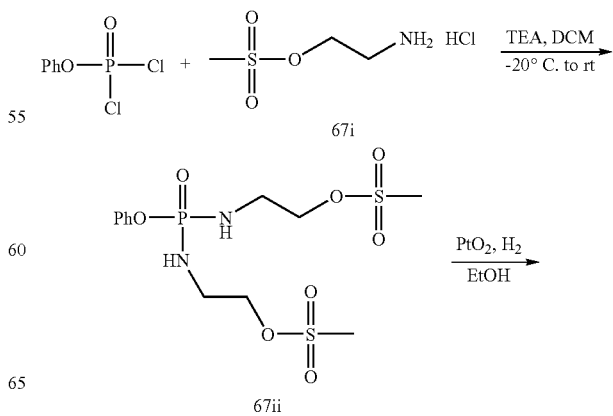

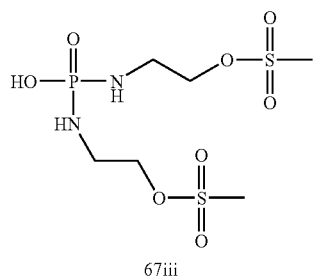

67iii

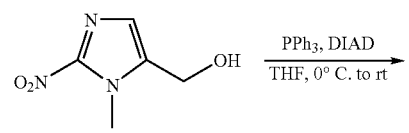

67

To a suspension of 67i (472 mg, 2.69 mmol) in DCM (20 ml) was added phenyldichlorophosphate (0.2 ml, 1.34 mmol) at −20° C., followed by the dropwise addition of TEA (0.75 ml, 5.38 mmol) and stirring. The reaction mixture was warmed up to rt, stirred at rt for 1 h, poured into brine, the organic layer separated, and the aqueous layer extracted with DCM. The combined organic layers were dried with $MgSO_4$ and concentrated. The residue was separated by column chromatography on silica gel employing as eluent EA/hexane (10-100%) to yield compound 67ii. To a solution of compound 67ii (42 mg) in EtOH (5 ml) was added platinum(IV) oxide (20 mg), the reaction mixture degassed, and vigorously stirred under hydrogen for 0.5 h. The reaction mixture was diluted with MeOH, filtered through a syringe filter, the filtrate concentrated under vacuum and coevaperated with toluene to yield compound 67iii. Compound 67iii was reacted with 1-N-methyl-2-nitroimidazole-5-methanol employing a Mitsunobu type reaction as described for the synthesis of Compound 36.

Example 15

Synthesis of Compounds 106 and 107

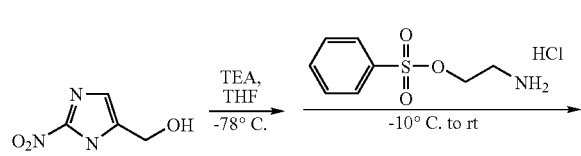

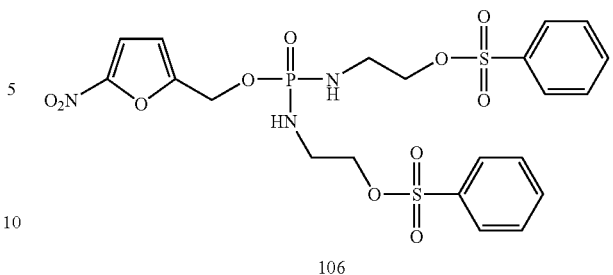

106

To a solution of 5-nitrofurfuryl alcohol (200 mg, 1.4 mmol) in THF (10 ml) was added $POCl_3$ (0.13 ml, 1.4 mmol) at −78° C., followed by the dropwise addition of TEA (0.216 ml, 1.54 mmol). The reaction temperature was warmed to −10° C. in 1 h, 2-(phenylsulfonyl)ethylamine hydrochloride (832 mg, 3.5 mmol) added to it, followed by the addition of TEA (1 ml, 7 mmol). The reaction was warmed to rt, stirred for 1 h, quenched with water and the organic layer separated. The aqueous layer was extracted with DCM twice, the combined organic layers were dried, concentrated to yield a residue which was separated by column chromatography on silica gel employing as eluent acetone\toluene (30 to 100%) to yield product 106. Compound 107:

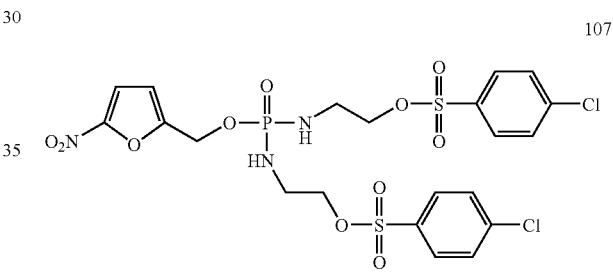

107 was synthesized using a similar method.

Compounds 108-112, shown below:

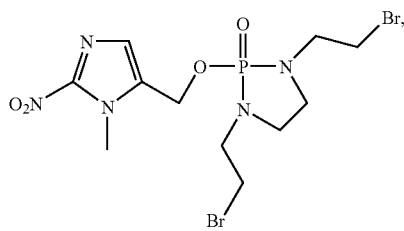

108

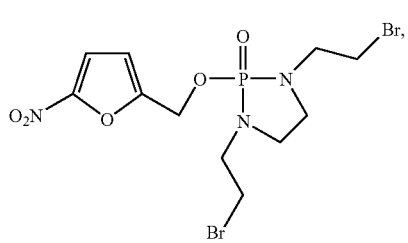

109

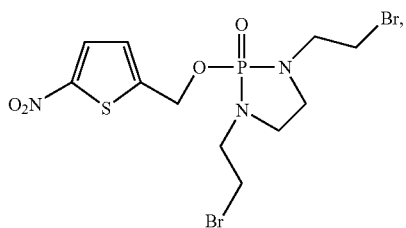

110

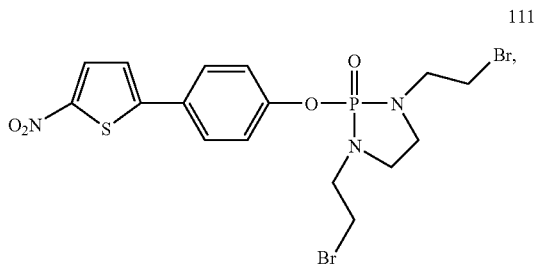

111

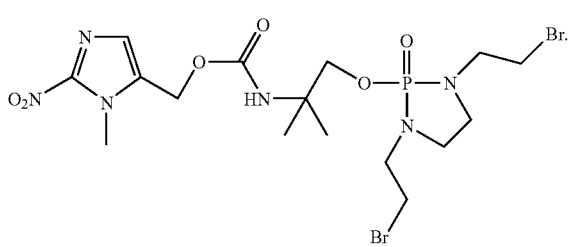

112 were synthesized employing the procedure described for the synthesis of compound 35 in Example 3 and substituting

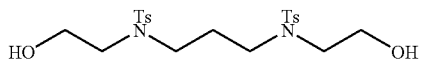

with

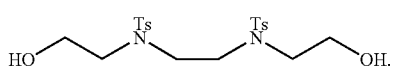

Example 16

Synthesis of Compounds 113-117

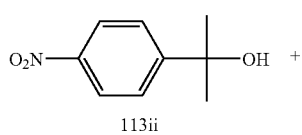

113ii

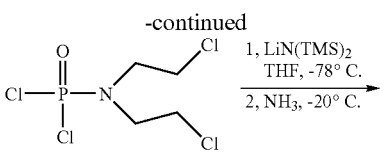

1i

113

Compound 113 was synthesized following a procedure described in Example 7 as described here. To a solution of 113ii (181 mg, 1.16 mmol) in THF (8 mL) was added dropwise LiN(TMS)$_2$ (1.2 mL, 1 M THF solution, 1.2 mmol) at −78° C., followed by the addition of 1i. The reaction mixture was warmed up to −20° C. and NH$_3$ bubbled through the reaction mixture for 5 minutes. Water (20 mL) was added to the reaction mixture and the reaction mixture extracted thrice with EA (30 mL). The combined organic layers were dried and concentrated to yield a residue which was separated by column chromatography on silica gel employing acetone\toluene (30-100%) to yield compound 113.

Compounds 114-117 were synthesized according to the method described for Compound 13 and substituting with the appropriate Trigger-OH as starting material.

114

115

116

117

Example 17

Synthesis of octadeutereated ifosfamide and Compound 64 (octadeuterated-Compound 25)

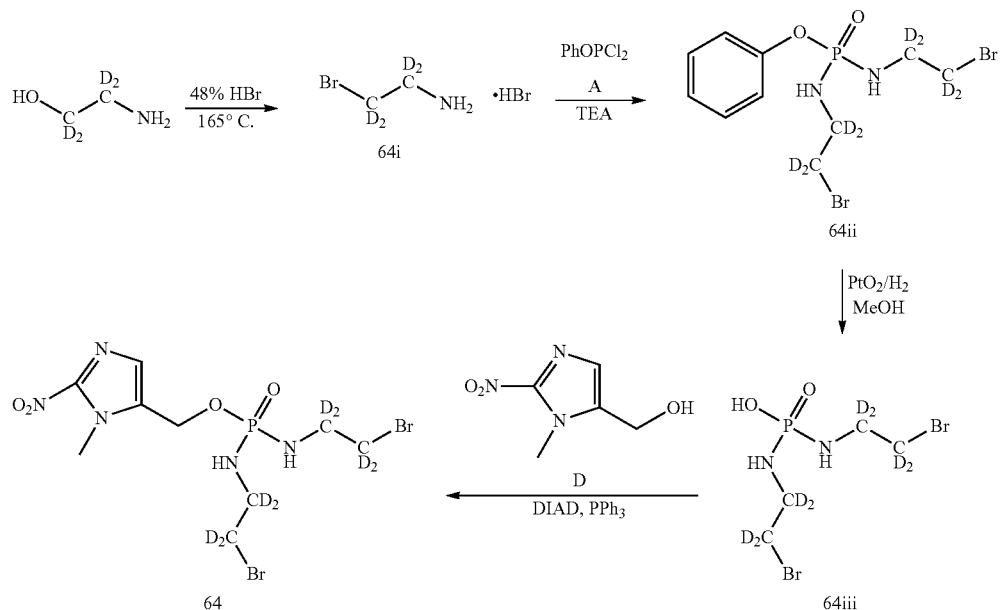

48% HBr (60 mL) was added dropwise to $d_4$-ethanolamine at 0° C. The reaction mixture was stirred for 1 hr at rt and then gently refluxed and slowly distilled, 16 mL liquid being collected in 2 hrs until 155° C. (oil bath). This was replaced twice with 60 mL of 48% HBr and the distillation continued for an additional 5 hr. 90 mL liquid was collected. The resultant solution was heated at 165° C. for 2 hr and evaporated under vacuum. The residue was recrystalled from an absolute ethanol (10 mL)-ethyl acetate (30 mL) to 11.3 g of $d_4$-2-bromoethamine hydrobromide (compound 64i). Compound 64i (19.5 mmol, 1.0 eq.) was added dropwise to a suspension of $d_4$-2-bromoethamine hydrobromide (40.0 mmol, 2.05 eq.) in dry DCM (100 mL) under argon, at −20° C., followed by the dropwise addition of TEA (81.9 mmol, 4.2 eq.) at −20° C. The reaction mixture was stirred at −20° C. for 0.5 h, and at rt for 2 h, poured into water, and extracted twice with DCM (30 mL). The combined organic layers were washed with brine, dried over $Na_2SO_4$, and concentrated under reduced pressure to yield a residue which was separated by column chromatography on silica gel employing as eluent Hexane/EA (100:70(v/v)) to yield 7.0 g of compound 64ii. $PtO_2$ (0.7 g) was added to a solution of compound 64ii (7.0 g) in MeOH (160 mL), the reaction mixture degassed and exchanged with $H_2$ thrice, stirred under $H_2$ for 3 h at rt, and diluted with MeOH until the white solid in the reaction mixture dissolved. The diluted reaction mixture was filtered, the filtrate concentrated under reduced pressure to yield a residue which was washed with anhydrous ether twice to yield 2.9 g of compound 64iii. To a suspension of compounds 64iii (1.92 g 1.0 eq.), 1-N-methyl-2-nitroimidazolemethanol (1.01 g, 1.1 eq.), and $PPh_3$ (2.39 g, 1.5 eq.) in THF (20 mL) was added DIAD (1.76 ml, 1.5 eq.), under argon, at 0° C. The reaction mixture was stirred for 2 hours while being warmed from 0° C. to rt, following which volatiles were removed under vacuum to yield a residue. The residue was separated by flash chromatography on silica gel employing as eluent Acetone/Toluene (100:70(v/v)) to yield 1.35 g of compound 64.

Example 18

Synthesis of Compound 2i

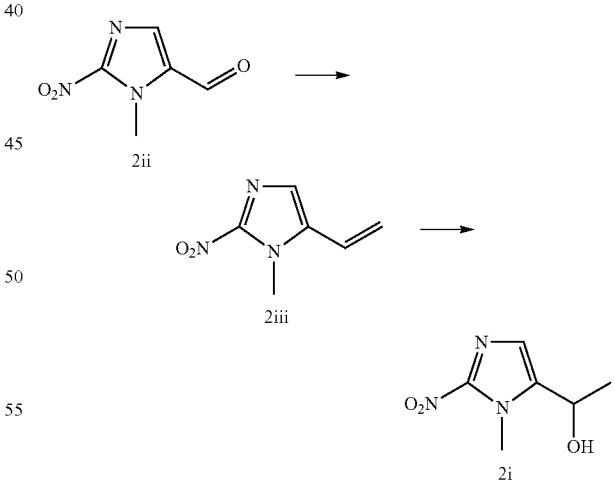

The vinyl derivative, 2iii, was synthesized according to the reference Cavalleri et al., *J. Het. Chem.*, 1972, 9: 979, and oxymercurated as follows. $Hg(OAc)_2$ (208 mg, 0.653 mmol) was dissolved in water (0.7 mL) and THF (0.7 mL), followed by the addition of compound 2iii (100 mg, 0.653 mmol). The reaction mixture was stirred at rt for 1.5 h, $NaBH_4$ (25 mg) added to it in portions, and after stirring for 15 min the reaction poured into water, extracted with EA, the EA layer dried and concentrated to yield a residue which was separated by silica gel column chromatography employing as eluent EA/Hexane (0-100%) to yield compound 2i (16 mg).

Example 22

Synthesis of 1-N-methyl-2-amino imidazole-5-carboxylic acid ethyl ester

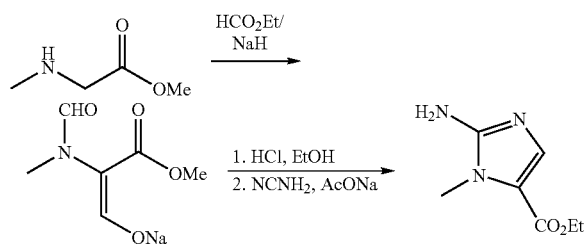

Ethyl formate (500 mL) was added to sarcosin methyl ester hydrochloride (82 g, 585.7 mmol, grounded into powder prior to reaction) contained in a 1-L round-bottomed flask. The reaction mixture was cooled in an ice-water bath, stirred, a gas outlet connected with the flask, NaH (60% oil suspension, 54 g, 1.35 mol) added slowly during a period of 2 h, and stirred at rt for about 14 h. Volatiles were removed using a rotary evaporator to yield a residue which was triturated twice with hexane (500 mL) to yield a sticky light brown paste which was dissolved in ethanol (400 mL) and conc. HCl (50 mL) and stirred at 110° C. for 1.5 h. After the reaction mixture cooled, the white precipitate was filtered off and the residue washed with 2×25 mL of ethanol. The filtrate was evaporated to yield a thick brown oil to which was added 10% aqueous HOAc, H$_2$NCN (45 g, 1.07 mol), and sodium acetate (88 g, 1.07 mol). The reaction mixture was stirred at 90-100° C. for 1.5 h to yield a clear solution which was cooled, its pH adjusted to 1 using concentrated HCl and the resulting solution concentrated to ⅕ its original volume using a rotary evaporator at a temperature not more than 45° C. The concentrated reaction mixture was carefully neutralized by addition of K$_2$CO$_3$ to a pH of 8-9 and extracted with EA (5×200 mL followed by 3×50 mL). The combined ethyl acetate layers were dried over MgSO$_4$, filtered, and volatiles removed to yield 48 g of 1-N-methyl-2-amino imidazole-5-carboxylic acid ethyl ester.

Example 23

Synthesis of 1-N-methyl-2-amino imidazole-5-carboxylic acid ethyl ester

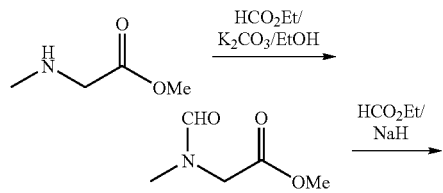

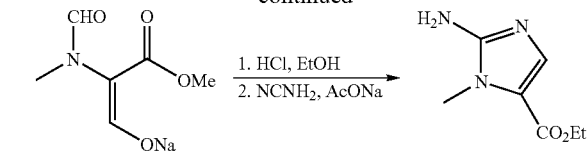

Ethyl formate (850 mL) was added to sarcosine methyl ester HCl salt (205 g, 1.46 mol, grounded into powder prior to use), potassium carbonate (205 g, 1.48 mol), and EtOH (800 mL, stirred overnight at rt, and filtered. The filtrate was concentrated in a rotary evaporator during which the residue separated into two layers. The upper layer was separated and the lower layer was extracted with EA. Combined EA extracts and the upper layer were dried over MgSO$_4$, filtered, and concentrated to yield 185 g (81%) of N-formyl sarcosine methyl ester which was used for the following reaction. NaH (60% oil suspension, 16.0 g, 0.4 mol) was carefully added in several portions in 1 h to a mixture of N-formyl sarcosine methyl ester (50 g, 0.34 mol) and ethyl formate (160 mL) cooled in an ice-water bath. The reaction mixture was stirred, the temperature raised to rt, and the stirring continued overnight. The reaction mixture was triturated twice with hexane (100 mL each time), the residue dissolved in EtOH (100 mL) and concentrated HCl (60 mL), and the reaction mixture stirred at 110° C. After 1 h, the reaction mixture was cooled, filtered, the residue washed with EtOH and the filtrate concentrated to yield a thick brown oil. The oil was added to 10% HOAc in water (200 mL), NH$_2$CN (35 g) and sodium acetate (90 g), stirred at 95° C. After 1 h the reaction mixture was concentrated to ⅓ its original volume in a rotary evaporator and its pH adjusted to about 9 by addition of sodium carbonate. The reaction mixture was then extracted with EA (8×100 mL), the combined EA layers dried, filtered, and concentrated to yield a residue which was purified by recrystallization to yield 1-N-methyl-2-amino imidazole-5-carboxylic acid ethyl ester ("amino ester").

Example 24

Synthesis of 1-N-methyl-2-nitroimidazole-5-carboxylic acid ethyl ester

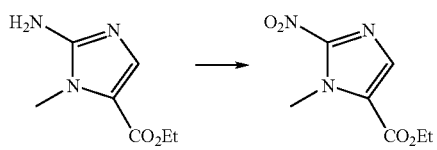

A solution of the amino ester (36.94 g, 0.218 mol) in 200 ml of acetic acid was added drop wise to a solution of sodium nitrite (100 g, 1.449 mol) and water (300 ml) cooled in an ice-water bath, and stirred. The temperature of the reaction mixture, which was measured to be around −5-10° C., was raised to rt and the reaction mixture stirred overnight. The reaction mixture was extracted with DCM (3×150 mL). The combined DCM layers were dried and evaporated to yield a reddish residue which was separated by column chromatography on silica gel employing as eluent EA/hexane (30%) to yield 1-N-methyl-2-nitroimidazole-5-carboxylic acid ethyl ester ("nitro ester") as a light brown solid (27 g, yield 62%).

This method described in Example 24 and employing aqueous acetic acid is an improvement of the method using about 7% sulfuric acid (v/v) for the diazonium ion formation from the amino ester. Using aqueous sulfuric acid, the reaction volume becomes large causing difficulty in stirring the reaction mixture effectively. For example, a reaction involving 150 g of the amino ester required a reaction mixture volume of about 12 L. The sticky nitro ester formed as product in aqueous sulfuric acid and disrupted the stirring of the reaction mixture.

Example 25

Synthesis of 1-N-methyl-2-nitroimidazole-5-carboxylic acid

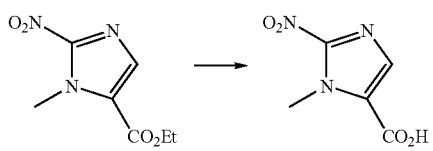

A suspension of the nitro ester (39.2 g, 196.9 mmol) in 1N NaOH (600 mL) and water (200 mL) was stirred at rt for about 20 h to give a clear light brown solution. The pH of the reaction mixture was adjusted to about 1 by addition of conc. HCl and the reaction mixture extracted with EA (5×150 mL). The combined ethyl acetate layers were dried over MgSO$_4$ and concentrated to yield 1-N-methyl-2-nitroimidazole-5-carboxylic acid ("nitro acid") as a light brown solid (32.2 g, 95%).

Example 26

Synthesis of 1-N-methyl-2-nitroimidazole-5-carboxylic acid

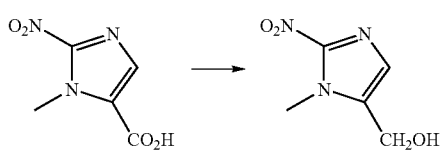

A mixture of the nitro acid (30.82 g, 180.23 mmol) and triethylamine (140 mL, 285 mmol) in anhydrous THF (360 mL) was stirred while the reaction mixture was cooled in a dry ice-acetonitrile bath (temperature <−20° C.). Isobutyl chloroformate (37.8 mL, 288 mmol) was added drop wise to this cooled reaction mixture during a period of 10 min and stirred for 1 h followed by the addition of sodium borohydride (36 g, 947 mmol) and dropwise addition of water during a period of 1 h while maintaining a temperature around or less than 0° C. The reaction mixture was warmed up to 0° C. The solid was filtered off and washed with THF. The combined THF portions were evaporated to yield 1-N-methyl-2-nitroimidazole-5-methanol as an orange solid (25 g) which was recrystallized from ethyl acetate.

Example 27

Synthesis of Compound 119

To a suspension of 1-N-methyl-2-nitroimidazole-5-methanol (50 mg, 0.32 mmol) in DME, LiN(TMS)$_2$ was added at −78° C. with vigorous stirring. After 10 min, compound 119i (67 mg, 0.32 mmol) was added and the reaction mixture was warmed to rt. After 1 h, the reaction mixture was concentrated and the residue was separated by chromatography on silica gel (0-100% acetone\toluene) to yield Compound 119.

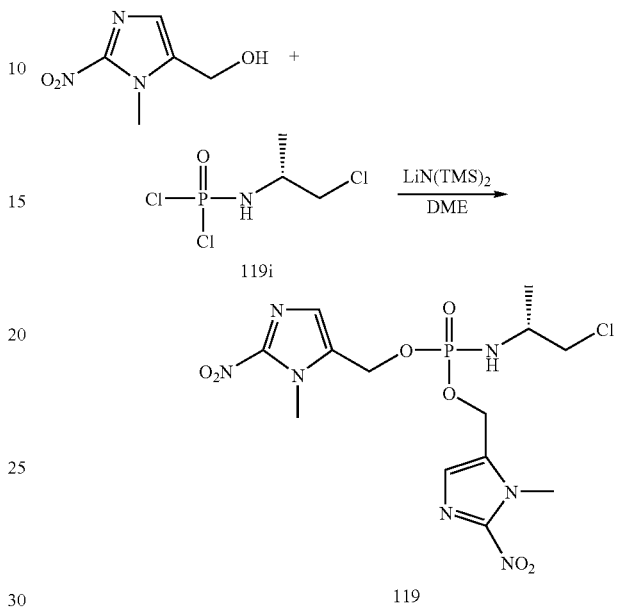

Examples 28A-28V

Compounds 134 to 155 were synthesized by employing the corresponding substituted phosphormamidate and hydroxy substituted Trigger (Trigger-OH), according to the procedures described in Examples 1-27 above.

Example 29A

The solubility of the following compounds is as listed below:

| Compound | Solubility (in saline at room temperature) |
| --- | --- |
| 10 | 10 mg/mL |
| 25 | 15 mg/mL |
| 73 | 10 mg/mL |
| 155 | <1 mg/mL |

Example 29B

Antiproliferation Assay

To determine the effect of phosphoramidate alkylator prodrugs on cell proliferation, the antiproliferative activity of these compounds was tested in a multi-well Alamar Blue-based assay. Cell growth in the presence and absence of the test compound was compared, as measured by a fluorescence plate reader at excitation 550 nm and emission 590 nm (see Biosource International Inc., Tech Application Notes, *Use of Alamar Blue in the measurement of Cell Viability and Toxicity*, Determining IC$_{50}$). The following cell lines were tested with 20,000 cells/well/5004 medium: NCI-H460 cells (ATCC HTB-177, RPMI medium (Gibco Products, Invitrogen Corporation, Carlsbad, Calif.)), HT29 cells (ATCC HTB-38, RPMI medium (Gibco)), MES-SA cells (ATCC CRL-1976, McCoy's 5a medium (ATCC)), MES-SA/Dx5 cells ((ATCC CRL-1977), McCoy's 5a medium (ATCC)), ACHN cells (ATCC CRL-1611, Minimum essential medium, Eagle (ATCC)), PC3 cells (ATCC CRL-1435, Ham's F12K medium (ATCC)). The cells were seeded in glass inserts placed in each well of a 24-well plate in the density and medium as specified above one day prior to compound testing. After 24 hours, these plates were divided into two groups—anoxia group and air group. A test compound was added to each well (2004, volume) in the treatment groups at concentrations varying from 100, 30, 10, 3, 1, 0.3, 0.1, 0.03, to 0.01 μM. All test compounds were serially diluted in complete medium with final DMSO concentrations less than or equal to 1% in each well. The cells in the anoxia treatment group were incubated for 2 hours in a Bactron II anaerobic chamber. The cells in the air treatment group were incubated for 2 hours in standard tissue-culture incubators. Following the 2 hour treatment with a test compound, the test compound was removed from each well, cells were washed with 500 μL, medium, and incubated for 3 days in 500 μL, fresh medium. After 3 days, cells were stained with 10% Alamar Blue for 2 hours after which the capacity of cells to proliferate was measured (as mentioned above), and the 50% growth inhibitory concentration ($GI_{50}$ (also referred to $IC_{50}$ herein)) of test compounds was calculated and tabulated in Table X below.

TABLE X

| | $IC_{50}$ values (μM) | | | | | |
|---|---|---|---|---|---|---|
| Compound | H460 Anoxia/Air | HT29 Anoxia/Air | MES-SA Anoxia/Air | MES-SA/Dx5 Anoxia/Air | ACHN Anoxia/Air | PC3 Anoxia/Air |
| P2 | 44/>100 | | | | | |
| 1 | 0.4/72 | 50/>100 | | 1/>100 | | |
| 23 | 0.04/5 | 7.5/— | | | | |
| 23 | 0.1/14 | | | | | |
| 154 | 0.9/2 | | | | | |
| 139 | 16/100 | | | | | |
| 140 | 5/65 | | | | | |
| 2 | 8/>100 | | | | | |
| 5 | 0.05/6 | 10/>100 | | | | |
| 22 | 0.7/16 | | | | | |
| 3 | >20/>100 | | | | | |
| 142 | >40/>100 | | | | | |
| 4 | 40/>100 | | | | | |
| 143 | 4.5/3.5 | | | | | |
| 6 | 0.7/>100 | 22/>100 | | 5/>100 | | |
| 144 | 7/>100 | | | | | |
| 145 | >100/>100 | | | | | |
| 147 | >100/>100 | | | | | |
| 7 | 0.14/25 | 7/>100 | | 0.59/83 | | |
| 11 | 5.2/>100 | | | | | |
| 12 | 1.7/>100 | | | | | |
| 9 | >10/>100 | | | | | |
| 8 | 0.013/0.6 | | | | | |
| 36 | 0.88/>100 | 55/>100 | 5/>100 | 7.5/>100 | | |
| 149 | 50/>100 | | | | | |
| 15 | 0.08/1 | | | | | |
| 16 | 1.6/>100 | | | | | |
| 17 | 1/9 | | | | | |
| 18 | 3.4/9 | | | | | |
| 14 | 8.5/>100 | | | | | |
| 150 | —/21 | | | | | |
| 25 | 0.15/86 | 16/>100 | 0.9/>100 | 0.3/>100 | 0.2/62 | 0.6/>100 |
| 26 | 0.1/35 | | | | | |
| 10 | 100/>100 | | | | | |
| 31 | 83/>100 | | | | | |
| 24 | 0.01/4 | | 0.1/2 | 0.1/0.8 | | |
| 27 | 25/100 | | | | | |
| 28 | 0.15/20 | | | | | |
| 32 | 50/100 | | | | | |
| 33 | 8/46 | | | | | |
| 34 | 0.01/1.8 | 0.8/57 | 0.13/10 | | | |
| 35 | 0.075/50 | | | | | |
| 35 | 0.05/55 | 1.8/>100 | 1/100 | | | |
| 74 | >100/>100 | | | | | |
| 75 | 9/26 | | | | | |
| 76 | 9/>100 | | | | | |
| 77 | 1.6/5.5 | | | | | |
| 78 | >100/>100 | | | | | |
| 79 | 3.5/3.5 | | | | | |
| 118 | >100/>100 | | | | | |
| 80 | >100/>100 | | | | | |
| 81 | 0.05/0.3 | | | | | |
| 82 | 0.03/0.02 | | | | | |
| 83 | 0.3/>100 | | | | | |
| 84 | 0.003/40 | | | | | |

TABLE X-continued

| Compound | H460 Anoxia/Air | HT29 Anoxia/Air | MES-SA Anoxia/Air | MES-SA/Dx5 Anoxia/Air | ACHN Anoxia/Air | PC3 Anoxia/Air |
|---|---|---|---|---|---|---|
| 85 | 0.7/100 | | | | | |
| 86 | 1.4/3 | | | | | |
| 119 | 0.3/>100 | | | | | |
| 37 | 0.36/>100 | | | | | |
| 87 | 22/>100 | | | | | |
| 88 | 0.03/0.53 | | | | | |
| 89 | 0.33/3.7 | | | | | |
| 90 | 0.01/3.4 | | | | | |
| 38 | 0.33/>100 | | | | | |
| 106 | 0.09/3.5 | | | | | |
| 107 | 0.06/2.8 | | | | | |
| 108 | 1.1/>100 | | | | | |
| 109 | 0.3/13 | | | | | |
| 110 | 0.3/21 | | | | | |
| 39 | 0.2/5 | | | | | |
| 91 | —/>100 | | | | | |
| 92 | >100/>100 | | | | | |
| 41 | —/7 | | | | | |
| 42 | 0.5/9 | | | | | |
| 93 | 0.1/3.8 | | | | | |
| 94 | 0.3/2 | | | | | |
| 95 | —/2.7 | | | | | |
| 96 | 0.1/0.1 | | | | | |
| 120 | 0.3/50 | | | | | |
| 121 | 0.04/1 | | | | | |
| 122 | 0.04/1.3 | | | | | |
| 43 | 2/60 | | | | | |
| 44 | 3/100 | | | | | |
| 45 | 6/>100 | | | | | |
| 46 | 5/>100 | | | | | |
| 47 | 4/>100 | | | | | |
| 48 | —/>100 | | | | | |
| 97 | 0.01/0.1 | | | | | |
| 49 | —/>100 | | | | | |
| 50 | 0.1/3 | | | | | |
| 98 | 0.1/2 | | | | | |
| 51 | 3/7 | | | | | |
| 52 | 15/20 | | | | | |
| 53 | 3/10 | | | | | |
| 99 | 0.1/1 | | | | | |
| 100 | 0.5/35 | | | | | |
| 54 | 1/60 | | | | | |
| 55 | 5/12 | | | | | |
| 56 | 0.5/10 | | | | | |
| 123 | 100/>100 | | | | | |
| 57 | 14/100 | | | | | |
| 124 | —/0 | | | | | |
| 125 | —/100 | | | | | |
| 126 | —/0 | | | | | |
| 111 | 50/100 | | | | | |
| 58 | 5/10 | | | | | |
| 59 | 2/6 | | | | | |
| 60 | 15/15 | | | | | |
| 61 | 0.3/4 | | | | | |
| 62 | 2/45 | | | | | |
| 63 | 1/8 | | | | | |
| 127 | 0.02/5 | | | | | |
| 128 | 0.02/10 | | | | | |
| 112 | 70/>100 | | | | | |
| 103 | 0.02/2 | | | | | |
| 113 | 1/100 | | | | | |
| 65 | 25/75 | | | | | |
| 114 | 1/80 | | | | | |
| 129 | 1/100 | | | | | |
| 115 | 0.5/5 | | | | | |
| 116 | 0.5/15 | | | | | |
| 130 | 0.7/20 | | | | | |
| 66 | 0.3/100 | | | | | |
| 67 | 48/>100 | | | | | |
| 68 | 100/>100 | | | | | |
| 69 | 71/>100 | | | | | |
| 70 | 2/65 | | | | | |
| 117 | 8/70 | | | | | |
| 71 | 0.1/0.1 | | | | | |

TABLE X-continued

| | IC$_{50}$ values (μM) | | | | | |
|---|---|---|---|---|---|---|
| Compound | H460 Anoxia/Air | HT29 Anoxia/Air | MES-SA Anoxia/Air | MES-SA/Dx5 Anoxia/Air | ACHN Anoxia/Air | PC3 Anoxia/Air |
| 72 | 0.5/12 | | | | | |
| 131 | >100/>100 | | | | | |
| 132 | 3/3 | | | | | |
| 133 | 22/>100 | | | | | |
| 104 | 0.4/12 | | | | | |
| 105 | <0.1/1 | | | | | |

Example 30

Antiproliferation Assay

Oxygen Dependence

To determine the oxygen dependence of phosphoramidate alkylator prodrugs, the antiproliferative activity of these compounds was tested in a multi-well Alamar Blue-based assay as previously described (see Example 29). NCI-H460 cells (ATCC HTB-177, RPMI medium (Gibco)) or HT29 (ATCC HTB-38, RPMI medium (Gibco)) were seeded at 20,000 cells/well/500 μL medium in glass inserts in 24-well plates one day prior to testing. The cells were incubated for 2 hours in a Bactron II anaerobic chamber flushed with gasses of the desired oxygen concentrations varying from anoxia, 0.1%, 0.3%, 0.6%, 1%, 10% oxygen, and air. The calculated IC$_{50}$ values (μM) are tabulated in Table Y1 (H460 cells) or Table Y2 (HT29 cells) below.

TABLE Y1

| | IC$_{50}$ values (μM) in H460 cells | | | | | | |
|---|---|---|---|---|---|---|---|
| Compound | N$_2$ | 0.1% O$_2$ | 0.3% O$_2$ | 0.6% O$_2$ | 1% O$_2$ | 10% O$_2$ | Air |
| 1 | 0.3 | | 10 | 7 | 50 | | 100 |
| 23 | 0.05 | 5 | | 6 | 5 | | 5 |
| 5 | 0.03 | 1 | | 1 | 10 | 5 | 40 |
| 36 | 1 | 30 | | 60 | 60 | >100 | >100 |
| 16 | 0.3 | 10 | | 10 | | 100 | >100 |
| 25 | 0.1 | 1 | 3 | 5 | 10 | 25 | 55 |
| 26 | 0.3 | 3 | | 6 | 5 | 10 | 40 |
| 10 | >100 | >100 | | >100 | >100 | | >100 |
| 24 | 0.007 | | | 0.85 | | | >1 |
| 34 | 0.01 | | 1 | | | | 5 |
| 35 | 0.05 | | 6 | 5 | 40 | | 50 |
| 84 | 0 | | | 3 | | | 40 |
| 119 | 0.3 | | | >100 | | | >100 |
| 37 | 0.5 | | | 25 | | | >100 |
| 88 | 0.03 | | 0.5 | 0.2 | | | 0.5 |
| 38 | 0.4 | | | 45 | >100 | | |
| 106 | 0.1 | | | 0.7 | | | 4 |
| 108 | 1 | | | >100 | | | >100 |
| 109 | 0.3 | | | 10 | | | 15 |
| 110 | 0.3 | | | 3 | | | 25 |
| 44 | | | | 45 | | | >100 |
| 46 | | | | 50 | | | 100 |
| 47 | | | | 60 | | | 100 |
| 97 | 0.006 | | | 0.01 | | | 0.02 |
| 49 | | | | 100 | | | 100 |
| 50 | | | | 3 | | | 3 |
| 98 | | | | 0.5 | | | 2 |
| 51 | | | | 7 | | | 7 |
| 52 | | | | 10 | | | 20 |
| 53 | | | | 5 | | | 10 |
| 99 | | | | 0.5 | | | 1 |
| 100 | 0.5 | | | 10 | | | 35 |
| 54 | 1 | | | 30 | | | 60 |
| 55 | 5 | | | 8 | | | 12 |
| 56 | 0.5 | | | 8 | | | 10 |
| 123 | >100 | | | >100 | | | >100 |
| 61 | 0.3 | | | 4 | | | 4 |
| 62 | 2 | | | 30 | | | 45 |
| 63 | 1 | | | 15 | | | 8 |
| 127 | 0.02 | | | 1 | | | 5 |
| 128 | 0.02 | | | 1 | | | 10 |
| 113 | 1 | | | >100 | | | >100 |
| 114 | 1 | | | 5 | | | 80 |
| 66 | 0.3 | | | 20 | | | 100 |
| 70 | 2 | | | 30 | | | 65 |

TABLE Y2

IC$_{50}$ values (μM) in HT29 cells

| Compound | N$_2$ | 0.1% O$_2$ | 0.3% O$_2$ | 0.6% O$_2$ | 1% O$_2$ | 10% O$_2$ | Air |
|---|---|---|---|---|---|---|---|
| 25 | 2 | | | 25 | | | >100 |

Example 31

Clonogenic Assay

Oxygen Dependence

To determine the oxygen dependence of phosphoramidate alkylator prodrugs, a clonogenic survival assay was performed. Cells were plated in 60 mm glass dishes (5×10$^5$ cells per dish in 5 mL of medium) 2 days prior to compound testing. The following cell lines were tested: NCI-H460 cells (ATCC HTB-177, RPMI medium (Gibco)), HT29 cells (ATCC HTB-38, RPMI medium (Gibco)), PC3 cells (ATCC CRL-1435, Ham's F12K medium (ATCC)). A solution of the test compound was made in complete medium immediately before the test and added directly to cells (2 mL volume). Anoxia or hypoxia (less than 200 ppm O$_2$) was achieved by exposing the glass dishes in a Bactron II anaerobic chamber or in aluminum vessels (see Example 33) for 2 hours. For the anaerobic chamber, desired levels of oxygenation between 200 ppm and air were achieved by flushing the anaerobic chamber with pre-calibrated gases prior to experimentation. For the aluminum vessels, anoxia or hypoxia was achieved by exposing the glass dishes in pre-warmed, air tight aluminum jigs to a series of five rapid evacuations and flushings with 95% nitrogen plus 5% carbon dioxide in a 37° C. water bath on a shaking platform (controls are flushed as well). After the fifth evacuation and flushing, the platform (with water bath and jigs) was shaken for 5 minutes, after which one more evacuation and flushing was performed, and the jigs were transferred to a shaker in a 37 degree C. incubator for the remainder of the 1 to 2 hour drug exposure. Levels of oxygenation between 200 ppm and air were achieved by varying the degree and number of evacuations. The oxygen concentrations in the medium and gas phases were checked using an oxygen electrode (Anima, Phoenixville, Pa.) in a specially modified aluminum jig that allowed for monitoring of both gas and liquid phases. Following the exposure to drug, the glass dishes were removed from the chamber or aluminum vessels and the drug was washed off the cells by rinsing with medium. The cells were then trypsinized and plated for clonogenic survival in plastic Petri dishes. Ten to 14 days later, the dishes were stained with crystal violet (0.25% in 95% ethanol), and colonies containing more than 50 cells were counted (see Example 33). The 90% growth inhibitory concentration (IC$_{90}$, 90% killing, 10% survival) of test compounds was calculated and tabulated in Table Y3 below.

TABLE Y3

IC$_{90}$ values (μM)

| Compound (Cell Line) | N2 | 0.1% O2 | 0.6% O2 | Air |
|---|---|---|---|---|
| 23 (H460) | 0.3 | | 0.6 | 5 |
| 25 (H460) | 0.1 | 0.4 | 5 | 30 |
| 25 (HT29) | 0.2 | | 3 | 40 |
| 25 (PC3) | 0.3 | | | 50 |
| 24 (H460) | 0.07 | | 0.25 | 14 |
| 35 (H460) | 0.5 | | 3 | 30 |

TABLE Y3-continued

IC$_{90}$ values (μM)

| Compound (Cell Line) | N2 | 0.1% O2 | 0.6% O2 | Air |
|---|---|---|---|---|
| 37 (H460) | 0.2 | | 5 | 90 |
| 70 (H460) | 2 | | 8 | 20 |

Example 32

Electrochemistry

To determine the electrochemical properties and reduction potentials of phosphoramidate alkylator prodrugs, cyclic voltammograms of these compounds were generated by Bioanalytical Systems, Inc. All experiments were conducted with glassy carbon (3.0 mm diameter) working electrodes, Ag/AgCl reference electrodes, and platinum wire auxiliary electrodes. Compounds were dissolved in 1 mL methanol to make final drug concentrations between 0.5 and 1.5 mM after the addition of 9 mL Phosphate Buffered Saline (PBS). The solution was added to an electrochemical cell vial and sparged with Argon for 5 minutes to remove most of the oxygen. Cyclic voltammetry was performed at 100 mV/sec and at 10,000 mV/sec scan rates at a glassy carbon working electrode. One test run was performed at a CGME mercury electrode (CGME in SMDE mode, 150 μm bore capillary, size 8 drop), but little difference was observed between mercury and glassy carbon voltammograms, so the mercury electrode was not used further. The single electron or multiple electron reduction potentials of compounds were generated at each scan rate and are tabulated in the table below.

TABLE

Reduction Potentials (mV)

| Compound | 100 mV/sec | 10,000 mV/sec |
|---|---|---|
| 1 | −596 | −638 |
| 5 | −606 | −634 |
| 36 | −609 | −634 |
| 25 | −594 | −626 |
| 24 | −568 | −636 |
| 34 | −584 | −663 |
| 78 | −704 | −746 |
| 82 | −428, −610 | −414, −769 |
| 88 | −559 | −629 |
| 108 | −614 | −593 |
| 103 | −638, −769, −875 | −756 |
| 2-NO$_2$-Imidazole | −634 | −693 |
| 5-NO$_2$-Furan | −487 | −638 |
| 4-NO$_2$-Benzene | −712, −1106 | −735, −1268 |

Example 33

Clonogenic Survival Assay

The phosphoramidate alkylator prodrugs of the invention were tested in the assay as follows. Exponentially growing human H460 cells (obtained from the ATCC) were seeded into 60 mm notched glass plates at a density of between 2.5 and 5×10$^5$ cells per plate and grown in RPMI medium supplemented with 10% fetal bovine serum for 2 days prior to initiating drug treatment. On the day of the test, drug stocks of known concentrations were prepared in complete medium, and 2 ml of the desired stock added to each plate. To achieve complete equilibration between the surrounding gas phase and the liquid phase, the lid of the glass plate was removed and the plate shaken for 5 minutes on an orbital shaker. The plates were recovered and stored inside a glove-box. The glove-box was evacuated and gassed with either a certified anoxic gas mixture (95% nitrogen and 5% carbon dioxide) or with an aerobic (normoxic) gas mixture (95% air and 5% carbon dioxide). Cells were then incubated with the drug for 2 hours at 37° C.

At the end of prodrug treatment, plates were removed from each vessel, and the prodrug was promptly removed from the cells. Plates were washed with phosphate buffered saline and a solution of trypsin-EDTA and then trypsinized for 5 minutes at 37° C. Detached cells were neutralized with medium plus serum and collected by centrifugation for 5 min at 100×g. Cells were resuspended at approximately $1\times10^6$ cells/ml and diluted 10 fold to yield stock concentrations for plating. The concentration of each stock was determined by counting with a Coulter Z2 particle counter. Known numbers of cells were plated, and the plates were placed in an incubator for between 7 and 10 days. Colonies were fixed and stained with a solution of 95% ethanol and 0.25% crystal violet. Colonies of greater than 50 cells were counted, and the surviving fraction was determined.

HT 29 and cell based clonogenic assays were performed in the same way as described above and in Example 31.

Cytotoxicity of compounds (Tables 1A and 1B) were determined in hypoxia and in normoxia by clonogenic assay employing H460 and HT29 cell lines as provided in Example 31 and this example and expressed as $IC_{90}$ in μM, and by anti-proliferation assay performed by modifying a multi-well assay described by Hay et al., *J. Med. Chem.*, 2003, 46:169-82 employing H460, HT29, HCT116, and DX-5 cell lines and expressed as $IC_{50}$ in μM (see Example 29). The ratio of $IC_{50}$ or $IC_{90}$ determined in normoxia and hypoxia is called hypoxia cytotoxicity ratio (HCR) and can be a measure of the hypoxia selective cytotoxicity of the prodrugs of the present invention.

TABLE 1A

| Cpd # | logP | Hypoxia P | Hypoxia C | Normoxia P | Normoxia C | HCR P | HCR C |
|---|---|---|---|---|---|---|---|
| P3 |  |  | 0.25 | 10 |  | 40 | 40 |
| P2 |  | 44.0 |  | >100.0 |  | >5 |  |
| S1 |  | >40 |  | >100 |  | >3 |  |
| S2 |  | 7 |  | >100 |  | >14 |  |
| 1 |  | 0.4 | 0.35 | 72.0 | 75.0 | 180 | 200 |
| 2 |  | 8 |  | >100 |  | >12 |  |
| 3 |  | >20 |  | >100 |  | >5 |  |
| 4 |  | 40 |  | >100 |  | >2 |  |
| 5 | 1 | 4.5 |  | 3.5 |  | 1 |  |
| 6 | 0.9 | 0.7 |  | >100 |  | >140 |  |

TABLE 1A-continued

| Cpd # | logP | Hypoxia P | Hypoxia C | Normoxia P | Normoxia C | HCR P | HCR C |
|---|---|---|---|---|---|---|---|
| P22 |  | 4.5 |  | 3.5 |  | ca. 1 |  |
| 7 | 1.4 | 0.14 |  | 25 |  | 180 |  |
| 8 |  | 0.01 |  | 0.6 |  | 60 |  |
| 9 |  | >10 |  | >100 |  | >10 |  |
| 10 |  | 100 |  | >100 |  | >1 |  |
| 11 |  | 5.2 |  | >100 |  | >20 |  |
| 12 |  | 1.7 |  | >100 |  | >50 |  |
| 14 |  | 8.5 |  | >100 |  | >12 |  |
| 15 |  | 0.08 |  | 1 |  | 12 |  |
| 16 | 0.5 | 1.6 | 0.2 | 100 | 35 | 60 | 175 |
| 17 |  | 1 |  | 9 |  | 9 |  |
| 18 |  | 3.4 |  | 9 |  | 3 |  |
| 20 |  | 1 |  | 8.5 |  | 8 |  |
| 21 |  | 0.25 |  | 7.8 |  | 26 |  |
| 22 |  | 0.7 |  | 16 |  | 23 |  |
| 23 |  | 0.04 | 0.2 | 5 | 10 | 125 | 50 |
| 24 |  | 0.01 |  | 4 |  | 400 |  |
| 25 |  | 0.05 |  | 50 |  | 1000 |  |
| 26 |  | 0.1 |  | 35 |  | 350 |  |
| 27 |  | 2.5 |  | 100 |  | 40 |  |
| 31 |  | 83 |  | >100 |  | >1 |  |
| 32 |  | 50 |  | 100 |  | 2 |  |
| 34 |  | <0.01 |  | 1.8 |  | >180 |  |
| 35 |  | 0.075 |  | 50 |  | 625 |  |
| 36 | −0.1 | 0.88 | 0.2 | >100 | >100 | >110 | >500 |

S1

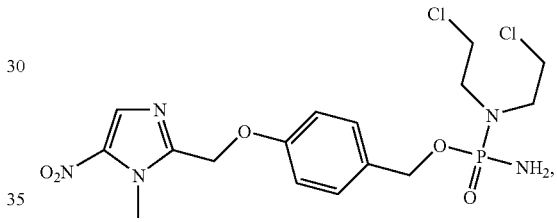

S2

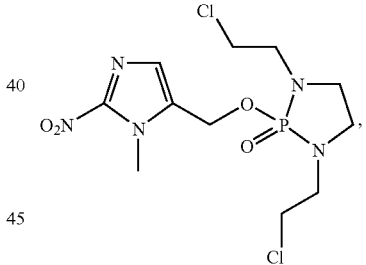

TABLE 1B

| Comp No. | HT29 P H | HT29 P N | HT29 C H | HT29 C N | HT29 HCR P | HT29 HCR C | DX-5 P H | DX-5 P N | DX-5 HCR | HCT116 P H | HCT116 P N | HCT116 HCR |
|---|---|---|---|---|---|---|---|---|---|---|---|---|
| 1 | 50 | 100 | 0.4 | 100 | >2 | >100 | 1 | >100 | >100 |  |  |  |
| 23 | 7.5 |  | 2 |  |  |  |  |  |  |  |  |  |
| 5 | 10 | >100 |  |  | >10 |  |  |  |  |  |  |  |
| 6 | 55 | >100 |  |  | >2 |  | 5 | >100 | >20 |  |  |  |
| 7 | 7(100) | >100 |  |  | >5(1) |  | 0.6 | 83 | 140 |  |  |  |
| 36 | 55(35) | >100 | 3 |  | >2 |  | 7.5 | >100 | >13 | 5 | >100 | >20 |
| 25 | 16 | >100 |  |  | >6 |  | 1 | >100 | >100 | 0.9 | >100 | >100 |
| 34 | 0.8 | 57 |  |  | 70 |  |  |  |  | 0.13 | 10 | 77 |

P = Proliferation;
C = Clonogenic;
H = Hypoxia;
N = Normoxic

Example 34

Effect of Compound 25 on Cell Cycle Distribution

Cells (H60, PC3 and HT29) were seeded at a density of $1.0 \times 10^6$ cells/3 ml medium per 60 mm dish. After 24 h attachment, cells were exposed to Compound 25 at the indicated concentrations for 2 h under either normoxia (air) or anoxia (nitrogen). Cells were washed twice, and incubated for an additional 22 h in fresh medium. Cells were trypsinized, centrifuged, and fixed in 75% ethanol at least for 24 h at $-20°$ C. Cell cycle distribution was determined using Guava Cell Cycle reagent (Guava, Hayward, Calif.) by flow cytometry (Guava, Hayward, Calif.). The data demonstrate that Compound 25 induces cell cycle arrest in an oxygen- and concentration-dependent manner in multiple human cancer cell lines.

| μM | | $G_0/G_1$ | S | $G_2/M$ |
|---|---|---|---|---|
| | | H460 cells | | |
| 0 | Air | 56 | 12 | 30 |
| | Nitrogen | 59 | 11 | 26 |
| 0.005 | Air | 38 | 18 | 42 |
| | Nitrogen | 50 | 12 | 38 |
| 0.05 | Air | 58 | 11 | 28 |
| | Nitrogen | 30 | 7 | 59 |
| 0.5 | Air | 58 | 11 | 28 |
| | Nitrogen | 23 | 31 | 40 |
| 5 | Air | 42 | 6 | 59 |
| | Nitrogen | 47 | 15 | 17 |
| 50 | Air | 14 | 19 | 65 |
| | Nitrogen | 33 | 14 | 11 |
| | | PC3 cells | | |
| 0 | Air | 54 | 13 | 33 |
| | Nitrogen | 60 | 12 | 28 |
| 0.0005 | Air | 55 | 12 | 32 |
| | Nitrogen | 59 | 10 | 31 |
| 0.005 | Air | 52 | 13 | 34 |
| | Nitrogen | 56 | 11 | 32 |
| 0.05 | Air | 55 | 12 | 33 |
| | Nitrogen | 43 | 12 | 44 |
| 0.5 | Air | 55 | 13 | 32 |
| | Nitrogen | 21 | 33 | 46 |
| 5 | Air | 55 | 12 | 32 |
| | Nitrogen | 35 | 38 | 26 |
| | | HT29 cells | | |
| 0 | Air | 50 | 14 | 36 |
| | Nitrogen | 47 | 13 | 39 |
| 0.005 | Air | 52 | 12 | 35 |
| | Nitrogen | 46 | 14 | 40 |
| 0.05 | Air | 50 | 15 | 35 |
| | Nitrogen | 37 | 11 | 52 |
| 0.5 | Air | 48 | 14 | 37 |
| | Nitrogen | 8 | 8 | 84 |
| 5 | Air | 47 | 13 | 39 |
| | Nitrogen | 14 | 50 | 36 |
| 5 | Air | | | |
| | Nitrogen | | | |

Example 35

Spheroid Model

Two human cancer cell lines were used in these spheroid studies to determine the efficacy of the hypoxic activated phosphoramidate alkylator prodrugs. HT29 colorectal adenocarcinoma (colon carcinoma) cells were seeded directly into a 125 ml spinner flask at 10,000 cells/mL and grown in RPMI medium supplemented with 10% FBS and antibiotics. As these cells divided, they adhered to each other and formed spheroids. H460 lung carcinoma cells were seeded into a flask coated with a non-adherent surface to form small balls of cells that can be seeded into a spinner flask. To initiate H460 cell seeds, 150 $cm^2$ tissue culture flasks were coated with 1% agarose and then 10,000 cells per flask were added and allowed to grow in RPMI medium supplemented with 10% FBS and antibiotics for 3 to 5 days before seeding into spinner cultures. For both cell lines, growth medium was changed every day after the spheroids became visible to the eye.

In order to determine the morphology and the location of hypoxic regions within an intact spheroid, whole spheroids were prepared for histology. For frozen sections, intact spheroids were washed in phosphate buffered saline (PBS) and embedded in OCT and rapidly frozen in a dry ice/2-methylbutane solution before being stored at $-80°$ C. For paraffin embedded sections, intact spheroids were fixed in a freshly prepared solution of 4% paraformaldehyde in PBS and subsequently embedded and sectioned.

To assess the ability of a phosphoramidate alkylator prodrug to penetrate to the inner hypoxic cancer cells, become activated, release the phosphoramidate alkylator, and kill those inner cancer cells, the clonogenic survival of spheroids exposed to drug for 2 h was measured.

Spheroids were placed in a new growth medium and incubated for at least 1 h before beginning experiments. Spheroids between 500 and 600 μm were isolated by filtering the spheroid culture through a series of sterile mesh filters of defined size. Between 10 and 20 spheroids were placed on a siliconized notched 60 mm Pyrex dish in 3 mL of medium with the desired concentration of the test compound. The dishes were placed in sealed aluminum vessels and exposed to a series of evacuations and gassings with certified gases containing 5% $CO_2$ and a defined amount of $O_2$ (0% $O_2$, 3% $O_2$, 10% $O_2$ or air). Spheroids were incubated in a shaking water bath to ensure both the equilibrium of the dissolved $O_2$ in solution and the integrity of the spheroids in solution for 2 h. The test compound was removed and the spheroids were washed before being completely digested with trypsin. Since the necrotic core contains cellular debris a treatment with DNase I was required to yield a uniform single cell-suspension. Cells were resuspended at $10^6$/mL and plated for clonogenic survival.

Initial dose response experiments were performed in monolayer cells under nitrogen, 0.6% $O_2$, or air to establish the appropriate dose range and the oxygen dependence of phosphoramidate alkylator release from a phosphoramidate alkylator prodrug. Clonogenic survival was the end point and the data are summarized by the $IC_{90}$ values (the inhibitory concentration required to kill 90% of the cells and yield 10% survival). Daunorubicin and cisplatin, each of which penetrates into speroids to a different extent, were employed to kill the outer aerobic cancer cells of the spheroid. Daunorubicin was used to penetrate the outer layers of a multicellular spheroid due to its high affinity toward cells and cisplatin was used at doses appropriate kill only the outer aerobic cancer cells. As a control for a bioreductive drug that killed cells under hypoxia in monolayer cultures, but not in multicellular cell culture due to its high reactivity and poor penetration, Tirapazamine was used both in monolayer based experiments and in spheroids as tabulated below for H460 cells exposed for 2 h.

$IC_{90}$ values for H460 cells exposed as monolayers or spheroids

|  | Monolayer | | | Spheroid |
|---|---|---|---|---|
| Drug | N2 | 0.6% O2 | Air | 10% O2 |
| Cisplatin | 4.2 μM | 7.7 μM | 7.3 μM | 8.0 μM |
| Daunorubicin | 0.16 μM | | | 19 μM |
| Tirapazamine | 14 μM | 27 μM | >100 μM | >200 μM |

A series of phosphoramidate alkylator prodrugs were tested in spheroids to determine their ability to penetrate into the inner lying hypoxic cancer cells, become activated, and kill the hypoxic cells. The results are tabulated below.

$IC_{90}$ for H460 cells exposed as monolayers or spheroids to phosphoramidate prodrugs for 2 h.

|  | Monolayer | | | Spheroid |
|---|---|---|---|---|
| Compound | N$_2$ | 0.6% O$_2$ | Air | 10% O$_2$ |
| 25 | 0.1 μM | 0.6 μM | 20 μM | 15 μM |
| 24 | 0.07 μM | 0.25 μM | 4 μM | 3 μM |
| 97 | | | | 13 μM |
| 70 | 1.25 μM | | | 25.5 μM |
| 1 | 0.35 μM | | 75 μM | >>100 μM |
| 36 | 1 μM | | 100 μM | >>100 μM |
| 35 | | | | 22 μM |

Similar results for the efficacy of Compound 25 were demonstrated in the HT29 spheroids as tabulated below:

|  | Monolayer | | | Spheroid |
|---|---|---|---|---|
| Compound | N2 | 0.6% O2 | Air | 10% O2 |
| 25 | 0.2 μM | 3 μM | 40 μM | 29 μM |

The phosphoramidate alkylator prodrug was combined simultaneously with cisplatin or daunorubicin and the spheroids exposed for 2 h to the combination, followed by measurement of clonogenic survival. The results are tabulated below:

| Compound | IC50 (μM) |
|---|---|
| Daunorubicin | 17 |
| Compound 25 | 9 |
| Daunorubicin + Compound 25 | 2.3 |

| Compound | IC50 (μM) | IC99 (μM) |
|---|---|---|
| Cisplatin | 14 | |
| Compound 25 | 12 | |
| Cisplatin + Compound 25 | 2.3 | 5.4 |

Phosphoramidate alkylator prodrugs demonstrate the ability to penetrate into the inner lying cells in the spheroid and kill hypoxic cancer cells alone and in combination with another agent that targets aerobic cancer cells.

Example 36

Antiproliferation Assay

DNA Mutant Repair Cells

Chinese hamster ovary cells mutant to specific DNA repair pathways were obtained from ATCC. The following cell lines were tested with 2,500 or 3,000 cells/well/5004 Dulbecco's Modified Eagle Medium (Gibco) supplemented with 10% fetal bovine serum and antibiotics: AA8 cells (ATCC CRL-1859), EM9 cells (ATCC CRL-1861), UV41 cells (ATCC CRL-1860), UV135 cells (ATCC CRL-1867), IRS1SF cells. All cell lines were initially screened with an anti-proliferation assay and those demonstrating sensitivity were retested with the clonogenic assay (as previously described) to confirm the proliferation results. Cells were exposed to selected doses of phosphoramidate alkylator prodrugs of the present invention for 2 h under hypoxic or aerobic conditions, the test compound was removed, and the cells assayed. The following table lists the cell lines, the pathway mutated, and the specific gene defect:

| Cell line | Mutant pathway | Gene defect |
|---|---|---|
| AA8 | None (Wild type) | (None) |
| EM9 | Base excision repair | XRCC1 |
| UV135 | Nucleotide excision repair | XPG |
| UV41 | Nucleotide excision repair and Homologous recombination | XPF |
| Irs1SF | Homologous recombination | XRCC3 |

The following table lists the effect of exposure of various cell lines to Compounds 25 and 36 under anoxic or aerobic conditions and assayed by proliferation as measured by $IC_{50}$.

| Compound | AA8 (Anoxia/Air) | EM9 (Anoxia/Air) | UV41 (Anoxia/Air) | UV135 (Anoxia/Air) | IRS1SF (Anoxia/Air) |
|---|---|---|---|---|---|
| 36 | 2/>100 | 4/>100 | 0.03/20 | 2/>100 | 0.3/59 |
| 25 | 8/>100 | 7/>100 | 0.2/95 | 6/>100 | 2/>100 |

The following table lists the $IC_{90}$ values for clonogenic survival for selected cells exposed to Compound 25 under anoxic or aerobic conditions.

|  | $IC_{90}$ (μM) | |
|---|---|---|
| Cell Line | N$_2$ | Air |
| AA8 | 0.85 | >300 |
| UV41 | 0.02 | 17 |
| Irs1SF | 0.02 | 20 |

Only cell lines defective in homologous recombination were sensitive to Compound 25 under hypoxia. Since UV41 participates in both the nucleotide excision repair pathway as well as with the homologous recombination repair pathway, Compound 25 possibly also produced a significant amount of monoadducts. However, UV135 which is also involved in nucleotide excision repair was not sensitive to Compound 25. The predominant lesions produced by Compound 25 were DNA interstrand crosslinks. These results were confirmed in UV41 and irs1SF cells with the clonogenic assay. The exposure under aerobic conditions produced the same spectrum of sensitivities as seen under hypoxia, indicating that the aerobic toxicity was also caused by DNA interstrand crosslink formation. Compound 36 exhibited a similar pattern of sensitivity in the mutant cell lines, indicating that Compound 36 also produced DNA interstrand crosslinks.

Example 37

Multilayered Cell Culture Assay

This example demonstrates the effect of Compound 25 on tissue penetration using multilayered cell culture (MCC) and to assess any bystander effect. MCCs were incubated with oxygenated media (20% $O_2$ & 5% $O_2$) or hypoxic media (approximately 0% $O_2$) and the test compound was exposed from one side (exposed surface, normoxic side) while the other side was temporarily closed off (far side, hypoxic side). When MCC's are incubated in media at 20% $O_2$ or 5% $O_2$ a gradient in oxygen develops from the surface exposed to the media towards the far surface of the culture. The furthest 50 µm of tissue becomes depleted of oxygen. The extent of $O_2$ depletion is greater with 5% than the 20% $O_2$ gassed media; incubation with 5% $O_2$ reflects the in vivo situation most closely. Incubating MCCs with media at 0% $O_2$ models perfusion limited hypoxia, where tumor blood vessels become completely depleted of oxygen and test compound must penetrate extensive distances to reach all cells. This situation therefore poses a greater barrier to drug penetration, if binding of activated drug acts to limit its penetration.

MCC based experiments were carried out with media gassed with 0, 5 or 20% $O_2$ for 45 minutes prior to and during incubation with the test compound. HCT116 cells were grown to a thickness of 150 µm on a solid support and one side of the culture was clamped off to develop diffusion limited hypoxia. Cultures were exposed to test compound for 1 hr under 0% $O_2$, 5% $O_2$ or 20% $O_2$ and efficacy assessed by measuring the inhibition of BrdU incorporation. The cultures were incubated for a second hour in fresh media at 20% $O_2$ and removed from the apparatus and returned to a normal growth chamber, where media flows over both sides of the MCC. Cultures were incubated for 24 hours prior to BrdUrd labeling and subsequent cryosectioning. BrdUrd labeling on the exposed and far sides of the MCC were analyzed using immunohistochemical staining, microscope imaging and computer image analysis to assess the effect of Compound 25 on cell proliferation.

When cultures were exposed to graded doses of Compound 25 under 20% $O_2$, 5 fold less compound was required on the far (hypoxic) side compared to the exposed (normoxic) side to produce comparable results, demonstrating penetration and hypoxic activation of Compound 25. When MCC's were exposed to test compound under a more physiologically relevant condition of 5% $O_2$, Compound 25 was 10 fold more effective at inhibiting BrdU incorporation on the hypoxic side as compared to the normoxic side. Normoxic sides of cultures at 5% & 20% $O_2$ were equally affected by exposure to Compound 25.

Compound 25 is more effective on the hypoxic side of cultures under 5% $O_2$ than with 0% $O_2$. Comparison of normoxic versus hypoxic sides of cultures under 5% $O_2$ demonstrated that Compound 25 penetrates effectively through relatively well oxygenated tissue. Compound 25 is capable of killing hypoxic cells located about 150 µm from functional blood vessels. Approximately 3-fold reduction in exposure to Compound 25 to the hypoxic side was observed under 0% $O_2$ relative to the exposure under 5% $O_2$ conditions. Bystander effect was observed only at the highest concentration.

The following table lists the effect of Compound 25 as measured by $IC_{50}$ (concentration to inhibit BrdU incorporation by 50%).

| Side | 0% $O_2$ (µM) | 5% $O_2$ (µM) | 20% $O_2$ (µM) |
|---|---|---|---|
| Hypoxic | ~1.1 | 0.7 | 2.6 |
| Normoxic | ~1.7 | 8.0 | >10 |

Example 38

Metabolism of Compound 25 By Human and Mouse Microsomal Protein

An in vitro assessment of metabolic stability of a phosphoramidate alkylator prodrug (Compound 25) was performed using human (HLM), rat (RLM) and mouse (MLM) liver microsomal proteins containing cytochrome P450 enzymes. A solution of Compound 25 (500 µL, 5 µM) was prepared by diluting a DMSO stock solution 100 fold in a water:methanol bridge solution, adding microsomal protein (1 mg/mL) in PBS/$MgCl_2$, and enzymatic reactions initiated by adding an NADPH solution. 50 µl of the reaction mixture was withdrawn at 0, 10, 20, and 30 minutes after addition of the NADPH solution, the proteins were precipitated with acetonitrile and the clear supernatant was analyzed for the amount of Compound 25 by reversed phase LC-MS/MS. Nifedipine and testosterone were used as positive controls. The first study compared RLM to MLM (Table 1) and the second study compared HLM to RLM (Tables 2A and 2B)

TABLE 1

| Compound | Metabolic stability (% at 30 min) | |
|---|---|---|
| | RLM | MLM |
| 25 | 84% | 89% |
| Nifedipine | 6% | 4% |
| Testosterone | 0% | 6% |

TABLE 2A

| Compound | Metabolic stability (% at 30 min) | |
|---|---|---|
| | HLM | RLM |
| 25 | 127% | 137% |
| Nifedipine | 22% | 2% |
| Testosterone | 65% | 33% |

TABLE 2B

| Comp. No. | Metabolic stability (MLM) (% at 30 min) | Plasma stability (% at 30 min) | MTD (mg/ml) | Intravenous administration in mice | | | | | Intraperitoneal administration in mice | | |
|---|---|---|---|---|---|---|---|---|---|---|---|
| | | | | t ½ (hr) | Cmax (μg/ml) | AUC (μg/ml × hr) | Vss (l/kg) | CL (ml/min/kg) | t ½ (hr) | Cmax (μg/ml) | AUC (μg/ml × hr) |
| 1 | 90 | 100 | | 0.26 | 35 | 12.5 | 1.48 | 4.0 | 0.25 | 29.9 | |
| 5 | 5 (20) | 100 (85) | | 0.08 | 16.9 | 4.5 | 1.25 | 185 | | 3 | 1.0 |
| 6 | 0 | 60 | 250 | | | | | | | | |
| 7 | 0 | 85 | 250 | | | | | | | | |
| 16 | 40 | | | | | | | | | | |
| 23 | 71 | 84 | | 0.15 | 7.8 | 2.3 | 3.3 | 368 | 0.16 | 8.5 | 3.5 |
| 25 | 92 | 102 (at 20 min) | | 0.11 (6.7 min) | 27.5 | | | | 0.18 (11 min) | 22.9 | |
| 26 | 56 | 85 | | | | | | | | | |
| 34 | 28 | 85 (at 20 min) | | | | | | | | | |
| 35 | 56 | 85 | | | | | | | | | |
| 36 | 90 | 60 | 400 | 0.24 | 27.7 | 10.8 | 1.27 | 77.4 | 0.18 | 44 | 26.1 |

Example 39

Iv Vivo Pharmacokinetics of Phosphoramidate Alkylator Prodrugs

Various plasma pharmacokinetic parameters of phosphoramidate alkylator prodrugs were determined in CD-1 mice except where noted as listed below in Table 3.

TABLE 3

| Drug | Dose (mg/kg) | Route | Formulation | $T_{max}$ (min) | $C_{max}$ (μg/mL) | AUC (μg·h/mL) | Half-life (min) |
|---|---|---|---|---|---|---|---|
| 23 | 50 | i.p. | 25% PEG/75% Saline | 5.00 | 8.50 | 210 | 9.60 |
| 23 | 50 | i.v. | 25% PEG/75% Saline | 5.00 | 7.80 | 136 | 8.87 |
| 36 | 50 | i.p. | 25% PEG/75% Saline | 15.0 | 44.0 | 1439 | 11.0 |
| 36 | 50 | i.v. | 25% PEG/75% Saline | 5.00 | 27.7 | 646 | 14.1 |
| 1[a] | 50 | i.p. | 25% PEG/75% Saline | 15.0 | 29.9 | — | — |
| 1[a] | 50 | i.v. | 25% PEG/75% Saline | 5.00 | 35.0 | 12.5 | 15.3 |
| 5 | 50 | i.p. | 25% PEG/75% Saline | 5.00 | 3.00 | 57.4 | 2.56 |
| 5 | 50 | i.v. | 25% PEG/75% Saline | 5.00 | 16.9 | 270 | 4.67 |
| 37 | 20 | i.p. | Cremophore:Ethanol:Saline (1:2:7) | 2.00 | 12.6 | 196 | 23.2 |
| 37 | 20 | i.v. | Cremophore:Ethanol:Saline (1:2:7) | 2.00 | 15.0 | 172 | 9.00 |
| 85 | 25 | i.p. | 10% PEG | 5.00 | 3.93 | 89.1 | 10.0 |
| 128 | 25 | i.p. | 10% PEG | 5.00 | 3.85 | 102 | 8.31 |
| 24 | 50 | i.p. | Saline | 5.00 | 7.60 | 64.0 | 4.10 |

[a]Balb/c mice

Example 40

Iv Vivo Pharmacokinetics of Compound 25

Various plasma or tumor pharmacokinetic parameters of Compound 25 were determined in CD-1 mice except where noted as listed below in Table 4.

TABLE 4

| Dose (mg/kg) | Route | Formulation | $T_{max}$ (min) | $C_{max}$ (μg/mL) | AUC (μg·h/mL) | Half-life (min) | F[c] (%) |
|---|---|---|---|---|---|---|---|
| 150[a] | i.p. | Saline | 5.00 | 90.1 | 1239 | 58.7 | — |
| 150[a,b] | i.p. | Saline | 15.0 | 3.38 | 307 | ND | — |
| 100 | p.o. | Saline | 15.0 | 15.8 | 784 | 95.2 | — |
| 50 | i.p. | 30% PEG/70% Saline | 5.00 | 22.9 | 438 | 11.0 | — |
| 50 | i.v. | 30% PEG/70% Saline | 2.0 | 27.5 | 325 | 6.7 | — |
| 50 | i.p. | 30% PEG/70% Saline | 15.0 | 9.2 | — | — | — |
| 50 | i.v. | 30% PEG/70% Saline | 2.0 | 27.5 | 177 | 10.1 | — |
| 50 | i.p. | Saline | 5.00 | 38.5 | 635 | 7.91 | — |
| 50 | p.o. | Saline | 15.0 | 0.93 | 40.4 | 25.7 | 13.6 |
| 25 | i.p. | 10% PEG | 45.0 | 6.33 | 247 | 4.43 | — |

[a]Nude mice with H460 tumor
[b]Tumor PK
[c]Bioavailability

Example 41

Cytochrome P450 Inhibition of the Metabolism of Compound 25

Eight reaction wells with 100 μL of a solution containing 50 mM potassium phosphate, pH 7.4, 2.6 mM NADP+, 6.6 mM glucose-6-phosphate, 0.8 U/mL of glucose-6-phosphate dehydrogenase, and 1:3 serial dilutions of the test compound (such as Compound 25) were prepared along with eight wells of 1:3 serial dilutions of a suitable positive control inhibitor (such as furafylline for CYP1A2, sulfaphenazole for CYP2C9, N-benzylnirvanol for CYPC219, quinidine for CYP2D6 and ketoconazole for CYP3A4). The concentrations of test compound ranges from 0.0229 μM to 200 μM. The reactions were initiated by adding 100 μL of a pre-warmed enzyme/substrate solution. A zero time-point control reaction was prepared by adding 50 mL of 10% formic acid (400 mL of acetonitrile for 2C19) in water to 100 mL of cofactor solution to inactivate the enzymes, then adding 100 mL of enzyme/substrate solution. A control reaction with no inhibitor was also prepared. After a suitable incubation at 37° C., the reactions were terminated by the addition of 50 mL of 10% formic acid in water (400 mL of acetonitrile for 2C19). The reactions were prepared and analyzed for the metabolite forms of the probe substrate (phenacetin for CYP1A2, diclofenac for CYP2C9, (S)-mephenyloin for CYPC219, dextromethorphan for CYP2D6 and midazolam, testosterone and nifedipine for CYP3A4) using HPLC/MS/MS. Each assay was performed in duplicate. A summary of the IC50 values are listed below.

TABLE 5

| | IC50 (mM) | |
|---|---|---|
| Isoform | Control | Compound 25 |
| 1A2 | 8.6 | NI |
| 2C9 | 0.20 | ~10 |
| 2C19 | 6.0 | NI |
| 2D6 | 0.21 | >50 |
| 3A4 Midazolam | 0.049 | >50 |
| 3A4 Nifedipine | 0.03 | NI |
| 3A4 Testosterone | 0.10 | >50 |

NI = No significant inhibition detected

Example 42

Determination of the Potential Metabolites of Compound 25 Formed in Mouse, Rat, Dog and Human Hepatocytes Compound 25 is incubated with mouse, rat, dog, monkey and human cryopreserved hepatocytes at a concentration of 10 μM. The reactions are stopped at 0 (pre-incubation), 30, 60 and 120 minutes by quenching with acetonitrile prior to centrifugation and analysis by high-performance liquid chromatography (HPLC) in conjunction with tandem mass spectrometry (LC/MS/MS). Potential metabolites are identified by performing full scans from 100 to 520 amu. The product ion spectra of the potential metabolites are subsequently collected and compared to the product ion spectrum of the parent compound to determine whether each potential metabolite is related to Compound 25. The disappearance of the parent compound (Compound 25) and the appearance of potential metabolites over time are monitored by comparing the peak heights at each time point acquired.

Example 43

Determination of the In Vivo Pharmacokinetics of Compound 25 and its Metabolite (s) in Rat, Dog and Monkey Pharmacokinetic parameters of Compound 25 and its metabolite(s) in Sprague Dawley rats are determined following single intravenous administration of 5, 20, 50 and 100 mg/kg Compound 25. The pharmacokinetics of Compound 25 and its metabolite(s) will also be determined in beagle dogs and cynomolgus monkeys following single intravenous administration of 20 mg/kg Compound 25. Concentrations of Compound 25 and its metabolite(s) in plasma are determined by a LC/MS/MS method and mean pharmacokinetic parameters are computed.

Example 44

Mass Balance Study in Rats

Normal and bile-cannulated Sprague-Dawley rats are administered $^{14}$C-Compound 25 as a single intravenous dose. Blood plasma, urine, feces and are collected at specified times and concentrations of total radioactivity are determined by liquid scintillation counting (LSC).

Example 45

Quantitative Whole Body Autoradiography

Sprague-Dawley rats are administered a single intravenous dose of 14C-Compound 25. At specified times, one rat per time point is euthanized. Blood is centrifuged to obtain plasma, and the blood and plasma are analyzed for concentration of radioactivity. Frozen rat carcasses are embedded in 2% CMC, frozen into a block and sectioned at 40 μm an in a Leica CM 3600 cryomicrotome. Collected sections are freeze-dried, mounted and exposed on phosphorimaging plates along with $^{14}$C autoradiographic standards for subsequent calibration of the image analysis software. Exposed screens are scanned using a Molecular Dynamics Storm 820 or 860. The concentration of radioactivity in select tissues including adipose (brown and white), adrenal gland, blood, brain (cerebrum, cerebellum, medulla) bone, bone marrow, cecum and contents, epididymis, esophagus, eyeball (Uveal tract, aqueous humor, lens), Harderian gland, heart, kidney (cortex, medulla, papilla and entire section), large intestine and contents, liver, lung, lymph node submaxillary), pancreas, pituitary gland, prostate gland, salivary gland, seminal vesicles, skeletal muscle, skin, stomach (and contents), small intestine (and contents), spleen, spinal cord, trachea, thyroid and urinary bladder (and contents) are measured by image analysis. Autoradioluminographs and digital images are produced for each animal.

Example 46

Plasma Protein Binding of Compound 25

The protein binding in mouse, rat, dog, monkey and human plasma of Compound 25 is determined using ultrafiltration. Ultrafiltration is performed by aliquoting plasma spiked at three concentrations with Compound 25 into a Centrifree® device in triplicate. All plasma samples are then equilibrated to 37° C. The Centrifree® apparatus is centrifuged at 37° C. for 30 minutes at 2500×g. A 75 μL aliquot of the ultrafiltrate is spiked with the I.S. (deuterated Compound 25) and analysed using LC/MS/MS. The ultrafiltrates are analyzed and quantified using human ultrafiltrate standards for the calibration curve.

Example 47

Example 47 demonstrates the usefulness of a compound of this invention in treating cancer employing a HT-29 human colon carcinoma xenograft mouse model.

Female CB17/SCID mice (purchased from Charles River, Cambridge, Mass.), 7-8 weeks of age, were allowed to acclimatize for at least three days, and handled under pathogen-free conditions. Human colon carcinoma cell line HT-29 was obtained from the American Type Culture Collection. The cell lines were cultured in RPMI 1640 media supplemented with 10% fetal bovine serum. Cells were maintained in a 37° C. incubator with 5% $CO_2$. The HT-29 cells were harvested from culture and inoculated at $3\times10^6$ cells/animal in the peritoneal subcutaneous space. When the tumors grew to an average volume of 100 $mm^3$ (day 8), each group of 10 mice was administered, for three weeks, vehicle alone (saline and PEG (10 mL/kg each), Group 1), Compound 36 alone (dissolved in 30% cyclodextrin in PBS) at a daily dose of 20, 60, or 200 mg/kg (Groups 2, 3 and 4, respectively), and Compound 36 at a daily dose of 20, 60, and 200 mg/kg given 2-3 hours after a dose of 10 mg/kg of 5FU (in saline) (Group 5, 6 and 7, respectively) and compared to a group receiving only 5FU at 10 mg/kg (Group 8) as tabulated below.

The body weight of each mouse was recorded twice per week. Growth of each xenograft was monitored by externally measuring tumors in two dimensions using a digital caliper twice per week. Tumor volume (V) was determined by the following equation: $V=(L\times W^2)/2$, where L is the length and W is the width of a xenograft. Tumor volumes were measured twice weekly.

Administration of Compound 36 at 20, 60, and 200 mg/kg/day each reduced tumor growth compared to administration of vehicle alone. Administration of a combination of Compound 36 and 5FU resulted in greater and dose related inhibition of tumor growth compared to vehicle. In addition combinations of 60 and 200 mg/kg of Compound 36 reduced tumor growth to a greater degree than 5FU alone.

| Group | Treatment (mg/kg) | % Inhibition vs Group 1 | % Inhibition vs Group 8 |
|---|---|---|---|
| 2 | 20 | 34.6 | — |
| 3 | 60 | 16.1 | — |
| 4 | 200 | 20.2 | — |
| 5 | 20 + 5FU | 35.7 | 3.3 |
| 6 | 60 + 5FU | 46.9 | 13.3 |
| 7 | 200 + 5FU | 58.2 | 23 |
| 8 | 5FU | 38.7 | — |

Associated with these anti-tumor effects, there was some degree of weight loss and occasional mortality, particularly in the group treated with the high dose of Compound 36 but in other groups as well. Overall, Compound 36 showed varying rates of tumor growth inhibition.

Example 48

Example 48 demonstrates the usefulness of a compound of this invention in treating cancer employing a NCI H460, human non small cell lung carcinoma xenograft mouse model.

Female CB17/SCID mice (purchased from Charles River, Cambridge, Mass.), 7-8 weeks of age, were allowed to acclimatize for at least three days, and handled under pathogen-free conditions. Human colon carcinoma cell line NCI H460 was obtained from the American Type Culture Collection. The cell lines were cultured and harvested according to the procedure described in Example 47 and inoculated at $1\times10^6$ cells/animal in the peritoneal subcutaneous space. When the tumors grew to an average volume of 100 $mm^3$ (day 8), each group of mice was administered, for three weeks, as tabulated in the table below: Compound 25 (2.5 mg/ml in 10% PEG; administration route—i.p.) and Taxol (1 mg/ml in 5% EtOH, 5% Cremophor and 90% saline; administration—i.v. 2 h after administration of Compound 25). The body weight and tumor volumes were measured as described in Example 47 above.

| Group (n = 10) | Treatment | Dose (mg/kg) | Regimen |
|---|---|---|---|
| 1a* | Not Applicable (NA) | NA | NA |
| 1b* | Saline | NA | (q1d × 5)/week × 2 weeks |
| 2 | Vehicle | NA | (q1d × 5)/week × 2 weeks |
| 3 | Compound 25 | 25 | (q1d × 5)/week × 2 weeks |
| 4 | Compound 25 | 50 | (q2d × 3)/week × 2 weeks |
| 5 | Compound 25 | 100 | (q7d × 1)/week × 2 weeks |
| 6 | Taxol | NA | (q2d × 3)/week × 2 weeks |
| 7 | Compound 25 | 25 | (q1d × 5)/week × 2 weeks |
|   | Taxol | 10 | (q2d × 3)/week × 2 weeks |
| 8 | Compound 25 | 50 | (q2d × 3)/week × 2 weeks |
|   | Taxol | 10 | (q2d × 3)/week × 2 weeks |
| 9 | Compound 25 | 100 | (q7d × 1)/week × 2 weeks |
|   | Taxol | 10 | (q2d × 3)/week × 2 weeks |

Groups 1a and 1b, n = 5;
q1d/qd = every day;
q2d = every second day;
q7d = every seventh day.

Results are presented in Table X2 based on tumor volume measurement on day 29 when vehicle treated mice had reached a volume of 946 $mm^3$. Groups of 5 mice receiving saline or no treatment were added in order to indicate any vehicle effects but are not used for comparisons in this analysis.

TABLE X2

| Group | % Inhibition vs Group 2 | % Inhibition vs Group 6 |
|---|---|---|
| 3 | 50.1 | — |
| 4 | 52 | — |
| 5 | 46.7 | — |
| 7 | 65.9 | 38.8 |
| 8 | 63.1 | 31.7 |
| 9 | 52.6 | 12.5 |
| 6 | 46 | — |

The results demonstrate that all three regimens for dosing Compound 25 provided similar degrees of tumor growth inhibition and that combination therapy, particularly with every day dosing provided additional benefit. Each combination therapy was associated with some degree of weight loss but not large enough to cause any mortality. Overall the results indicate that Compound 25 is efficacious in this model of lung cancer and provides additional benefit to that provided by the standard chemotherapeutic agent, taxol.

Using the mouse to HED conversion, Compound 25 can be administered at a therapeutically effective dose of about 2 to about 8 mg/kg/day, for the treatment of cancer, particularly lung cancer, alone or in combination with Taxol™, wherein the daily dose can be administered with a decreasing frequency of dosing for higher doses compared to lower doses.

Example 49

Example 49 describes the usefulness of a compound of this invention in treating cancer as demonstrated employing a H460, non-small lung carcinoma xenograft mouse model. Female CB17/SCID mice (purchased from Charles River, Cambridge, Mass.), 7-8 weeks of age, were allowed to acclimatize for at least three days, and handled under pathogen-free conditions. Human non-small lung carcinoma cell line NCI H460 was obtained from the American Type Culture Collection. The cell lines were cultured and harvested as described in Example 47 above, and inoculated at $3\times10^6$ cells/animal in the peritoneal subcutaneous space. When the tumors grew to an average volume of 100 mm$^3$ (day 8), each group of mice (ten per group) was administered, for three weeks, as tabulated in the table below: Compound 25 (2.5 mg/ml in 10% PEG; administration route—i.p.); Compound 24 (0.3, 0.1 mg/ml in 10% PEG, administration route—i.p.) and Taxol (1 mg/ml in 5% EtOH, 5% Cremophor and 90% saline; administration—i.v. 2 h after administration of the test compound).

Treatment protocol

| Group | No. of Mice | Treatment | Dose (mg/kg) | Regimen |
|---|---|---|---|---|
| 1 | 10 | Vehicle* | NA | (q1d × 5 d)/week × 3 week |
| 2 | 8 | Taxol | 10 | (q2d × 3)/week × 2 week |
| 3 | 8 | Compound 24 | 3 | (q1d × 5 d)/week × 3 week |
| 4 | 9 | Compound 24 | 1 | (q1d × 5 d)/week × 3 week |
|   |   | Taxol | 10 | (q2d × 3)/week × 2 week |
| 5 | 8 | Compound 24 | 3 | (q1d × 5 d)/week × 3 week |
|   |   | Taxol | 10 | (q2d × 3)/week × 2 week |
| 6 | 8 | Compound 25 | 25 | (q1d × 5 d)/week × 3 week |
|   |   | Taxol | 10 | (q2d × 3)/week × 2 week |

*50% PEG

The body weight and tumor volume were determined as described in Example 47 above. Results for tumor growth inhibition measured on day 27 are as tabulated below. Comparisons were made on day 27 because that was the last day of measurements for the vehicle group and those animals were sacrificed.

| | % Inihibition vs | |
|---|---|---|
| Group | Group 1 | Group 2 |
| 3 | 39.9 | — |
| 4 | 16 | -32.7 |
| 5 | 51.5 | 23.3 |
| 6 | 56.8 | 31.7 |
| 2 | 36.7 | — |

These results demonstrate that daily doses of 3 mg/kg of Compound 24 and 25 mg/kg of Compound 25 inhibited tumor growth and that Compound 25 had a slightly greater benefit both as monotherapy and in combination with taxol. These effects were accompanied by mild weight reductions, particularly in the Compound 25+ taxol group.

Using the mouse to HED conversion, Compound 25 can be administered at a therapeutically effective dose of 2 mg/kg/day, for the treatment of cancer, particularly lung cancer, alone or in combination with Taxol™, and Compound 24 can be administered at a therapeutically effective dose of 0.25 mg/kg/day, for the treatment of cancer, particularly lung cancer, alone or in combination with Taxol™.

Example 50

Example 50 describes the usefulness of a compound of this invention in treating cancer as demonstrated employing a HT-29, human colon carcinoma xenograft mouse model. Female CB17/SCID mice (purchased from Charles River, Cambridge, Mass.), 7-8 weeks of age, were allowed to acclimatize for at least three days, and handled under pathogen-free conditions. Human colon carcinoma cell line HT29 was obtained from the American Type Culture Collection. The cell lines were cultured and harvested as described in Example 47 above, and inoculated at $3\times10^6$ cells/animal in the peritoneal subcutaneous space. When the tumors grew to an average volume of 100 mm$^3$ (day 8), each group of mice (ten per group) was administered, for three weeks, as tabulated in the table below: Compound 24 (in 10% PEG), administration route—i.p., administrated 2 h before 5-FU or cisplatin (CDDP; in saline) on the days the combination therapy was scheduled; 5FU alone (in saline), or CDDP alone.

Treatment protocol

| Group | # mice | Test Article | Dose (mg/kg) | Routes, Regimens |
|---|---|---|---|---|
| 1* | 8 | Saline | 10 ml/kg | iv, q3d × 4 |
| 2* | 8 | 5-FU | 50 | iv, q3d × 4 |
| 3* | 4 | No treatment | N/A | N/A |
| 4** | 9 | Vehicle (saline) | 10 ml/kg | ip, (q1d × 5)/week × 3 week |
| 5** | 9 | 5-FU | 50 | iv, q3d × 4 |
| 6** | 9 | CDDP | 5 | iv, once |
| 7** | 9 | Compound 24 | 3 | ip, (q1d × 5)/week × 3 week |
| 8** | 9 | Compound 24 | 6 | ip, (q1d × 5)/week × 3 week |
| 9** | 9 | Compound 24 | 6 | ip, (q1d × 5)/week × 2 week |
|   |   | 5-FU | 50 | iv, q3d × 4 |
| 10** | 9 | Compound 24 | 3 | ip, (q1d × 5)/week × 3 week |
|   |   | CDDP | 5 | iv, once |
| 11** | 9 | Compound 24 | 6 | ip, (q1d × 5)/week × 3 week |
|   |   | CDDP | 5 | iv, once |
| 12** | 8 | No treatment | N/A | N/A |

*tumor location flank;
**tumor location peritoneum;
Q3d = every third day

In control groups, tumors were implanted in two locations as part of a separate study of effect of location on control group tumor growth. These results had no impact on the interpretation of the study and all treatments were compared to the vehicle group with tumors on the same area of the body. The body weight and tumor volume were measured as described in Example 47. Tumor growth inhibition measured on day 25 when vehicle tumors had reached the maximal size and animals in that group were sacrificed is tabulated below.

| Group | % Inhibition vs | |
|---|---|---|
| | Group 4 | Group 6 |
| 7 | 44.1 | — |
| 8 | 42.1 | — |
| 9 | 71.1 | 28.9 |
| 10 | 53.2 | 24.8 |
| 11 | 50.7 | 20.9 |
| 5 | 59.3 | — |
| 6 | 37.4 | — |

The results demonstrate that Compound 24 as monotherapy resulted in tumor growth inhibition of slightly more than 40% whereas combining Compound 24 administered in combination with CDDP or 5FU provided about 50-70% growth inhibition. According to this Example, the most therapeutically effective combination was that of Compound 24 and 5FU. The effects on tumor growth were associated with minor decreases in weights of the mice during treatment; however, the mice recovered the lost weight after the end of treatment.

Using the mouse to HED conversion, Compound 24 can be administered at a therapeutically effective dose of about 0.25 to about 0.50 mg/kg/day, for the treatment of cancer, particularly colon cancer, alone or in combination with 5FU or CDDP.

Example 51

Figure 2:
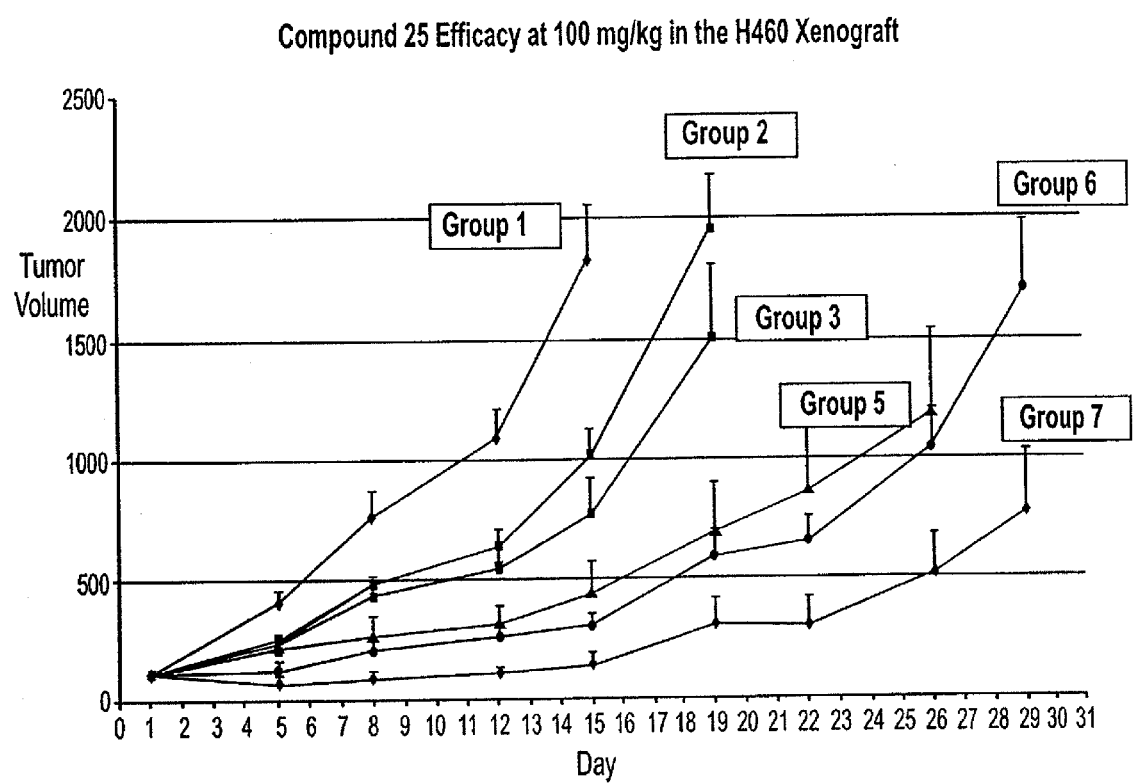
FIG. 2 demonstrates the effect of Compound 25 (100 mg/kg) on tumor growth in the H460 xenograft mouse model.

Example 51 describes the usefulness of a compound of this invention in treating cancer as demonstrated employing an H460, non-small lung carcinoma xenograft mouse model. Female CB17/SCID mice (purchased from Charles River, Cambridge, Mass.), 7-8 weeks of age, were allowed to acclimatize for at least three days, and handled under pathogen-free conditions. Human non-small cell lung carcinoma cell line NCI H460 was obtained from the American Type Culture Collection. The cell lines were cultured and harvested as described in Example 47 above, and inoculated at $3\times10^6$ cells/animal in the peritoneal subcutaneous space. When the tumors grew to an average volume of 100 mm³, treatment was initiated in which groups of 10 mice received vehicle (Group 1), CDDP at 3 or 6 mg/kg (Groups 2 and 3, respectively, IV one time), Compound 25 at 50 mg/kg in saline 5 times per week for two weeks (Group 4), Compound 25 at 100 mg/kg every three days for 5 times (Group 5) or the combination of each dose of Compound 25 with either 3 or 6 mg/kg of CDDP (Groups 6 and 7, respectively). Results for groups receiving 50 mg/kg of Compound 25 are illustrated in the FIG. 1. FIG. 2 shows similar results for 100 mg/kg of Compound 25.

These results performed with a saline formulated version of Compound 25 demonstrate significant dose related decrease in tumor volume and increase in tumor growth delay with a daily dose of 50 mg/kg, and 100 mg/kg with less frequent dosing compared to that employed for the 50 mg/kg daily dose. These data also demonstrate that both dosing regimens add to the effects of CDDP in this model.

Using the mouse to HED conversion, Compound 25 can be administered at therapeutically effective doses of about 4 to about 8 mg/kg/day, for the treatment of cancer, particularly lung cancer, alone or in combination with 5FU or CDDP, wherein the daily dose can be administered with a decreasing frequency of dosing for higher doses compared to lower doses.

Example 52

Example 52 describes the usefulness of a compound of this invention in treating cancer as demonstrated employing a HT-29, human colon carcinoma xenograft mouse model. Female CB17/SCID mice (purchased from Charles River, Cambridge, Mass.), 7-8 weeks of age, were allowed to acclimatize for at least three days, and handled under pathogen-free conditions. Human colon carcinoma cell line HT29 was obtained from the American Type Culture Collection. The cell lines were cultured and harvested as described in Example 47 and inoculated at $3\times10^6$ cells/animal in the peritoneal subcutaneous space. When the tumors grew to an average volume of 100 mm³ (day 8), each group of mice (ten per group) was administered for three weeks, as tabulated in the table below: Compound 25 in saline, administration route—i.p., administrated 2 h before CDDP on the days the combination therapy is scheduled and CDDP (in saline, IV).

| Treatment protocol | | | |
|---|---|---|---|
| Group (n = 9) | Test Article | Dose (mg/kg) | Administration Regimens |
| 1 | Saline | 10 ml/kg | (qd × 5)/week × 2 week |
| 2 | CDDP | 5 | Once |
| 3 | Compound 25 | 50 | (qd × 5)/week × 2 week |
| 4 | Compound 25 | 100 | (q2d × 3)/week × 2 week |
| 5 | Compound 25 | 100 | Q3d × 5 |
| 6 | Compound 25 | 100 | Q7d × 2 |
| 7 | Compound 25 CDDP | 50 5 | (qd × 5)/week × 2 week Once |
| 8 | Compound 25 CDDP | 100 5 | (q2d × 3)/week × 2 week Once |
| 9 | Compound 25 CDDP | 100 5 | q3d × 5 Once |
| 10 | Compound 25 CDDP | 100 5 | q7d × 2 Once |

The body weight and tumor volume were determined as described in Example 47. Data are based on tumor volumes at day 25 when tumors in the vehicle group had reached sufficient size to require that the mice be sacrificed. The results of inhibition of tumor growth are tabulated below.

| Group | % Inhibition vs | |
|---|---|---|
| | Group 1 | Group 2 |
| 3 | 28.2 | — |
| 4 | 30.1 | — |
| 5 | 31.3 | — |
| 6 | 48.1 | — |
| 7 | 50.7 | 30.8 |
| 8 | 44.2 | 27.5 |
| 9 | 36.2 | 21.5 |
| 10 | 51.8 | 33.2 |
| 2 | 24.2 | — |

The results demonstrate that monotherapy administering Compound 25, formulated in saline, at 50 mg/kg/day and 100 mg/kg/day with a variety of dose regimens results in inhibition of tumor growth in this model of colon cancer, and that treatment combination of Compound 25 and CDDP enhanced the effectiveness of Compound 25 for treatment of colon cancer in this model. These effects were accompanied by modest body weight loss, more so in the combination groups; the mice recovered the lost body weights after the treatment ended.

Using the mouse to HED conversion, Compound 25 can be administered at a therapeutically effective doses of about 4 to about 8 mg/kg/day, for the treatment of cancer, particularly non-small cell lung cancer, alone or in combination with CDDP, wherein the daily dose can be administered with a decreasing frequency of dosing for higher doses compared to lower doses.

Example 53

Example 53 describes the usefulness of a compound of this invention in treating cancer as demonstrated employing a H460, non-small cell lung carcinoma xenograft mouse model. Female CB17/SCID mice (purchased from Charles River, Cambridge, Mass.), 7-8 weeks of age, were allowed to acclimatize for at least three days, and handled under pathogen-free conditions. Human non-small cell lung cell line NCI H460 was obtained from the American Type Culture Collection. The cell lines were cultured and harvested as described in Example 47 and inoculated at $3\times10^6$ cells/animal in the peritoneal subcutaneous space. When the tumors grew to an average volume of 100 mm$^3$, treatment was initiated in which groups of 10 mice received vehicle (Group 1), CDDP at 6 mg/kg (IV one time, Group 2), Compound 25 at 150 mg/kg in saline, once a week for two weeks (i.p., Group 3), or the combination of the two agents (Group 4).

Figure 3:
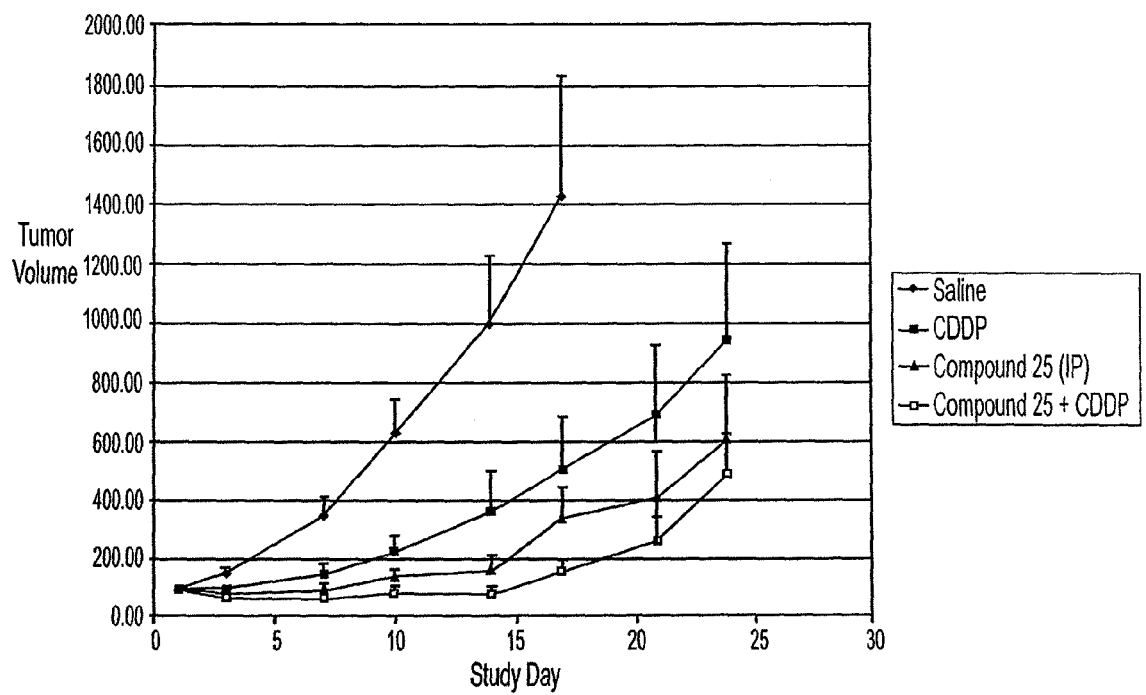
FIG. 3 demonstrates the effect of Compound 25 (150 mg/kg) dosed in combination with CDDP on tumor growth in the H460 xenograft mouse model.

The results shown in FIG. 3 demonstrate that 150 mg/kg per week of Compound 25 provided greater reduction in tumor growth than CDDP alone and that the combination of the two agents resulted in added benefit. These results also indicate that during the two week period of dosing mean tumor volume did not change indicating complete inhibition of tumor growth. These data indicate that Compound 25 administered at 150 mg/kg/day as monotherapy, once a week, is the most effective of all the dosing regimens described in the preceding examples (Examples 47-52). Little change in body weight was observed suggesting reduced toxicity with this dosing regimen.

Using the mouse to HED conversion, Compound 25 can be administered at a therapeutically effective dose of about 12 mg/kg/day, for the treatment of cancer, optionally administered at a frequency of once every week, particularly non-small cell lung cancer, alone or in combination with CDDP.

Example 54

Example 54 describes efficacy of Compound 25 via an ip bolus injection or ip infusion alone or in combination with Cisplatin in the H460 xenograft mouse model. Female Nu-Foxn1$^{nu}$ homozygous nu/nu mice (purchased from Charles River, Cambridge, Mass.), 6 weeks of age, were allowed to acclimatize for at least three days, and handled under pathogen-free conditions. Human H460 cells were obtained from the American Type Culture Collection. The cell lines were cultured and harvested as described in Example 47 and inoculated at $3\times10^6$ cells/animal in the peritoneal subcutaneous space. When the tumors grew to an average volume of 100 mm$^3$ (day 8), each group of mice (ten per group) was administered, for three weeks, as tabulated in the table below: Compound 25 (formulated as a 15 mg/ml saline solution, administration route—i.p., administrated 2 h before CDDP on the days the combination therapy is scheduled) and CDDP in saline, IV.

Treatment protocol

| Group | Test Article | Dose (mg/kg) | Regimens | Dose Concentration:Dose Volume |
|---|---|---|---|---|
| 1 | Saline | 10 | Q7d × 2 | 0 mg/mL:10 mL/kg |
| 2 | CDDP | 6 | Q7d × 2 | 0.6 mg/mL:10 mL/kg |
| 3 | Compound 25 | 150 | Q7d × 2 | 15 mg/mL:10 mL/kg |
| 4 | Compound 25 | 150 | q7d × 2 | 15 mg/mL:10 mL/kg |
|   | CDDP | 6 | q7d × 2 | 0.6 mg/mL:10 mL/kg |
| 5 | Compound 25 | 150 | Q7d × 2 | 10 mg/mL:15 mL/kg |
| 6 | Saline | 0.2 ml | 200 µL - 1 week × 2* | 0 mg/mL:1 µL/hr |
| 7 | Compound 25 | 15 mg/ml | 200 µL - 1 week × 2* | 15 mg/mL:1 µL/hr |

*Alzet pump, 200 µL for 1 week × 2 (re-implant new pump at the end of one week).

Figure 4:
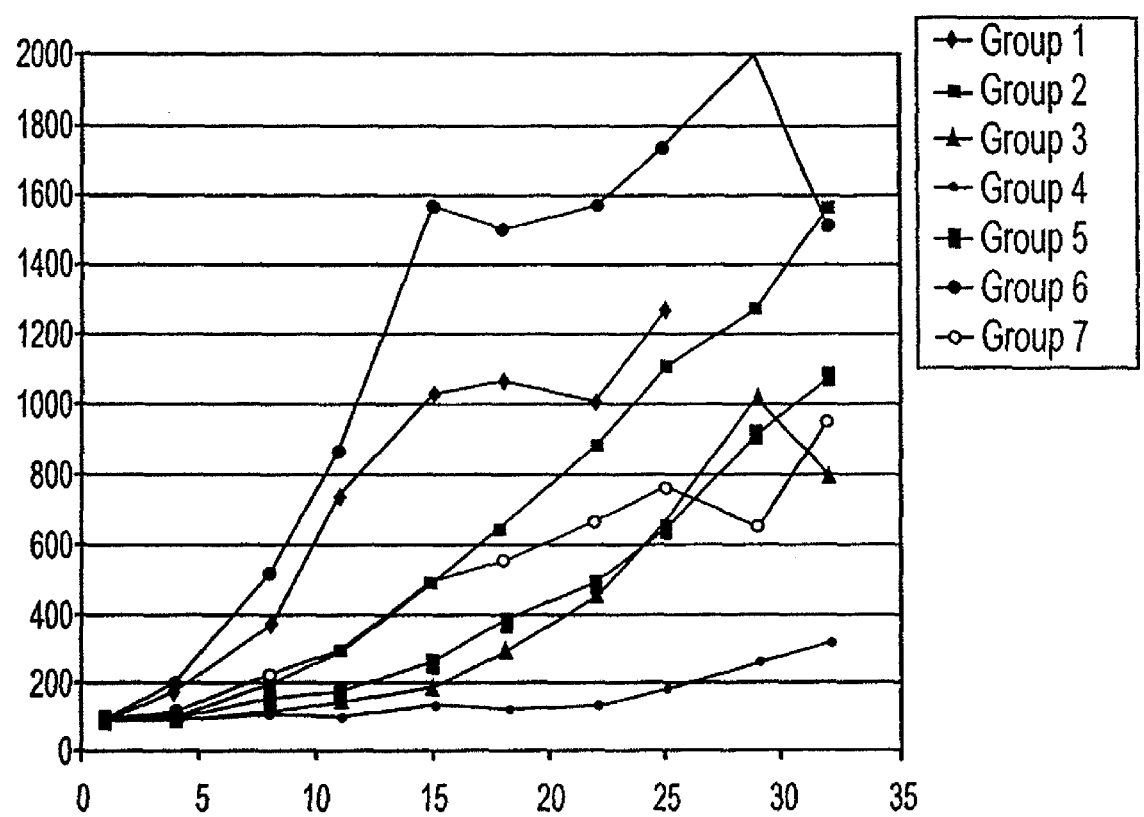
FIG. 4 demonstrates the effect of Compound 25 dosed in combination with CDDP on tumor growth in the H460 xenograft mouse model.

The body weight and tumor volume was determined as described in Example 47. The results are shown in FIG. 4. The data indicate that, while continuous application of Compound 25 alone or in combination with CDDP is efficacious, intermittent, such as once a week, dosing can provide greater therapeutic benefit in the treatment of certain cancers such as non-small cell lung cancer.

Example 55

Compound 25 And Gemcitabine Combination Therapy

A combination of Compound 25 and gemcitabine was administered to nude mice that were carrying tumors derived from type MiPaca2 human pancreatic cancer cells. Mia-Paca-2 tumor is a highly invasive, rapidly growing tumor that results in death within 20-30 days in untreated animals. The tumor cells had been transfected with the gene for red fluorescent protein. Mice were administered doses of vehicle control, gemcitabine, Compound 25, Compound 24, or gemcitabine/Compound 25 combinations or gemcitabine/Compound 24 were administered i.p., as tabulated below (8 mice/group). Compounds 24 and 25 were formulated in saline and provided by Threshold Pharmaceuticals, Inc., as a dry powder. Gemcitabine was obtained commercially and prepared freshly according to manufacturer's instructions.

Treatment protocol

| Group | Compound | Dose (mg/kg) | Schedule |
|---|---|---|---|
| 1 | Vehicle | 10 ml/kg | (qd* × 5)/week for 2 weeks |
| 2 | Gemcitabine | 200 | qw* × 3 weeks |
| 3 | Compound 25 | 30 | (qd × 5)/week for 2 weeks |
| 4 | Compound 24 | 6 | (qd × 5)/week for 2 weeks |

169
-continued

Treatment protocol

| Group | Compound | Dose (mg/kg) | Schedule |
|---|---|---|---|
| 5 | Gemcitabine | 200 | qw × 3 weeks |
|   | Compound 25 | 30 | (qd × 5)/week for 2 weeks |
| 6 | Gemcitabine | 200 | qw × 3 weeks |
|   | Compound 24 | 6 | (qd × 5)/week for 2 weeks |

*qd = every day; qw = every week.

Figure 5:
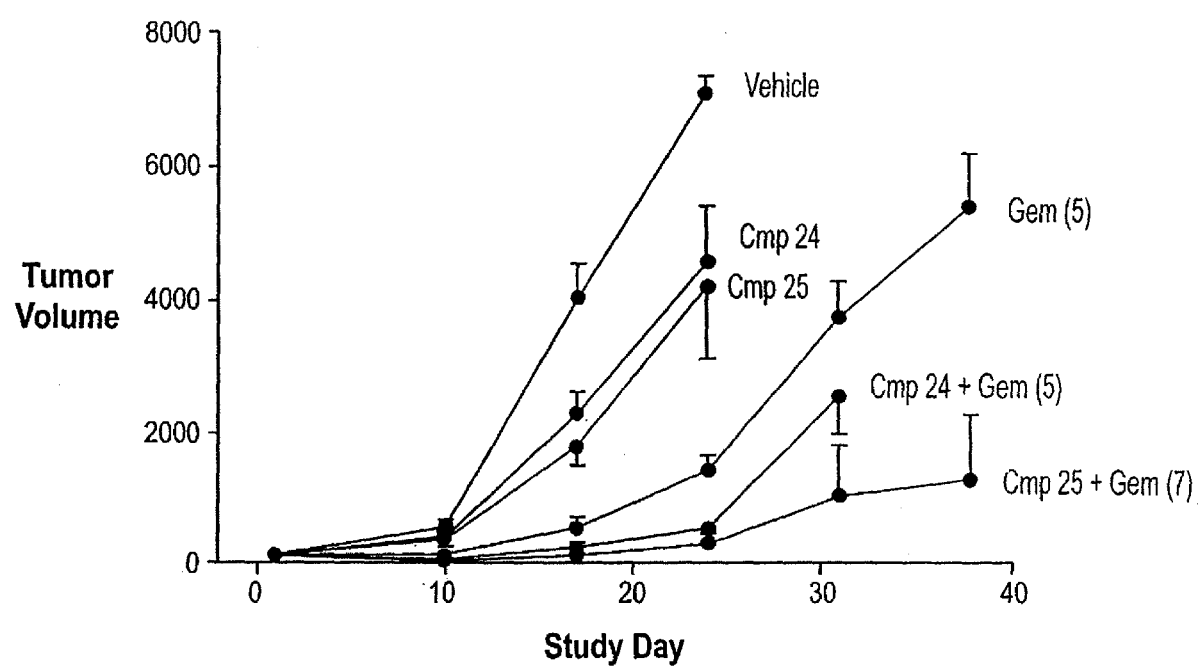
FIGS. 5, 6 and 7 demonstrate the effect of Compound 25 in combination with Gemcitabine on tumor growth in the H460 xenograft mouse model.
Figure 6:
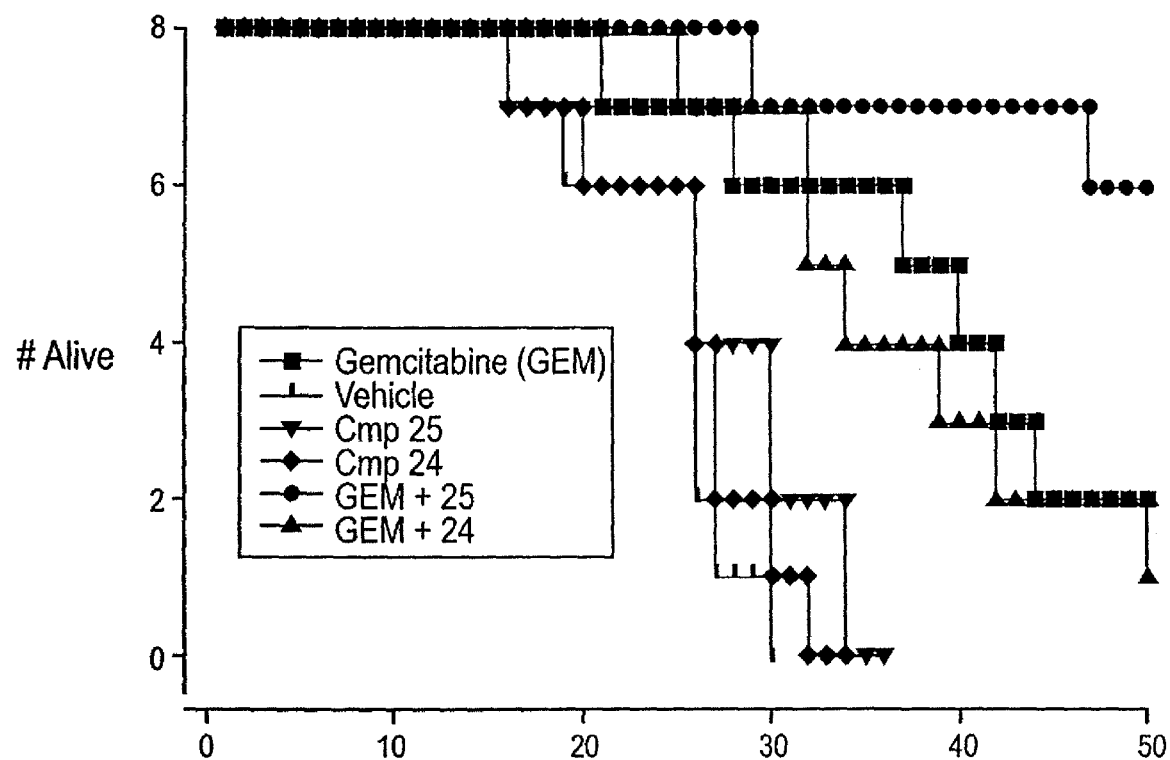

Tumors were imaged once weekly until the end of the study at which time open body images were obtained to confirm effects. In Group 1, the tumors grew rapidly (FIG. 5) and resulted in 100% lethality by day 30 (FIG. 6).

Figure 7:
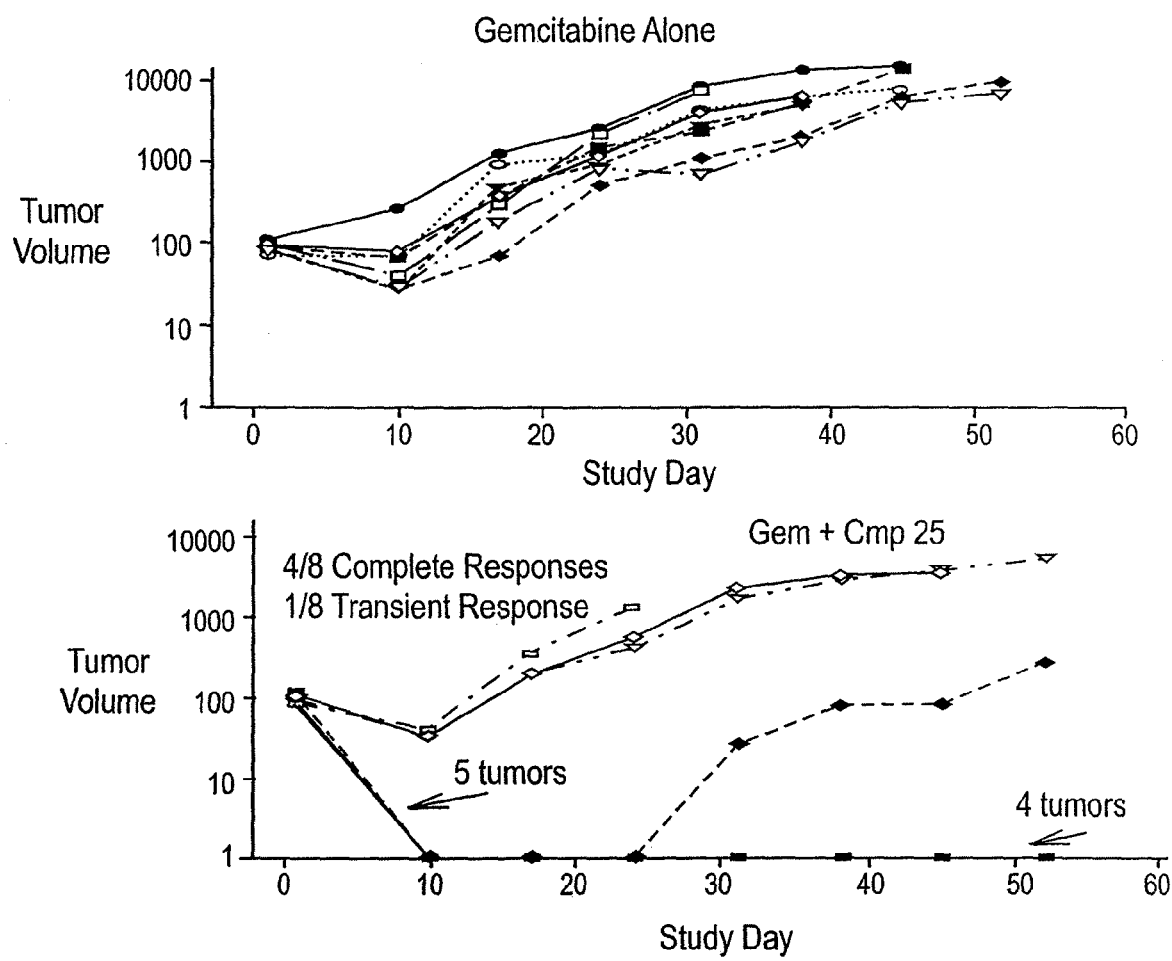

Groups 3 and 4 treatments resulted in minor effects on tumor volume and had little effect on survival. Group 2 treatment significantly reduced tumor volume and prolonged survival. Group 6 treatment provided modest reduction in tumor size but no additional effects on survival. In contrast, Group 5 treatment demonstrated significantly reduced tumor growth and significantly prolonged survival compared to Group 2 treatment. Five out of 8 tumors in Group 5 regressed rapidly after treatment and within a short period failed to emit fluorescence (FIG. 7).

Four of these tumors remained at zero fluorescence until the end of the experiment and the tumors were considered to be cured. No tumors in Group 2 were considered to be cured. These results demonstrate that combination treatment with Compound 25 and gemcitabine is of greater benefit in this model of cancer compared to monotherapy with the standard of care, gemcitabine. These results demonstrate that tumor reduction in animals administered a combination of Compound 25 at 30 mg/mg/day and gemcitabine is significantly greater than that in animals treated with gemcitabine as a single agent.

Using the mouse to HED conversion, Compound 25 can be administered at a therapeutically effective doses of about 2.5 mg/kg/day, for the treatment of cancer, particularly pancreatic cancer, in combination with gemcitabine.

Example 56

It is recognized that efficacious molecules for treatment of human diseases including cancer may be toxic at doses near or sometime much greater than doses necessary to achieve beneficial effects. To determine appropriate dose and route of administering such a compound, it is necessary to understand its toxicity. Routinely, initial approaches to determining the toxic dose involve the use of rodents such as mice to provide preliminary data that might support the design of similar studies in larger animals and humans. Test compounds (Compounds 24, 25 and 36) were tested in mice as preliminary experiments for determining doses to be used in larger animals. Compound 25 was tested at doses as high as 300 mg/kg as a single dose and found to cause renal toxicities such as tubular necrosis and protein spillage into the urine. Transient reductions in white blood cells were also observed. However, little toxicity was noticed at lower doses (100 and 200 mg/kg). These doses selected represent an approximation of doses that might be used in larger animals such as rats and dogs for the purpose of confirming that such toxicities exist and for predicting if renal function should be measured in humans.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A compound of formula (I):

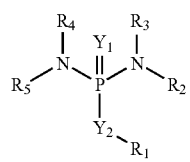

(I)

wherein $Y_2$ is O, S, $NR_6$, $NCOR_6$, or $NSO_2R_6$ wherein $R_6$ is ($C_1$-$C_6$) alkyl, $C_1$-$C_6$ heteroalkyl, aryl, or heteroaryl;

$R_3$ and $R_4$ are independently selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl;

$R_1$ has the formula L-$Z_3$;

L is C($Z_1$)$_2$; and each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$ heteroacyl, aroyl, or heteroaroyl; or L is:

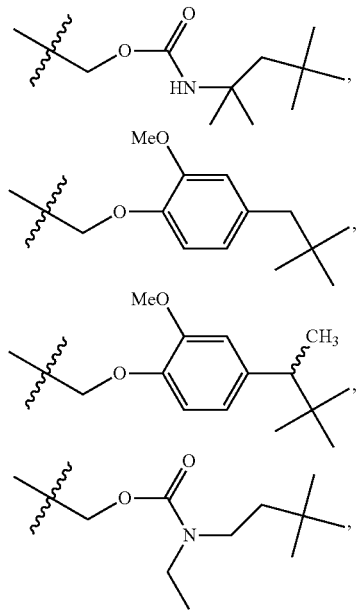

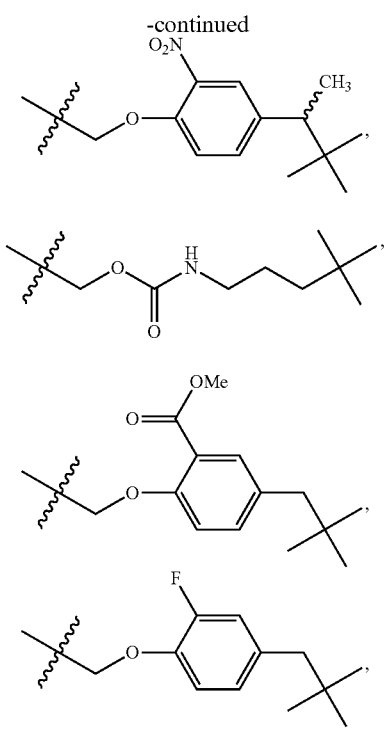

$Z_3$ is a bioreductive group having a formula selected from the group consisting of:

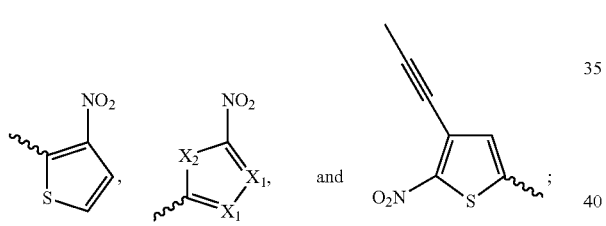

each $X_1$ is independently N or $CR_8$;
$X_2$ is $NR_7$, S, or O;
$R_7$ is independently selected from the group consisting of $C_1$-$C_6$ alkyl, $C_1$-$C_6$ heteroalkyl, $C_3$-$C_8$ cycloalkyl, heterocyclyl, aryl and heteroaryl;
$R_8$ is independently hydrogen, halogen, cyano, $CHF_2$, $CF_3$, $CO_2H$, amino, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$ heteroacyl, aroyl or heteroaroyl; or a pharmaceutically acceptable salt thereof.

2. The compound of claim 1, or a pharmaceutically acceptable salt thereof, wherein $Y_2$ is O.

3. The compound of claim 1 selected from one of the following formulae:

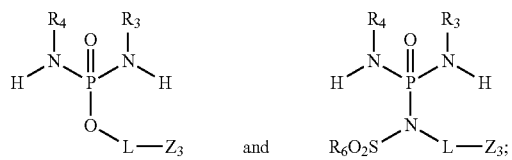

or a pharmaceutically acceptable salt thereof.

4. The compound of claim 1, or a pharmaceutically acceptable salt thereof, wherein the $Z_3$ is selected from the group consisting of:

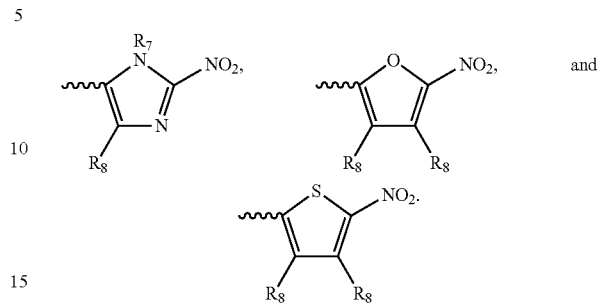

5. The compound of claim 3 selected from one of the following formulae:

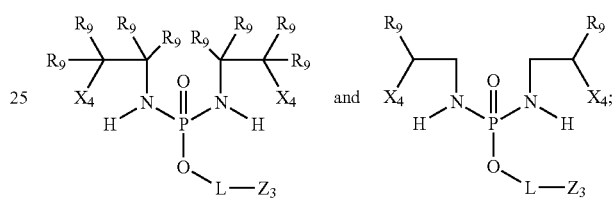

wherein each $R_9$ independently is hydrogen, $C_1$-$C_4$ alkyl or $C_3$-$C_8$ cycloalkyl;
$X_4$ is halo, alkylsulfonyloxy, heteroalkylsulfonyloxy, arylsulfonyloxy, or heteroalkylsulfonyloxy,
or a pharmaceutically acceptable salt thereof.

6. The compound of claim 5 of the formula:

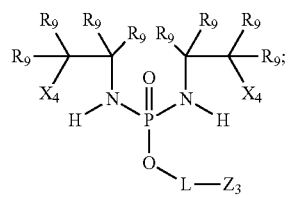

wherein each $R_9$ is independently hydrogen, methyl, ethyl, propyl, isopropyl, or cyclopropyl; or a pharmaceutically acceptable salt thereof.

7. The compound of claim 5 of the formula:

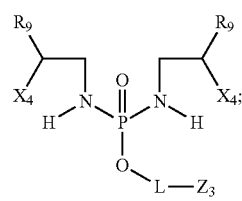

wherein each $R_9$ independently is hydrogen, methyl, ethyl, propyl, isopropyl, or cyclopropyl;
or a pharmaceutically acceptable salt thereof.

8. The compound of claim 1, or a pharmaceutically acceptable salt thereof, wherein L-$Z_3$ has the formula:

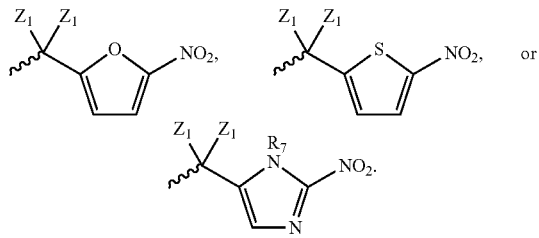

wherein each $Z_1$ independently is H or $C_1$-$C_6$ alkyl.

9. The compound of claim 5 of formula:

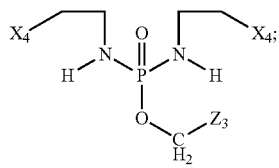

wherein each $X_4$ is selected from the group consisting of Cl, Br, alkylsulfonyloxy, heteroalkylsulfonyloxy, arylsulfonyloxy, and heteroarylsulfonyloxy; or a pharmaceutically acceptable salt thereof.

10. The compound of claim 1 of the formula:

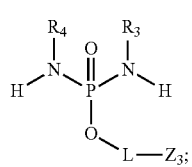

(I)

wherein L is —$CH_2$ or CH($Z_1$) wherein $Z_1$ is $C_1$-$C_6$alkyl; or a pharmaceutically acceptable salt thereof.

11. The compound of claim 5, or a pharmaceutically acceptable salt thereof, wherein L-$Z_3$ is selected from the group consisting of:

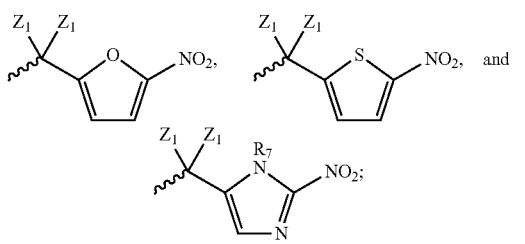

and $R_7$ is independently $C_1$-$C_6$ alkyl, $C_1$-$C_6$ heteroalkyl, $C_3$-$C_8$ cycloalkyl, heterocyclyl, aryl, or heteroaryl.

12. The compound of claim 11, or a pharmaceutically acceptable salt thereof, wherein $Z_1$ is hydrogen, methyl, or ethyl; $R_7$ is selected from the group consisting of methyl, trifluoroethyl, ethyl, propyl, and cyclohexyl; $R_9$ independently is hydrogen or $C_1$-$C_6$ alkyl and each $X_4$ is halo, alkylsulfonyloxy, heteroalkylsulfonyloxy, arylsulfonyloxy, or heteroarylsulfonyloxy.

13. The compound of claim 12, or a pharmaceutically acceptable salt thereof, wherein $R_9$ is hydrogen, methyl, ethyl, isopropyl, or isobutyl; and $X_4$ is chloro, bromo, or methanesulfonyloxy.

14. The compound of claim 1 of formula:

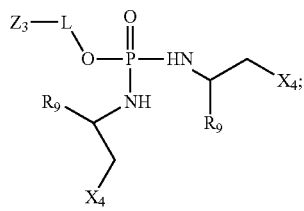

wherein;

L is $CH_2$, CHMe, $CMe_2$,

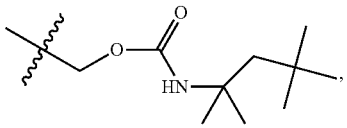

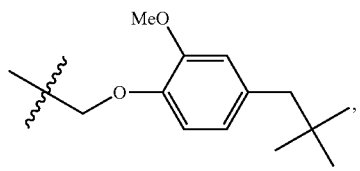

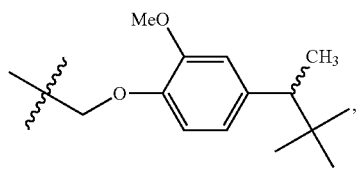

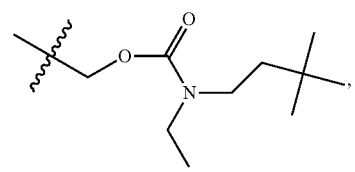

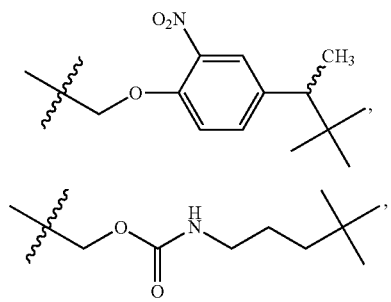

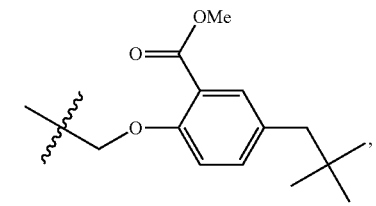

-continued

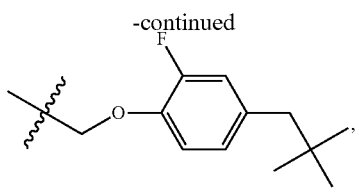

and Z₃ is selected from the group consisting of:

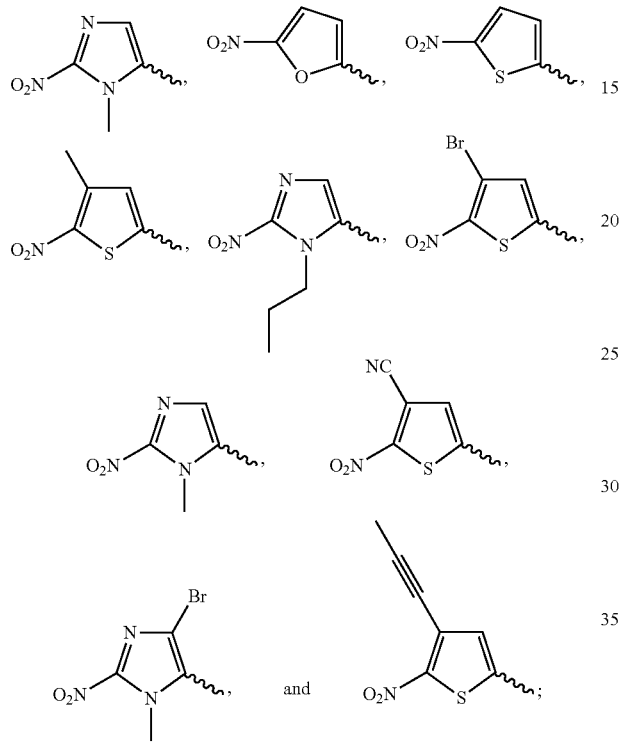

each R₉ is independently selected from the group consisting of hydrogen, methyl, ethyl, propyl, isobutyl, isopropyl and cyclopropyl; and
each X₄ is independently selected from the group consisting of Cl, Br, alkylsulfonyloxy, heteroalkylsulfonyloxy, arylsulfonyloxy and heteroarylsulfonyloxy;
or a pharmaceutically acceptable salt thereof.

15. A compound having the formula:

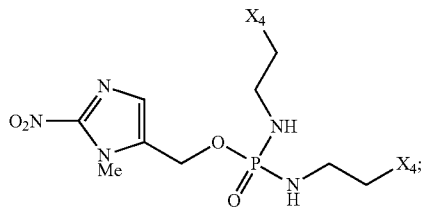

wherein both X₄ are Cl or both X₄ are Br.

16. The compound of claim 15 having the formula:

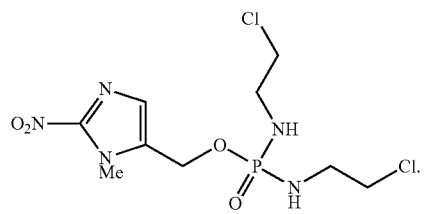

17. A compound having the formula:

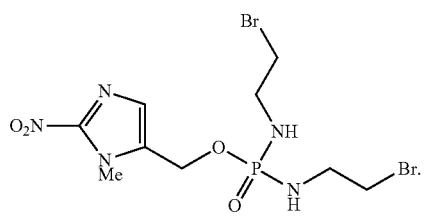

18. A pharmaceutical formulation comprising the compound of claim 15 and a pharmaceutically acceptable excipient, carrier, or diluent.

19. A pharmaceutical formulation comprising the compound of claim 16 and a pharmaceutically acceptable excipient, carrier, or diluent.

20. A pharmaceutical formulation comprising the compound of claim 17 and a pharmaceutically acceptable excipient, carrier, or diluent.

* * * * *

UNITED STATES PATENT AND TRADEMARK OFFICE
CERTIFICATE OF CORRECTION

| | | |
|---|---|---|
| PATENT NO. | : 8,003,625 B2 | Page 1 of 1 |
| APPLICATION NO. | : 11/993822 | |
| DATED | : August 23, 2011 | |
| INVENTOR(S) | : Matteucci et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this

Twentieth Day of December, 2011

David J. Kappos
*Director of the United States Patent and Trademark Office*

UNITED STATES PATENT AND TRADEMARK OFFICE
CERTIFICATE OF CORRECTION

PATENT NO. : 8,003,625 B2
APPLICATION NO. : 11/993822
DATED : August 23, 2011
INVENTOR(S) : Matteucci et al.

Page 1 of 1

It is certified that error appears in the above-identified patent and that said Letters Patent is hereby corrected as shown below:

In the Claims:

Claim 1, Column 170, Line 25: please delete " 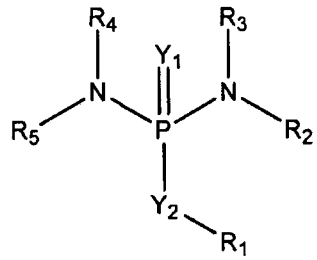 " and insert

-- 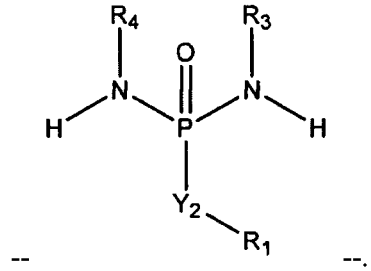 --.

Claim 1, Column 171, Line 20: please insert -- or -- after " 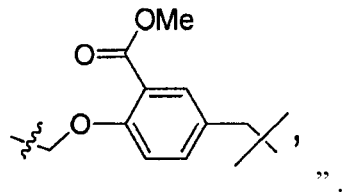 ".

Signed and Sealed this
Twenty-second Day of May, 2012

David J. Kappos
*Director of the United States Patent and Trademark Office*